(12) United States Patent
Amarasinghe et al.

(10) Patent No.: US 12,246,131 B2
(45) Date of Patent: Mar. 11, 2025

(54) PATIENT INTERFACE

(71) Applicant: RESMED PTY LTD, Bella Vista (AU)

(72) Inventors: Amal Shirley Amarasinghe, Sydney (AU); Ravikumar Baluchagi, Sydney (AU); Adam Francis Barlow, Sydney (AU); Andrew James Bate, Sydney (AU); Emily Elizabeth Blanch, Sydney (AU); David James Braund, Sydney (AU); Christopher Samuel Cullen, Sydney (AU); Errol Savio Alex D'Souza, Sydney (AU); Bruce Richard Davies, Sydney (AU); Craig David Edwards, Sydney (AU); Christopher Andrew Wakeley Gill, Sydney (AU); Lachlan Richard Goldspink, Sydney (AU); Thomas Kirby, Sydney (AU); Kishore Markapuram Chengalvarayan, Sydney (AU); Holly Elizabeth Miller, Sydney (AU); Lemmy Nga, Sydney (AU); Chia Ik Tan, Sydney (AU); Matthew Robin Wells, Sydney (AU)

(73) Assignee: RESMED PTY LTD, Bella Vista (AU)

( * ) Notice: Subject to any disclaimer, the term of this patent is extended or adjusted under 35 U.S.C. 154(b) by 0 days.

(21) Appl. No.: 17/533,941

(22) Filed: Nov. 23, 2021

(65) Prior Publication Data
US 2022/0126049 A1 Apr. 28, 2022

Related U.S. Application Data

(63) Continuation of application No. 15/759,348, filed as application No. PCT/AU2016/050891 on Sep. 23, 2016, now Pat. No. 11,278,692.

(Continued)

(51) Int. Cl.
*A61M 16/06* (2006.01)
*A61M 16/00* (2006.01)
*A61M 16/08* (2006.01)

(52) U.S. Cl.
CPC .... *A61M 16/0622* (2014.02); *A61M 16/0057* (2013.01); *A61M 16/0683* (2013.01);
(Continued)

(58) Field of Classification Search
CPC ............... A61M 16/06; A61M 16/065; A61M 16/0616; A61M 16/0683; A61M 16/0622;
(Continued)

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| CN | 1623610 A | 6/2005 |
| CN | 101455871 A | 6/2009 |

(Continued)

OTHER PUBLICATIONS

Extended European Search Report mailed Jun. 30, 2021 in European Application No. 20210909.6, 11 pages.
(Continued)

*Primary Examiner* — Bradley H Philips
*Assistant Examiner* — Savannah L Gabriel
(74) *Attorney, Agent, or Firm* — Nixon & Vanderhye P.C.

(57) ABSTRACT

A patient interface includes a frame assembly including connectors operatively attachable to headgear, a cushion assembly provided to the frame assembly and including a seal-forming structure structured to form a seal with the patient's nose and/or mouth, and an air delivery connector provided to the frame assembly and operatively connected to
(Continued)

an air delivery tube for supplying the air at positive pressure along an air flow path. The cushion assembly is structured to releasably connect to the frame assembly independently of the air delivery connector. The air delivery connector is structured to releasably connect to the frame assembly independently of the cushion assembly.

33 Claims, 109 Drawing Sheets

Related U.S. Application Data

(60) Provisional application No. 62/222,593, filed on Sep. 23, 2015, provisional application No. 62/376,961, filed on Aug. 19, 2016.

(52) U.S. Cl.
CPC ........ *A61M 16/08* (2013.01); *A61M 16/0816* (2013.01); *A61M 16/0875* (2013.01); *A61M 2210/0618* (2013.01); *A61M 2210/0625* (2013.01)

(58) Field of Classification Search
CPC .............. A61M 16/08; A61M 16/0057; A61M 16/0816; A61M 16/0875; A61M 16/0618; A61M 16/0625; A61M 16/42; A61M 16/0225; A62B 18/084
See application file for complete search history.

(56) References Cited

U.S. PATENT DOCUMENTS

| | | | |
|---|---|---|---|
| 6,532,959 B1 | 3/2003 | Berthon-Jones | |
| 6,581,594 B1 | 6/2003 | Drew et al. | |
| 6,907,882 B2 | 6/2005 | Ging et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,887,726 B2 | 11/2014 | Schulz et al. | |
| 9,480,809 B2 | 11/2016 | Guney | |
| 11,179,534 B2 | 11/2021 | Henry et al. | |
| 2003/0196655 A1 | 10/2003 | Ging | |
| 2005/0076913 A1* | 4/2005 | Ho | A61M 16/0633 128/207.13 |
| 2006/0042629 A1 | 3/2006 | Geist | |
| 2008/0178875 A1 | 7/2008 | Henry | |
| 2008/0314388 A1* | 12/2008 | Brambilla | A61M 16/0644 128/205.25 |
| 2009/0044808 A1* | 2/2009 | Guney | A61M 16/0622 128/207.18 |
| 2009/0050156 A1 | 2/2009 | Ng et al. | |
| 2009/0145429 A1 | 6/2009 | Ging et al. | |
| 2009/0217926 A1* | 9/2009 | Hine | A62B 18/02 128/201.25 |
| 2009/0241961 A1 | 10/2009 | McAuley et al. | |
| 2010/0000534 A1 | 1/2010 | Kooij et al. | |
| 2010/0000537 A1* | 1/2010 | McAuley | A61M 16/0683 128/205.25 |
| 2010/0224199 A1* | 9/2010 | Smith | A61M 16/06 128/863 |
| 2010/0319700 A1* | 12/2010 | Ng | A61M 16/0066 128/206.28 |
| 2011/0197341 A1* | 8/2011 | Formica | B32B 27/065 2/209.3 |
| 2011/0232649 A1* | 9/2011 | Collazo | A61M 16/0605 128/207.18 |
| 2012/0138063 A1* | 6/2012 | Eves | A61M 16/06 128/206.24 |
| 2012/0222680 A1 | 9/2012 | Eves | |
| 2013/0152938 A1 | 6/2013 | Jablonski | |
| 2015/0202397 A1 | 7/2015 | Pastoor | |
| 2015/0352308 A1 | 12/2015 | Cullen | |
| 2016/0030696 A1 | 2/2016 | Klenner | |
| 2017/0281894 A1* | 10/2017 | Walls | A61M 16/0683 |
| 2017/0304577 A1* | 10/2017 | Bearne | A61M 16/0622 |
| 2018/0071476 A1* | 3/2018 | Neff | A61M 16/0605 |
| 2018/0250486 A1 | 9/2018 | Amarasinghe et al. | |
| 2018/0256844 A1* | 9/2018 | Galgali | A61M 16/0605 |

FOREIGN PATENT DOCUMENTS

| | | |
|---|---|---|
| CN | 102596299 A | 7/2012 |
| CN | 204563187 U | 8/2015 |
| EP | 1 027 905 A2 | 8/2000 |
| JP | 2004-570 A | 1/2004 |
| JP | 2004-000570 A | 1/2004 |
| JP | 2009-501577 A | 1/2009 |
| JP | 2009-504320 A | 2/2009 |
| JP | 2013-523241 A | 6/2013 |
| JP | 2018-527152 A | 9/2018 |
| WO | 98/04310 | 2/1998 |
| WO | 98/34665 | 8/1998 |
| WO | 00/78381 | 12/2000 |
| WO | WO 2004/041342 | 5/2004 |
| WO | 2004/073778 | 9/2004 |
| WO | 2004/096332 A1 | 11/2004 |
| WO | 2005/063328 | 7/2005 |
| WO | WO 2005/063326 | 7/2005 |
| WO | 2006/074513 | 7/2006 |
| WO | 2006/130903 | 12/2006 |
| WO | 2009/052560 | 4/2009 |
| WO | WO 2009/055549 A1 | 4/2009 |
| WO | 2009/108995 A1 | 9/2009 |
| WO | 2010/135785 | 12/2010 |
| WO | 2011/022751 A1 | 3/2011 |
| WO | 2012/028995 | 3/2012 |
| WO | 2012/171072 A1 | 12/2012 |
| WO | 2013/020167 A1 | 2/2013 |
| WO | WO 2013/128377 A1 | 9/2013 |
| WO | WO 2014/110622 A1 | 7/2014 |
| WO | 2014/142681 A1 | 9/2014 |
| WO | 2014/165906 A1 | 10/2014 |
| WO | WO 2014/175753 A1 | 10/2014 |
| WO | 2015/006826 A1 | 1/2015 |
| WO | 2015/088362 | 6/2015 |
| WO | 2015/193833 A2 | 12/2015 |
| WO | 2016/041019 A1 | 3/2016 |
| WO | 2016/046776 A1 | 3/2016 |
| WO | 2016/141430 A1 | 9/2016 |
| WO | 2016/149769 A2 | 9/2016 |
| WO | 2017/049357 A1 | 3/2017 |
| WO | 2017/049358 A1 | 3/2017 |
| WO | 2017/049360 A1 | 3/2017 |
| WO | 2017/049361 A1 | 3/2017 |

OTHER PUBLICATIONS

Notice of Reasons for Rejection mailed Aug. 31, 2020 in Japanese Application No. 2018-533973, with English translation, 14 pages.
Notification of the Second Office Action mailed Oct. 12, 2020 in Chinese Application No. 201680064877.4, with English translation, 11 pages.
Notification of the First Office Action mailed Feb. 6, 2020, in Chinese Application No. 201680064877.4, with English translation, 17 pages.
First Examination Report mailed Dec. 2, 2019 in New Zealand Application No. 740771, 5 pages.
Extended European Search Report mailed May 6, 2019 in European Application No. 16847654.7, 10 pages.
West, John, "Respiratory Physiology", Lippincott Williams & Wilkins, 9th edition, pub. 2012.
International Search Report for PCT/AU2016/050891, mailed Jan. 25, 2017, 12 pages.
Written Opinion of the ISA for PCT/AU2016/050891, mailed Jan. 25, 2017, 8 pages.
Written Opinion of the IPEA for PCT/AU2016/050891, mailed Oct. 5, 2017, 7 pages.

(56) References Cited

OTHER PUBLICATIONS

International Preliminary Report on Patentability for PCT/AU2016/050891, mailed Jan. 18, 2018, 22 pages.
Notice of Reasons for Rejection and English translation thereof mailed Aug. 8, 2022 in corresponding JP Patent Application P2021-095885 (13 pages).
Patent Examination Report for corresponding New Zealand Application No. NZ 780024, five pages, dated Jun. 6, 2023.
Patent Examination Report for corresponding New Zealand Application No. NZ 780023, four pages, dated Jun. 14, 2023.
Notification of the First Office Action with English Translation for corresponding Chinese Application No. 2021107263671, 25 pages, dated Apr. 7, 2024.
Second Office Action with English Translation issued in corresponding CN Application No. 202110726367.1, 29 pages, dated Nov. 8, 2024.

* cited by examiner

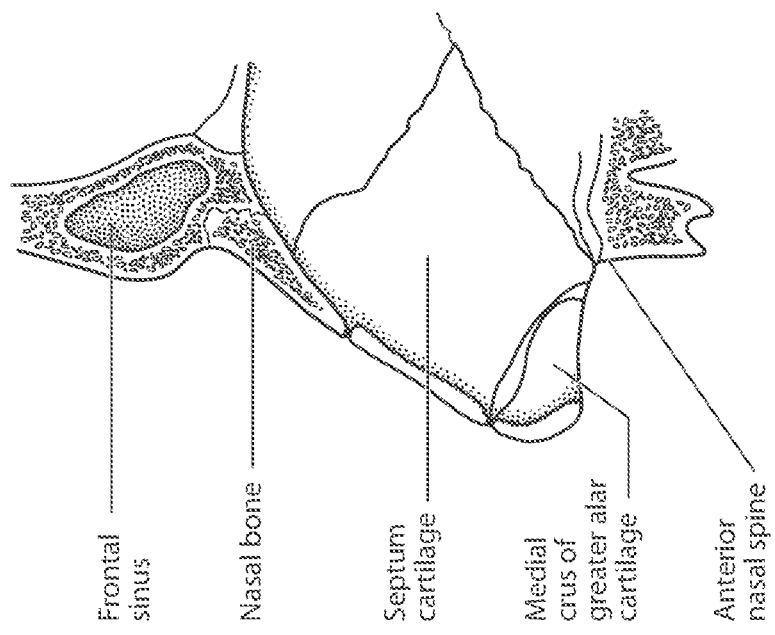
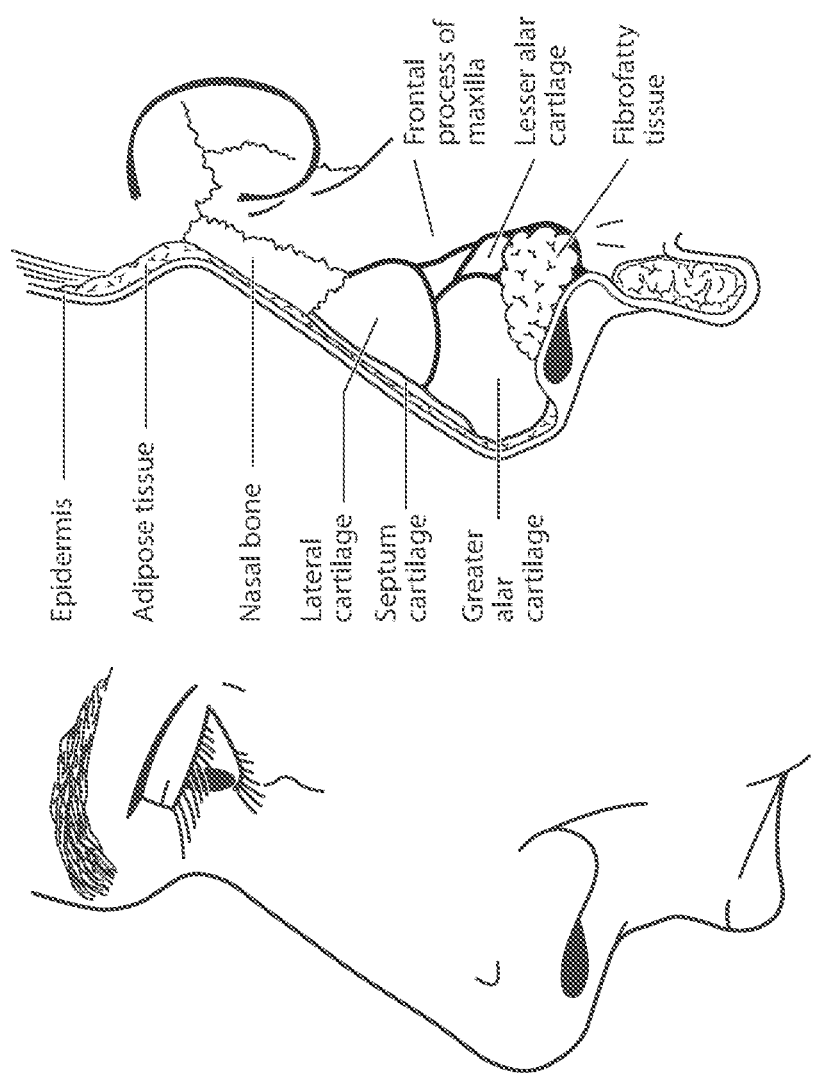
FIG. 2G   FIG. 2H   FIG. 2I

Relatively Large Positive Curvature

Relatively Small Positive Curvature

Zero Curvature

Relatively Small Negative Curvature

Relatively Large Negative Curvature

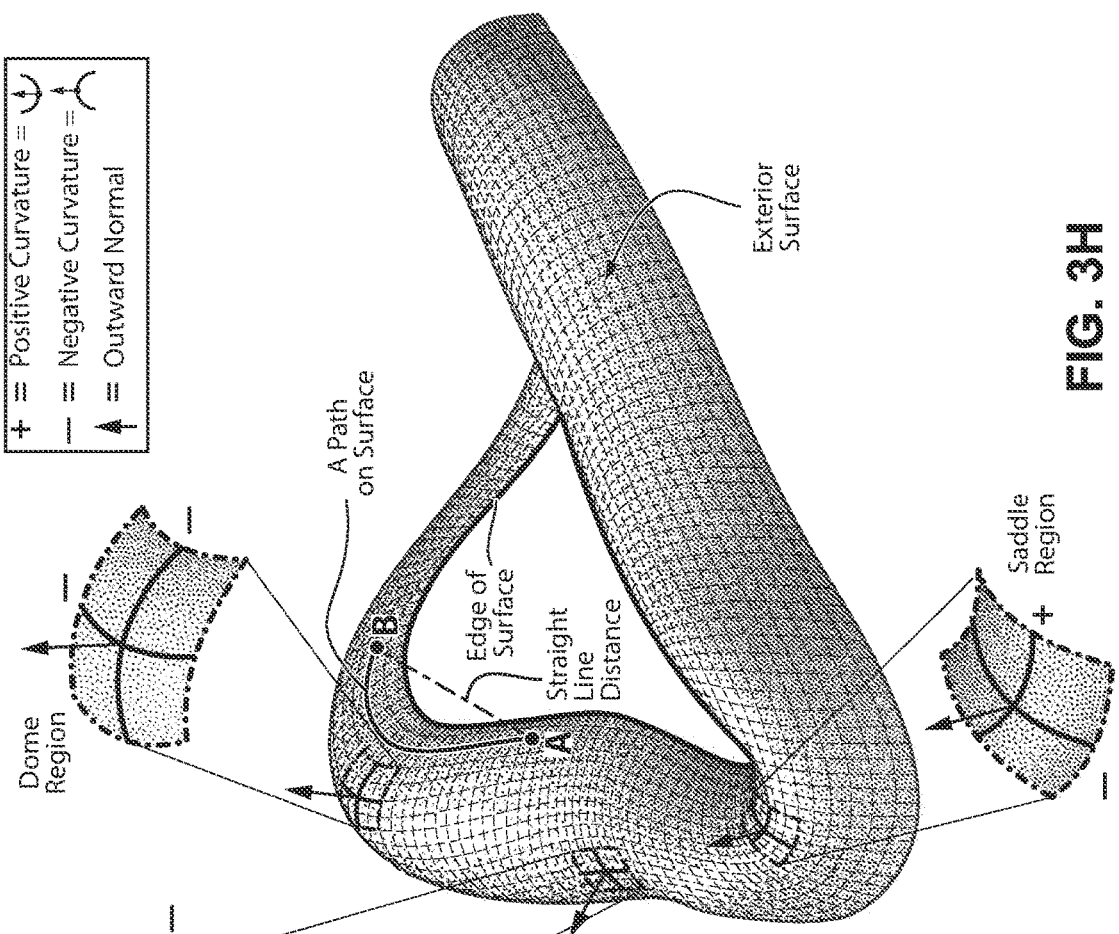
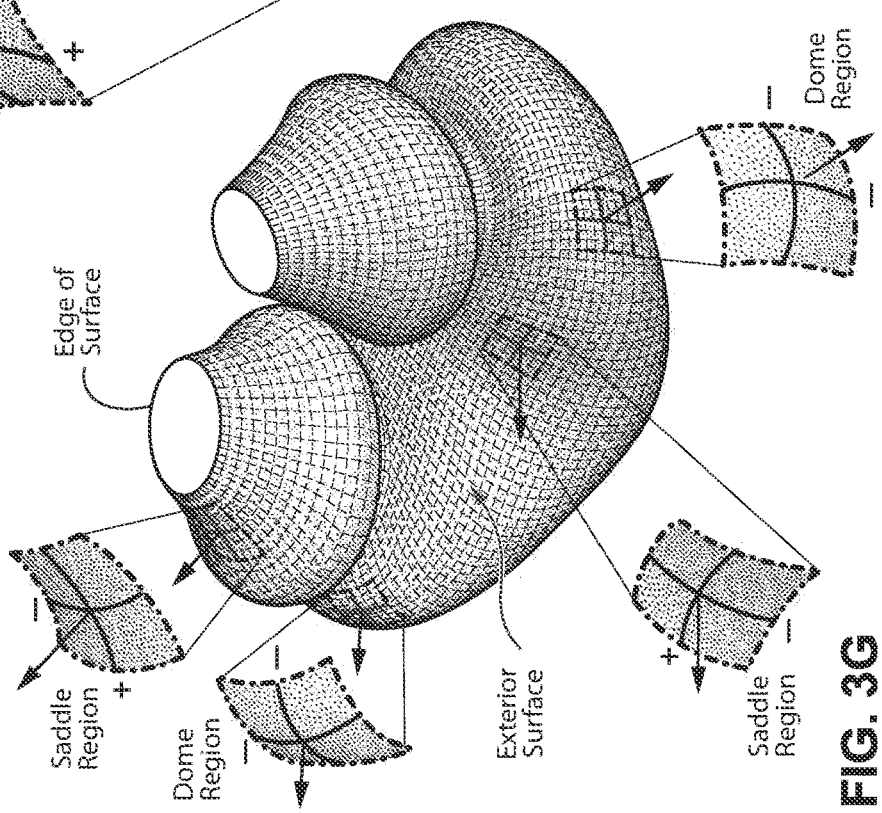
FIG. 3H
FIG. 3G

Left-hand rule

Right-hand rule

Left ear helix

Right-hand helix
Right-hand positive

Right ear helix

PATIENT INTERFACE

1 CROSS-REFERENCE TO RELATED APPLICATIONS

This application is a continuation of U.S. patent application Ser. No. 15/759,348, filed Mar. 12, 2018, which is the U.S. national phase of International Application No. PCT/AU2016/050891 filed Sep. 23, 2016, which designated the U.S. and claims the benefit of U.S. Provisional Application No. 62/222,593, filed Sep. 23, 2015, and U.S. Provisional Application No. 62/376,961, filed Aug. 19, 2016, the entire contents of each of which are hereby incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
| --- | --- | --- | --- | --- |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |

-continued

| Mask name | Mask type | A-weighted sound power level dB(A) (uncertainty) | A-weighted sound pressure dB(A) (uncertainty) | Year (approx.) |
|---|---|---|---|---|
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH$_2$O)Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a person in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

Clinical experts may be able to diagnose or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of the present technology relates to a patient interface including a frame assembly including connectors operatively attachable to headgear, a cushion assembly provided to the frame assembly, the cushion assembly including a seal-forming structure structured to form a seal with the patient's nose and/or mouth, and an air delivery connector provided to the frame assembly, the air delivery connector operatively connected to an air delivery tube for supplying the air at positive pressure along an air flow path. The cushion assembly is structured to releasably connect to the frame assembly independently of the air delivery connector. The air delivery connector is structured to releasably connect to the frame assembly independently of the cushion assembly.

In an example, a first seal for the air flow path may be formed between the air delivery connector and the frame assembly. In an example, a second seal may be formed between the frame assembly and the cushion assembly. In an example, the first seal comprises a dynamic diametric seal and a dynamic face seal. In an example, the second seal comprises a static diametric seal and a static face seal. In an example, the air delivery connector is structured to engage the cushion assembly to provide a seal for the air flow path. In an example, the cushion assembly includes a lip seal structured to provide the seal with the air delivery connector. In an example, the air delivery connector includes an elbow assembly. In an example, the elbow assembly is adapted to swivel relative to the frame assembly. In an example, the air delivery connector includes a vent adaptor connector. In an example, the air delivery connector includes a pair of quick release spring arms structured and arranged to releasably connect to the frame assembly. In an example, the cushion assembly includes a shell provided to the seal-forming structure, the shell and the seal-forming structure cooperating to form a plenum chamber. In an example, the frame assembly includes an upper headgear connector structured to connect to upper straps of the headgear and a lower headgear connector structured to connect to lower straps of the headgear. In an example, the upper headgear connector includes a pair of upper headgear connector arms, each of the arms including one or more flexible portions structured and arranged to conform to varying facial profiles. In an example, each of the flexible portions includes one or more slots structured to form one or more hinges. In an example, the lower headgear connector includes a pair of lower headgear connector arms, each of the lower headgear connector arms including a magnetic connector structured to connect to a magnetic headgear clip. In an example, each of the lower headgear connector arms comprises a slot structured to form a hinge portion. In an example, the frame assembly includes a relatively hard shroud, and the upper and lower headgear connectors are provided to the shroud. In an example, the shroud includes upper and lower grooves structured to receive respective upper and lower headgear connectors. In an example, the frame assembly is provided in one size and is structured to be selectively engageable with multiple sizes of the cushion assembly. In an example, the frame assembly includes a lockout feature along the air flow path structured and arranged to prevent direct connection or insertion of the air delivery tube. In an example, the lockout feature comprises a plurality of projections structured and arranged to extend towards the air flow path. In an example, the lockout feature comprises a single annular projection structured and arranged to extend towards the air flow path. In an example, the air delivery connector includes an elbow assembly comprising a plurality of vent holes and an anti-asphyxia valve assembly. In an example, the frame assembly is provided in the air flow path.

Another aspect of the present technology relates to a frame assembly for a patient interface including an upper headgear connector structured to connect to upper straps of headgear. The upper headgear connector includes a pair of upper headgear connector arms, each of the arms including one or more flexible portions structured and arranged to conform to varying facial profiles.

In an example, each of the flexible portions includes one or more slots structured to form one or more hinges. In an example, each upper headgear connector arm includes a first flexible portion and a second flexible portion between the first flexible portion and an upper headgear connection point structured to connect to a respective upper strap. In an example, the first flexible portion includes a single slot and the second flexible portion includes a plurality of slots. In an example, the frame assembly further comprises a lower headgear connector structured to connect to lower straps of headgear, the lower headgear connector including a pair of lower headgear connector arms.

In yet another example, there is a provided a frame assembly for a patient interface, comprising an upper headgear connector structured to connect to upper straps of headgear, the upper headgear connector including a pair of upper headgear connector arms, each of the arms including a plurality of flexible portions structured and arranged to conform to varying facial profiles, wherein each of the flexible portions forms a plurality of hinges.

Another aspect of the present technology relates to a patient interface including a frame assembly including connectors operatively attachable to headgear, a cushion assembly provided to the frame assembly, the cushion assembly including a seal-forming structure structured to form a seal with the patient's nose and/or mouth, and an air delivery connector (e.g., elbow assembly) provided to the frame assembly, the air delivery connector operatively connected to an air delivery tube for supplying the air at positive pressure. In an example, a first seal for the air flow path is formed between the elbow assembly and the frame assembly, and a separate second seal is formed between the frame assembly and the cushion assembly. For example, the elbow assembly is structured to establish a hard-to-hard connection and dynamic seal with the frame assembly, and the cushion assembly is structured to establish a separate hard-to-hard connection and static seal with the frame assembly.

Another aspect of the present technology relates to a patient interface including a frame assembly including connectors operatively attachable to headgear, a cushion assembly provided to the frame assembly, the cushion assembly including a seal-forming structure structured to form a seal with the patient's nose and/or mouth, and an air delivery connector (e.g., elbow assembly) provided to the frame assembly, the air delivery connector operatively connected to an air delivery tube for supplying the air at positive pressure. In an example, the frame assembly includes a lockout feature along the opening of the air flow path that is structured and arranged to prevent direct connection or insertion of the air delivery tube. This arrangement requires use of the elbow assembly to interconnect the frame assembly and the air delivery tube, thereby ensuring that the elbow assembly (e.g., and its vent and anti-asphyxia valve (AAV)) are present in the system.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

The methods/systems/devices/apparatus described herein can provide improved functioning in a processor, such as of a processor of a specific purpose computer, respiratory monitor and/or a respiratory therapy apparatus. Moreover, the methods/devices/apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

4.2 Respiratory System and Facial Anatomy

Figure 2A:
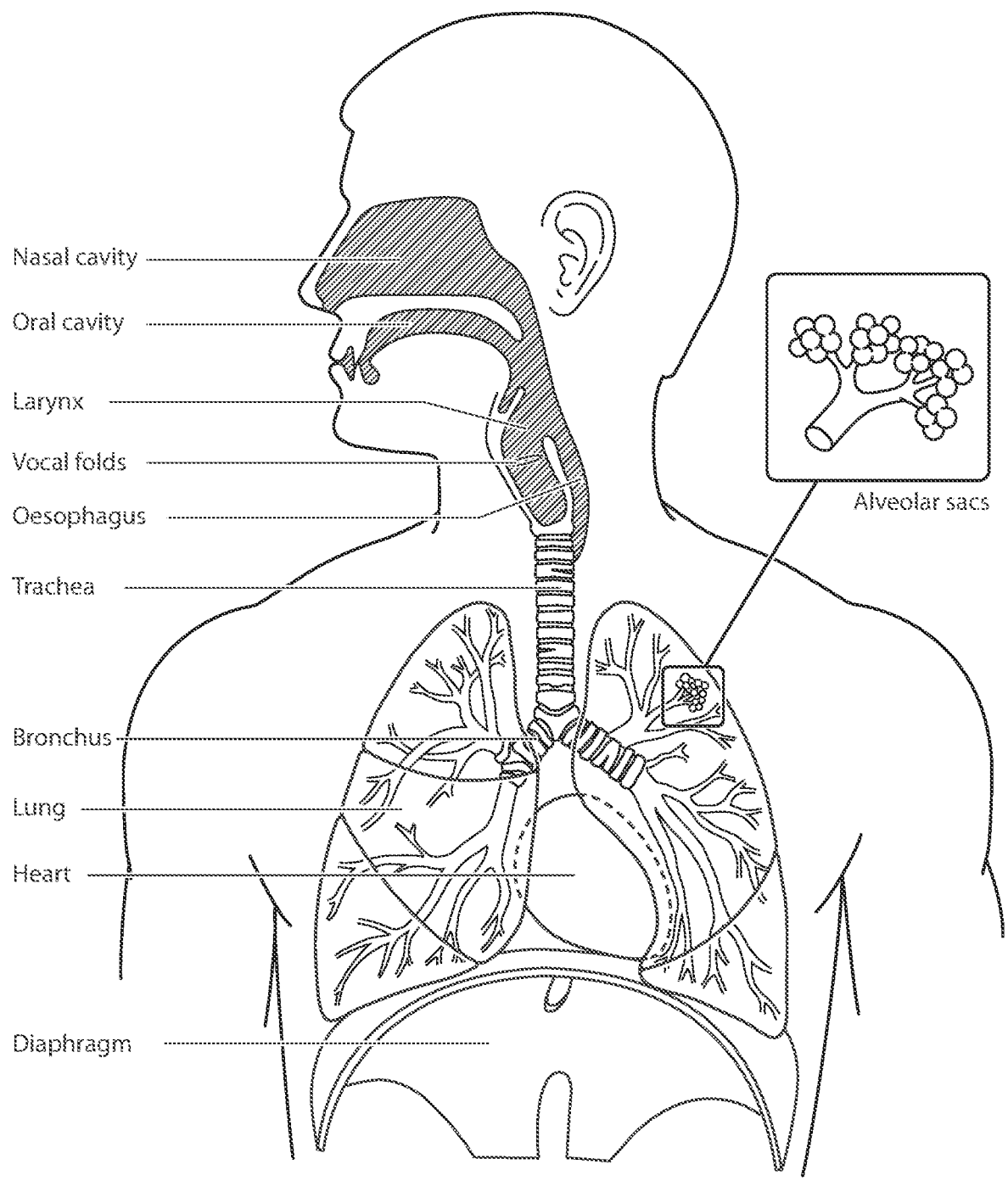

FIG. 2A shows an overview of a human respiratory system including the nasal and oral cavities, the larynx, vocal folds, oesophagus, trachea, bronchus, lung, alveolar sacs, heart and diaphragm.

Figure 2B:
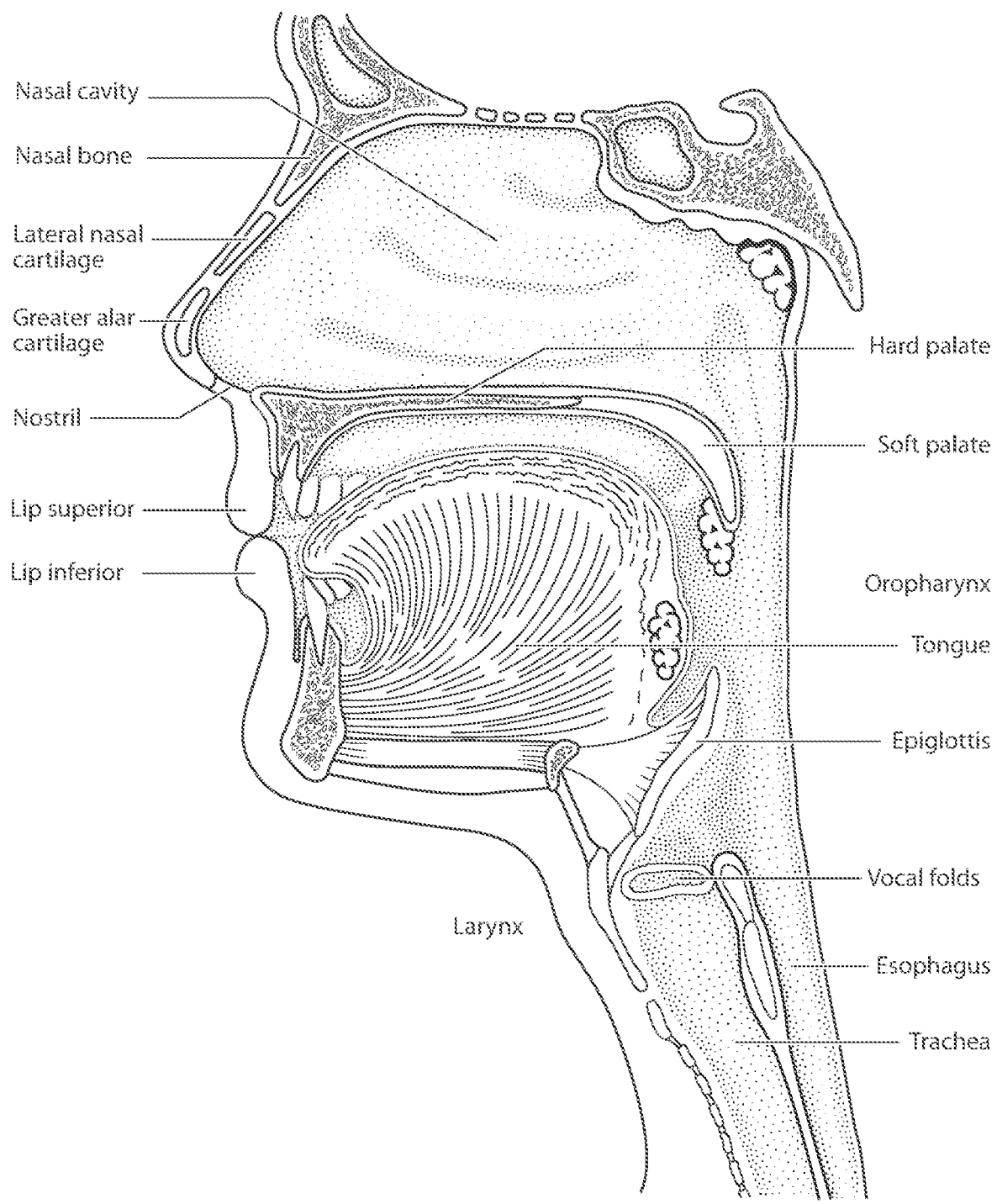

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
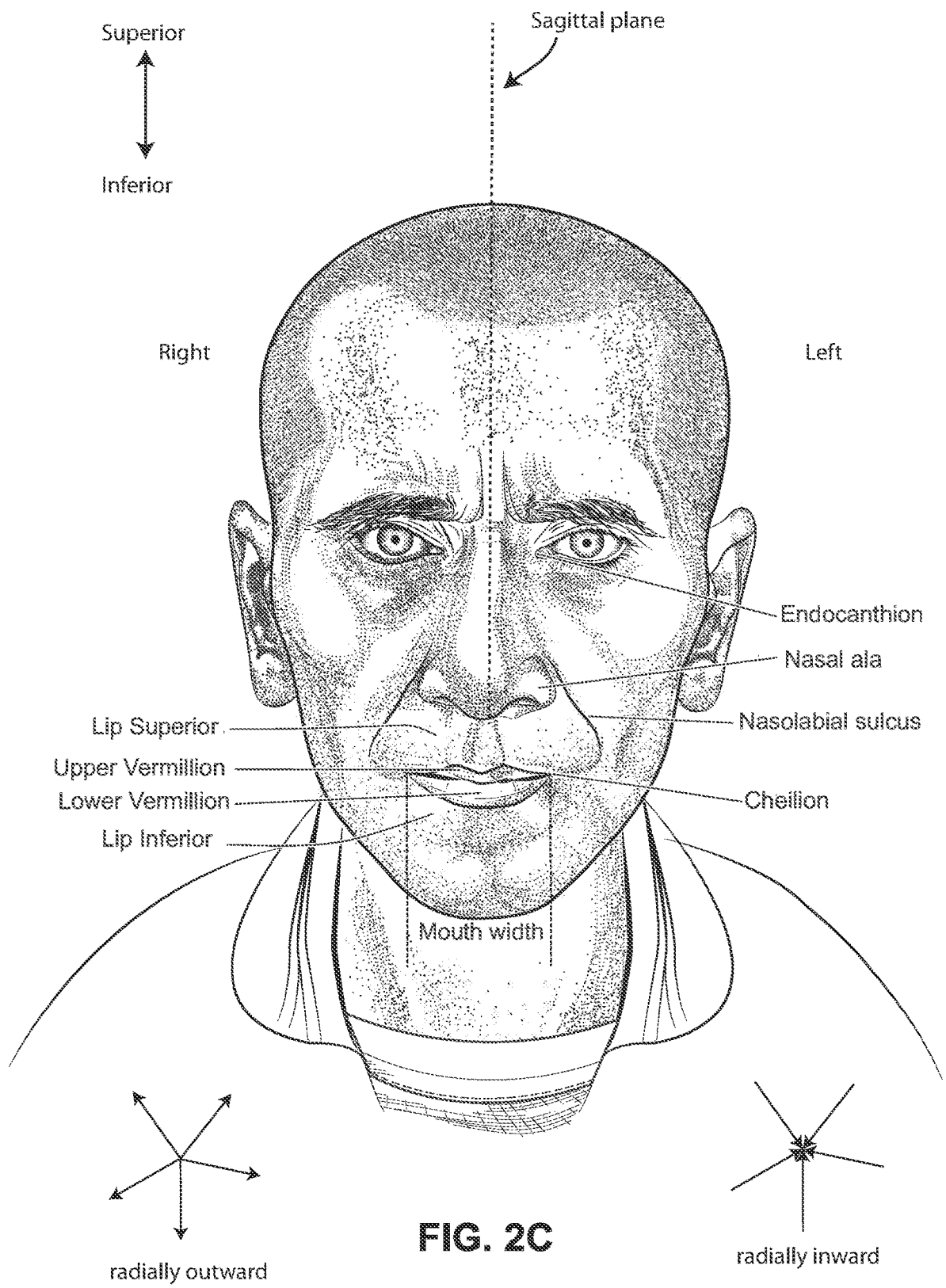

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
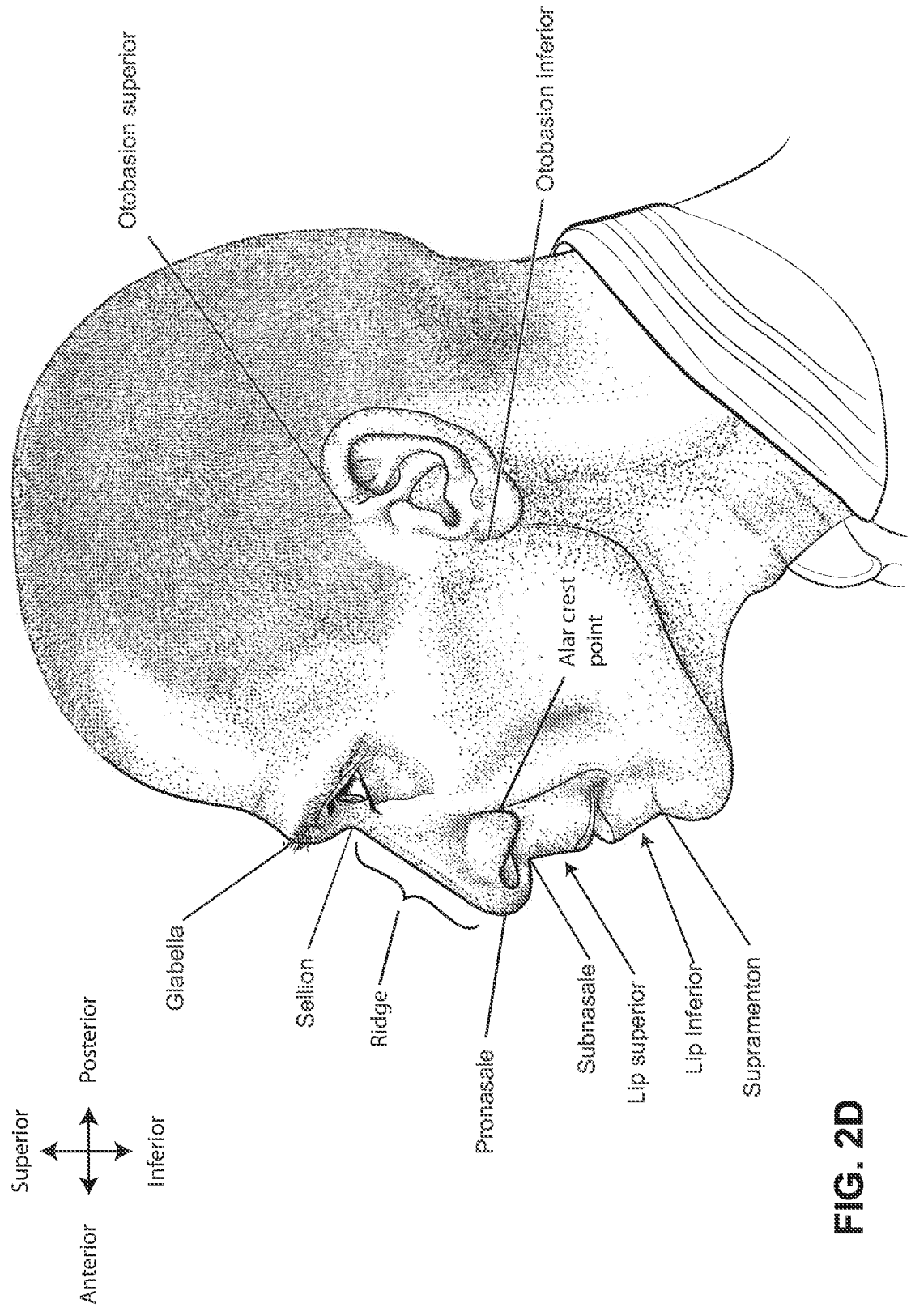

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
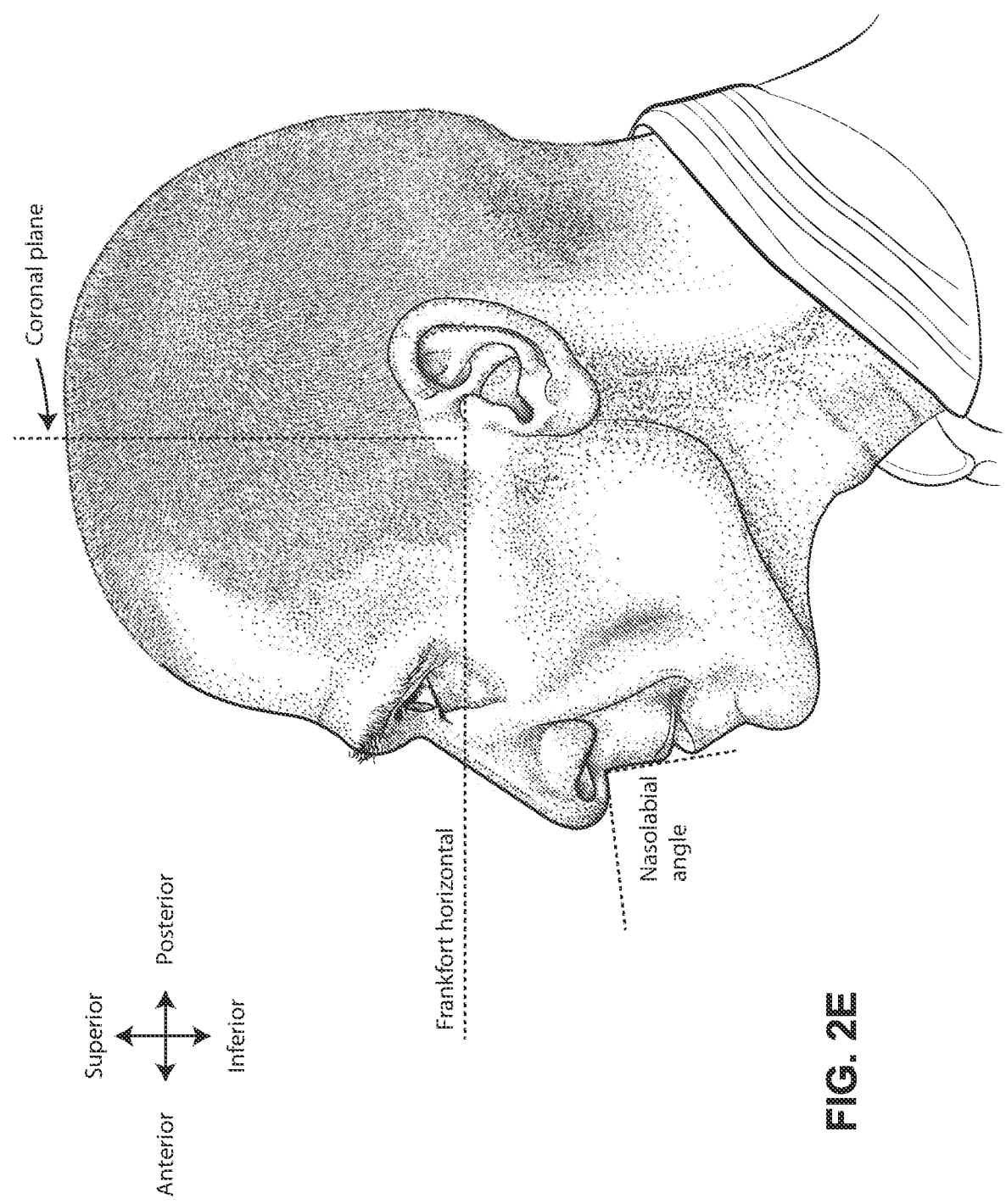

FIG. 2E is a further side view of a head. The approximate locations of the Frankfort horizontal and nasolabial angle are indicated. The coronal plane is also indicated.

Figure 2F:
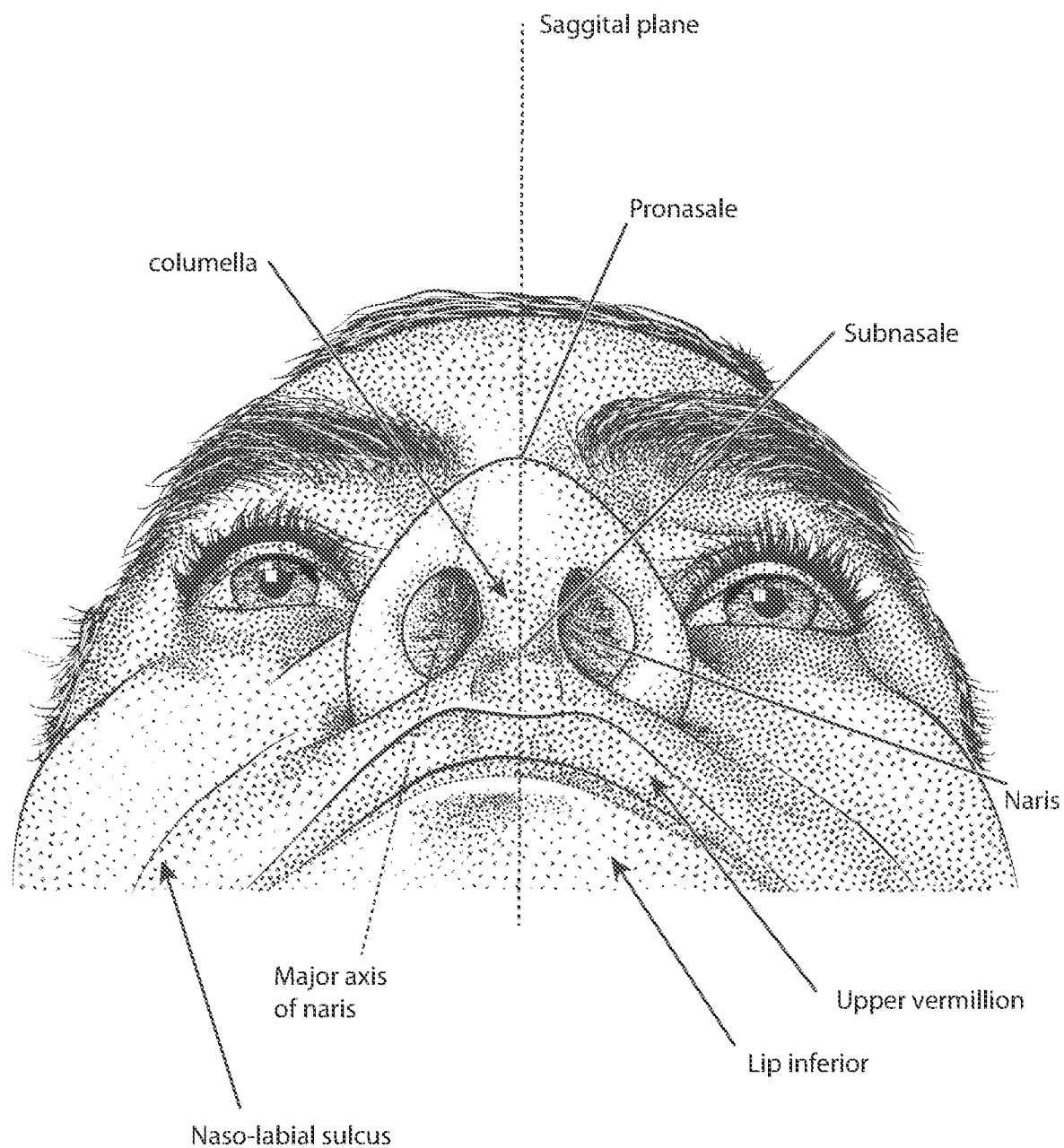

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
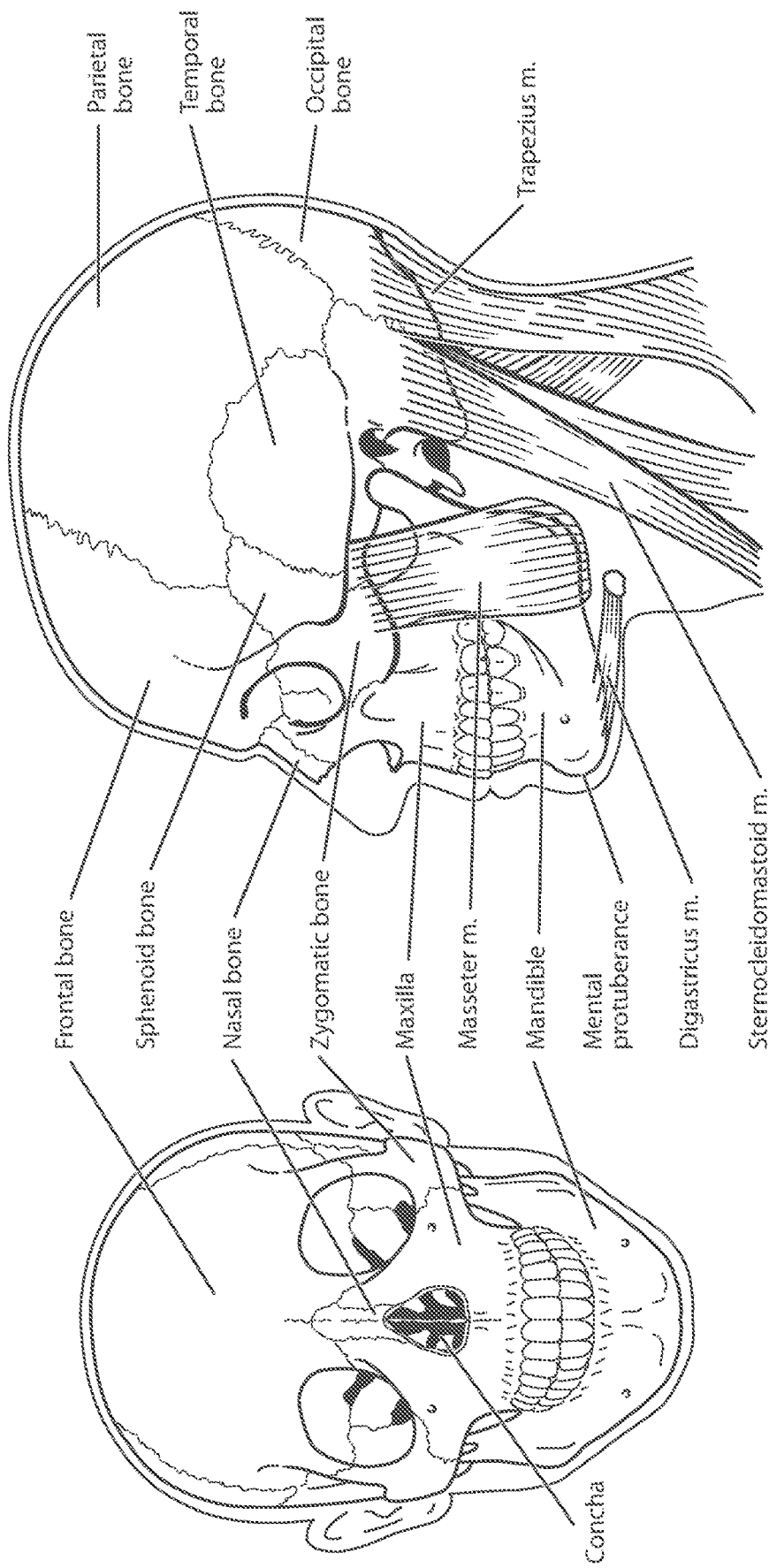

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
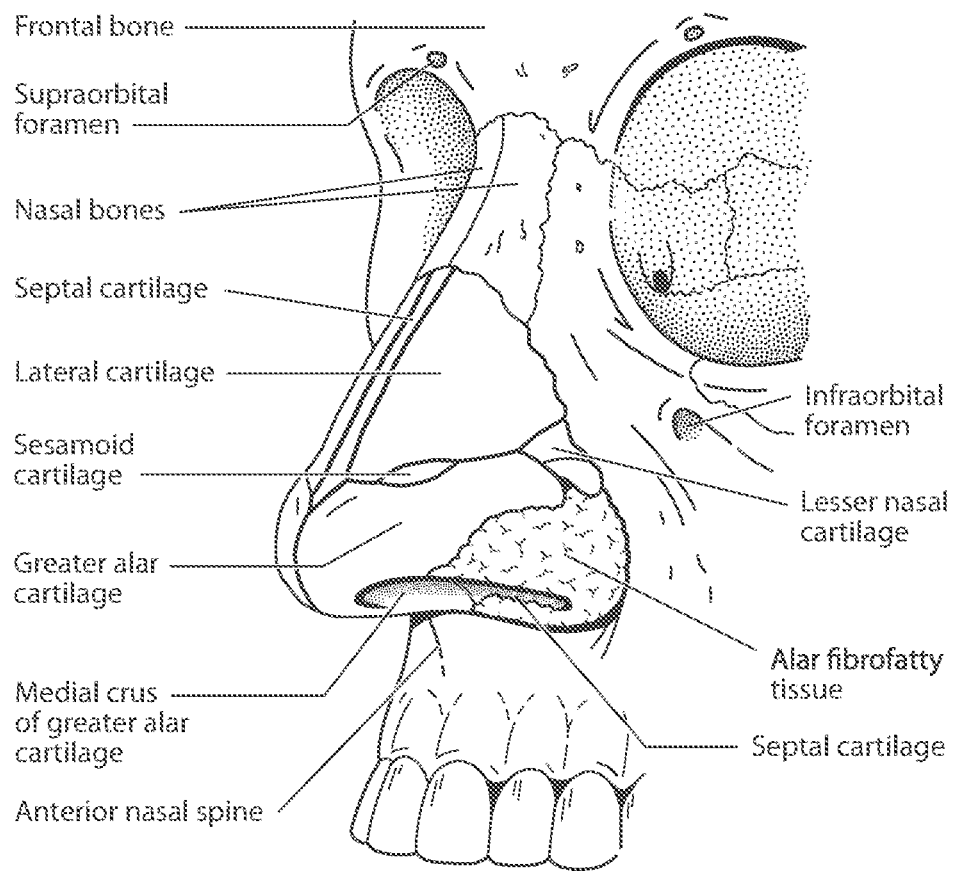

FIG. 2L shows an anterolateral view of a nose.

4.3 Patient Interface

Figure 3A:
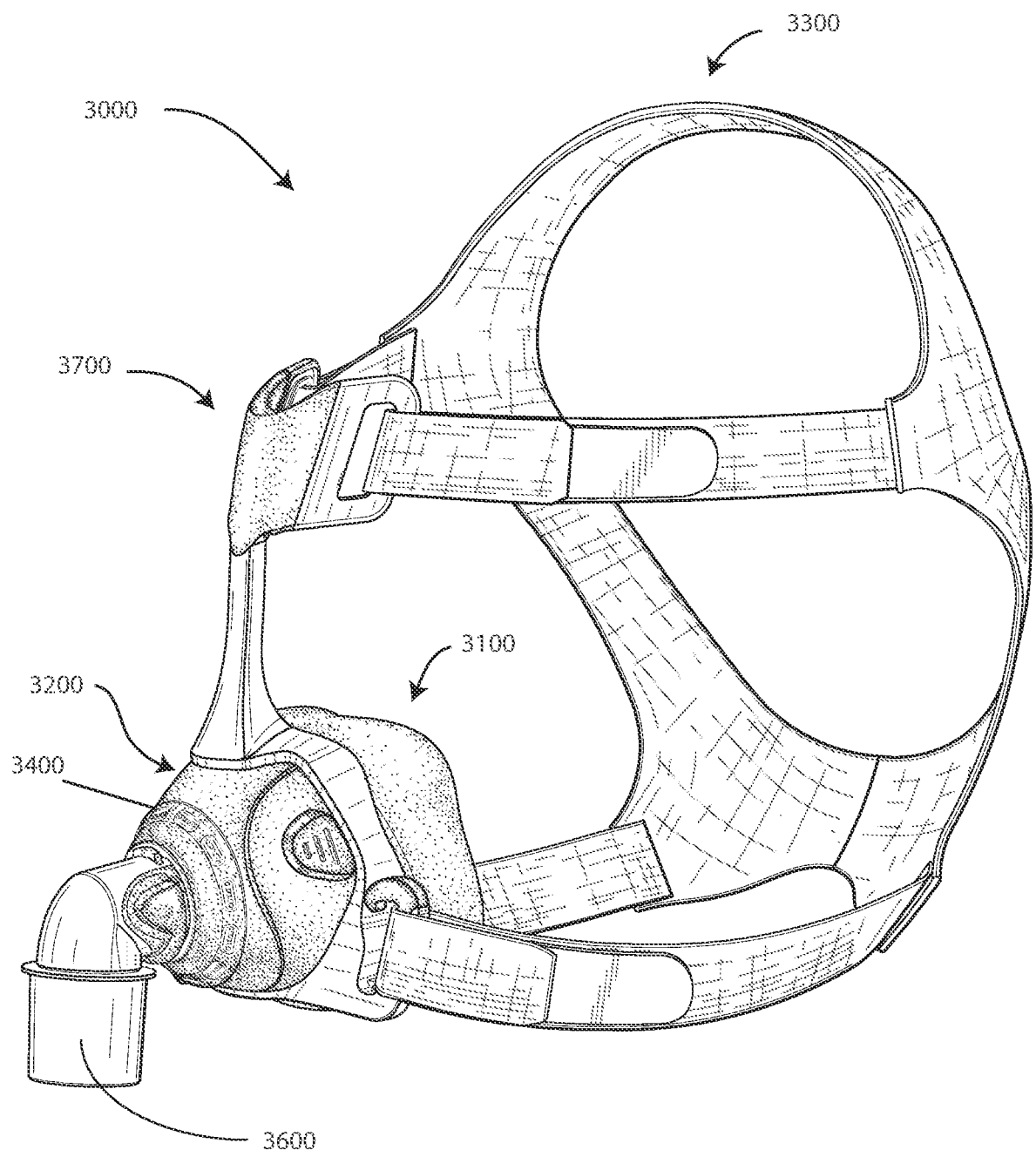

FIG. 3A shows a patient interface in the form of a nasal mask in accordance with one form of the present technology.

Figure 3B:
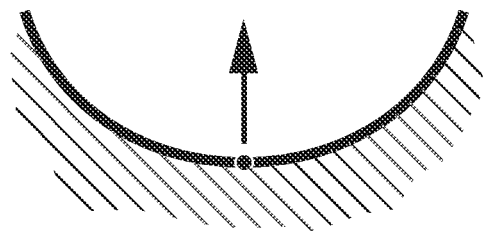

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
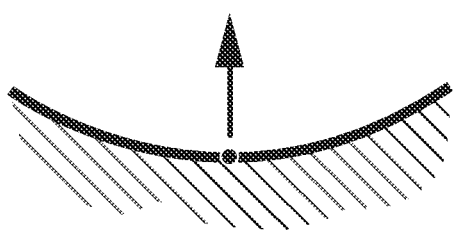

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
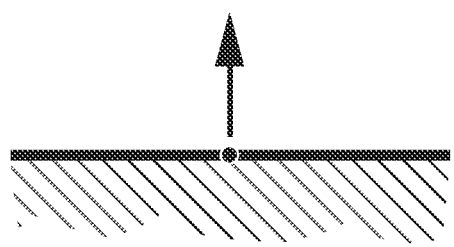

FIG. 3D shows a schematic of a cross-section through a structure at a point. An outward normal at the point is indicated. The curvature at the point has a value of zero.

Figure 3E:
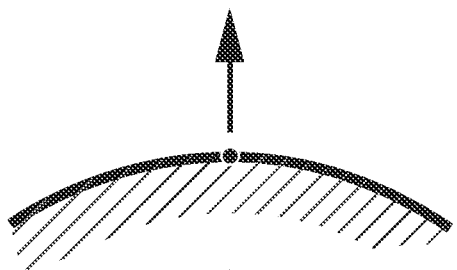

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
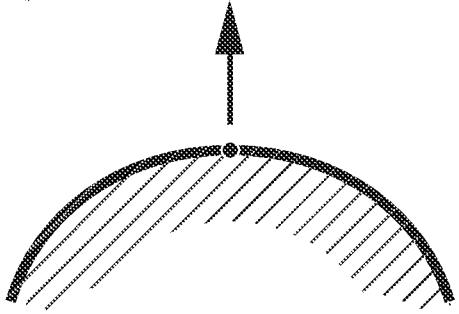

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
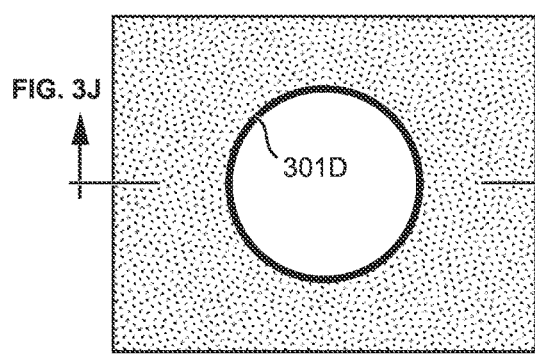

FIG. 3I shows the surface of a structure, with a one dimensional hole in the surface. Plane curve 301D forms the boundary of a one dimensional hole.

Figure 3K:
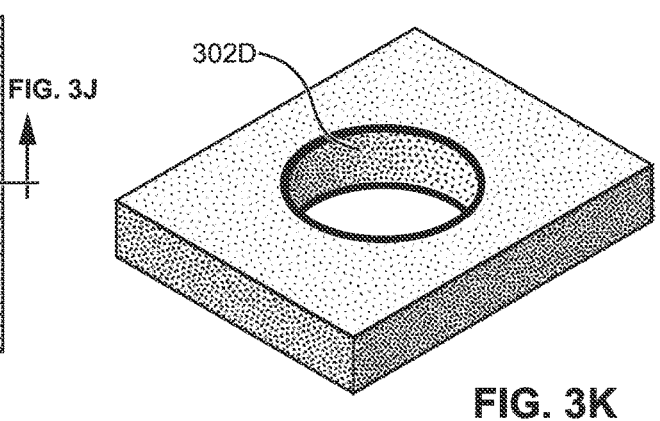
Figure 3J:
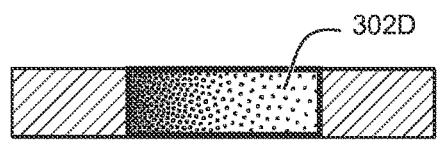

FIG. 3J shows a cross-section through the structure of FIG. 3I. Surface 302D that bounds a two dimensional hole in the structure of FIG. 3I is indicated.

FIG. 3K shows a perspective view of the structure of FIG. 3I, including the two dimensional hole and the one dimensional hole. Surface 302D that bounds a two dimensional hole in the structure of FIG. 3I is indicated.

Figure 3L:
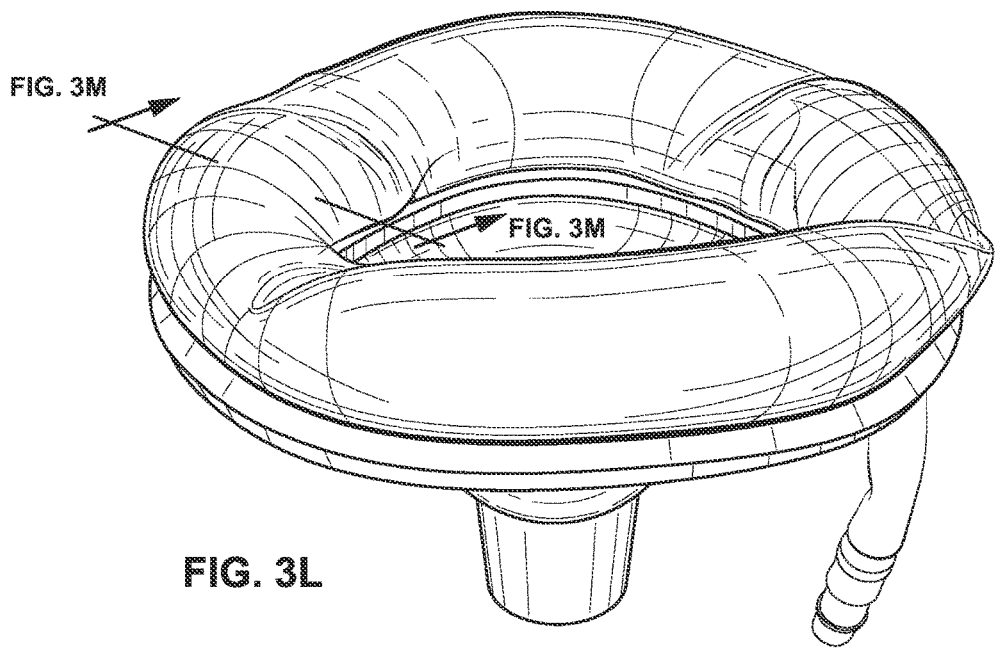

FIG. 3L shows a mask having an inflatable bladder as a cushion.

Figure 3M:
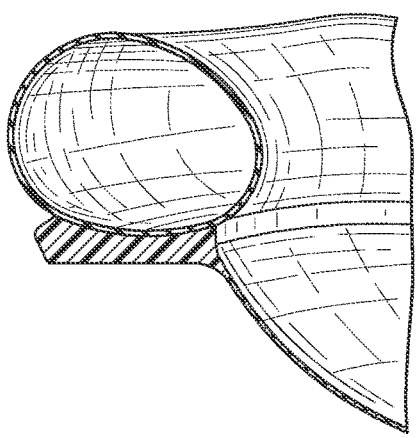

FIG. 3M shows a cross-section through the mask of FIG. 3L, and shows the inside surface of the bladder.

Figure 3N:
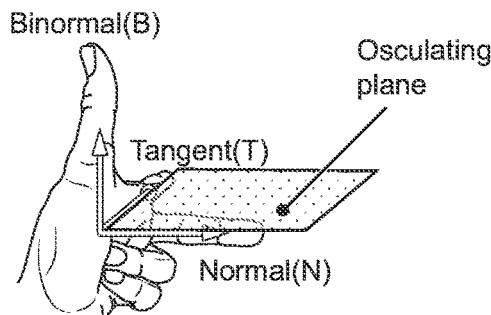

FIG. 3N illustrates a left-hand rule.

Figure 3O:
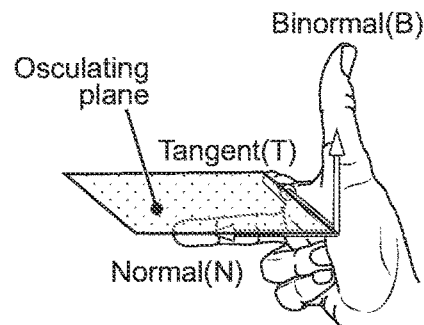

FIG. 3O illustrates a right-hand rule.

Figure 3P:
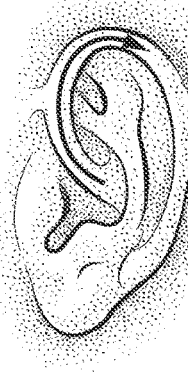

FIG. 3P shows a left ear, including a left ear helix.

Figure 3R:
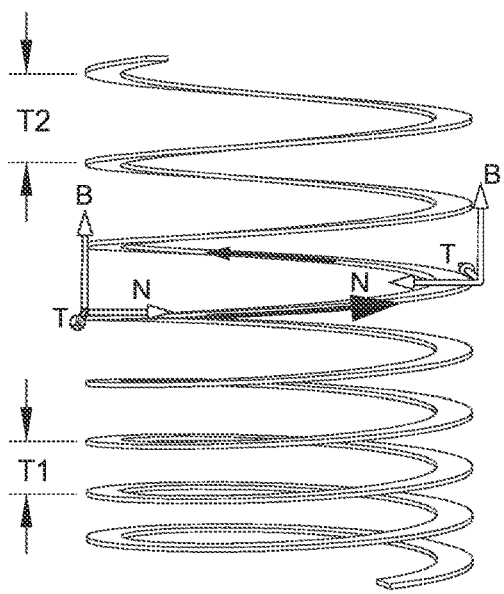
Figure 3Q:
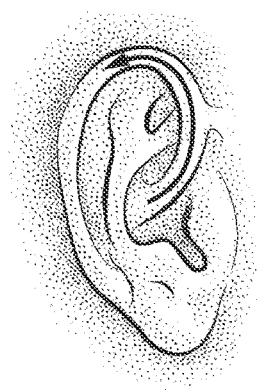

FIG. 3Q shows a right ear, including a right ear helix.

FIG. 3R shows a right-hand helix.

Figure 3S:
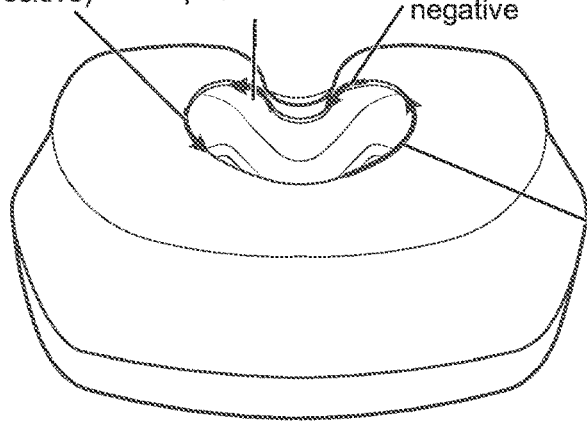

FIG. 3S shows a view of a mask, including the sign of the torsion of the space curve defined by the edge of the sealing membrane in different regions of the mask.

Figure 4:
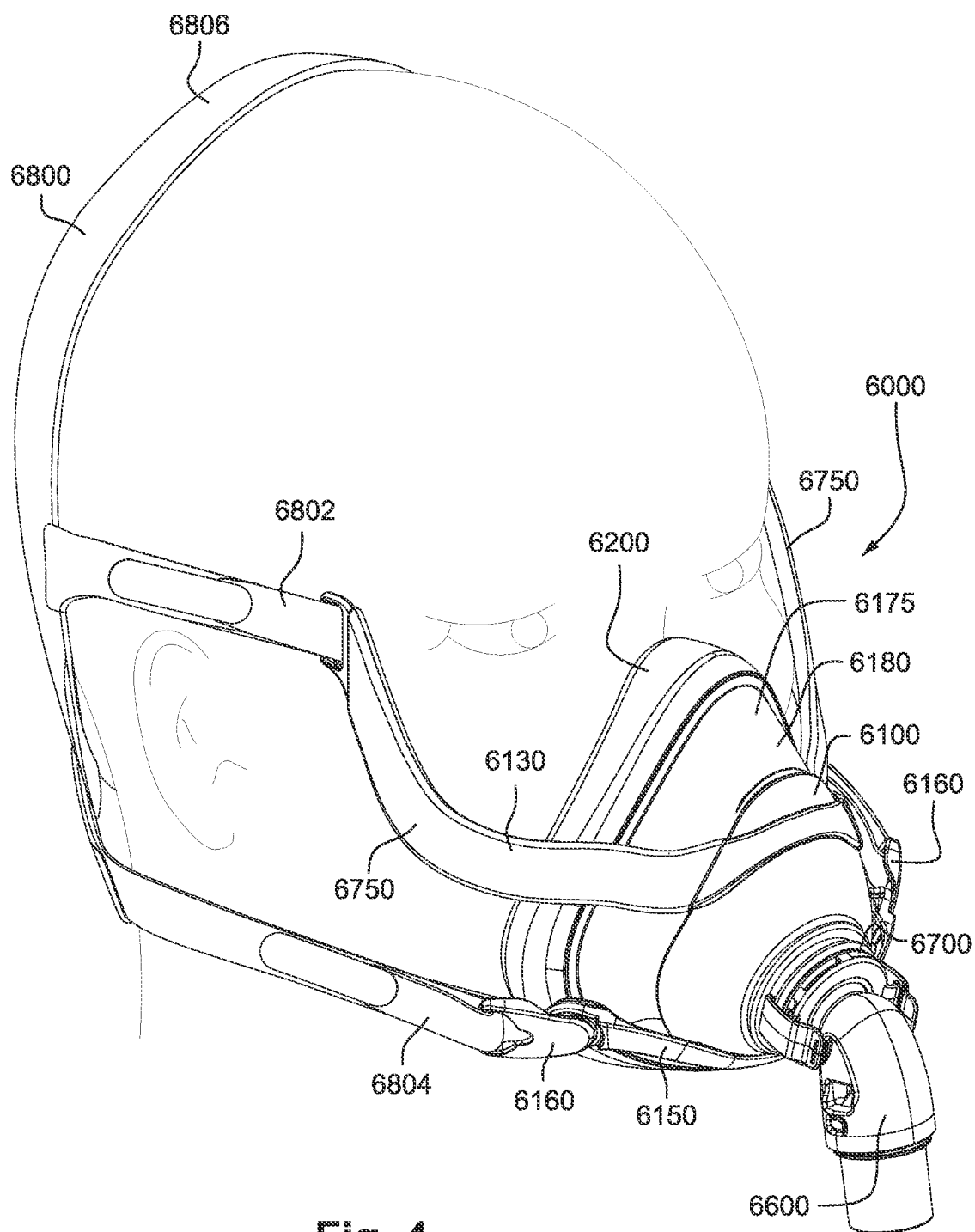

FIG. 4 is a perspective view of a patient interface shown on a patient's head according to an example of the present technology.

Figure 5:
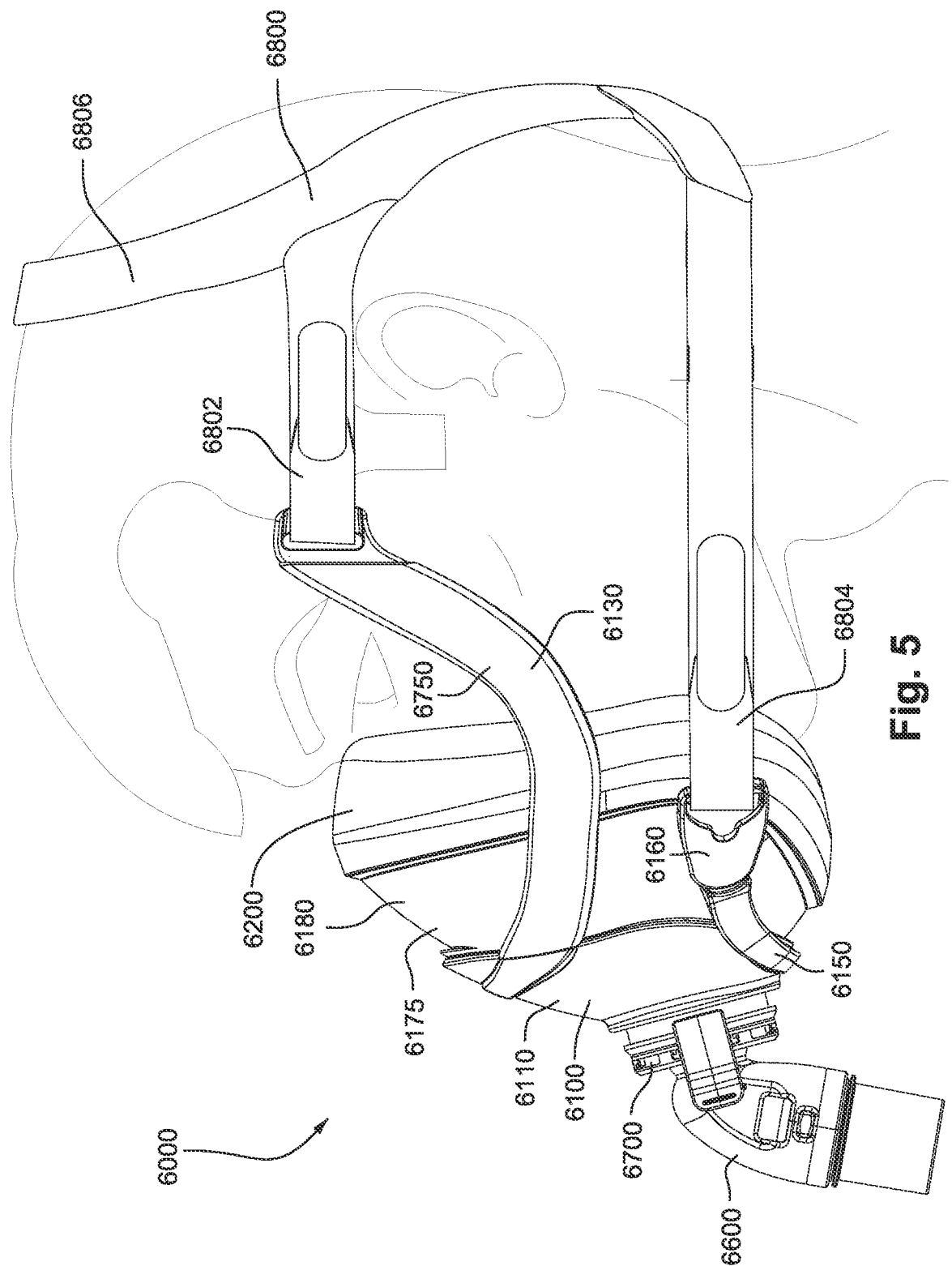

FIG. 5 is a side view of the patient interface shown in FIG. 4.

Figure 6:
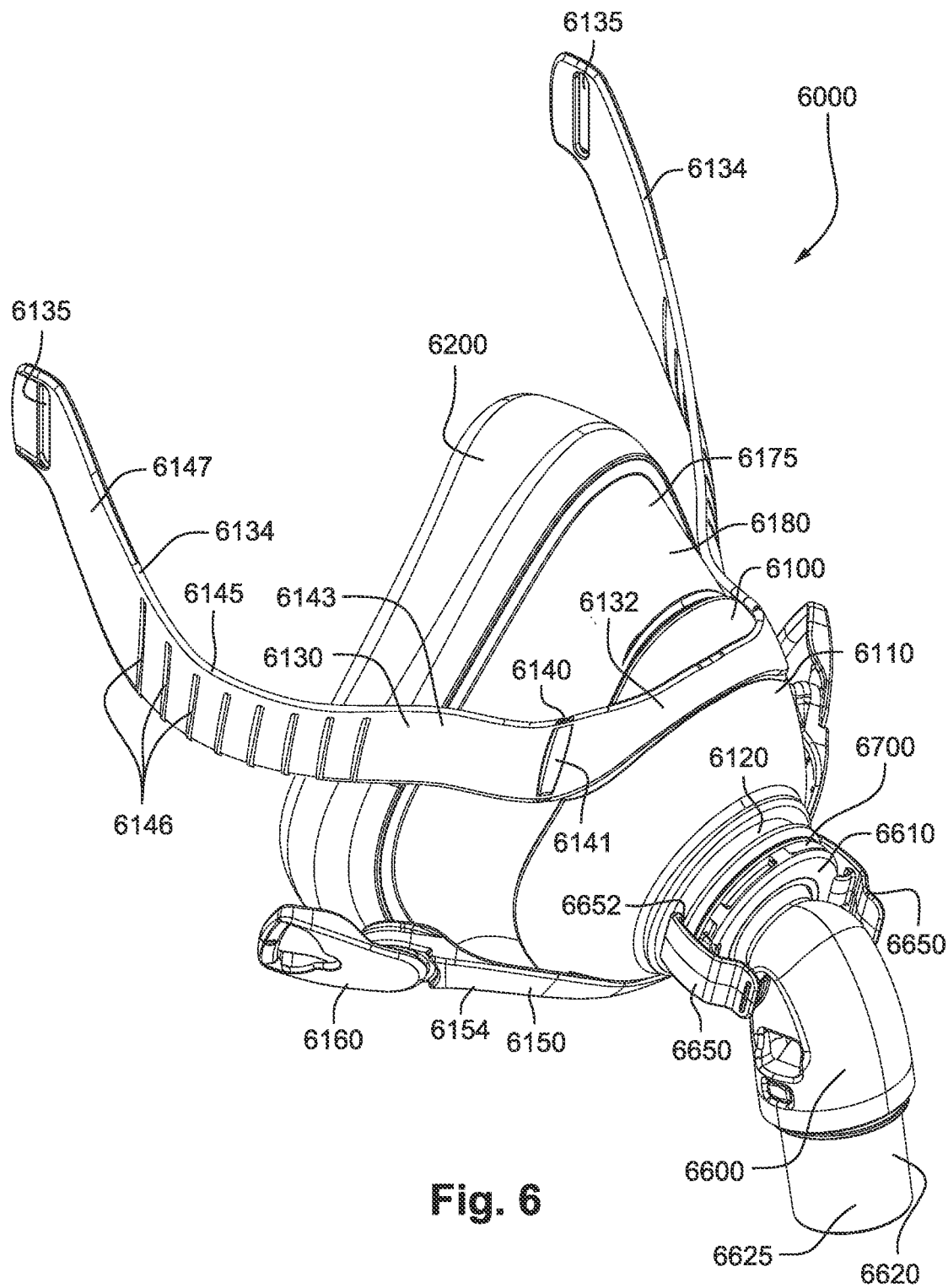

FIG. 6 is a perspective view of a patient interface according to an example of the present technology, the patient interface being shown with the headgear removed and arm covers for upper arms of the frame assembly removed.

Figure 7:
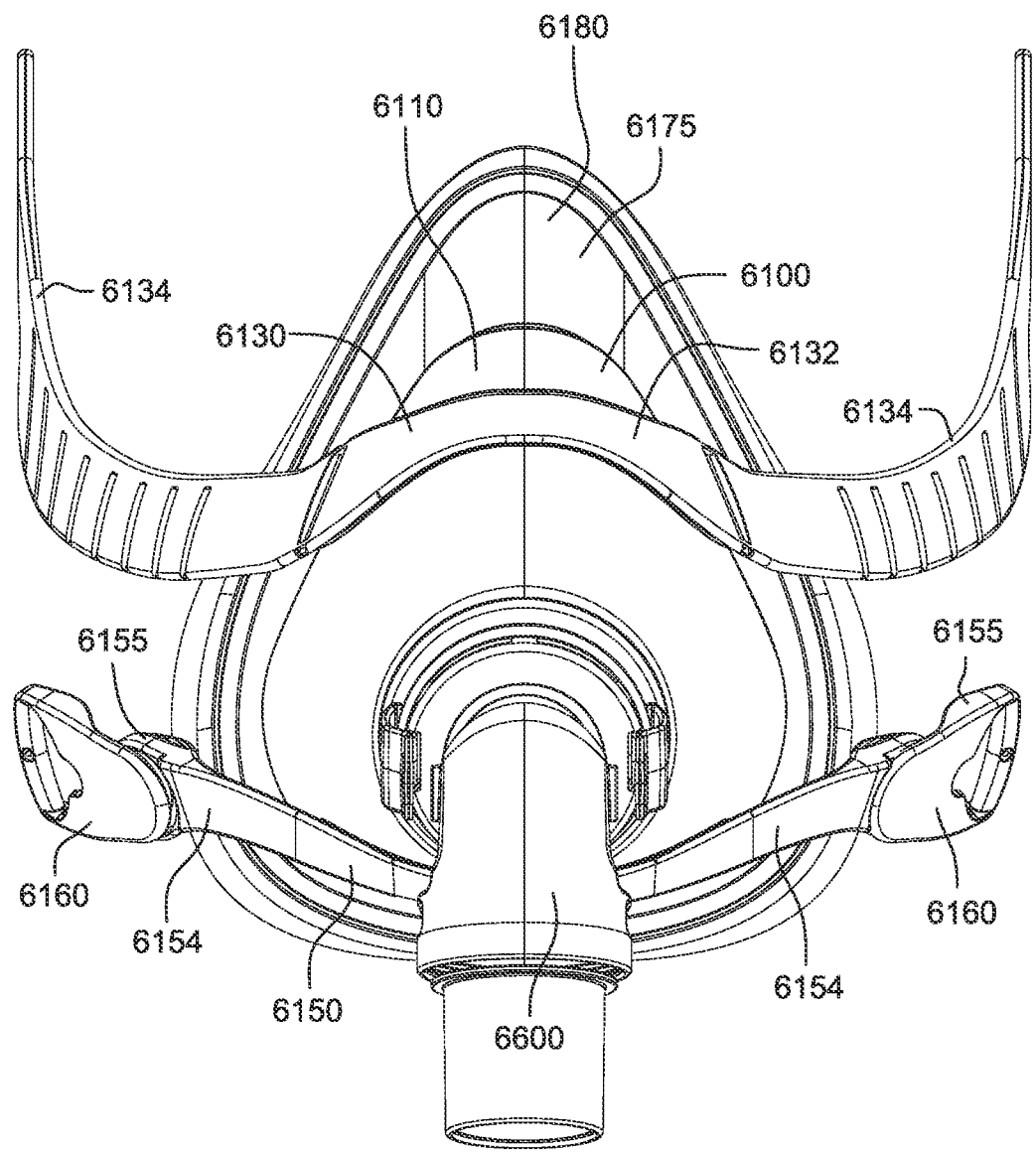

FIG. 7 is a front view of the patient interface shown in FIG. 6.

Figure 8:
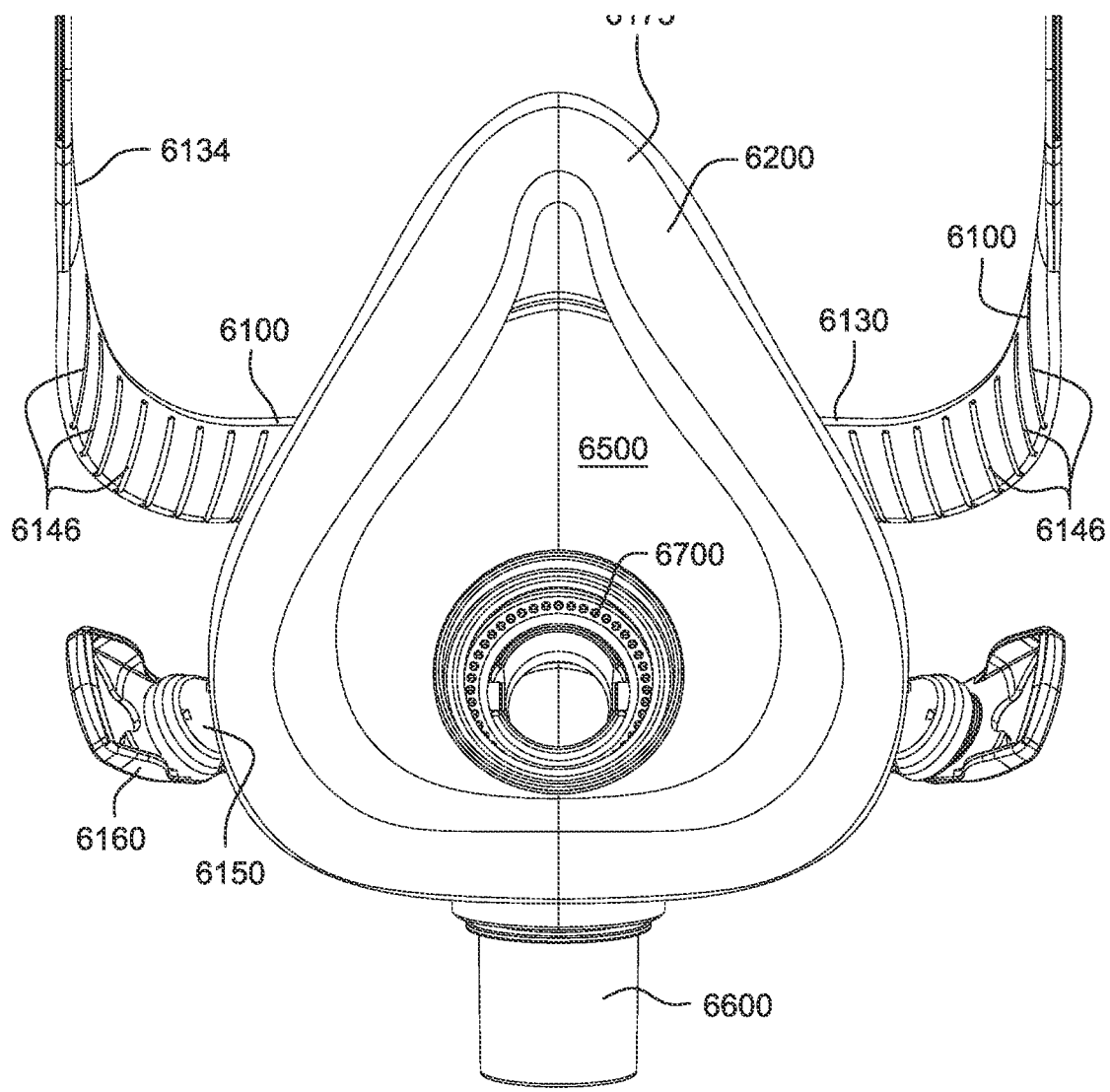

FIG. 8 is a rear view of the patient interface shown in FIG. 6.

Figure 9:
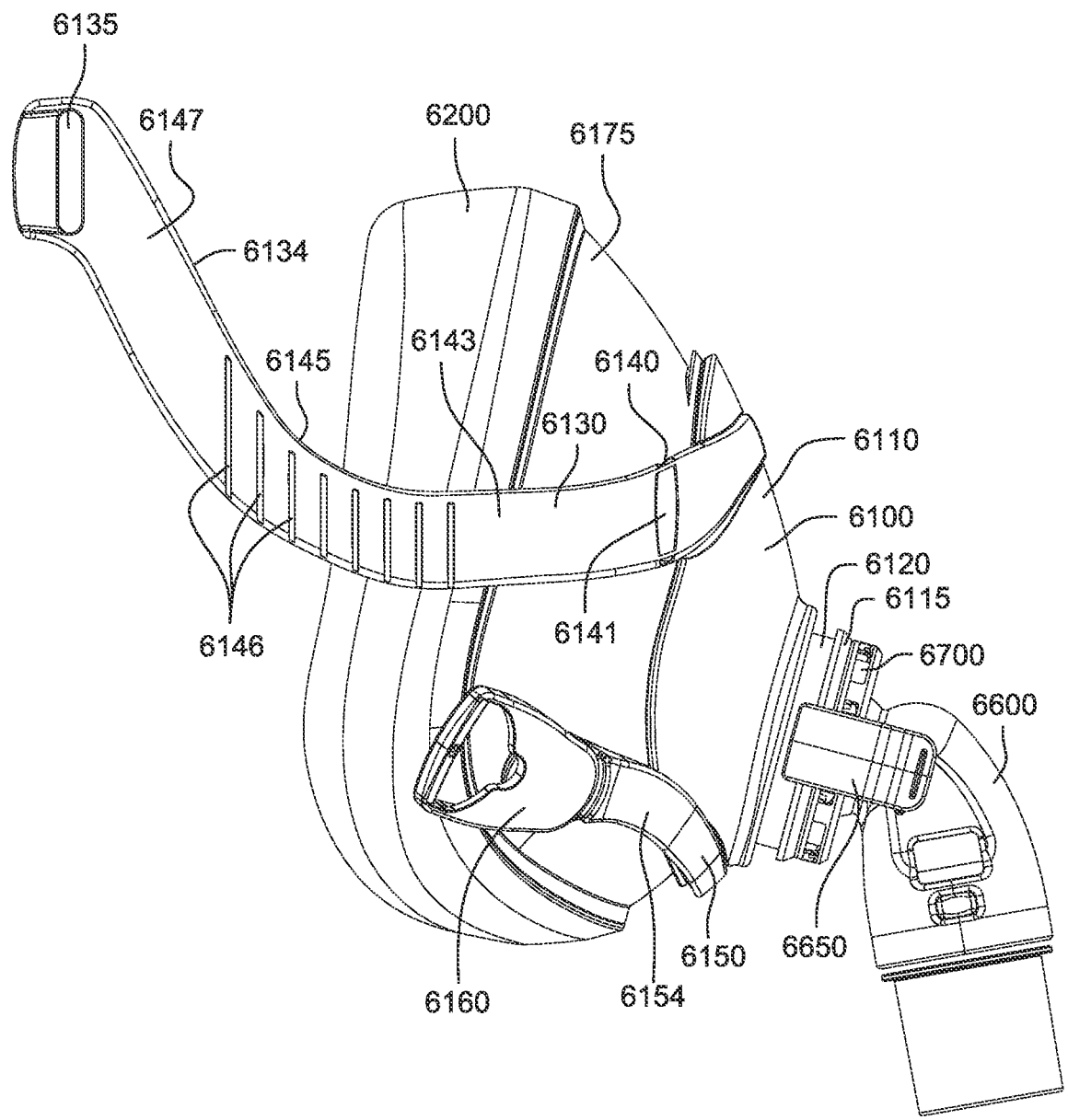

FIG. 9 is a side view of the patient interface shown in FIG. 6.

Figure 10:
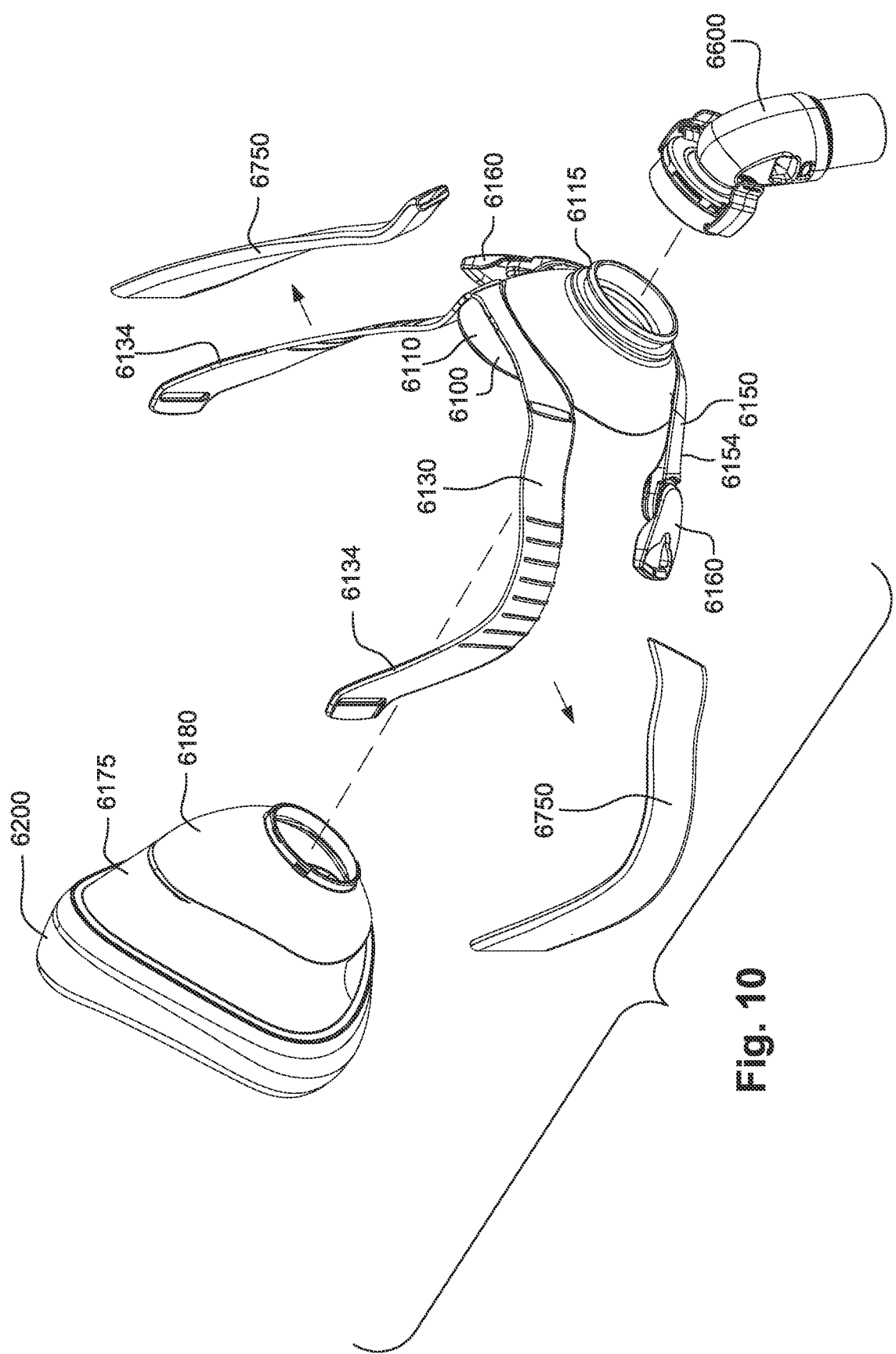

FIG. 10 is an exploded view of a patient interface according to an example of the present technology showing the cushion assembly, frame assembly, arm covers, and elbow assembly.

Figure 11:
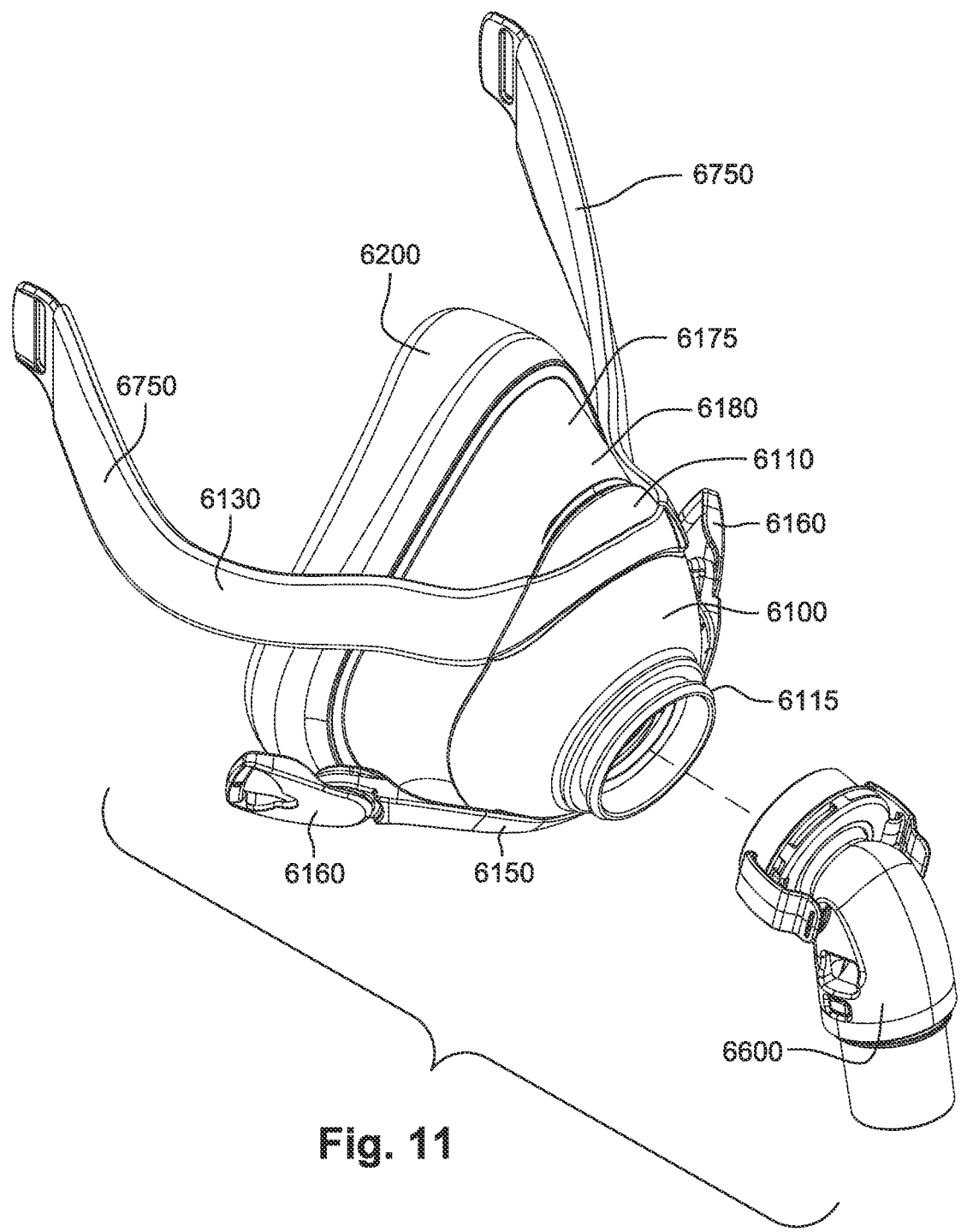

FIG. 11 is an exploded view of a patient interface according to an example of the present technology showing the cushion assembly and frame assembly removably connected with the elbow assembly removed.

Figure 12:
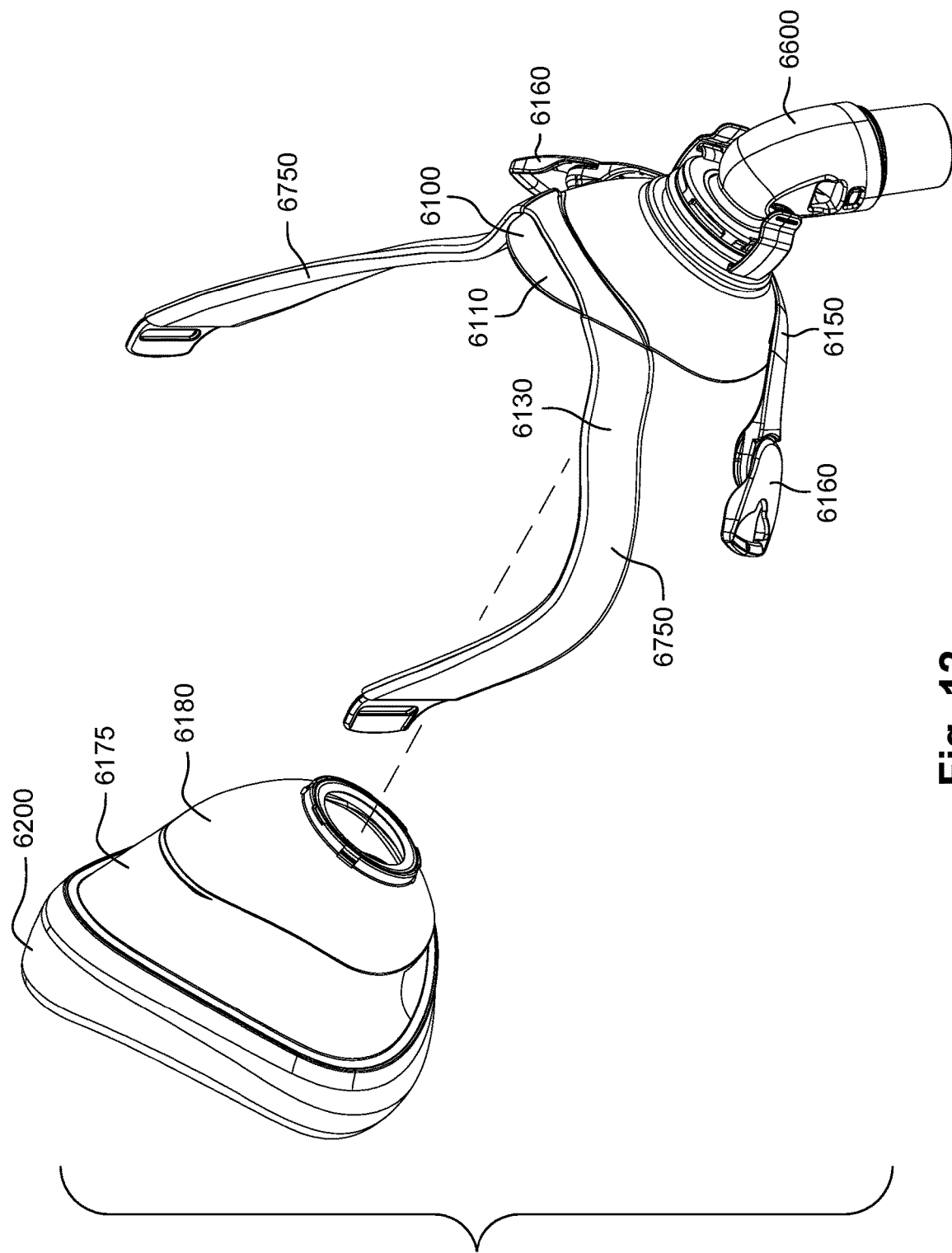

FIG. 12 is an exploded view of a patient interface according to an example of the present technology showing the frame assembly and elbow assembly removably connected with the cushion assembly removed.

Figure 13:
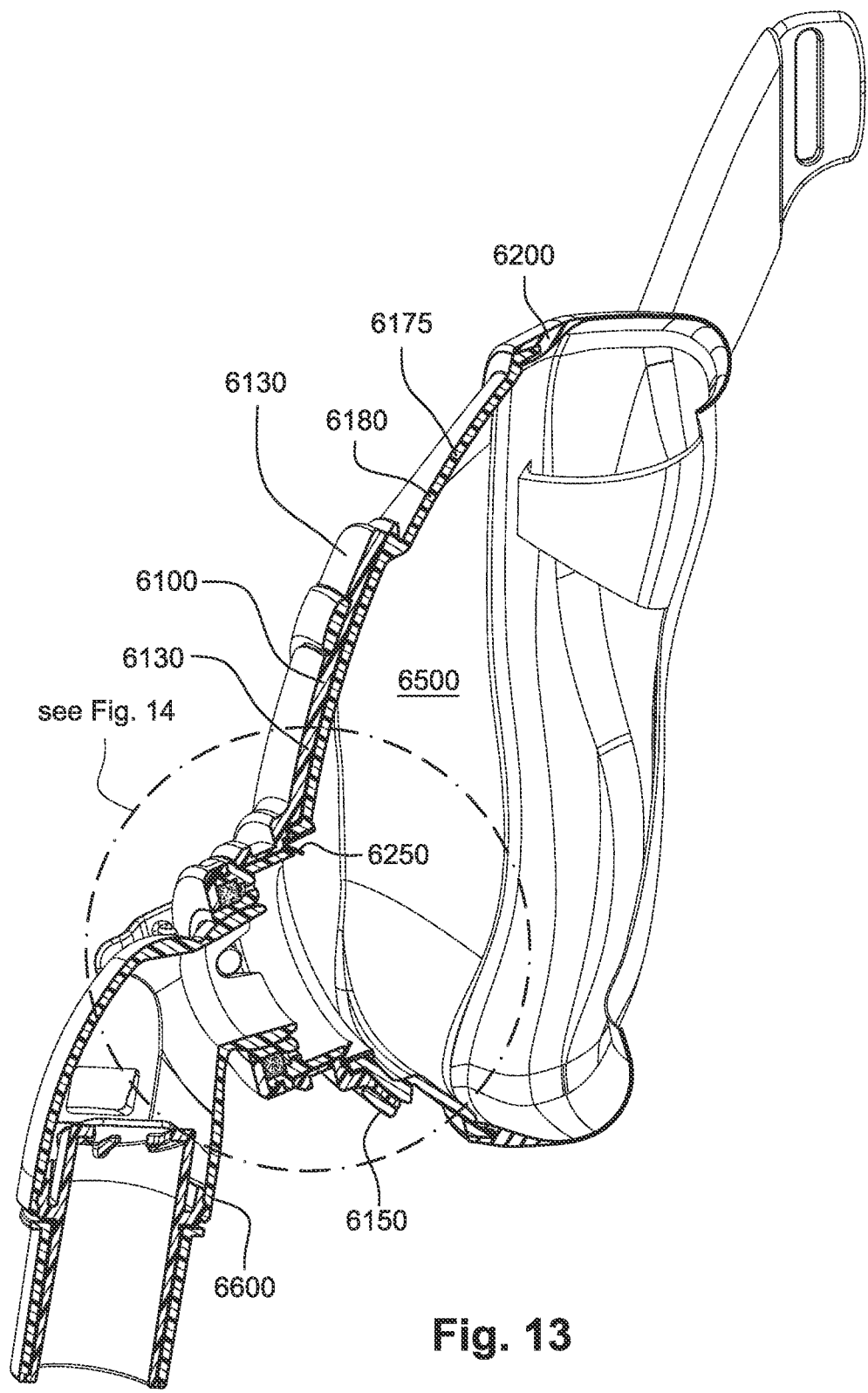

FIG. 13 is a cross-sectional view of a patient interface according to an example of the present technology.

Figure 14:
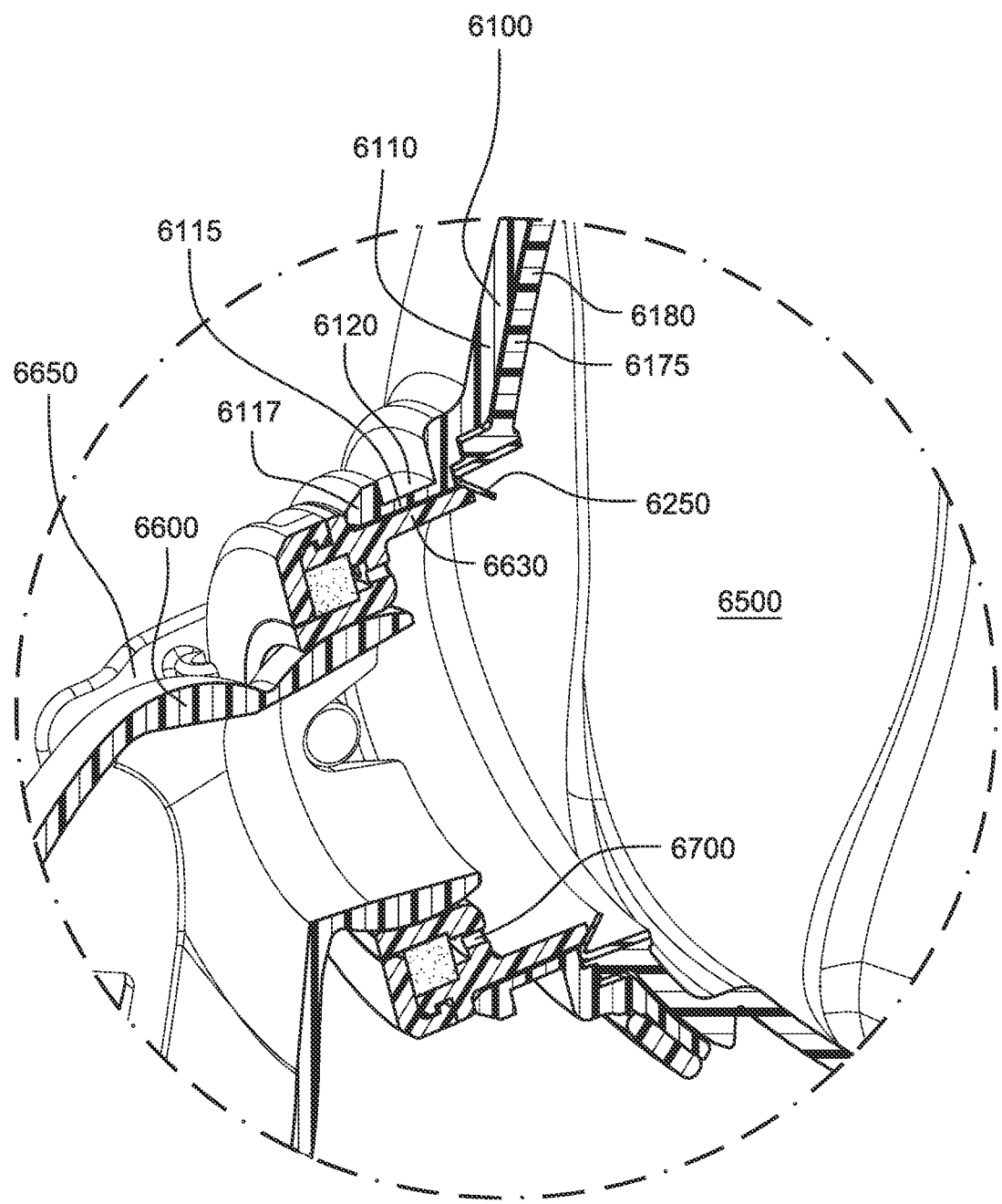

FIG. 14 is an enlarged view of the patient interface shown in FIG. 13.

Figure 15:
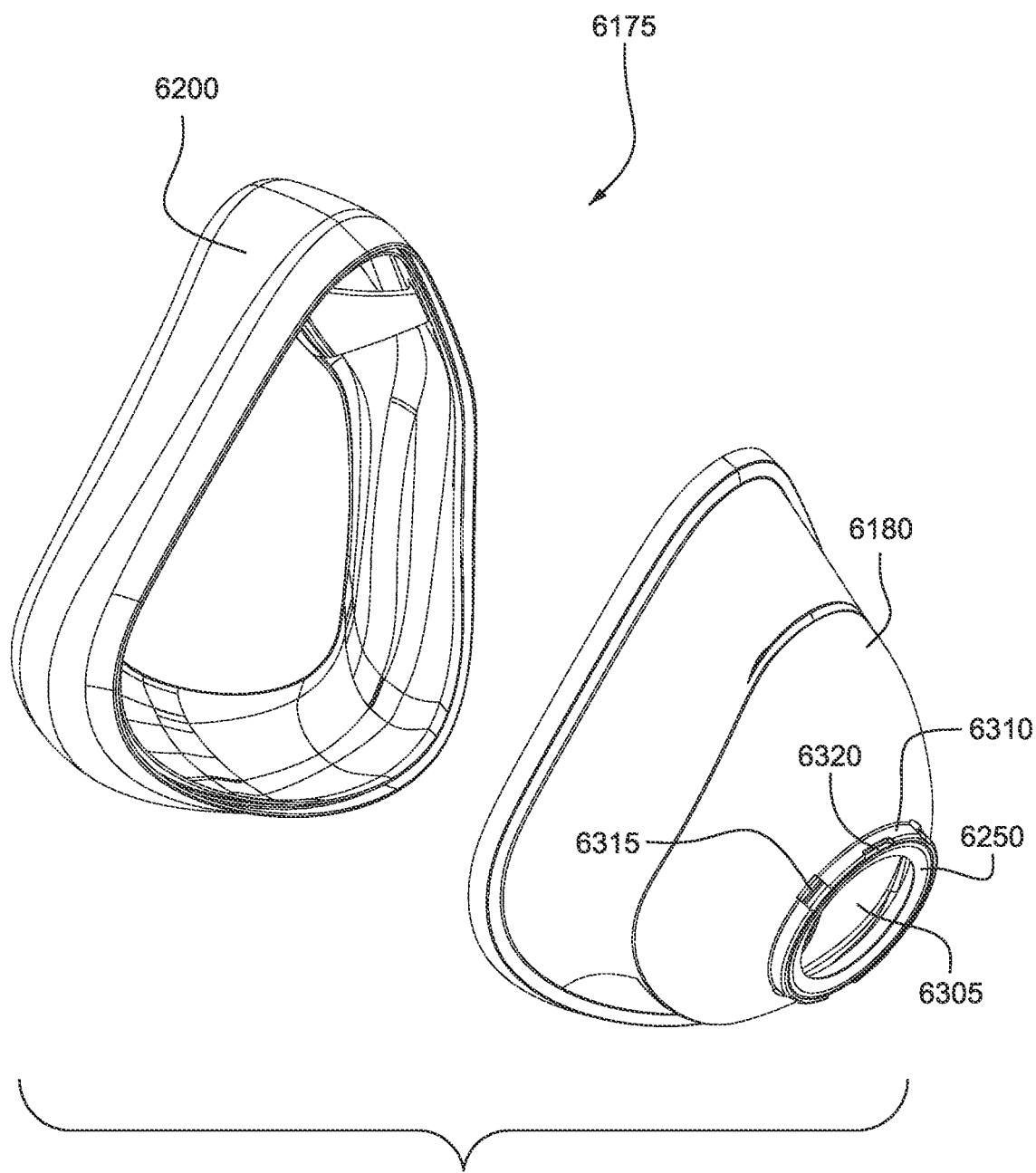

FIG. 15 is a front exploded view of a cushion assembly according to an example of the present technology.

Figure 16:
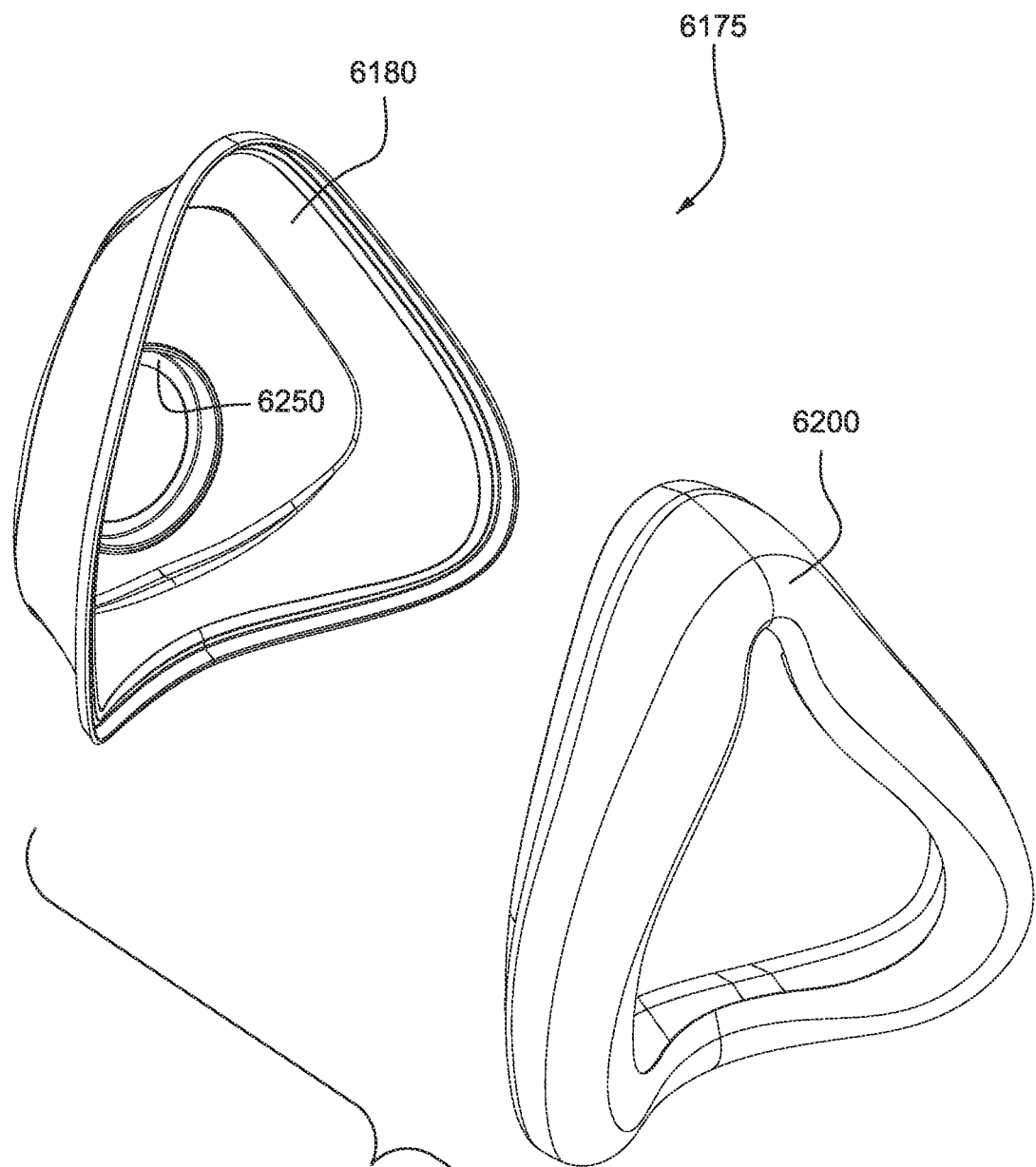

FIG. 16 is a rear exploded view of the cushion assembly shown in FIG. 15.

Figure 17:
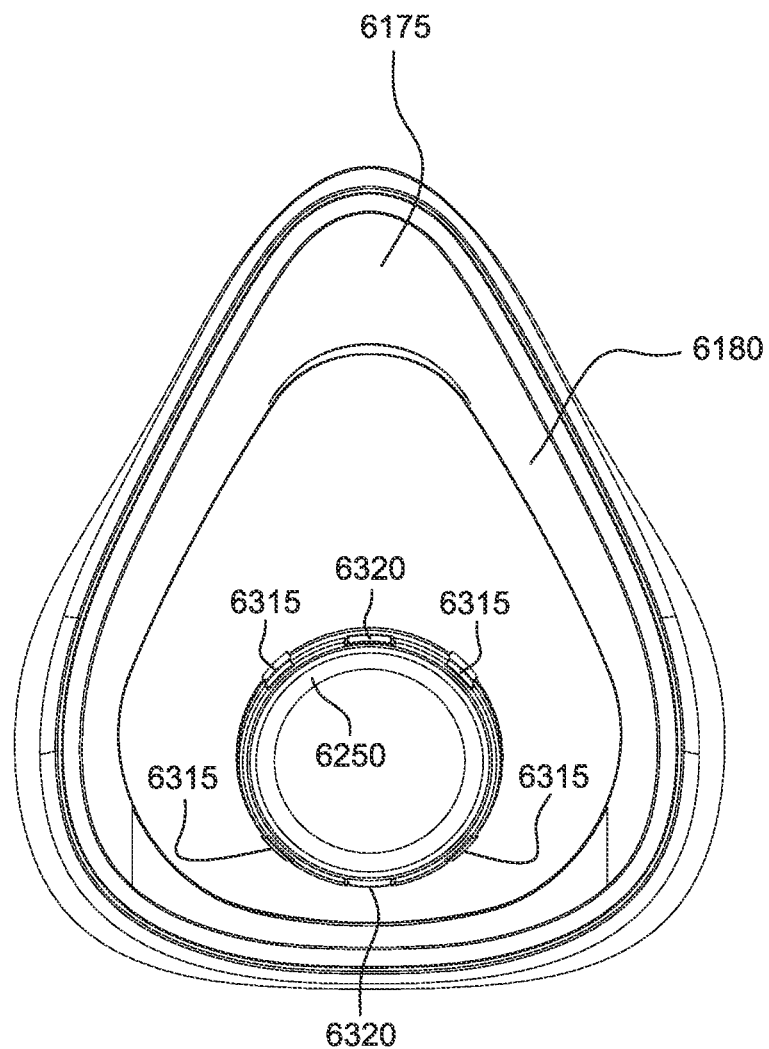

FIG. 17 is a front view of the cushion assembly shown in FIG. 15.

Figure 18:
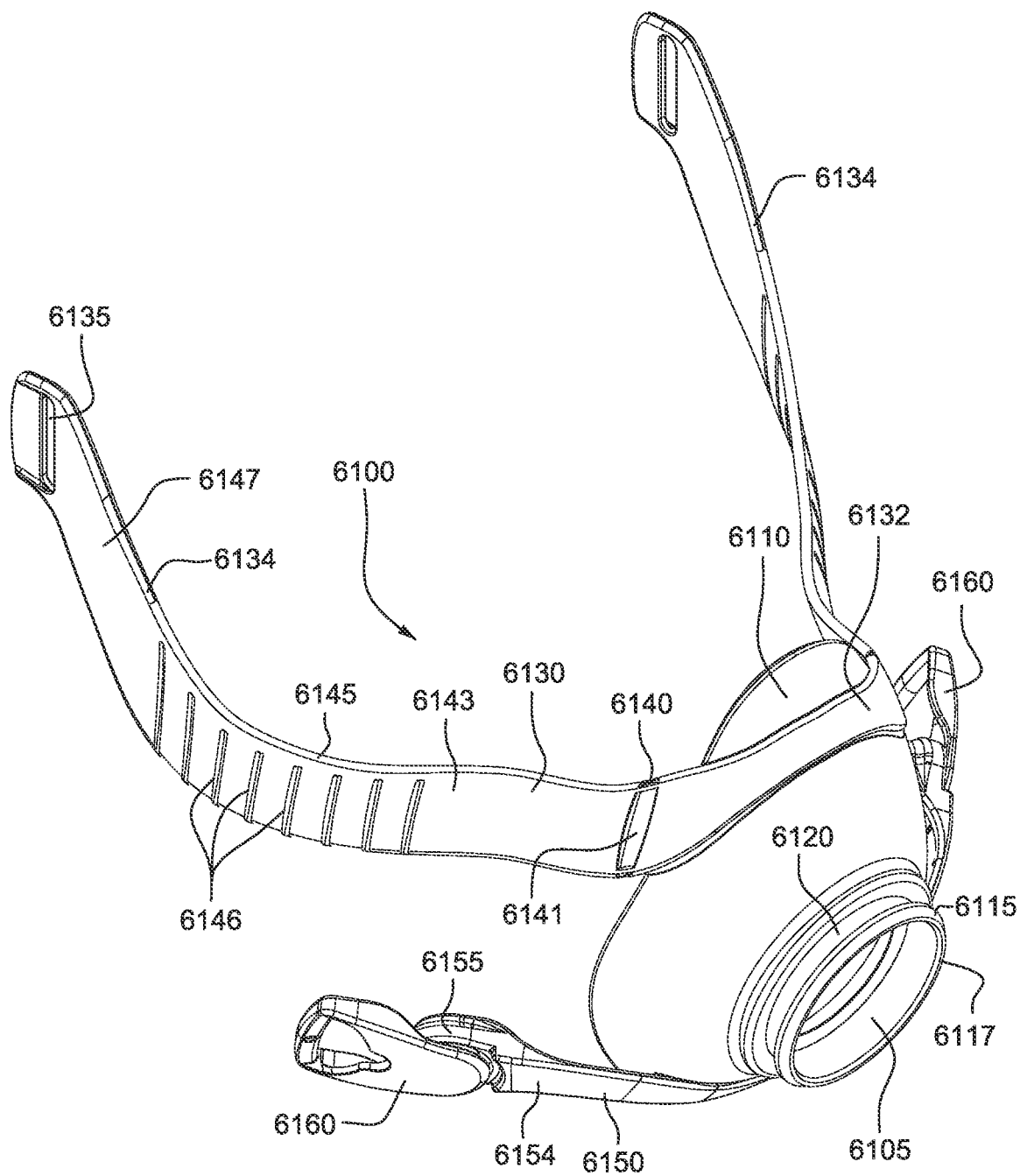

FIG. 18 is a front perspective view of a frame assembly according to an example of the present technology.

Figure 19:
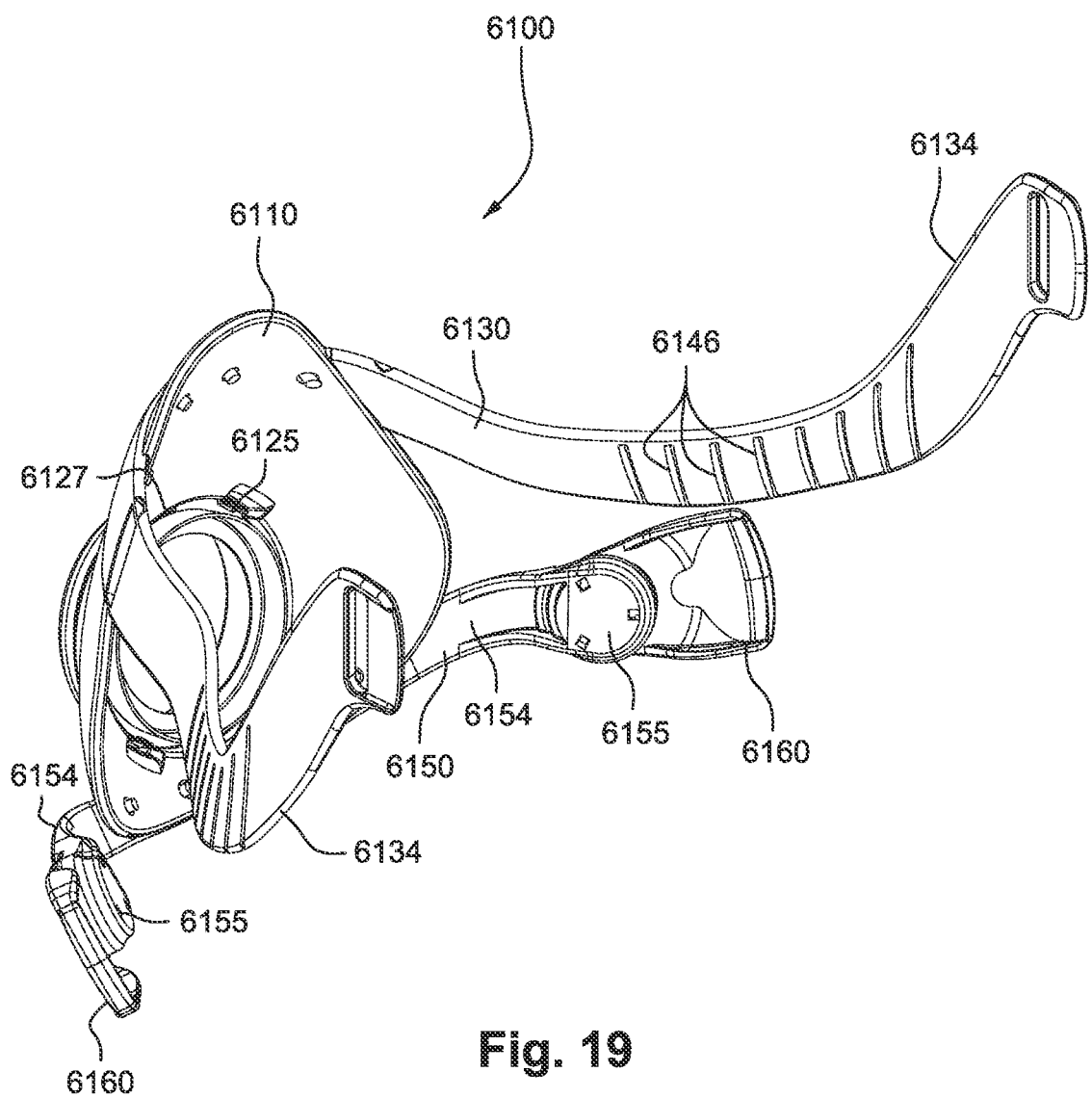

FIG. 19 is a rear perspective view of the frame assembly shown in FIG. 18.

Figure 20:
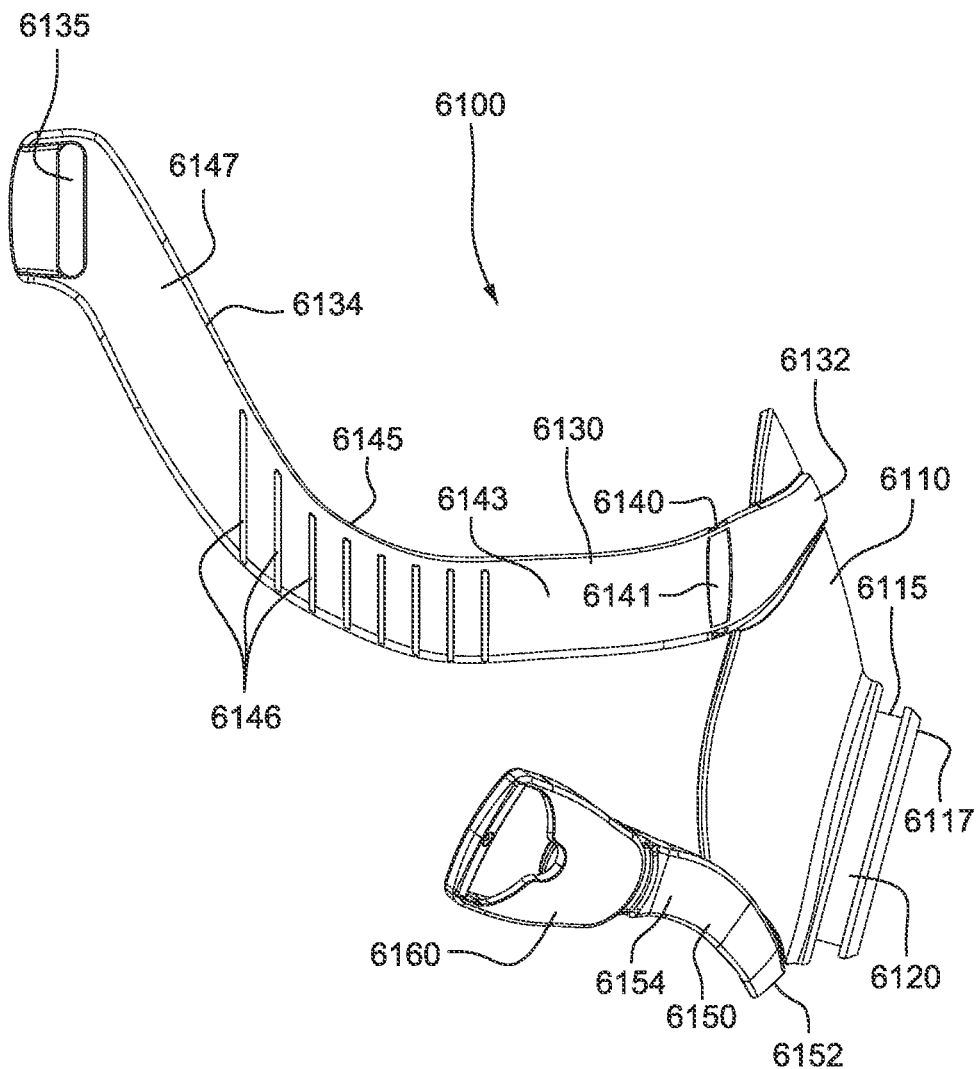

FIG. 20 is a side view of the frame assembly shown in FIG. 18.

Figure 21:
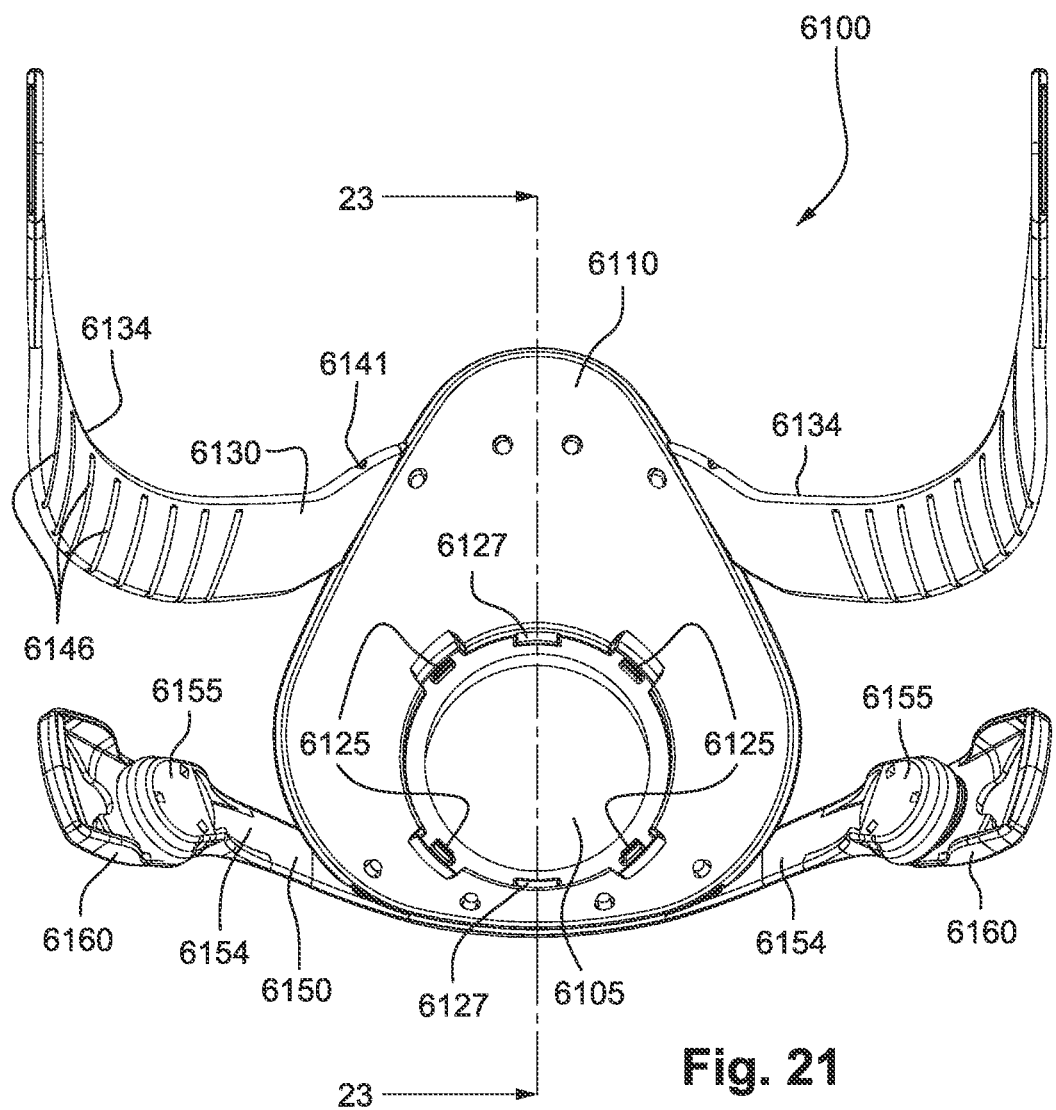

FIG. 21 is a rear view of the frame assembly shown in FIG. 18.

Figure 22:
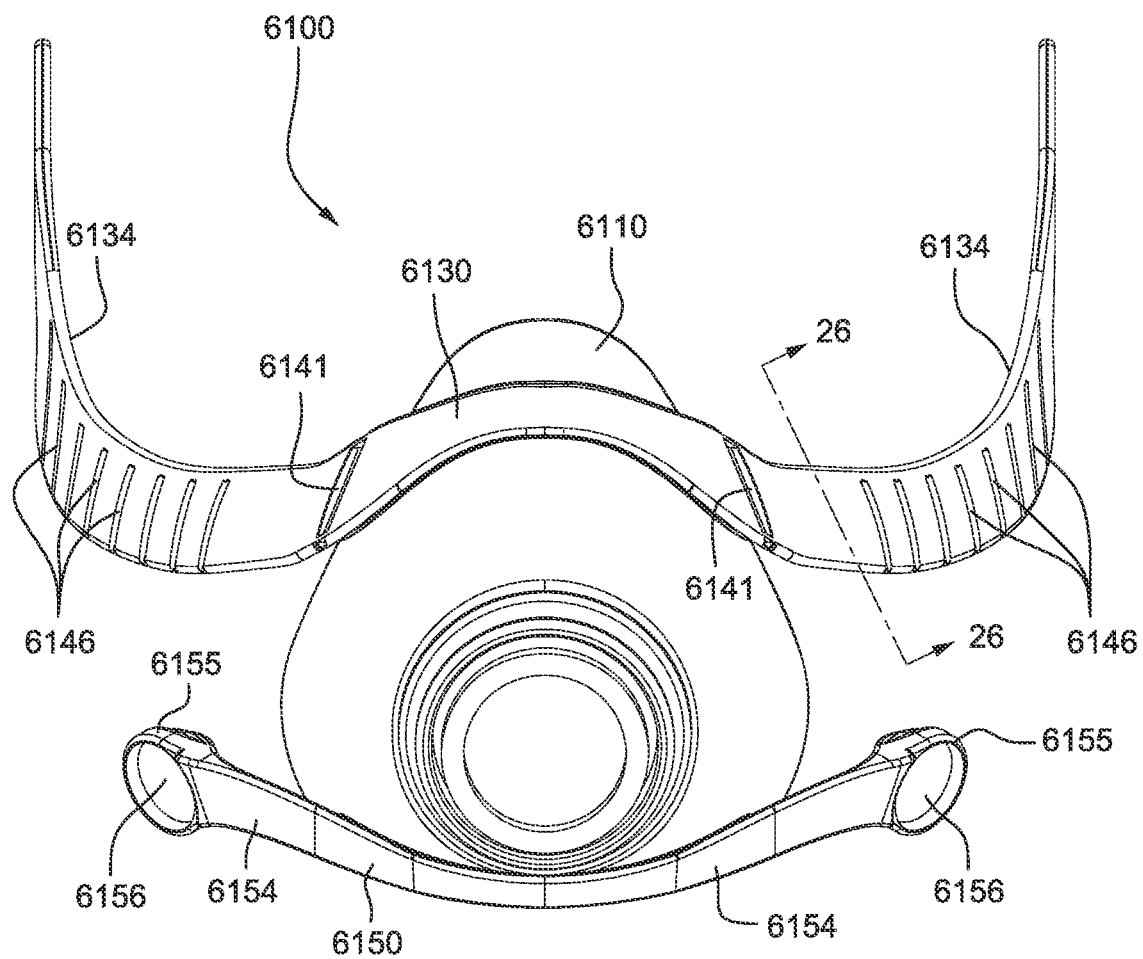

FIG. 22 is a front view of the frame assembly shown in FIG. 18.

Figure 23:
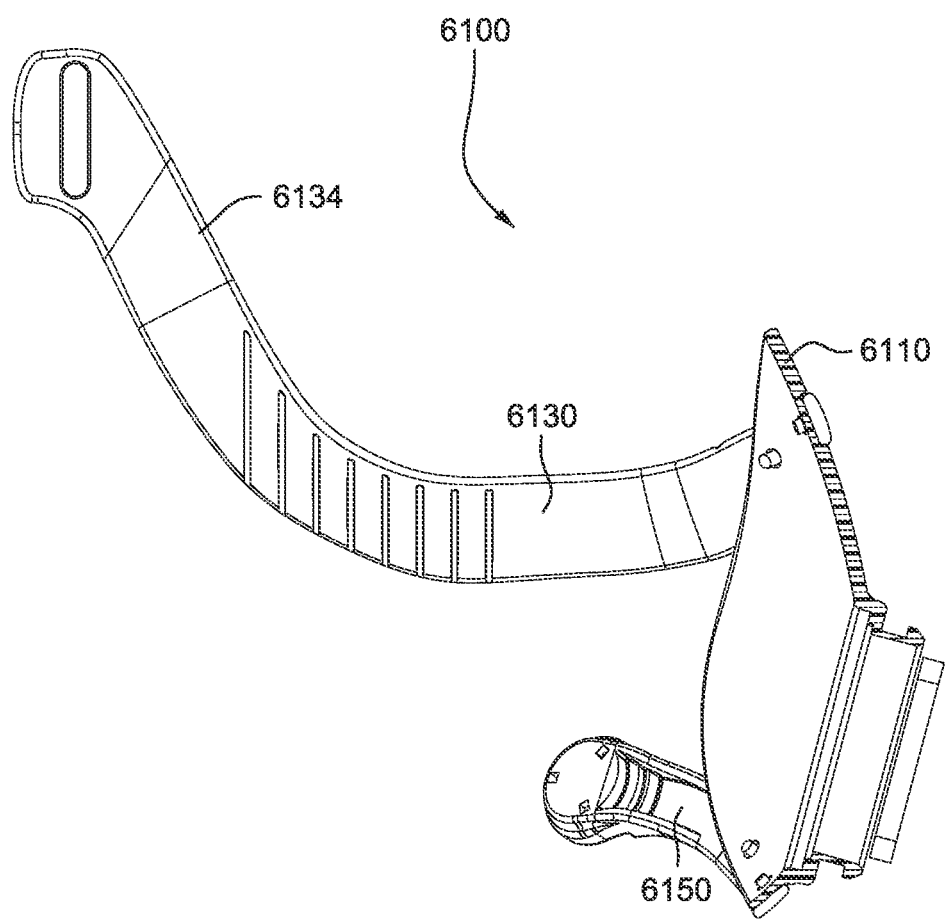

FIG. 23 is a cross-sectional view of the frame assembly shown in FIG. 21.

Figure 24:
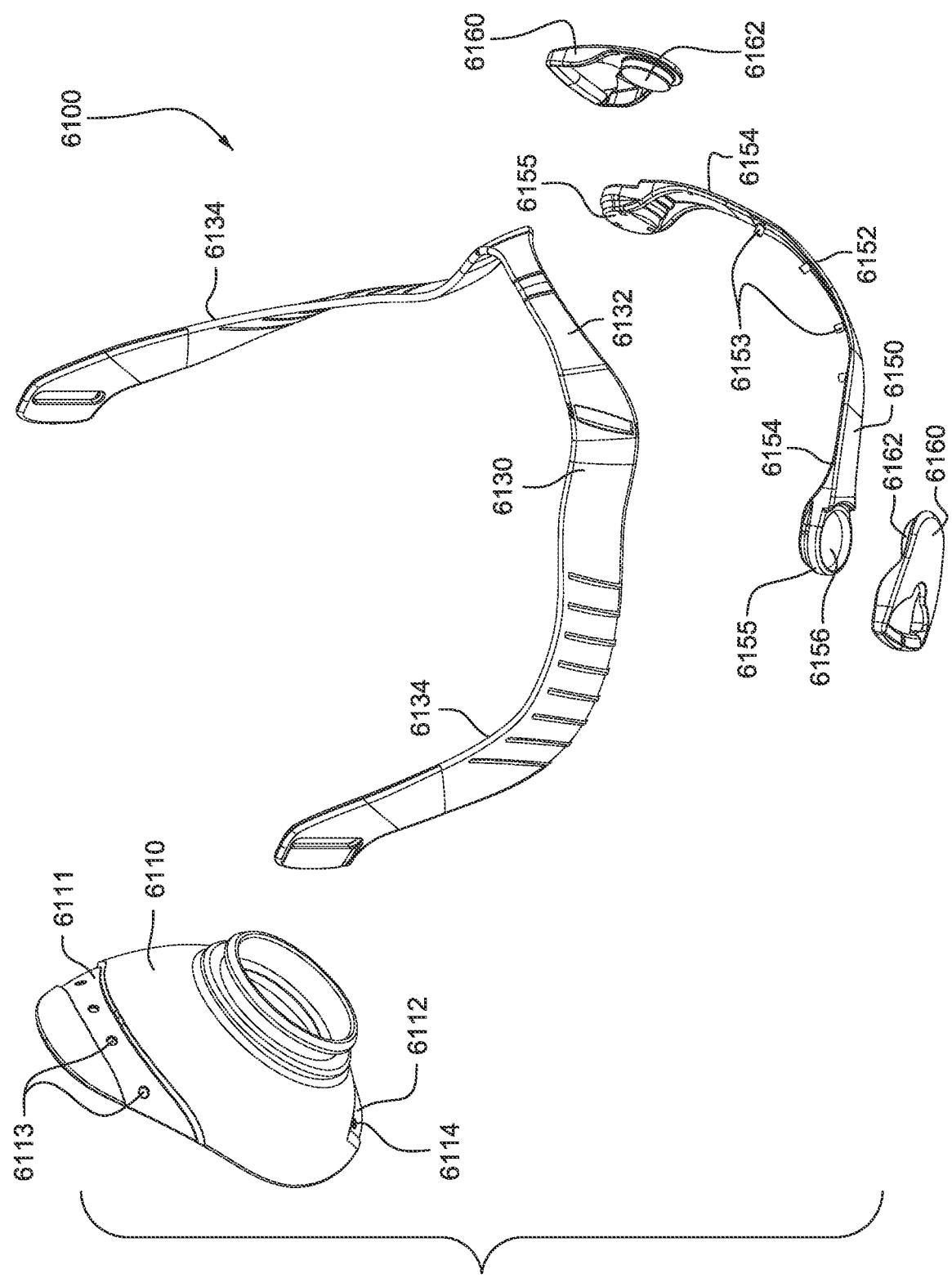

FIG. 24 is a front exploded view of the frame assembly shown in FIG. 18.

Figure 25:
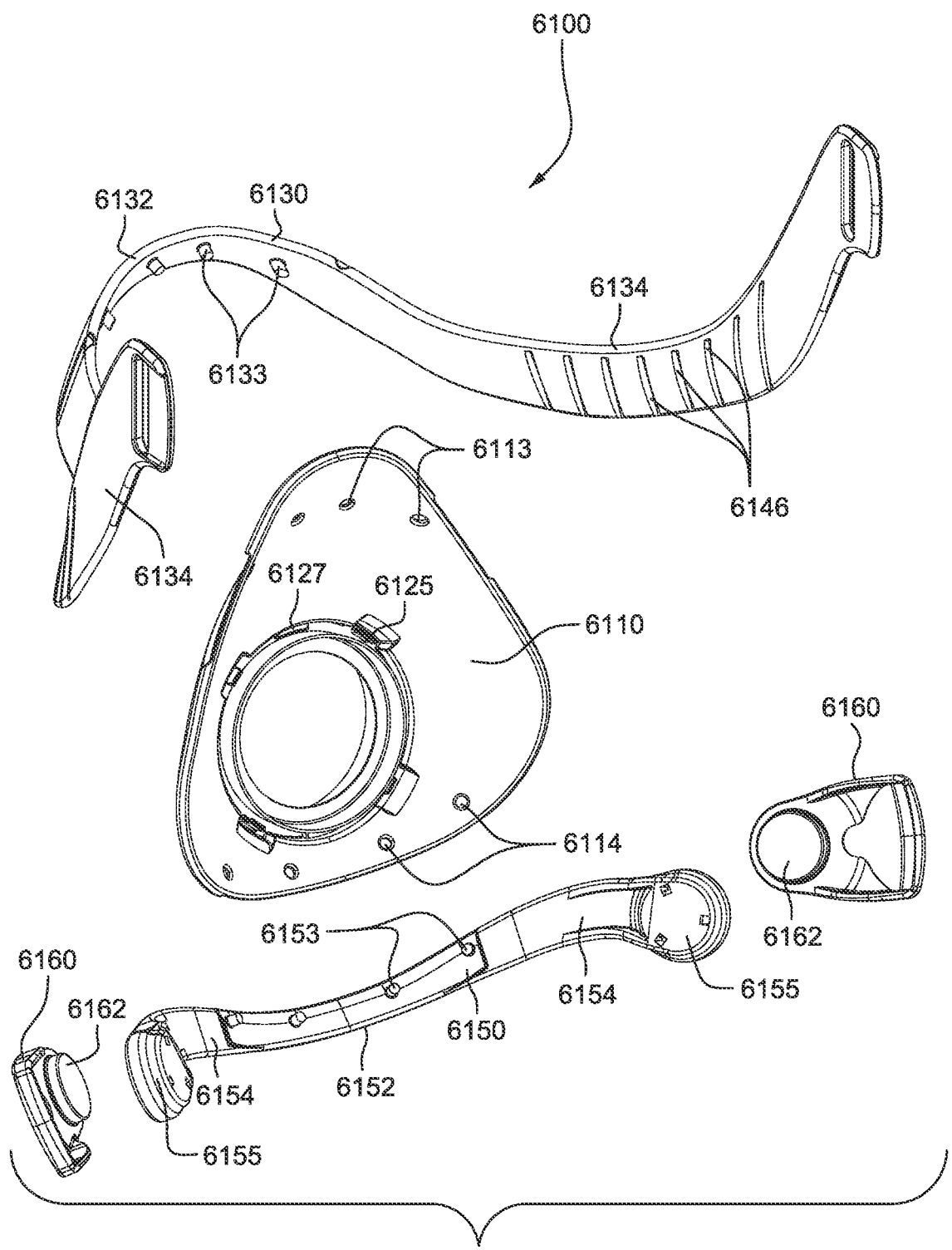

FIG. 25 is a rear exploded view of the frame assembly shown in FIG. 18.

Figure 26:
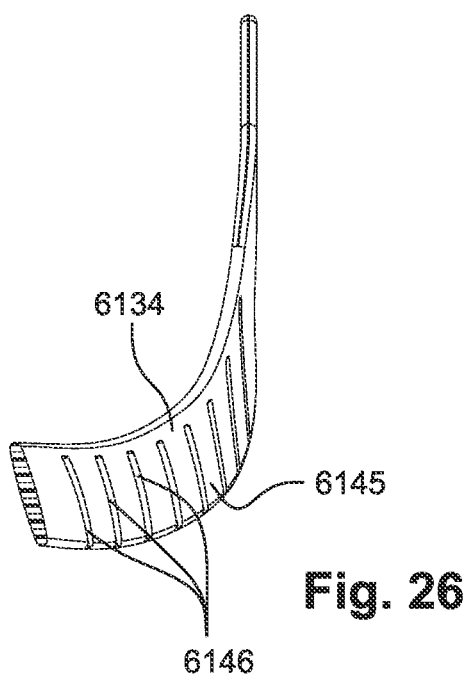

FIG. 26 is a cross-sectional view of the frame assembly shown in FIG. 22.

Figure 27:
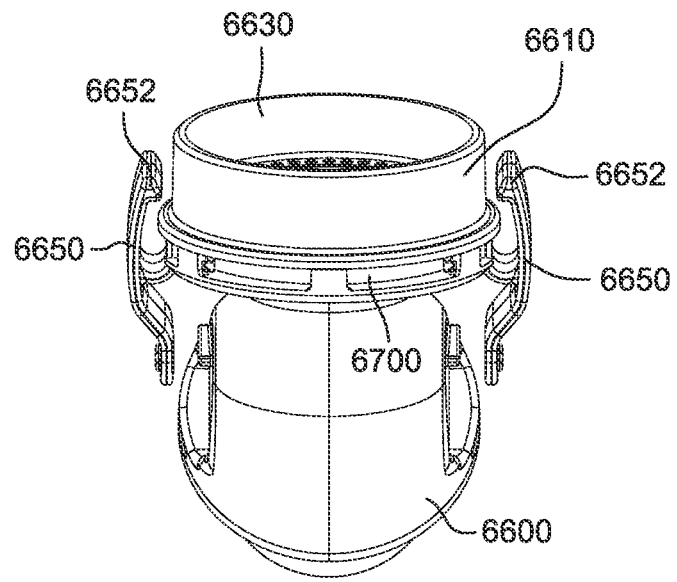

FIG. 27 is a top view of an elbow assembly according to an example of the present technology.

Figure 28:
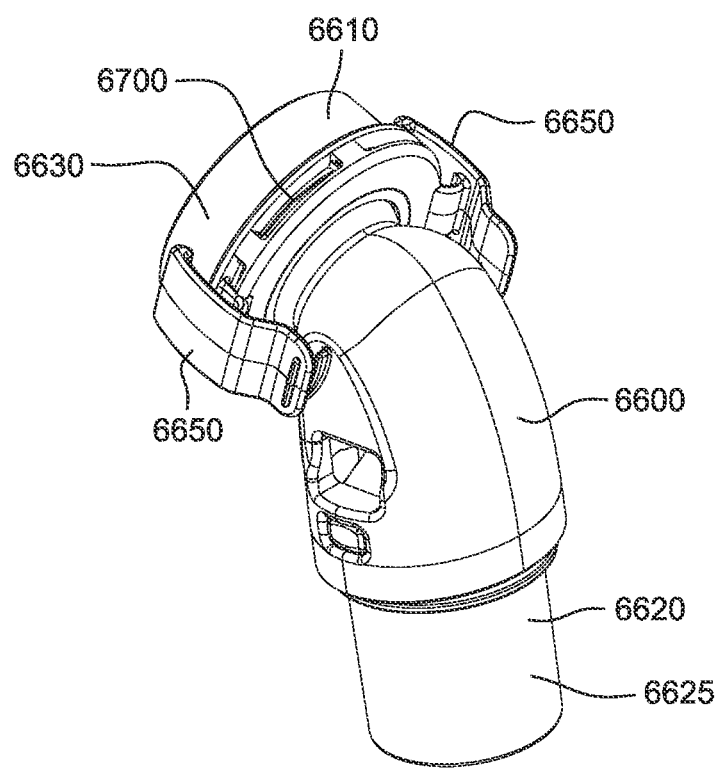

FIG. 28 is a perspective view of the elbow assembly shown in FIG. 27.

Figure 29:
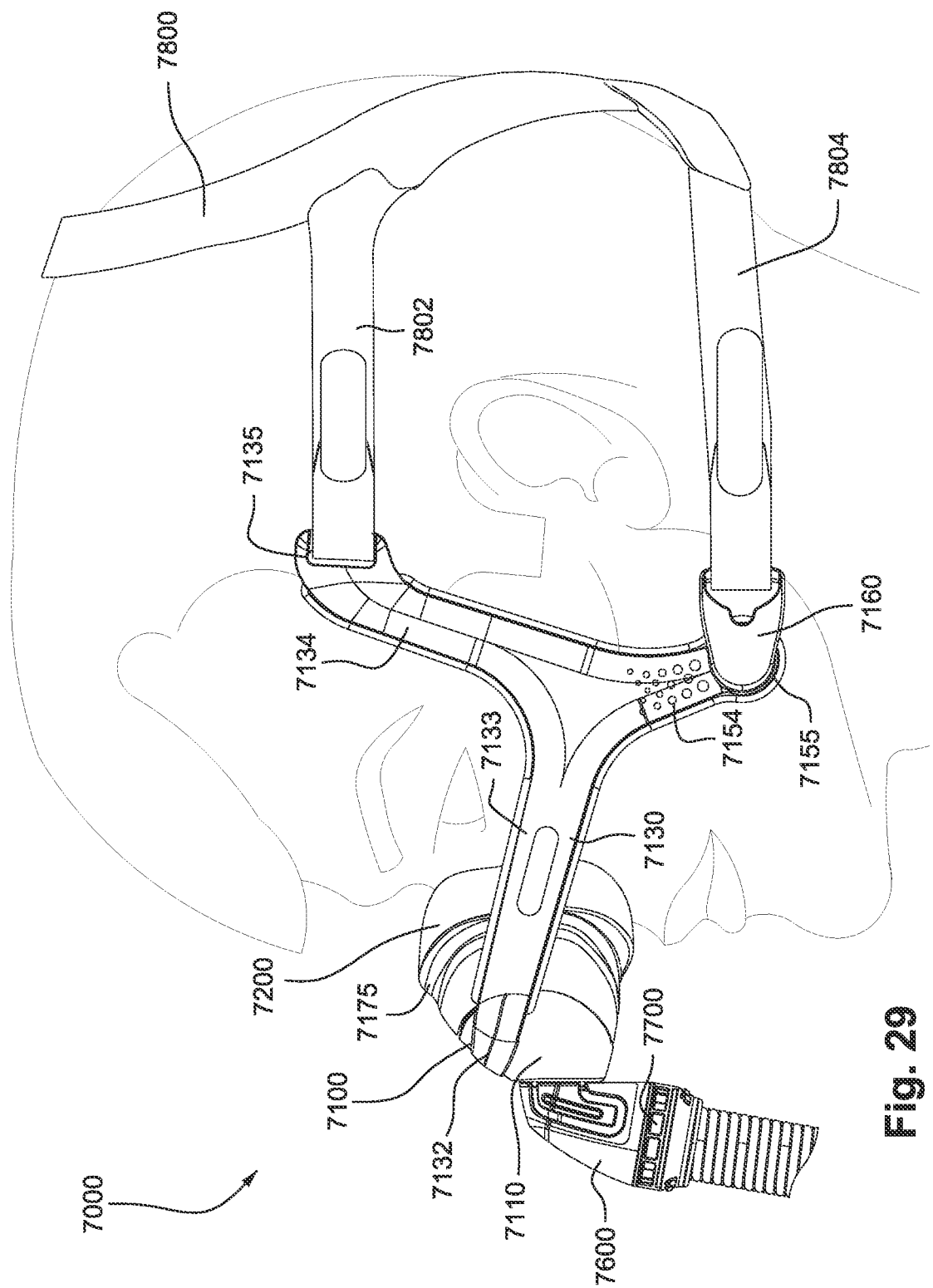

FIG. 29 is a side view of a patient interface shown on a patient's head according to an example of the present technology.

Figure 30:
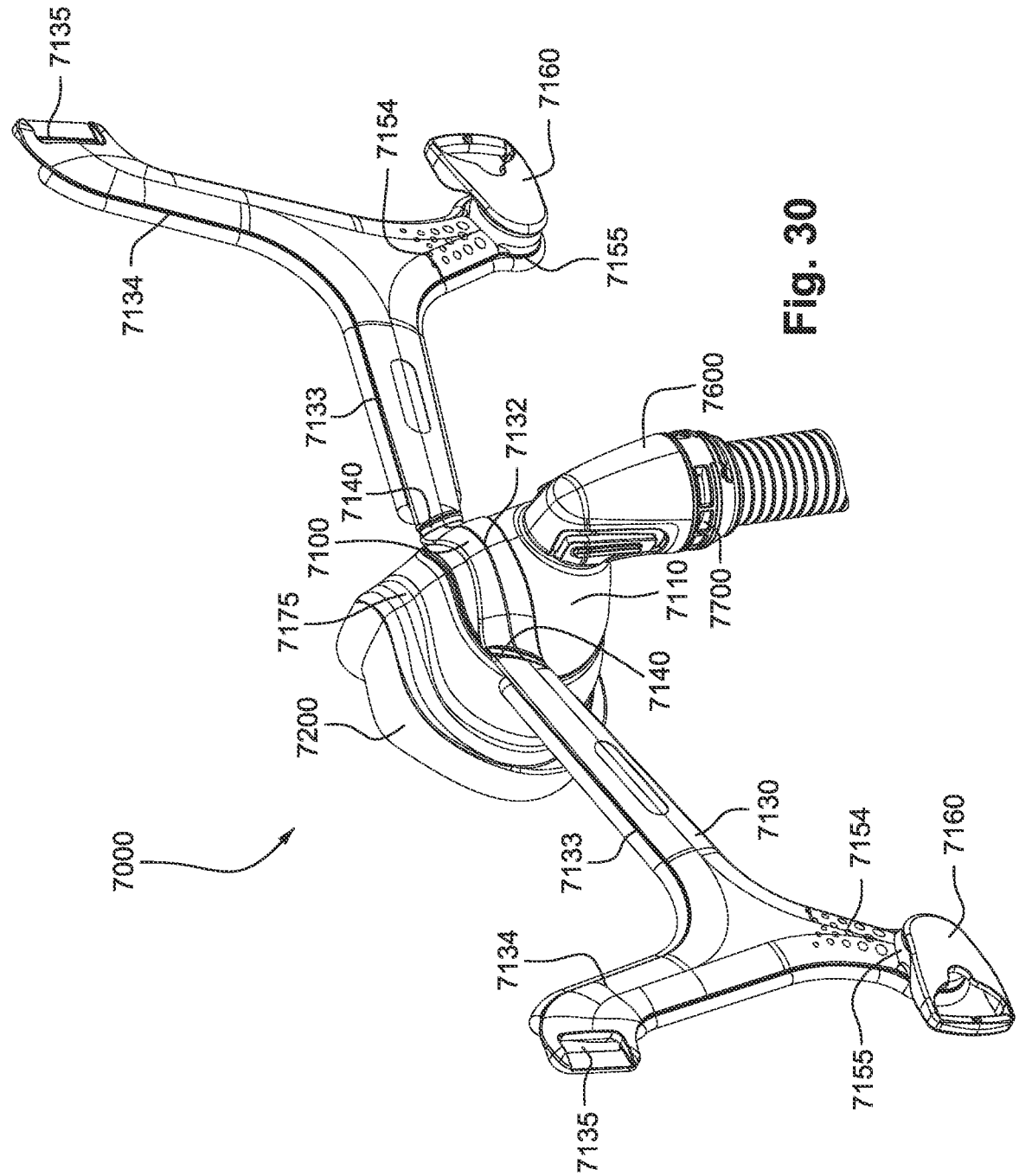

FIG. 30 is a perspective view of a patient interface according to an example of the present technology, the patient interface being shown with the headgear removed.

Figure 31:
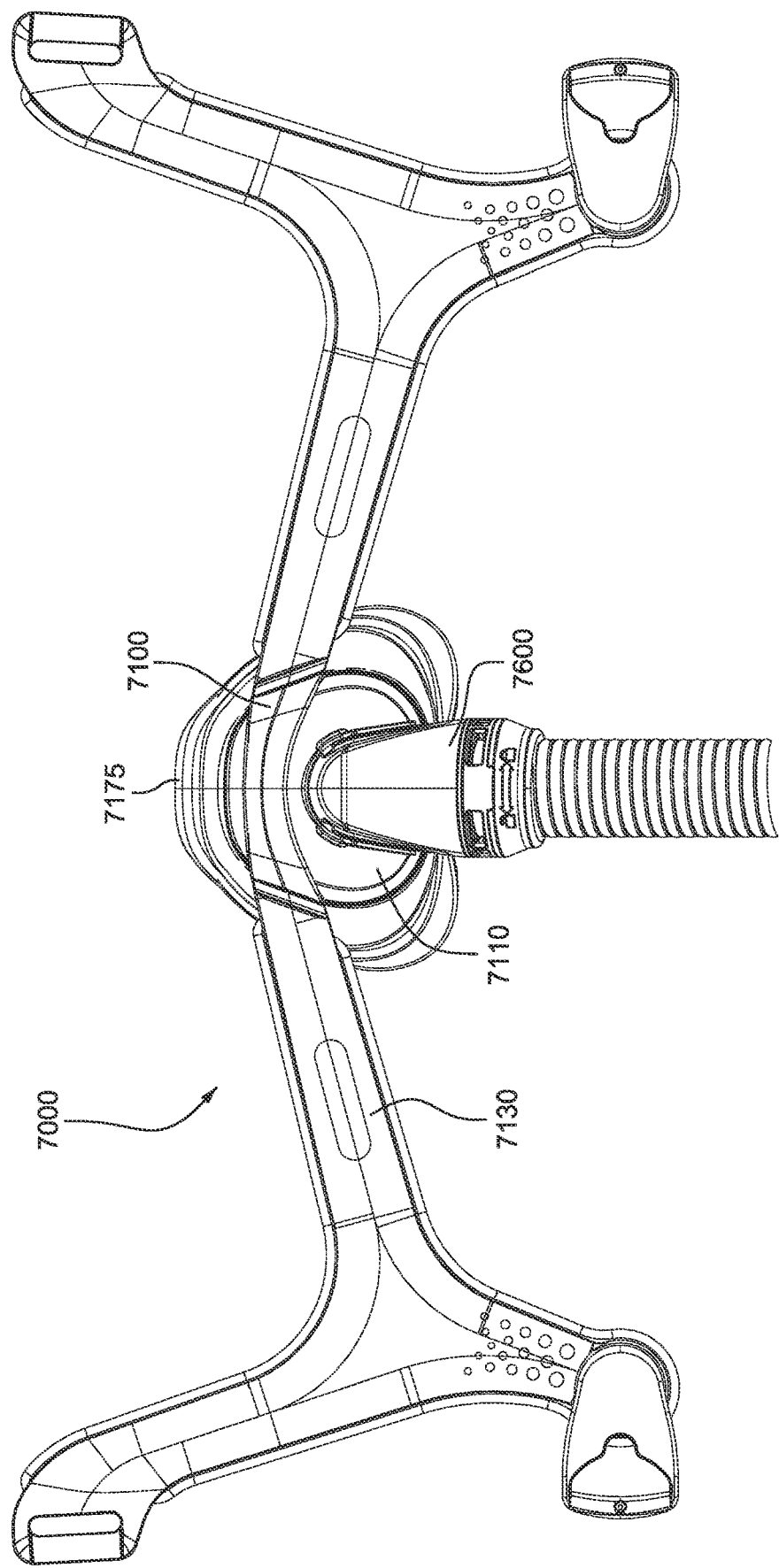

FIG. 31 is a front view of the patient interface shown in FIG. 30.

Figure 32:
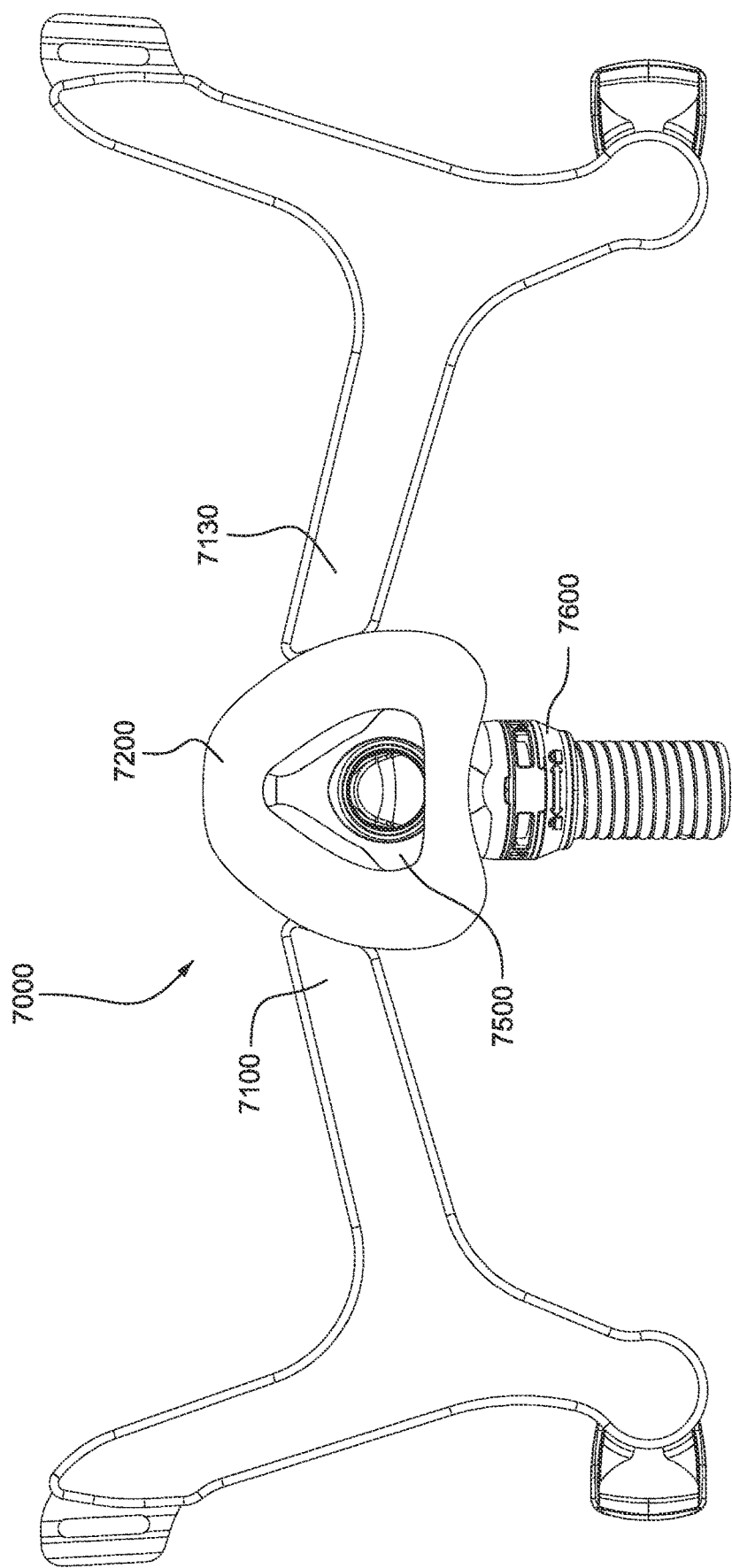

FIG. 32 is a rear view of the patient interface shown in FIG. 30.

Figure 33:
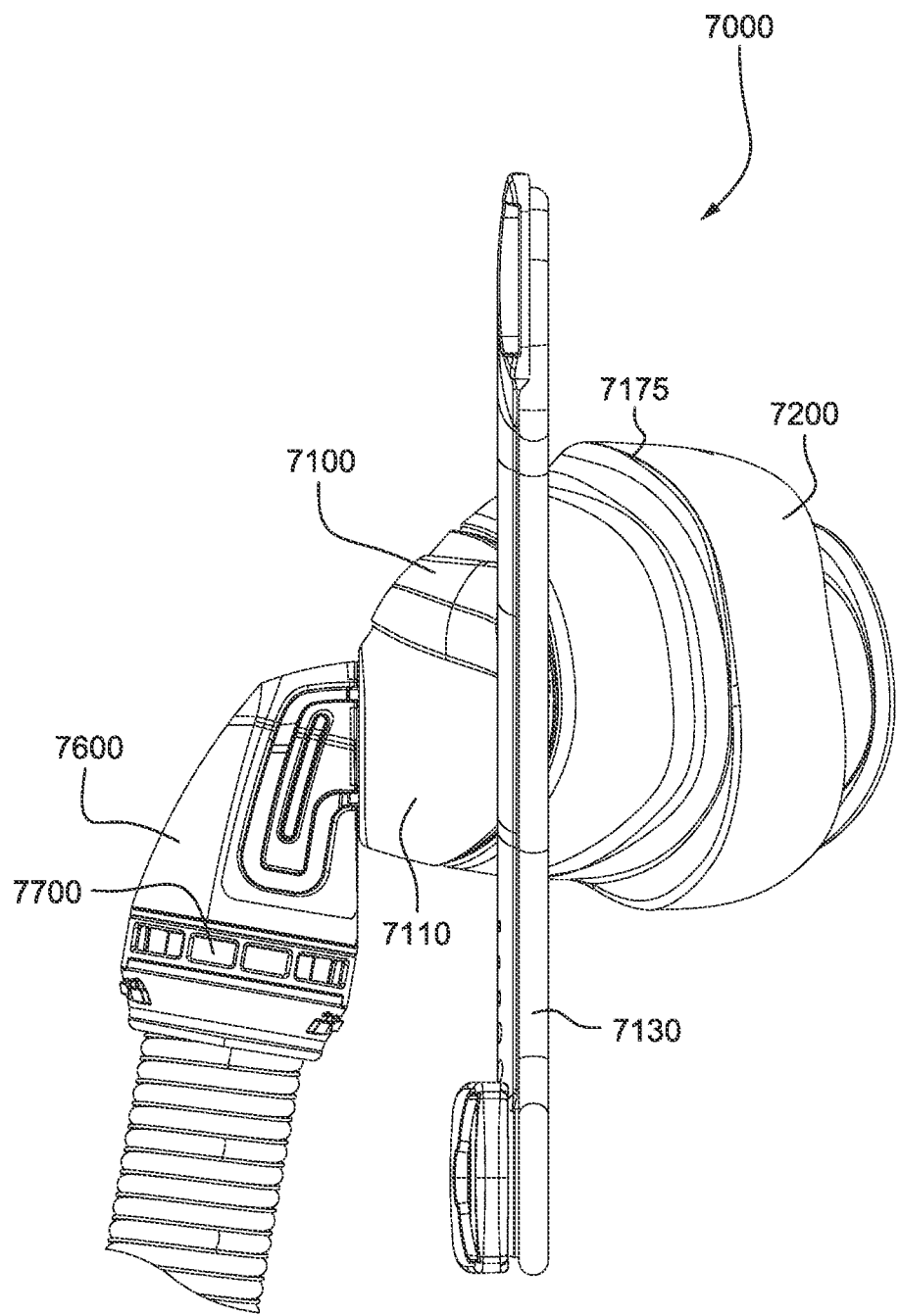

FIG. 33 is a side view of the patient interface shown in FIG. 30.

Figure 34:
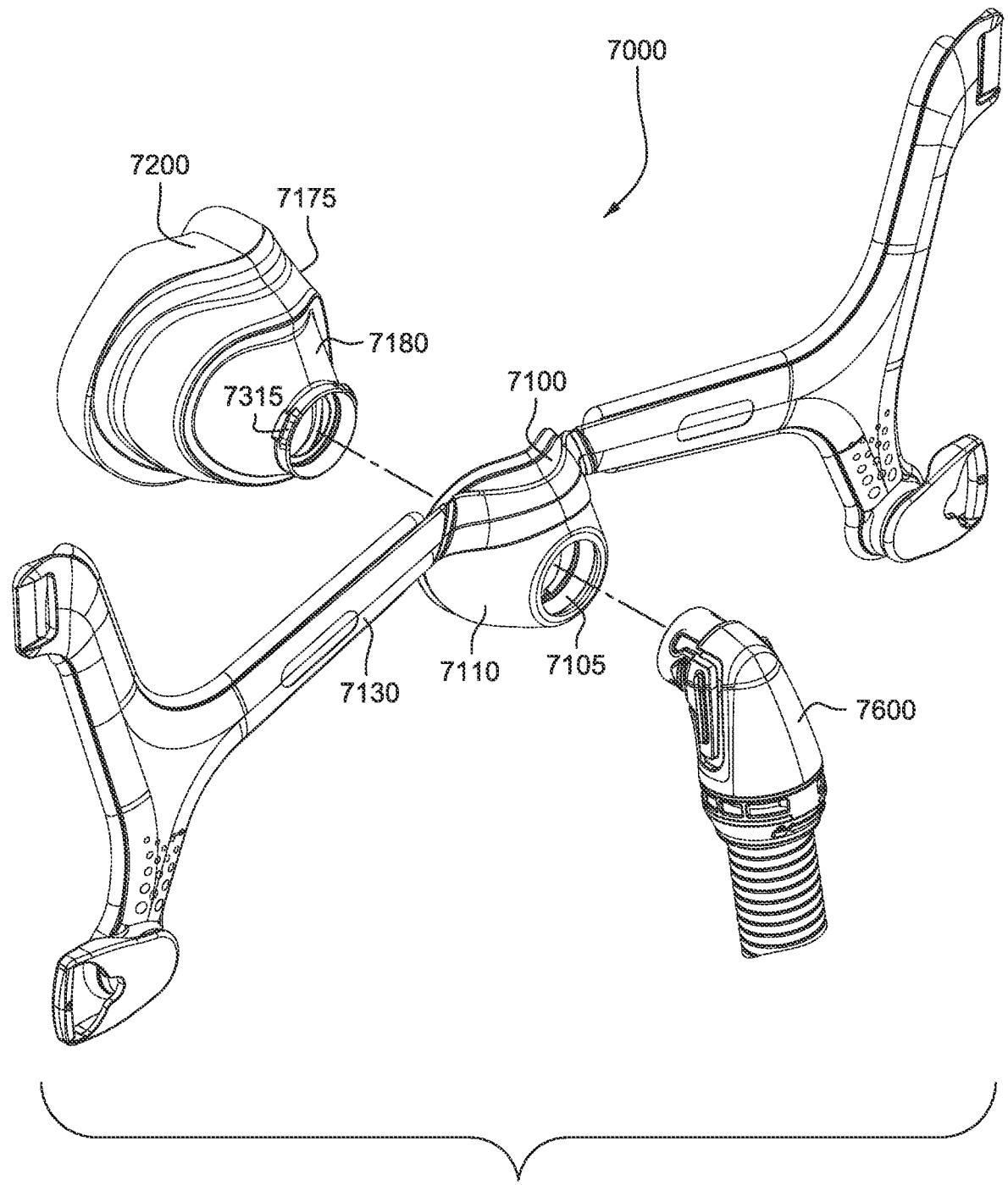

FIG. 34 is an exploded view of a patient interface according to an example of the present technology showing the cushion assembly, frame assembly, and elbow assembly.

Figure 35:
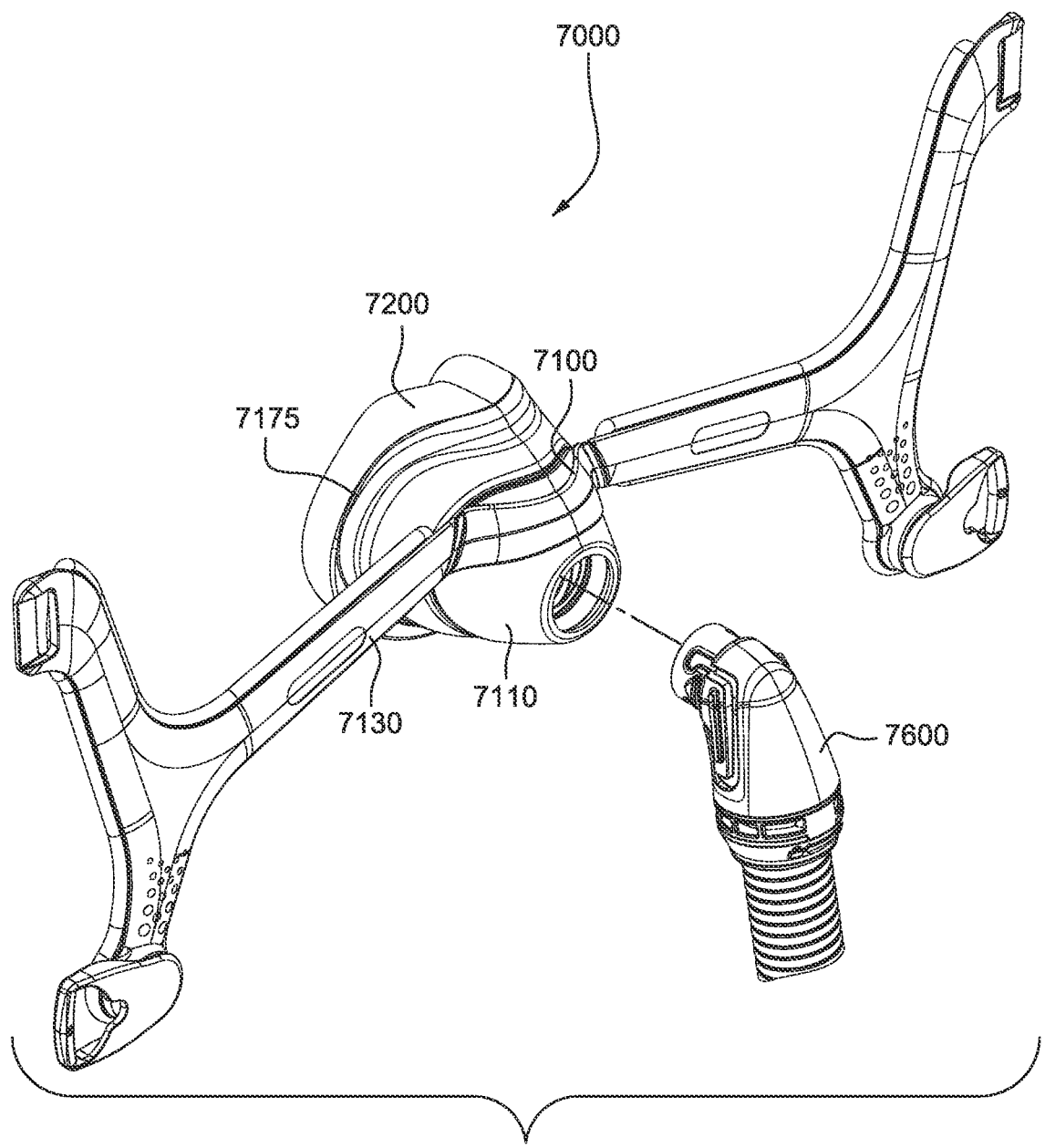

FIG. 35 is an exploded view of a patient interface according to an example of the present technology showing the cushion assembly and frame assembly removably connected with the elbow assembly removed.

Figure 36:
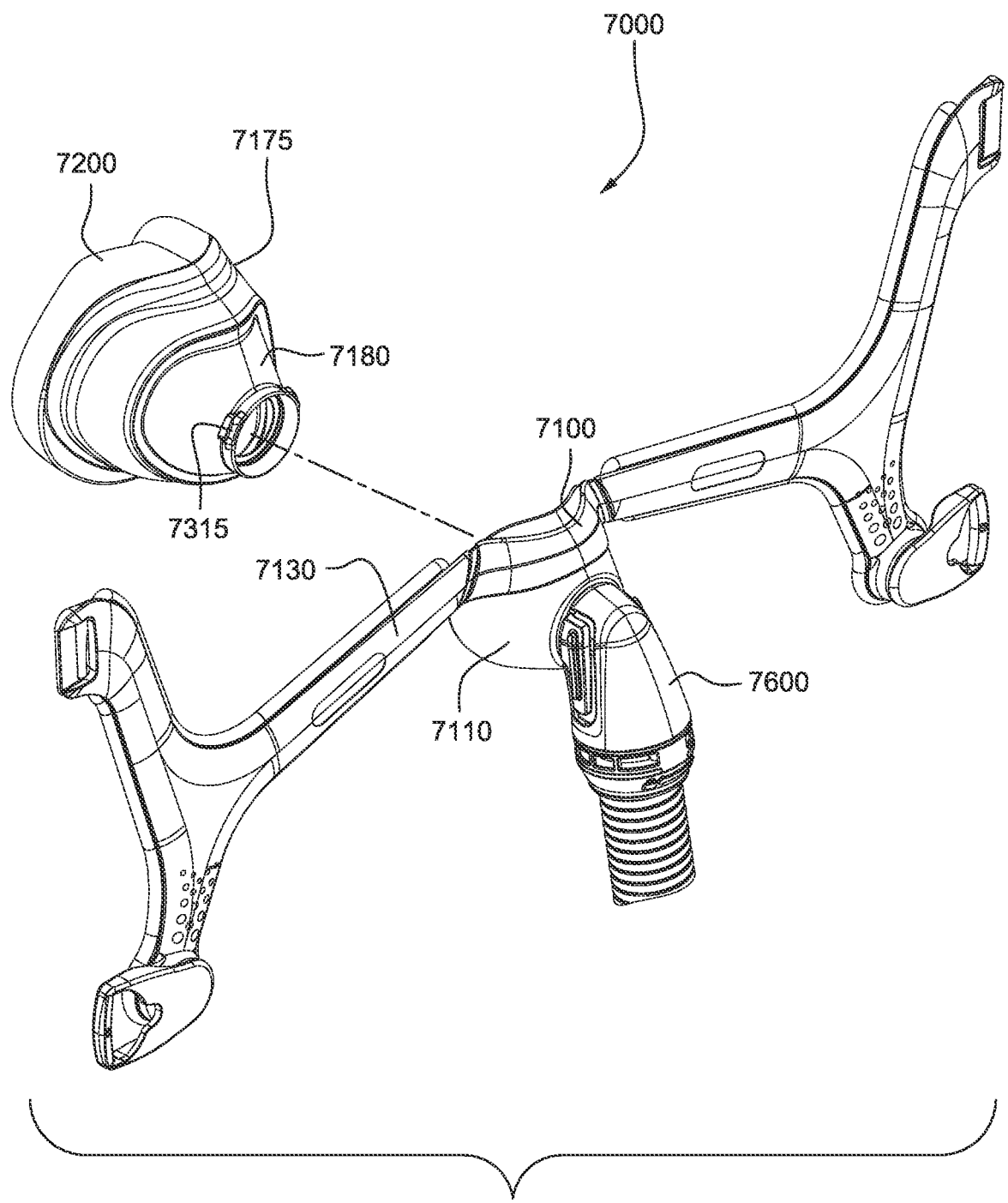

FIG. 36 is an exploded view of a patient interface according to an example of the present technology showing the frame assembly and elbow assembly removably connected with the cushion assembly removed.

Figure 37:
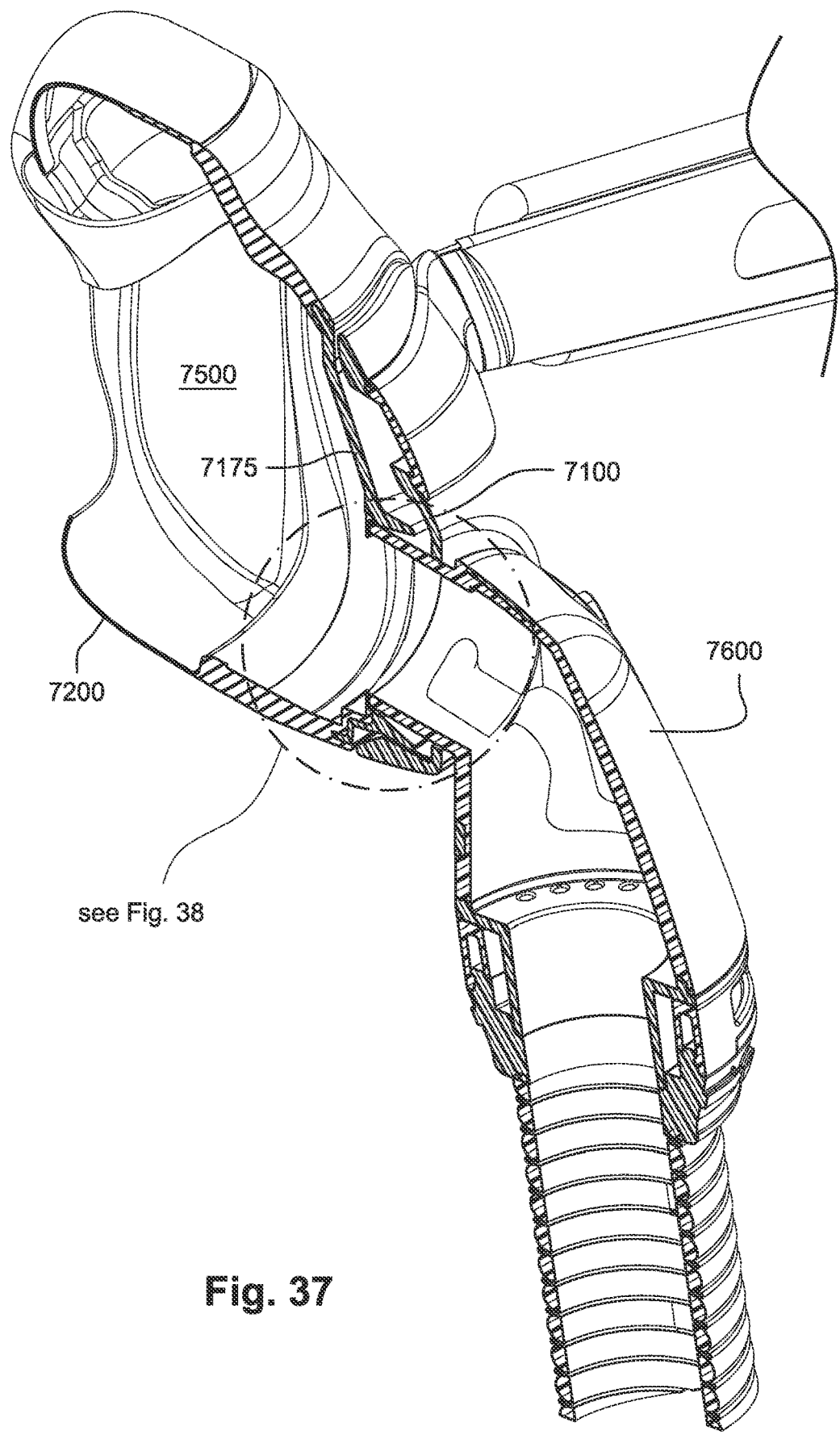

FIG. 37 is a cross-sectional view of a patient interface according to an example of the present technology.

Figure 38:
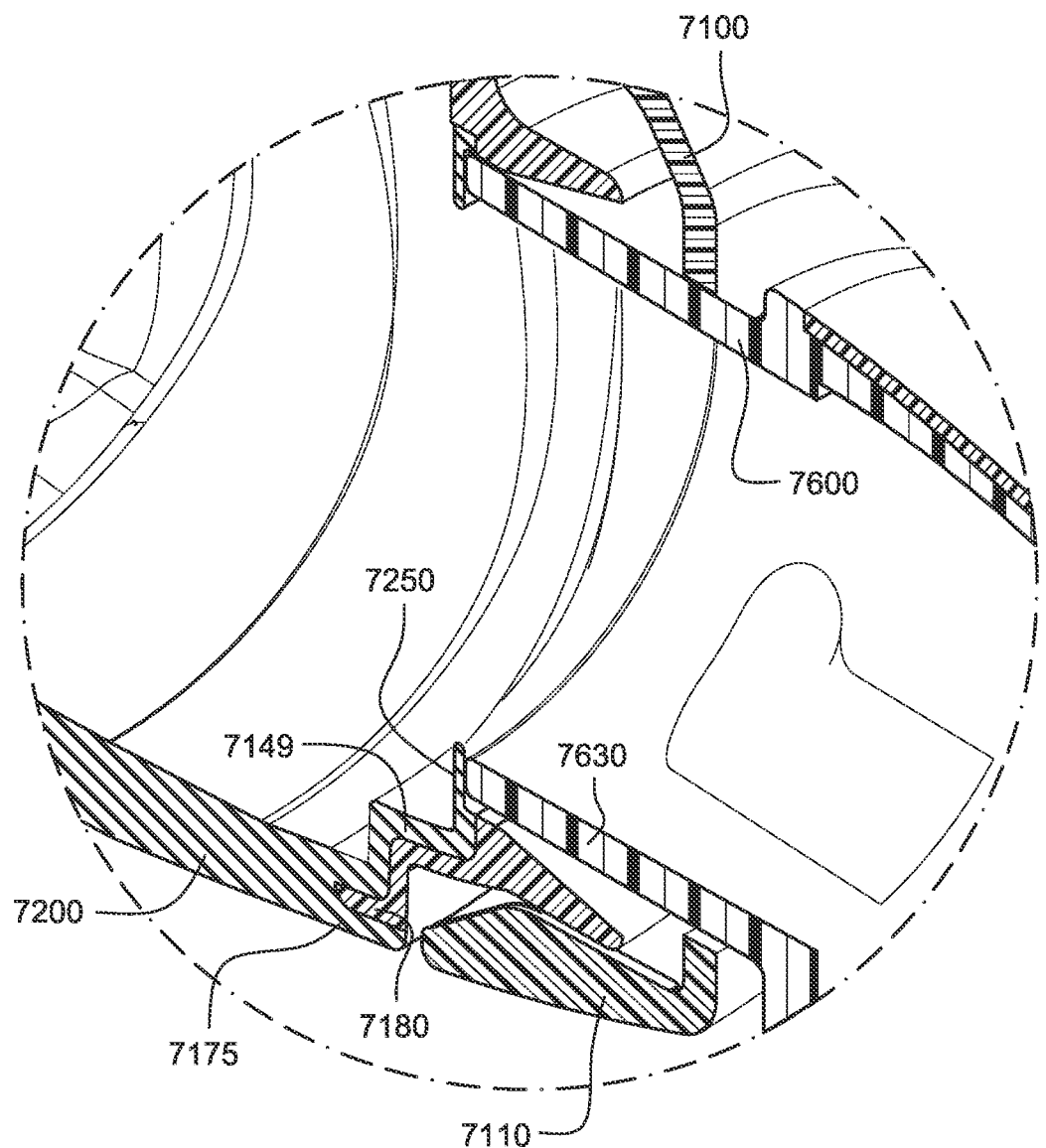

FIG. 38 is an enlarged view of the patient interface shown in FIG. 37.

Figure 39:
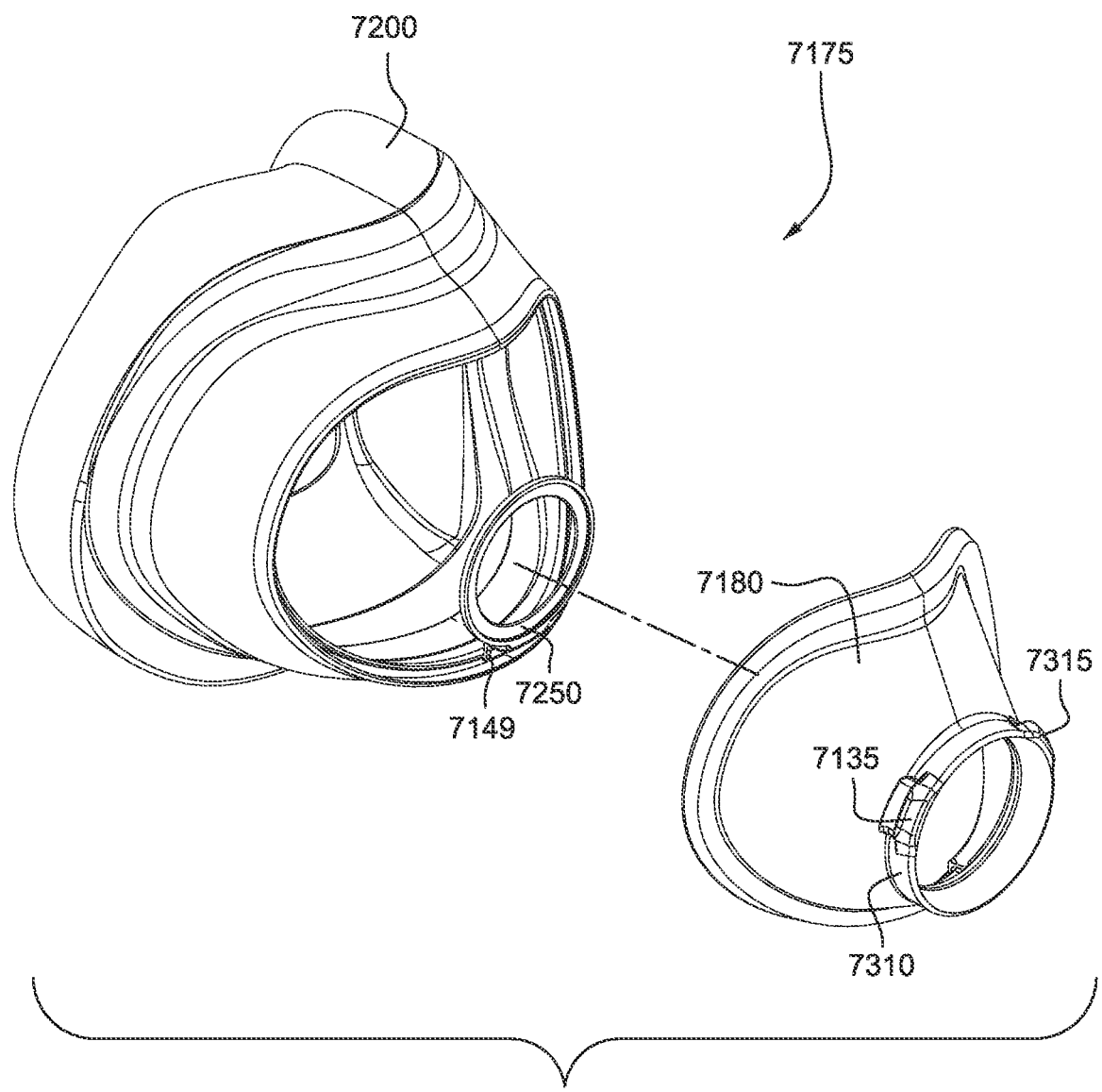

FIG. 39 is a front exploded view of a cushion assembly according to an example of the present technology.

Figure 40:
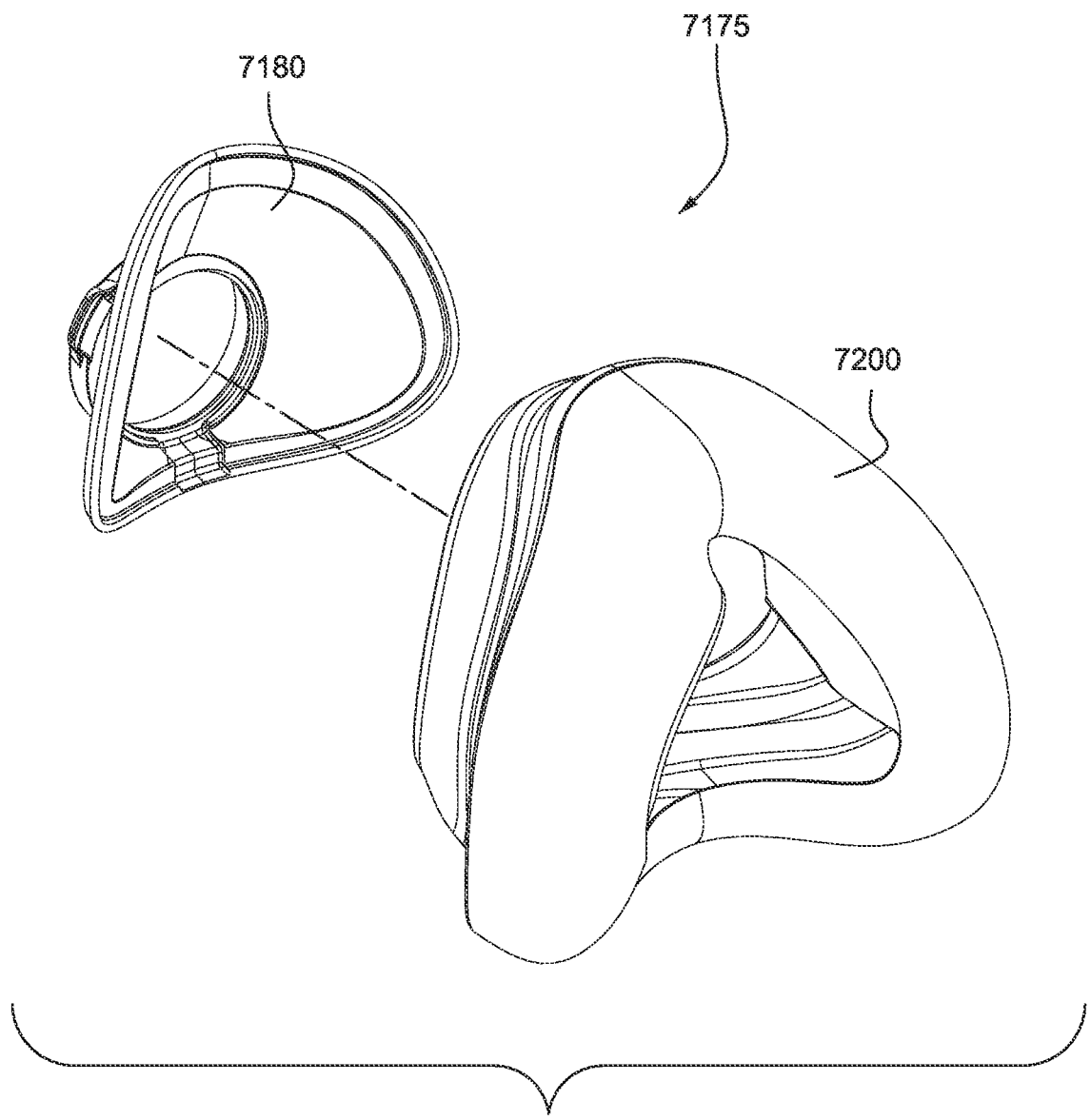

FIG. 40 is a rear exploded view of the cushion assembly shown in FIG. 39.

Figure 41:
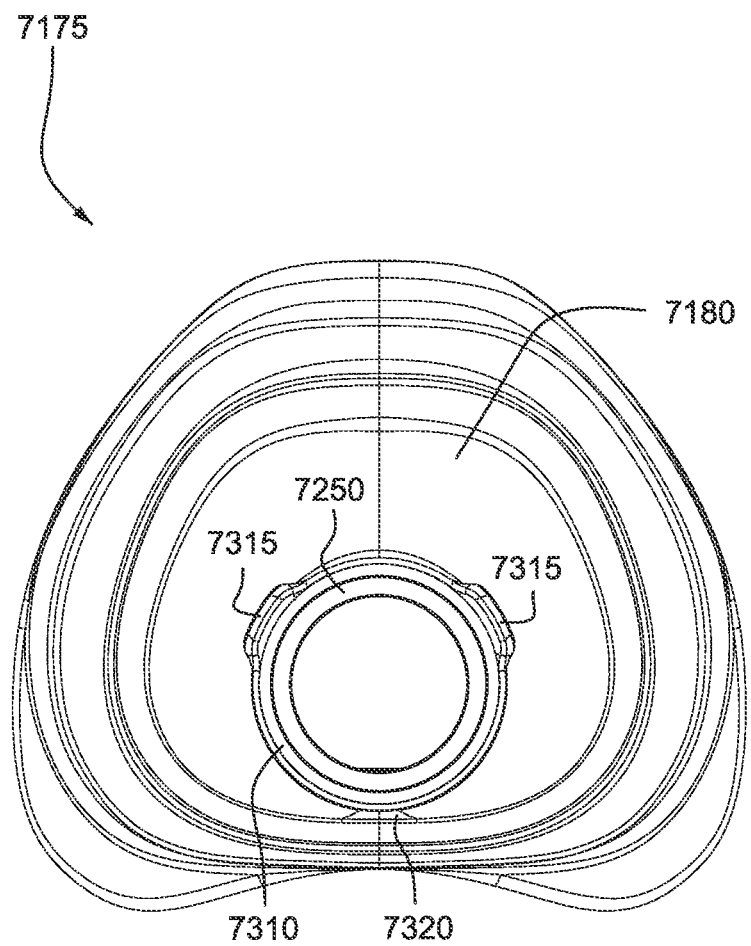

FIG. 41 is a front view of the cushion assembly shown in FIG. 39.

Figure 42:
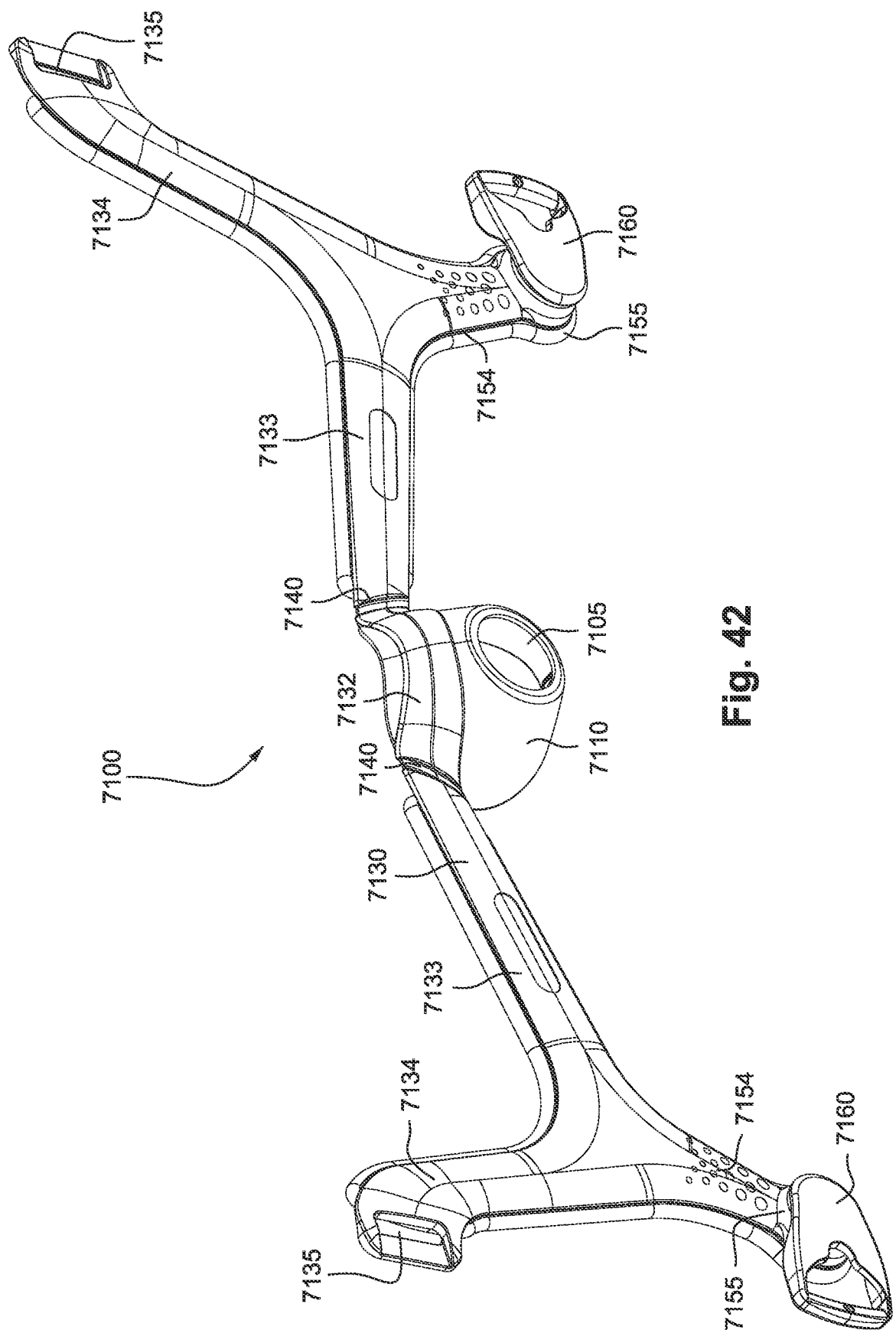

FIG. 42 is a front perspective view of a frame assembly according to an example of the present technology.

Figure 43:
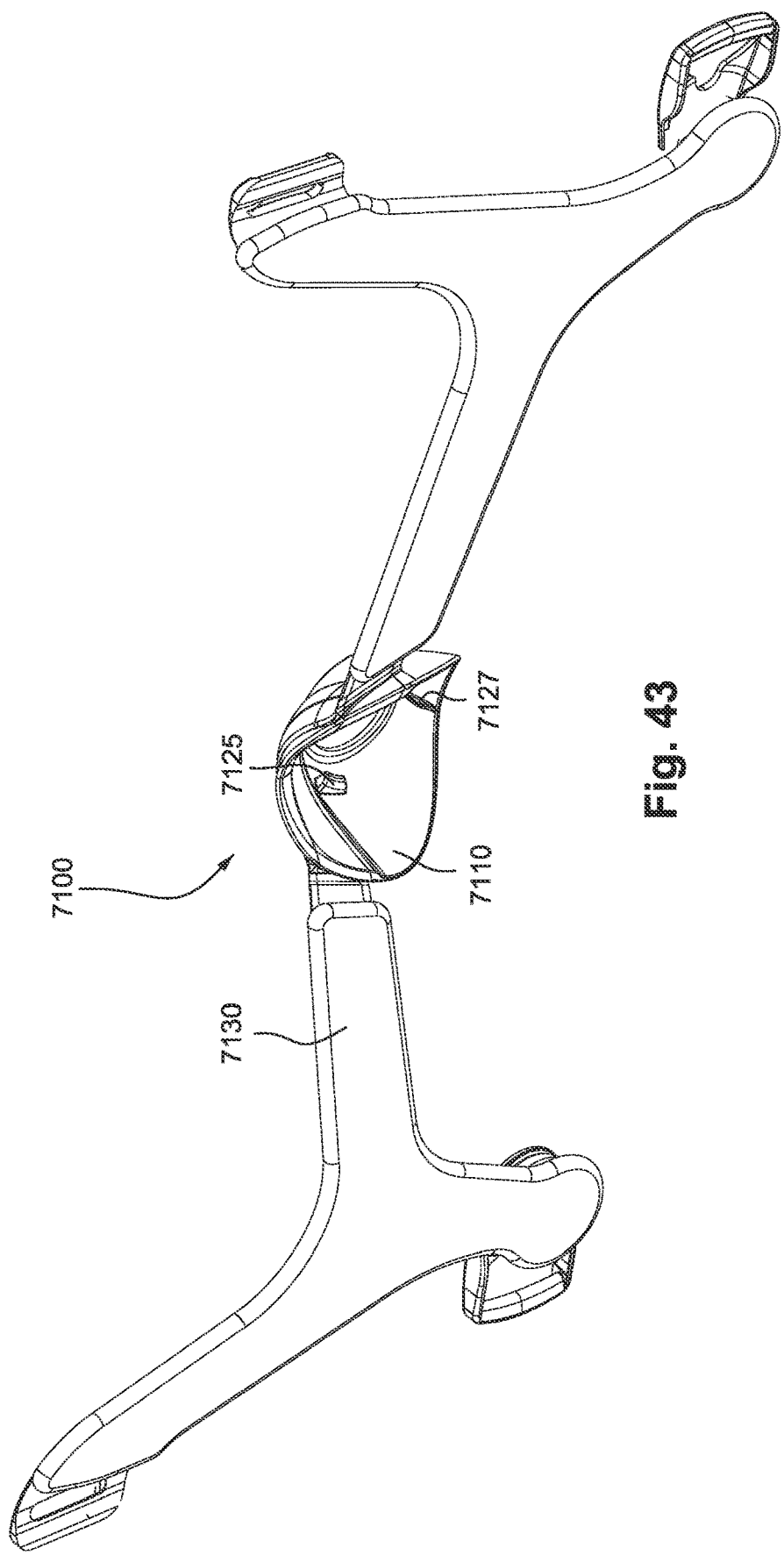

FIG. 43 is a rear perspective view of the frame assembly shown in FIG. 42.

Figure 44:
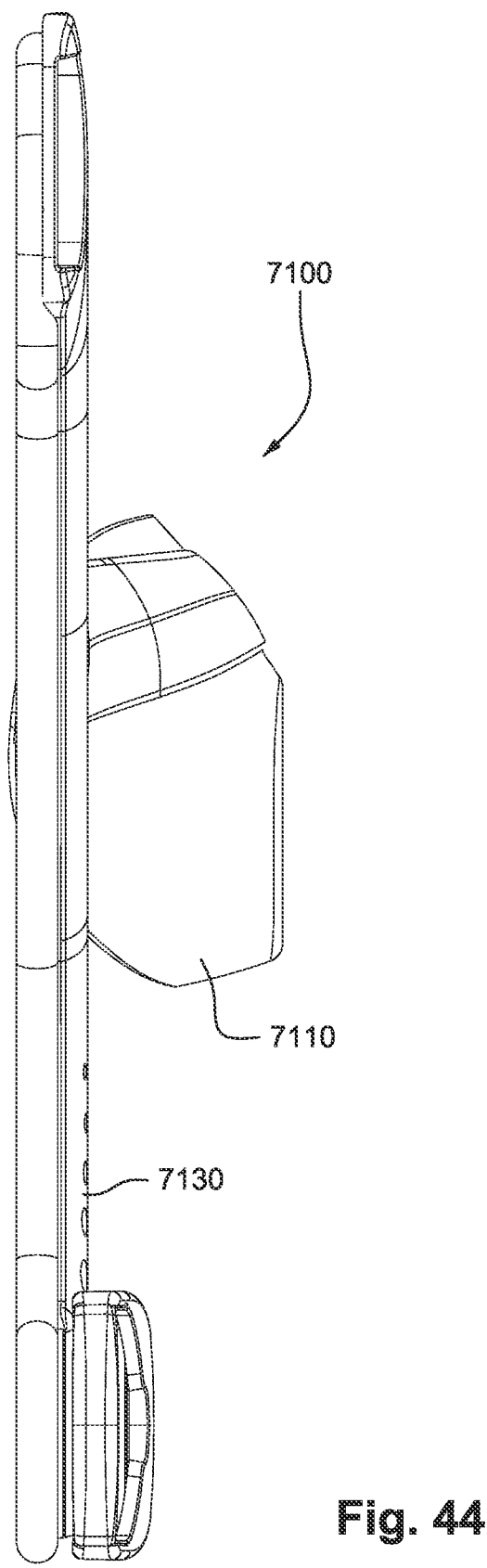

FIG. 44 is a side view of the frame assembly shown in FIG. 42.

Figure 45:
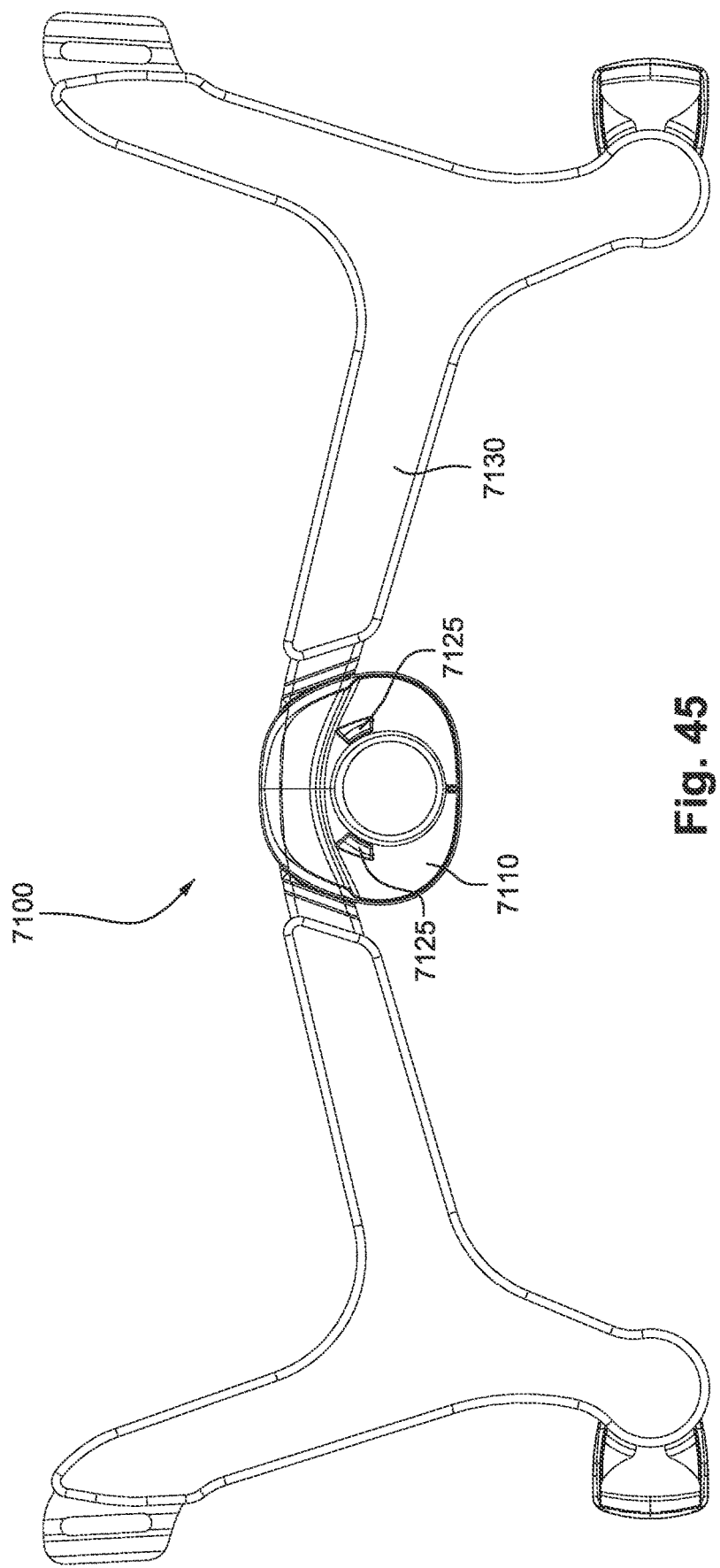

FIG. 45 is a rear view of the frame assembly shown in FIG. 42.

Figure 46:
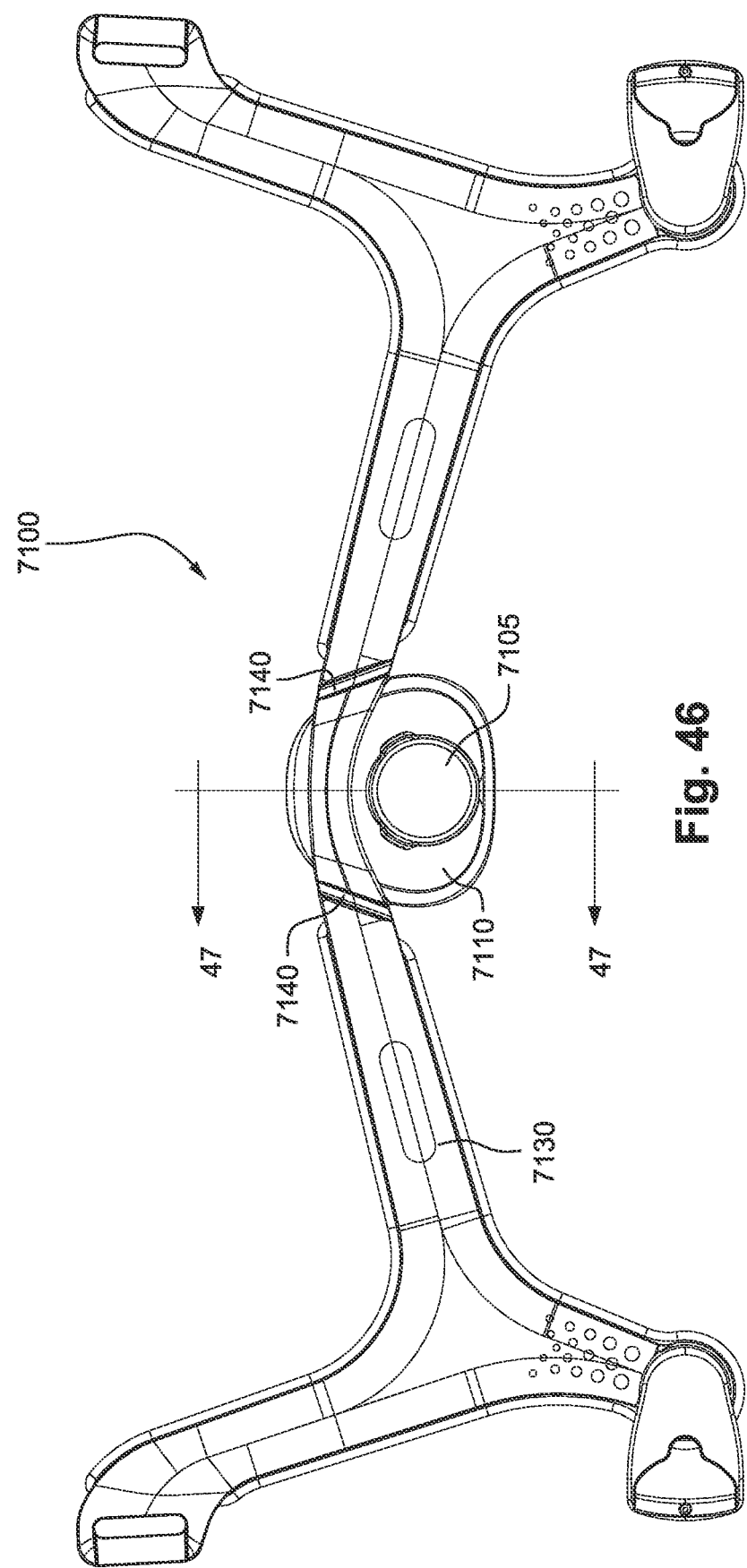

FIG. 46 is a front view of the frame assembly shown in FIG. 42.

Figure 47:
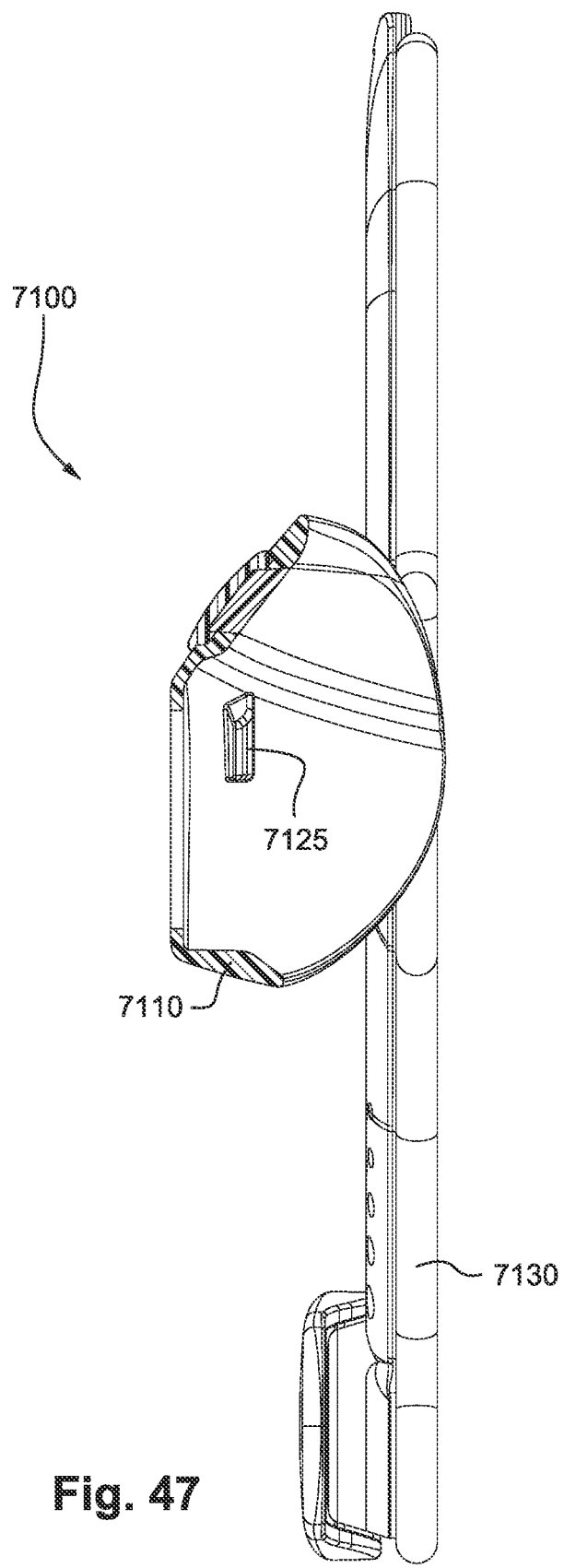

FIG. 47 is a cross-sectional view of the frame assembly shown in FIG. 46.

Figure 48:
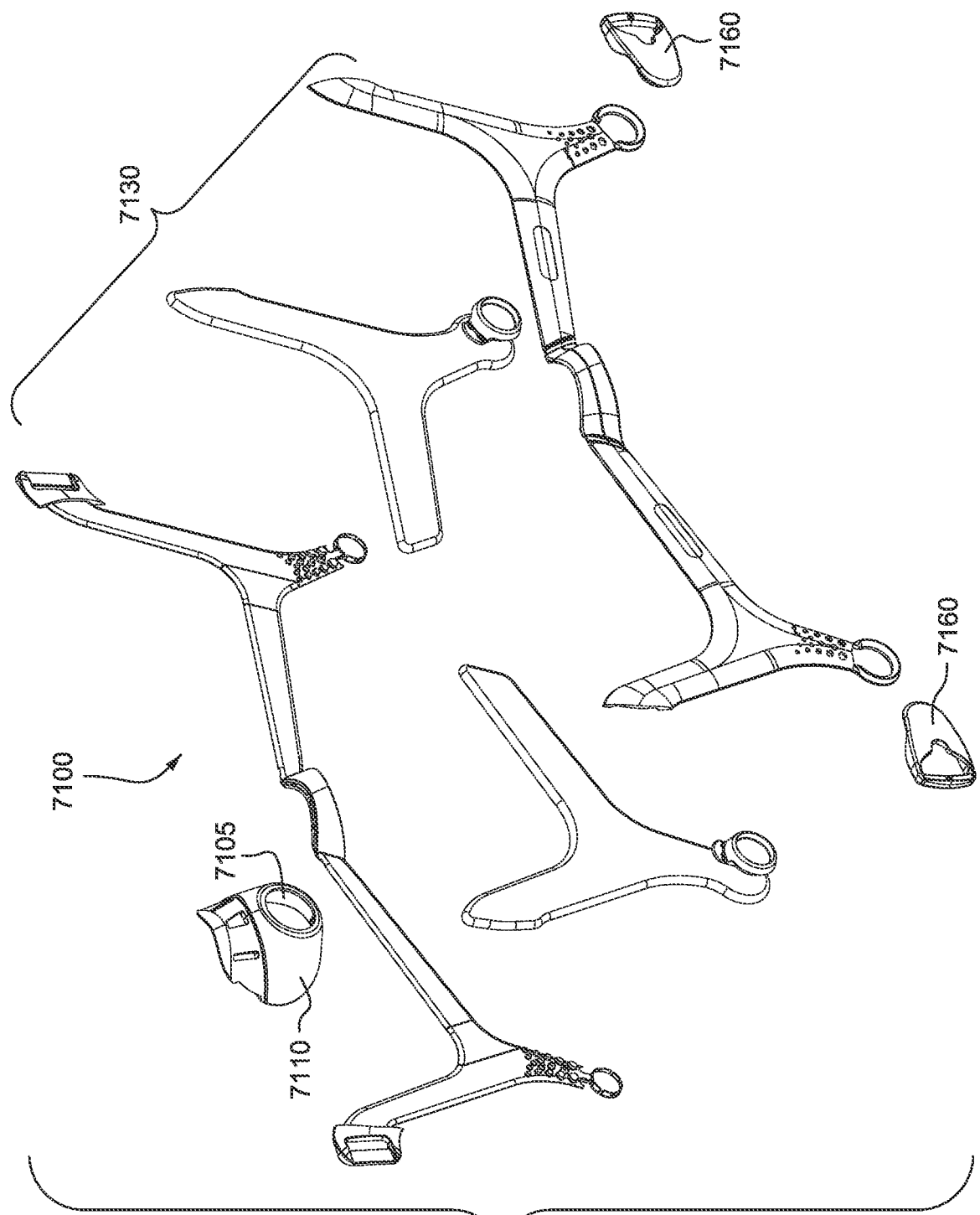

FIG. 48 is a front exploded view of the frame assembly shown in FIG. 42.

Figure 49:
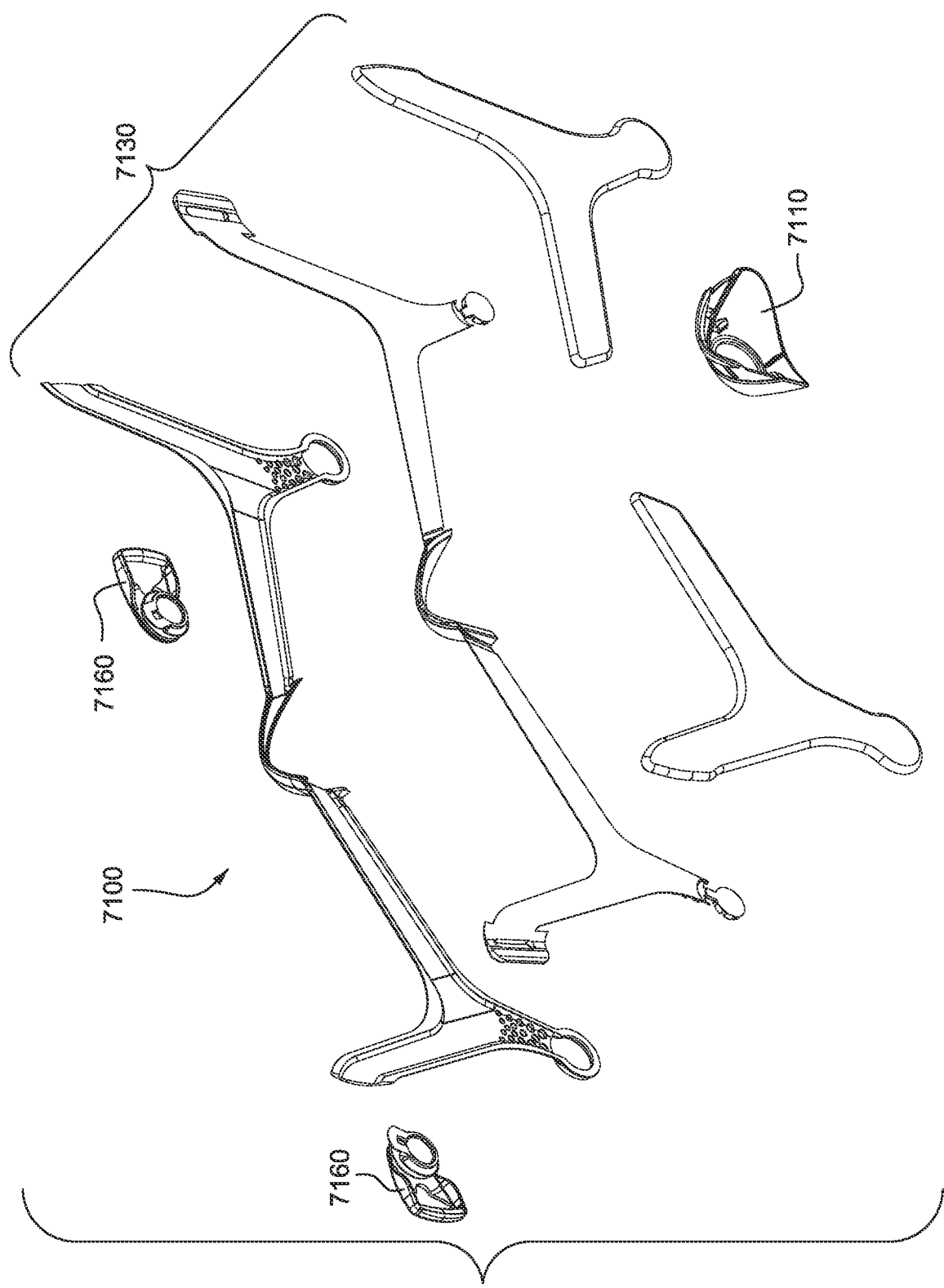

FIG. 49 is a rear exploded view of the frame assembly shown in FIG. 42.

Figures 50, 51:
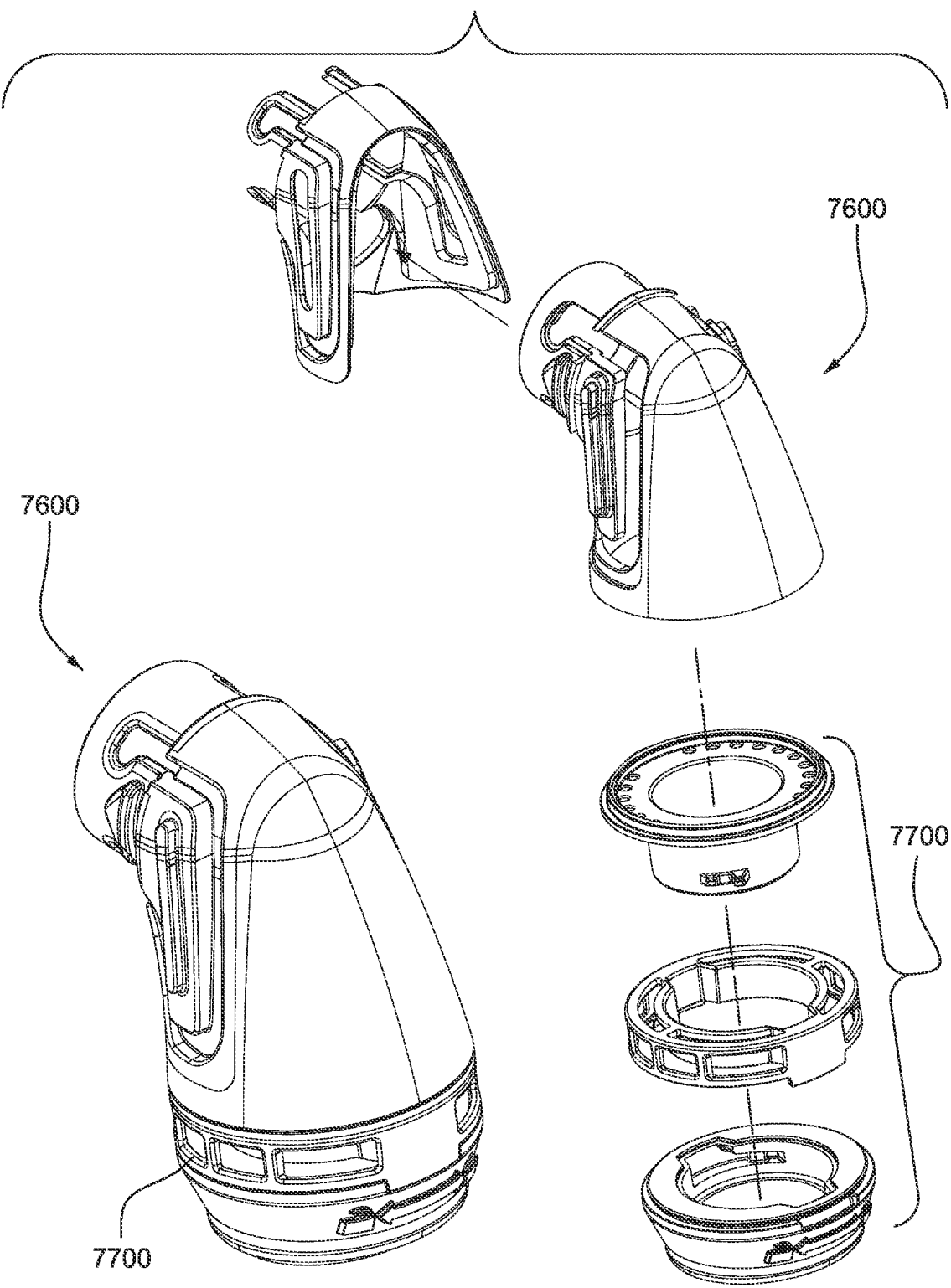

FIG. 50 is a perspective view of an elbow assembly according to an example of the present technology.

FIG. 51 is an exploded view of the elbow assembly shown in FIG. 50.

Figures 52, 53:
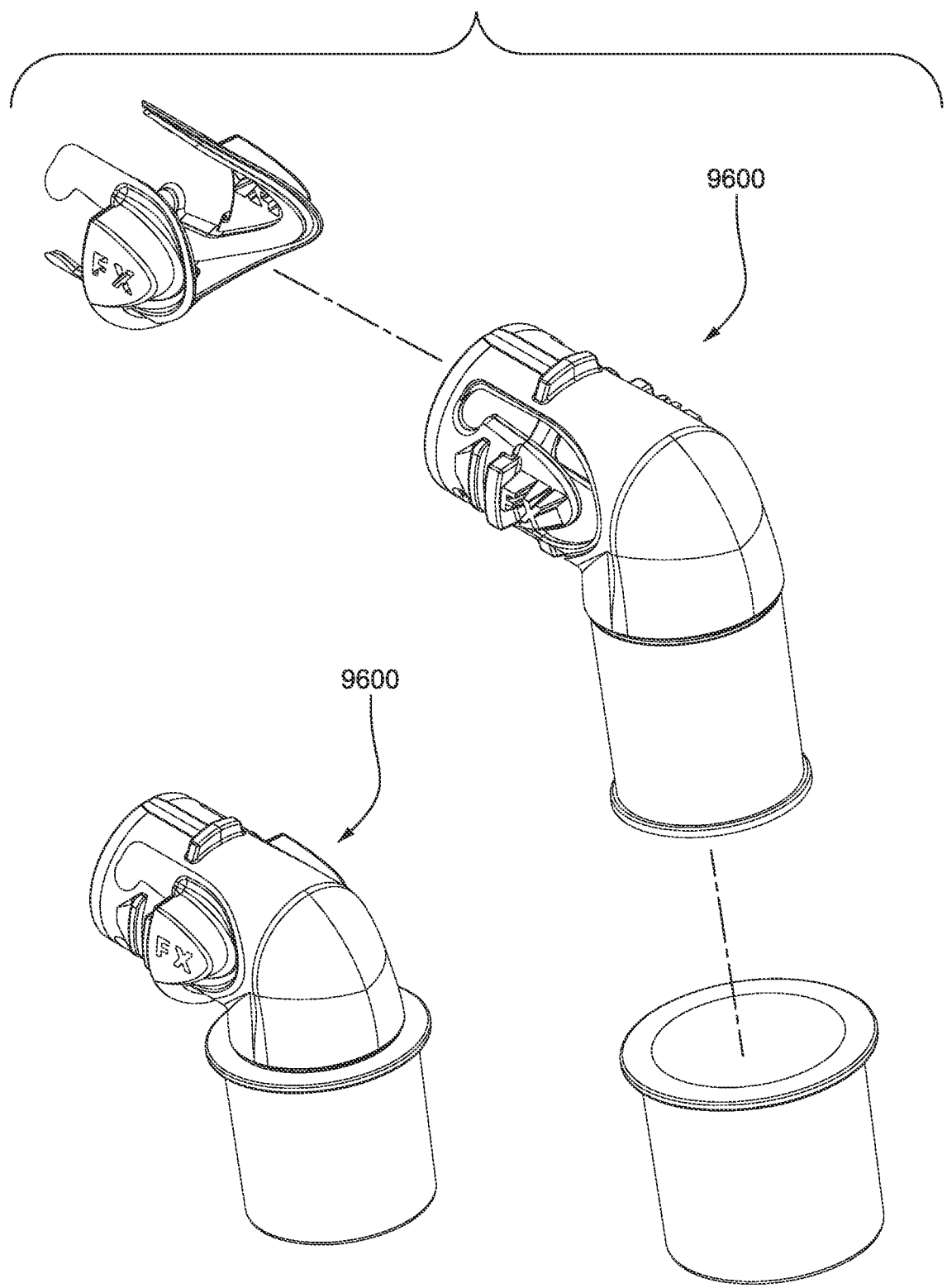

FIG. 52 is a perspective view of an elbow assembly according to an example of the present technology.

FIG. 53 is an exploded view of the elbow assembly shown in FIG. 52.

Figure 54C:
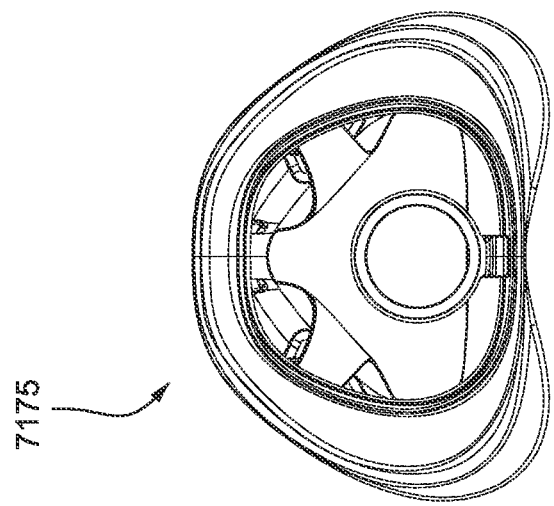
Figure 54B:
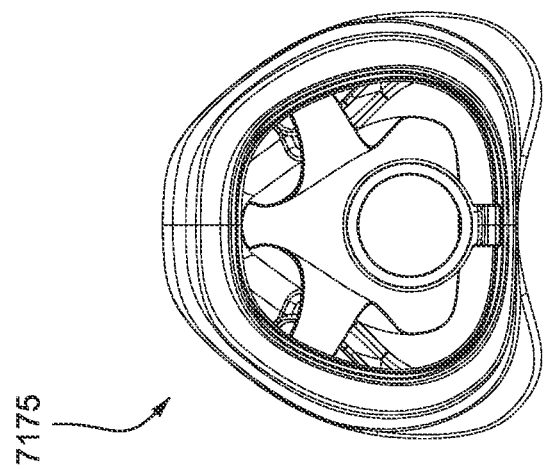
Figure 54A:
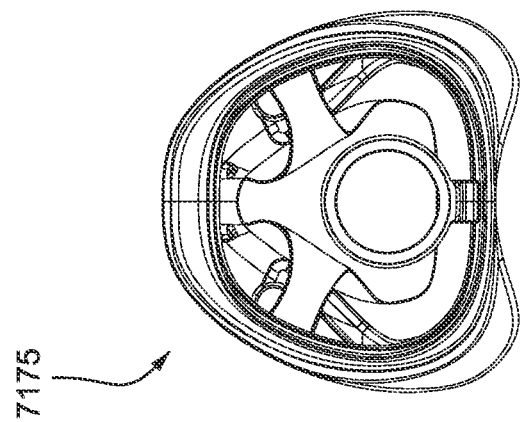

FIGS. 54A, 54B, and 54C are rear views of small, medium, and large cushion assemblies according to an example of the present technology.

Figure 55:
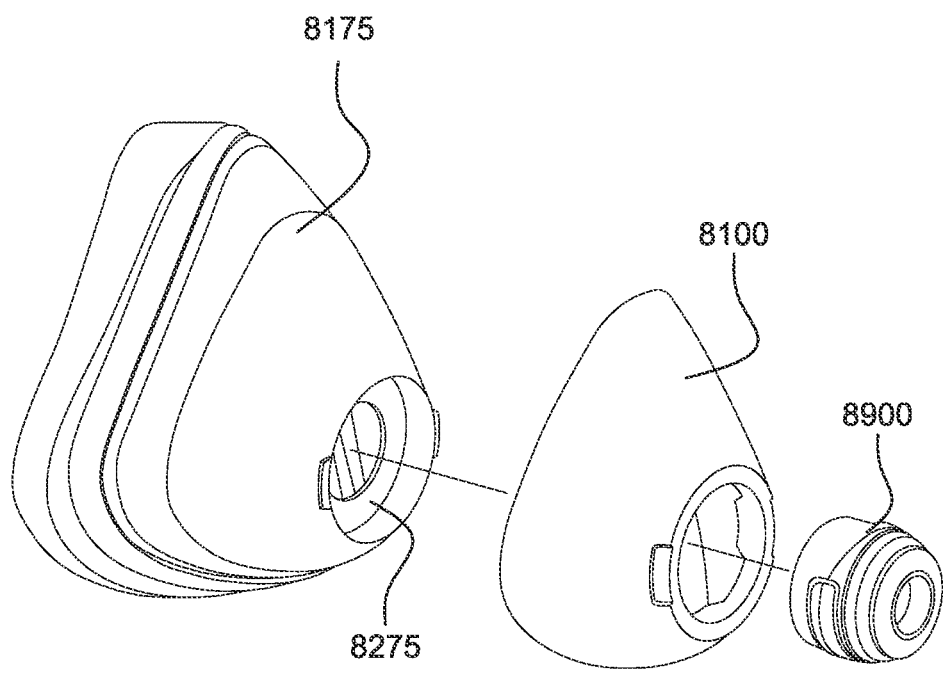

FIG. 55 is an exploded view of a patient interface according to an alternative example of the present technology.

Figure 56:
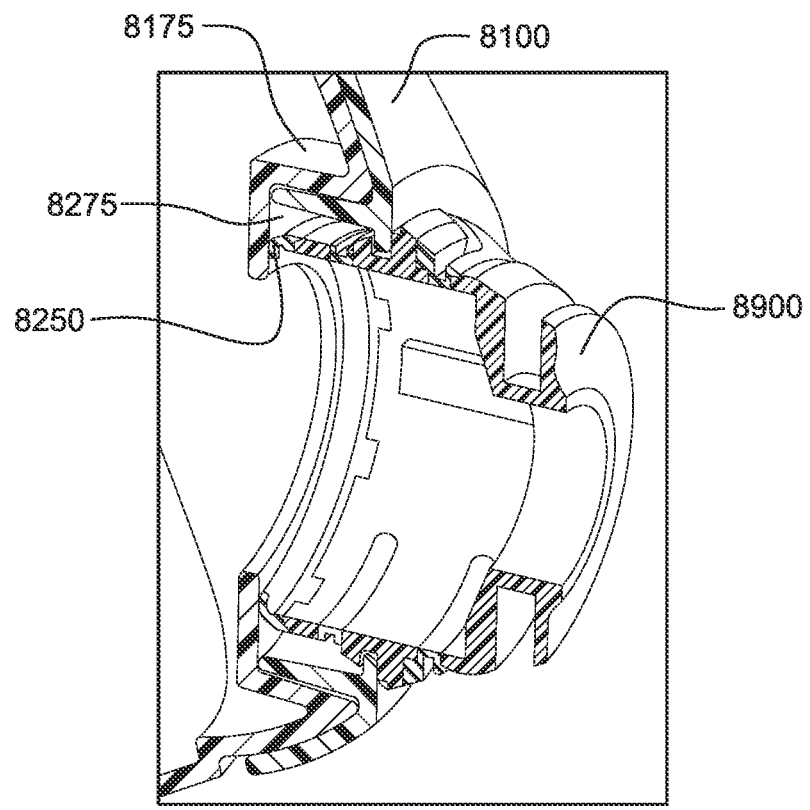

FIG. 56 is a cross-sectional view of the patient interface shown in FIG. 55.

Figure 57:
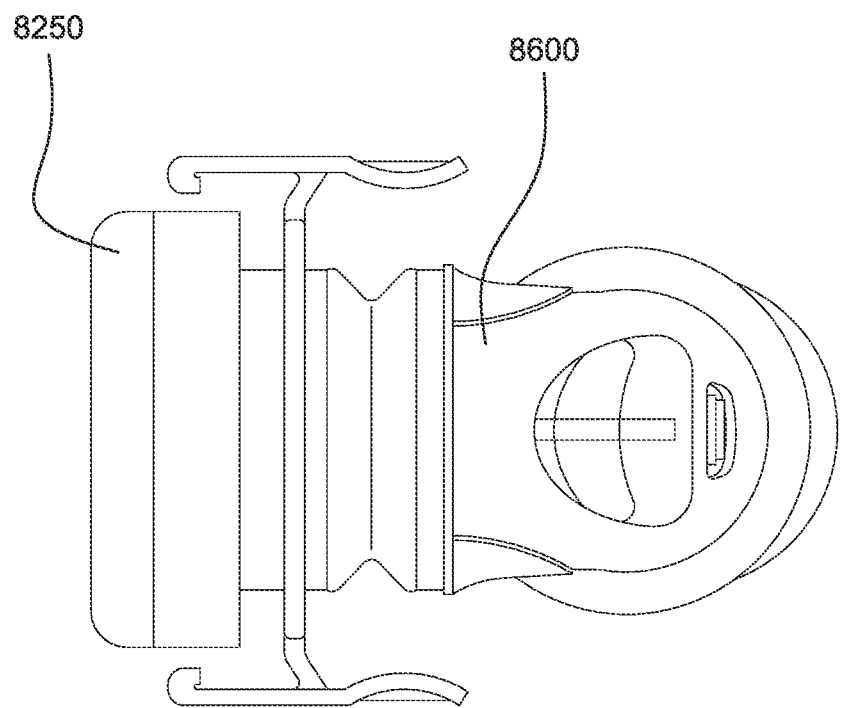

FIG. 57 is a top view of an elbow assembly according to an alternative example of the present technology.

Figure 58:
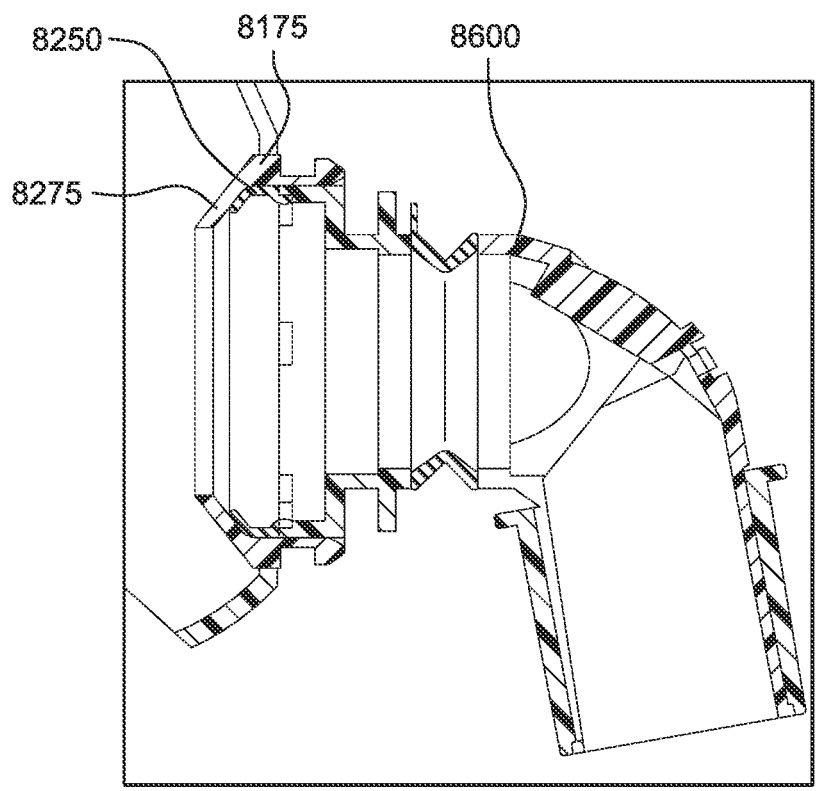

FIG. 58 is a cross-sectional view showing the elbow assembly of FIG. 57 attached to a patient interface according to an example of the present technology.

Figure 59:
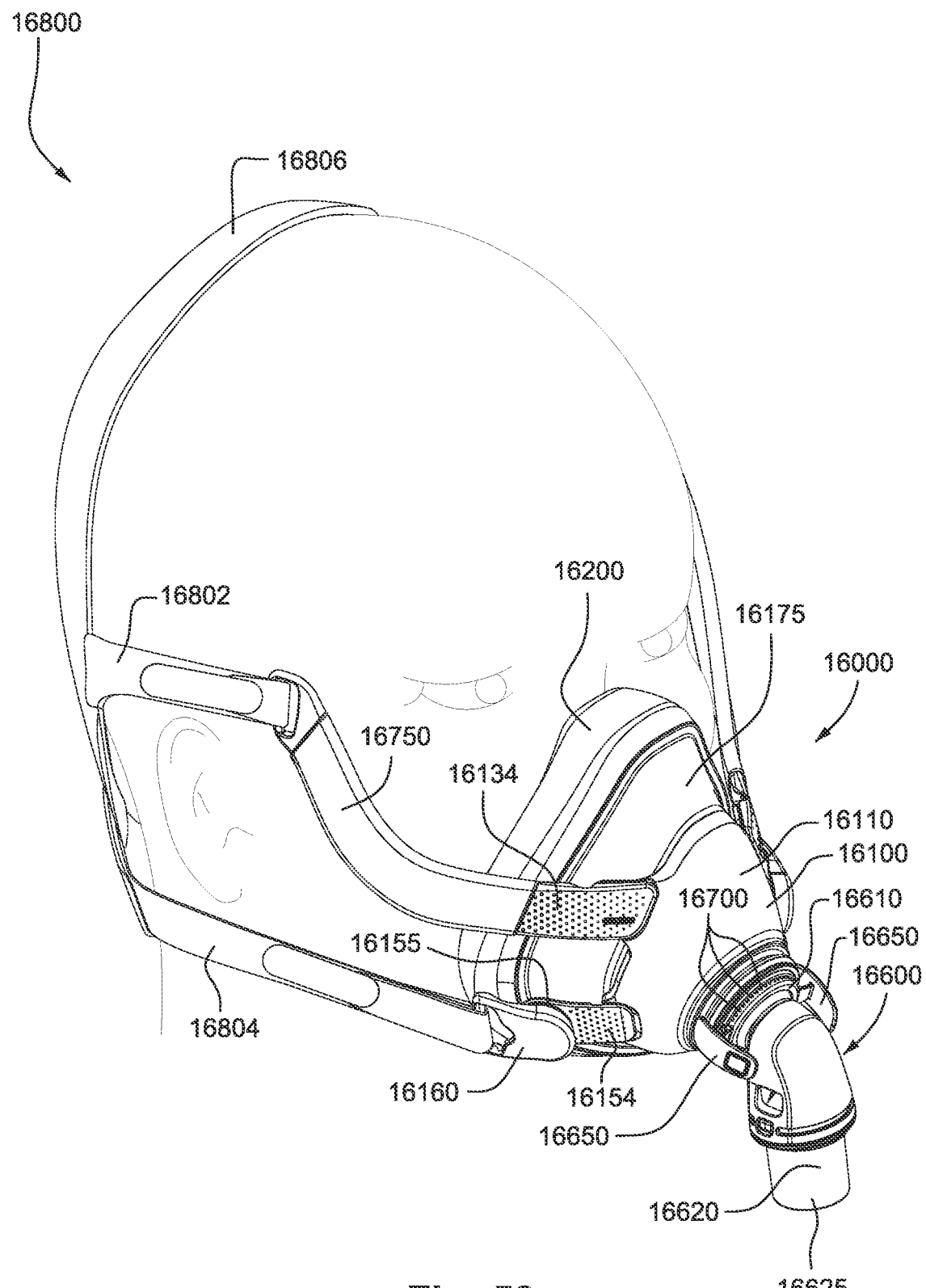

FIG. 59 is a perspective view of a patient interface shown on a patient's head according to an example of the present technology.

Figure 60:
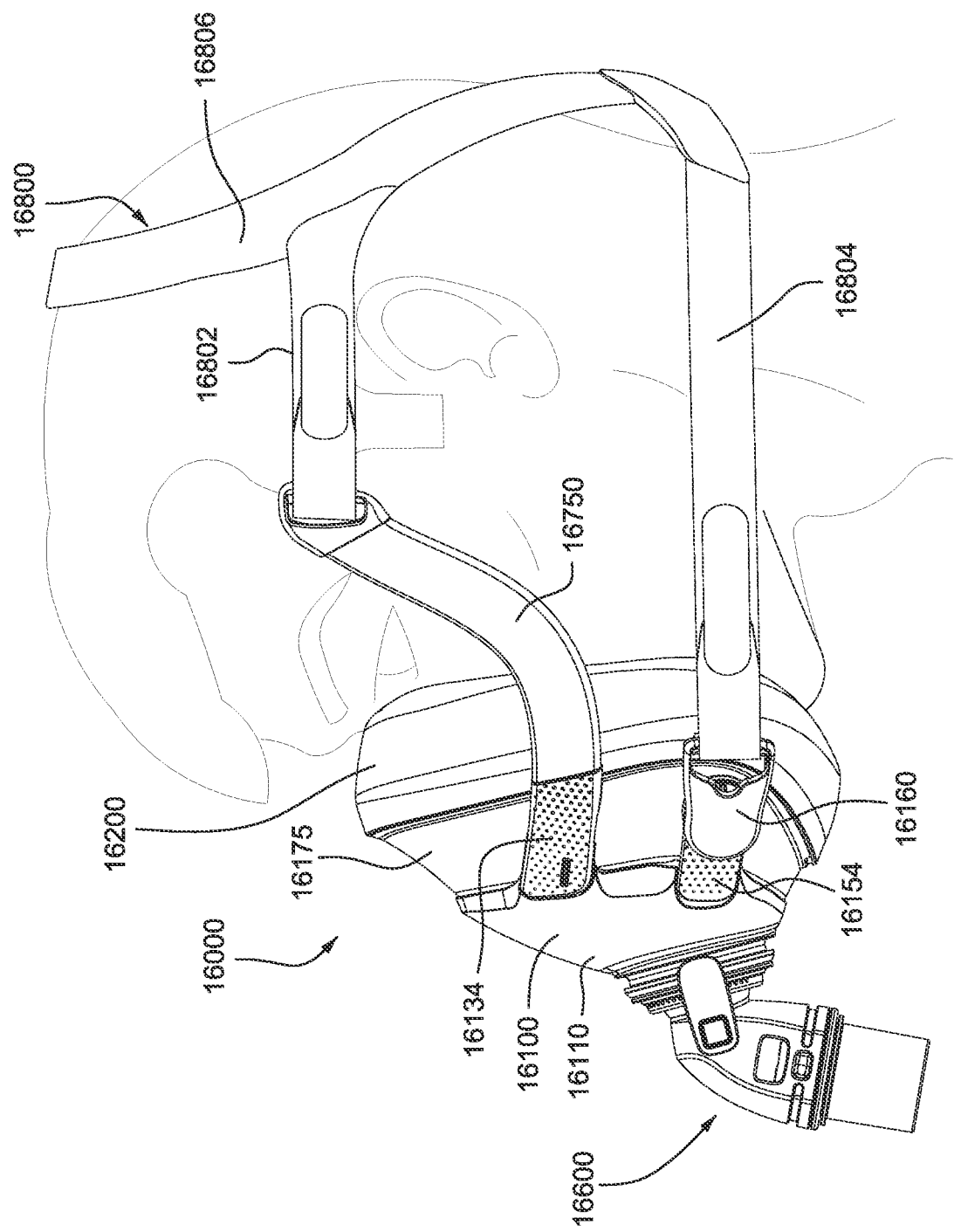

FIG. 60 is a side view of the patient interface shown in FIG. 59.

Figure 61:
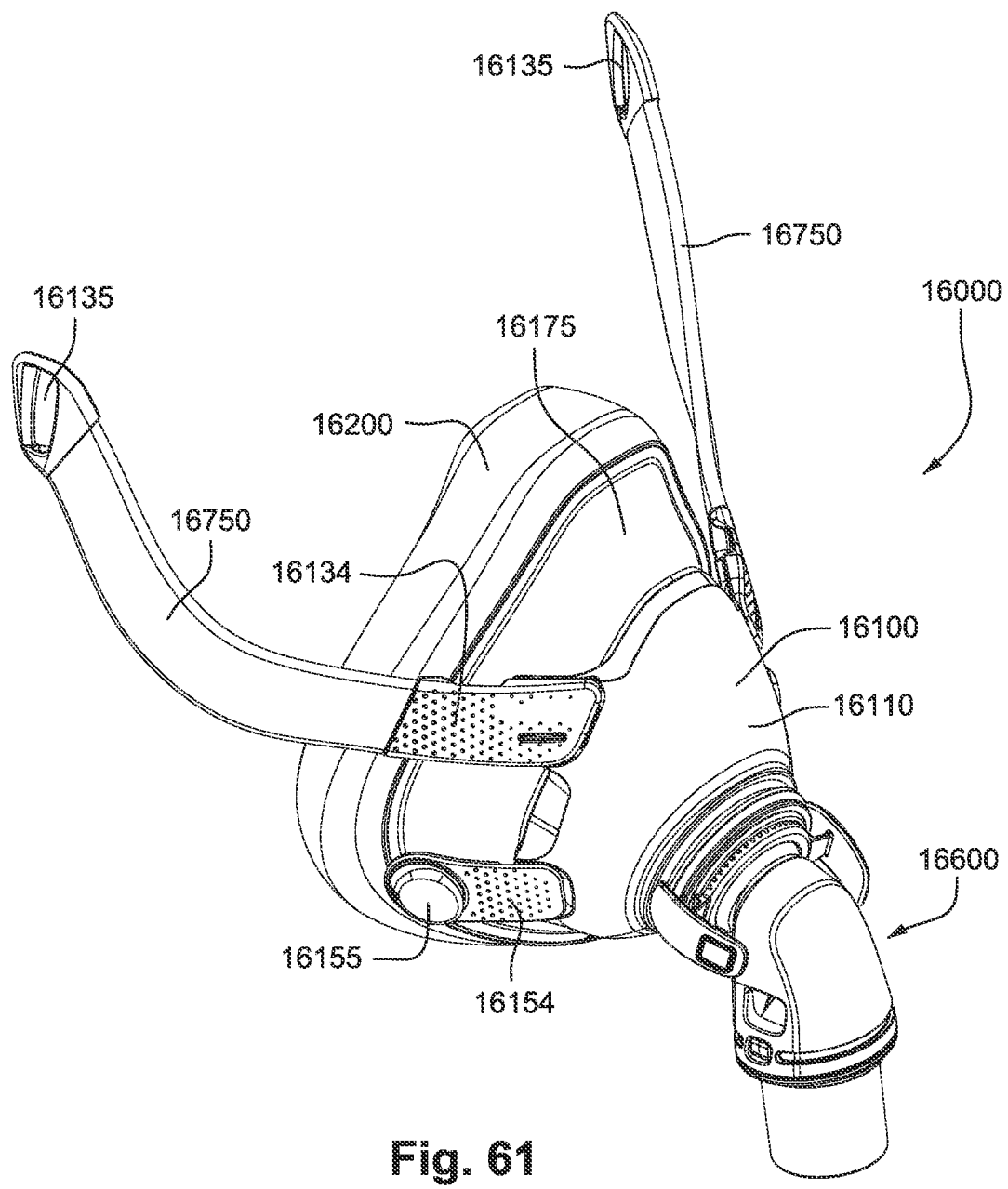

FIG. 61 is a perspective view of a patient interface according to an example of the present technology, the patient interface being shown with headgear removed.

Figure 62:
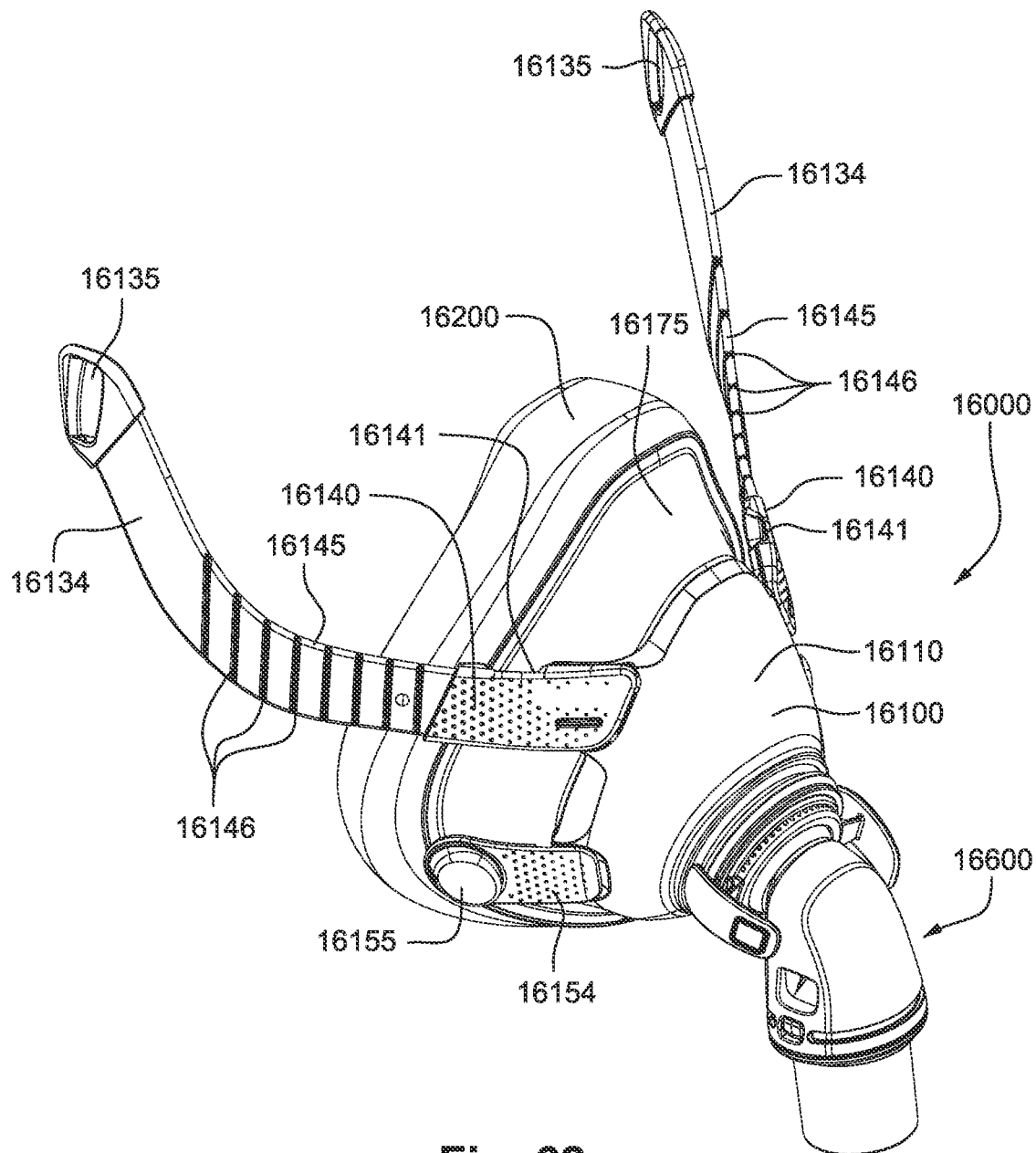

FIG. 62 is a perspective view of the patient interface shown in FIG. 61 with arm covers for upper arms of the frame assembly removed.

Figure 63:
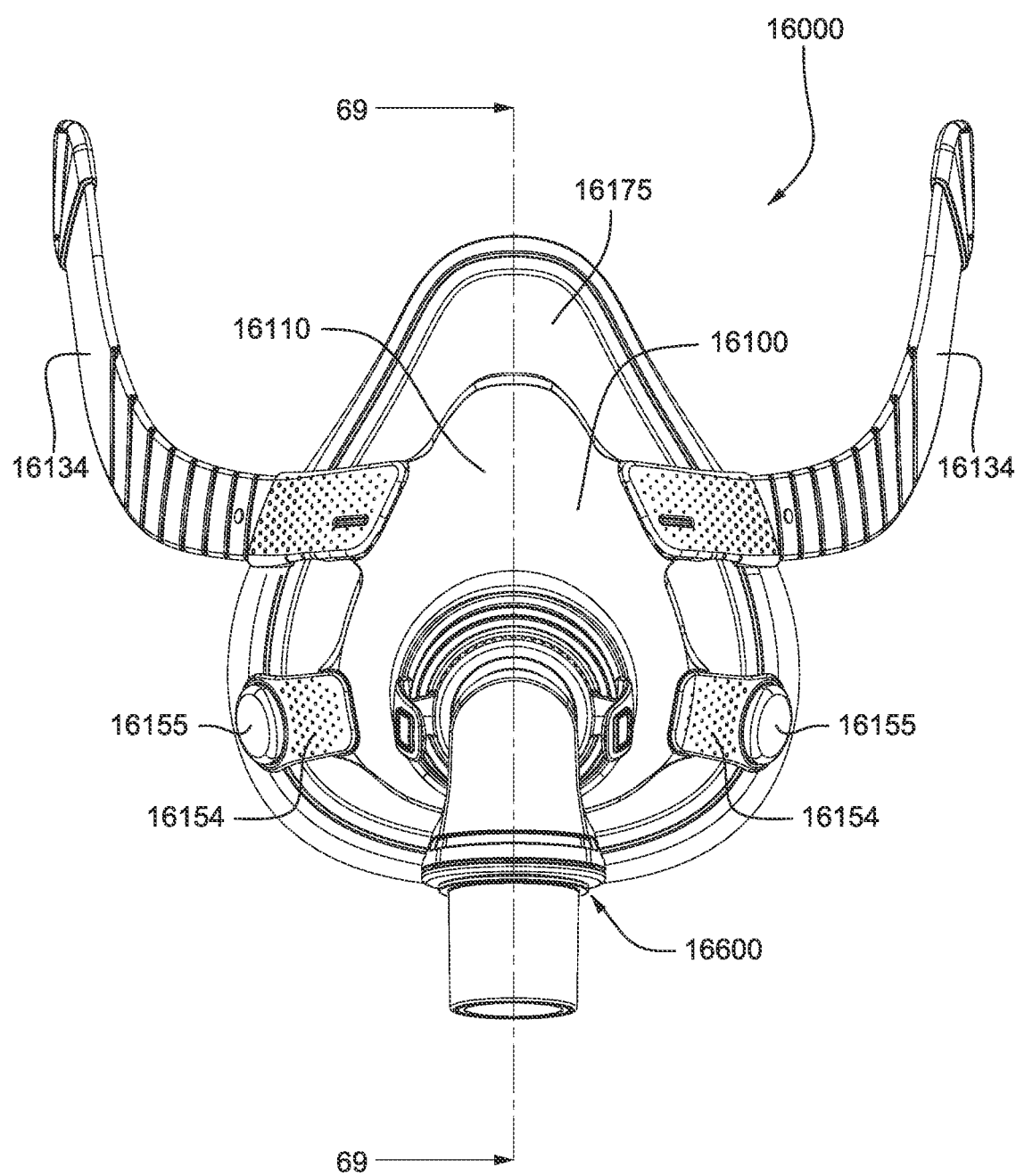

FIG. 63 is a front view of the patient interface shown in FIG. 62.

Figure 64:
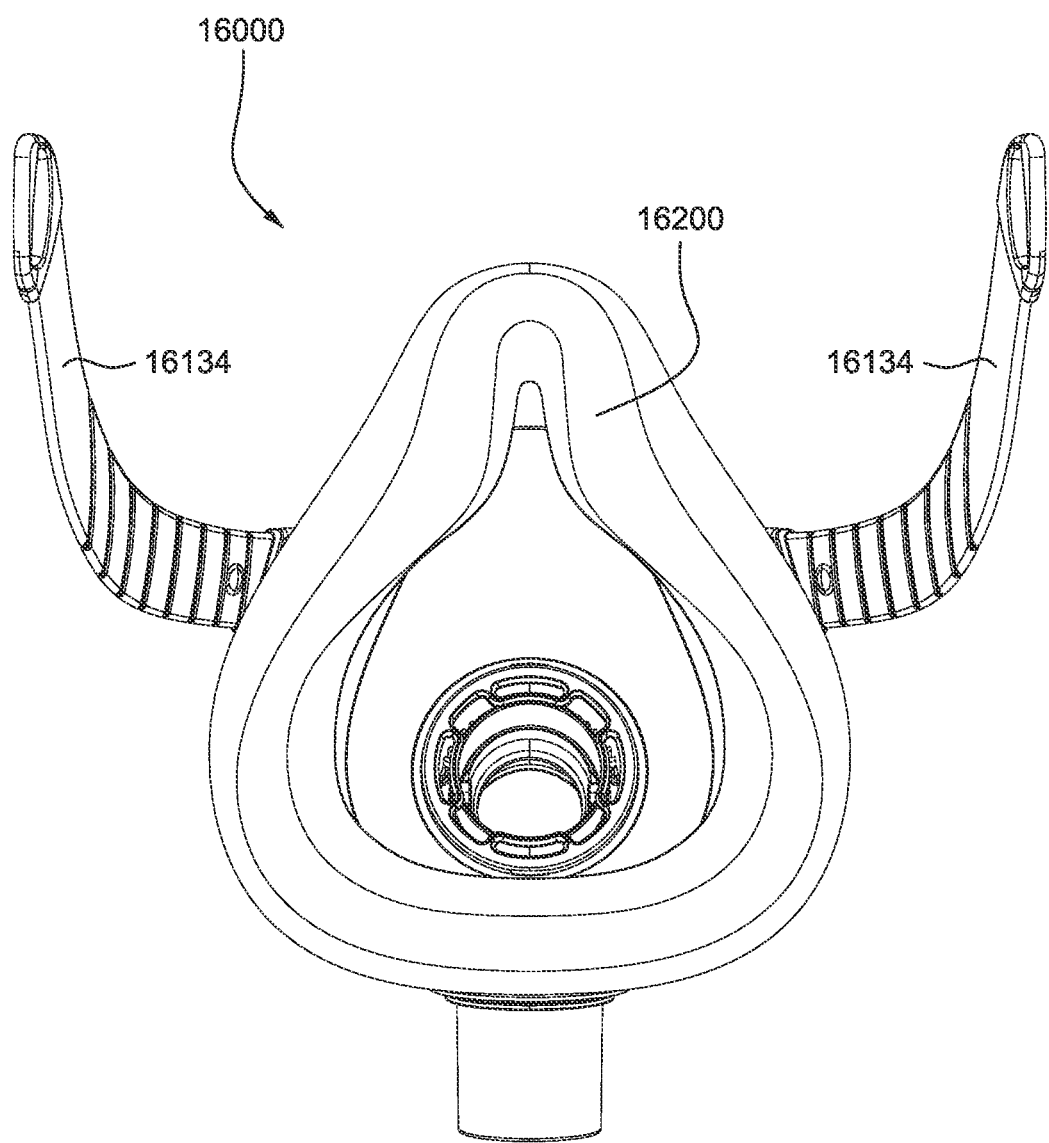

FIG. 64 is a rear view of the patient interface shown in FIG. 62.

Figure 65:
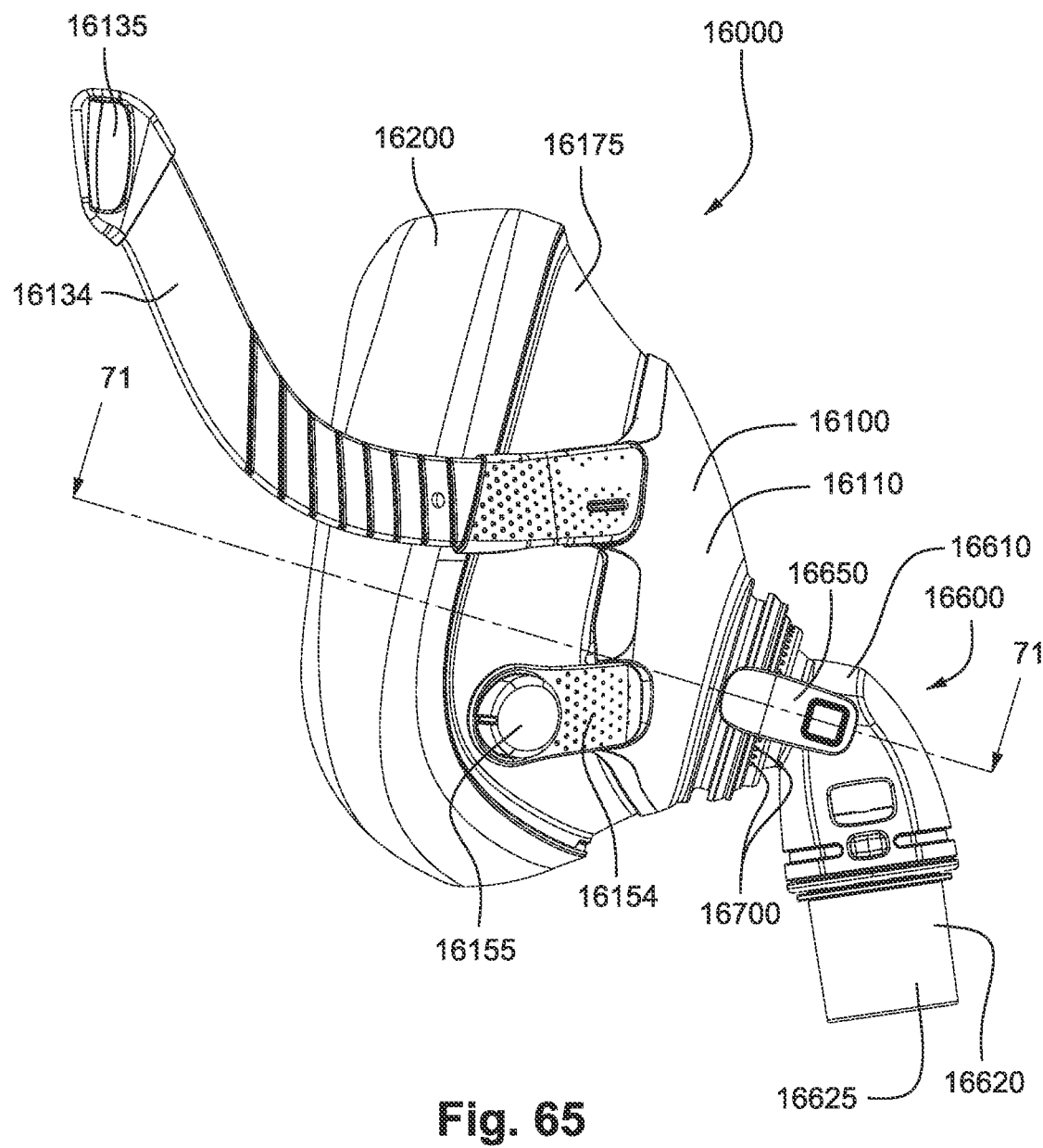

FIG. 65 is a side view of the patient interface shown in FIG. 62.

Figure 66:
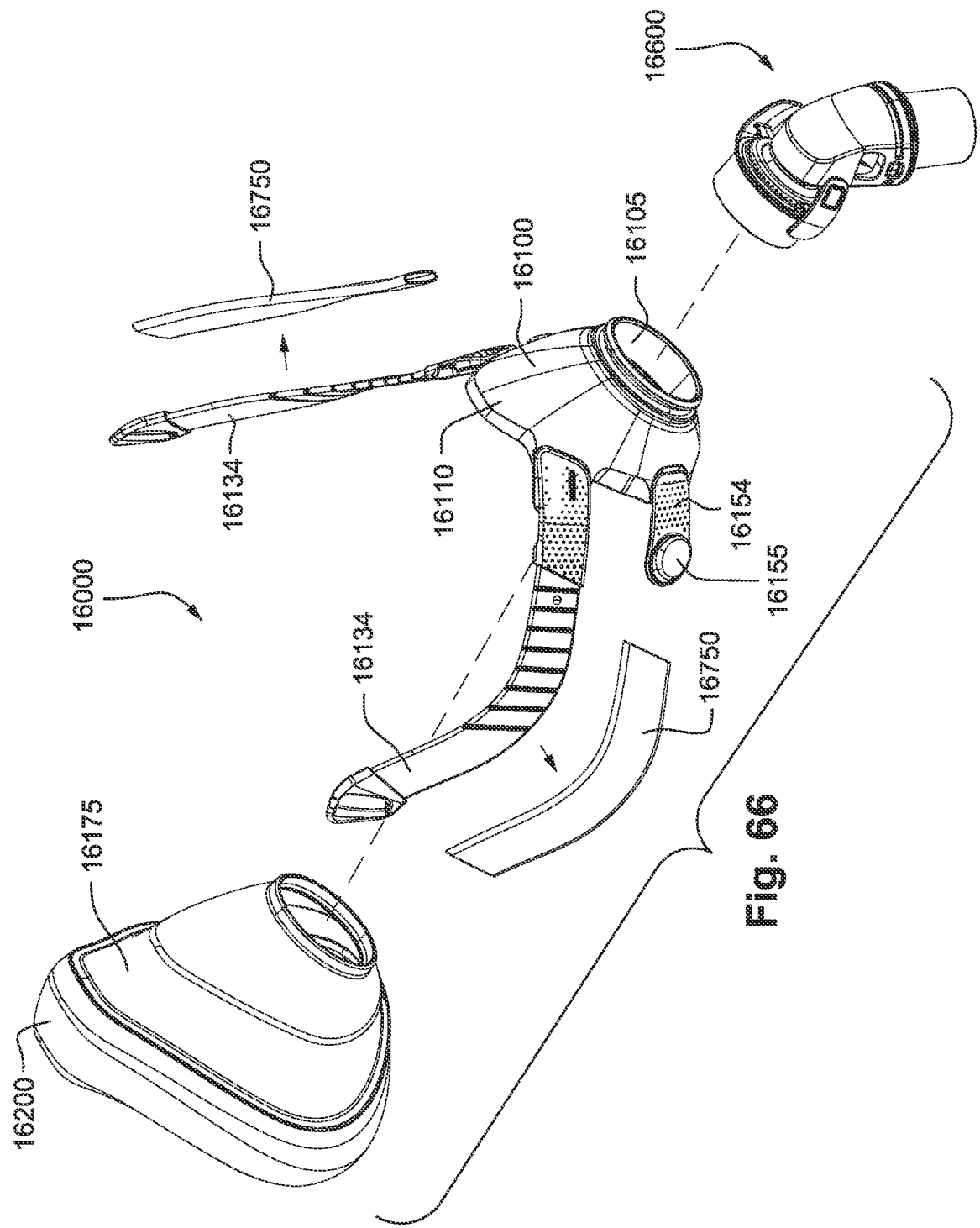

FIG. 66 is an exploded view of the patient interface shown in FIG. 61 showing the cushion assembly, frame assembly, arm covers, and elbow assembly.

Figure 67:
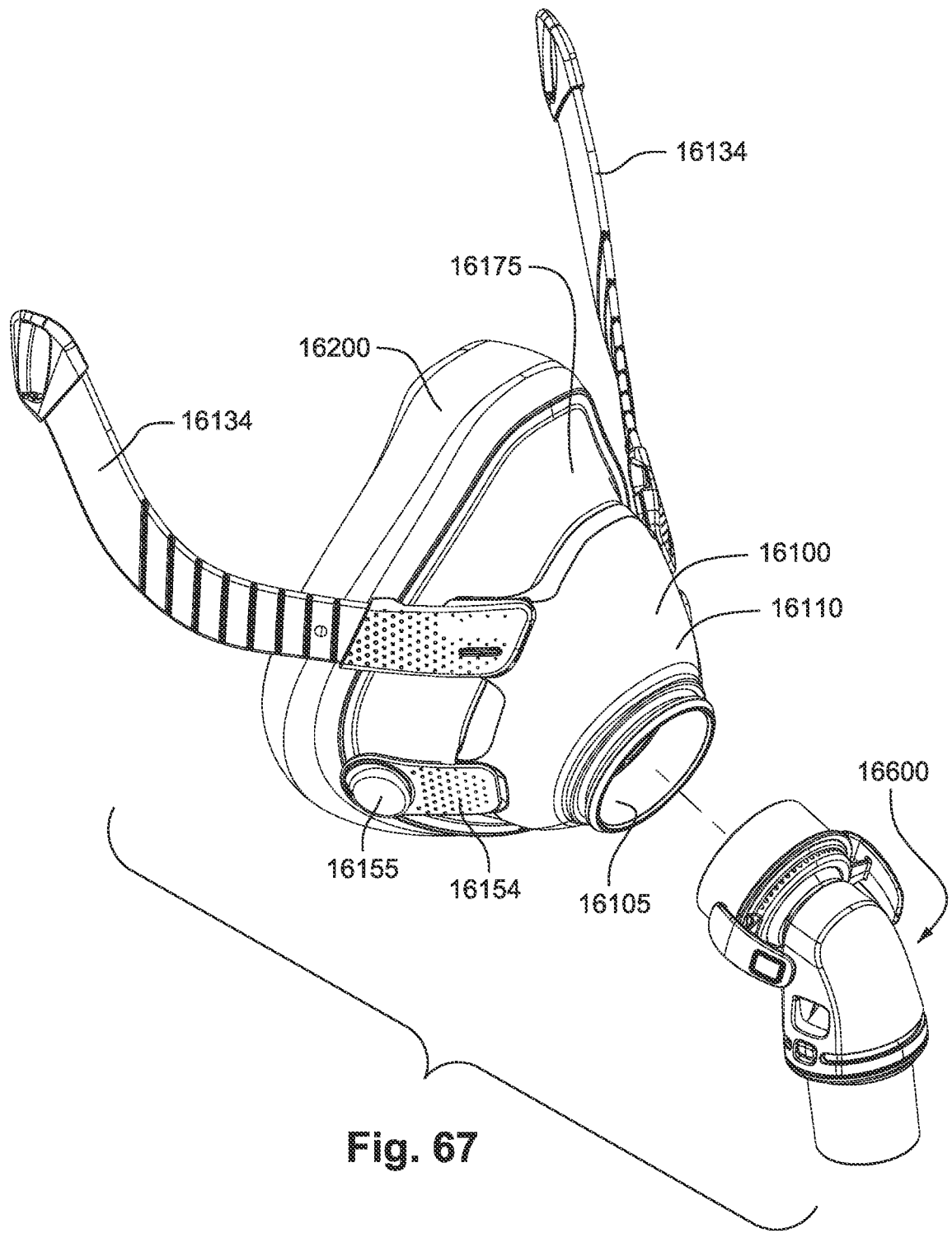

FIG. 67 is an exploded view of the patient interface shown in FIG. 62 showing the cushion assembly and frame assembly removably connected with the elbow assembly removed.

Figure 68:
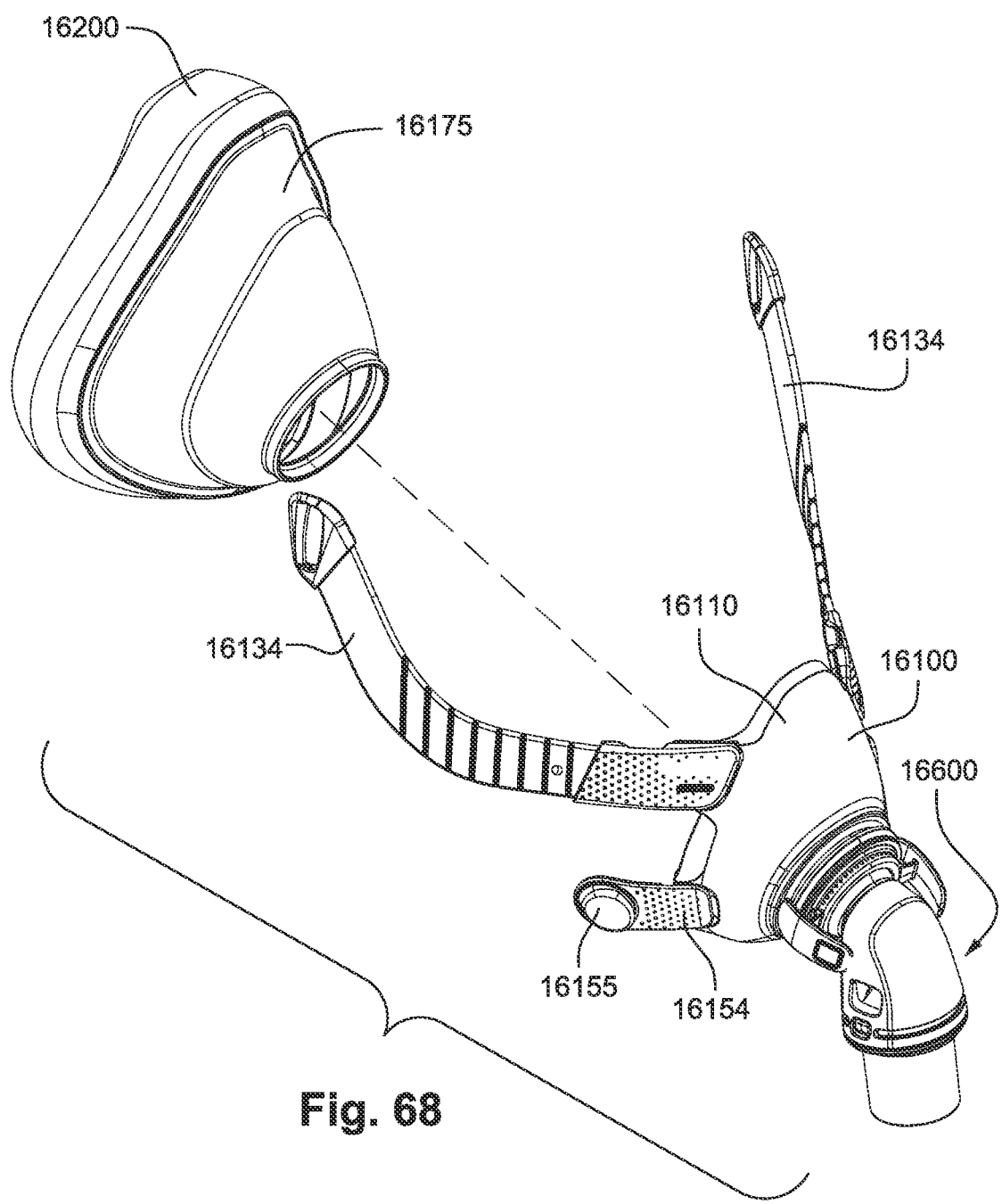

FIG. 68 is an exploded view of a patient interface shown in FIG. 62 showing the frame assembly and elbow assembly removably connected with the cushion assembly removed.

Figure 69:
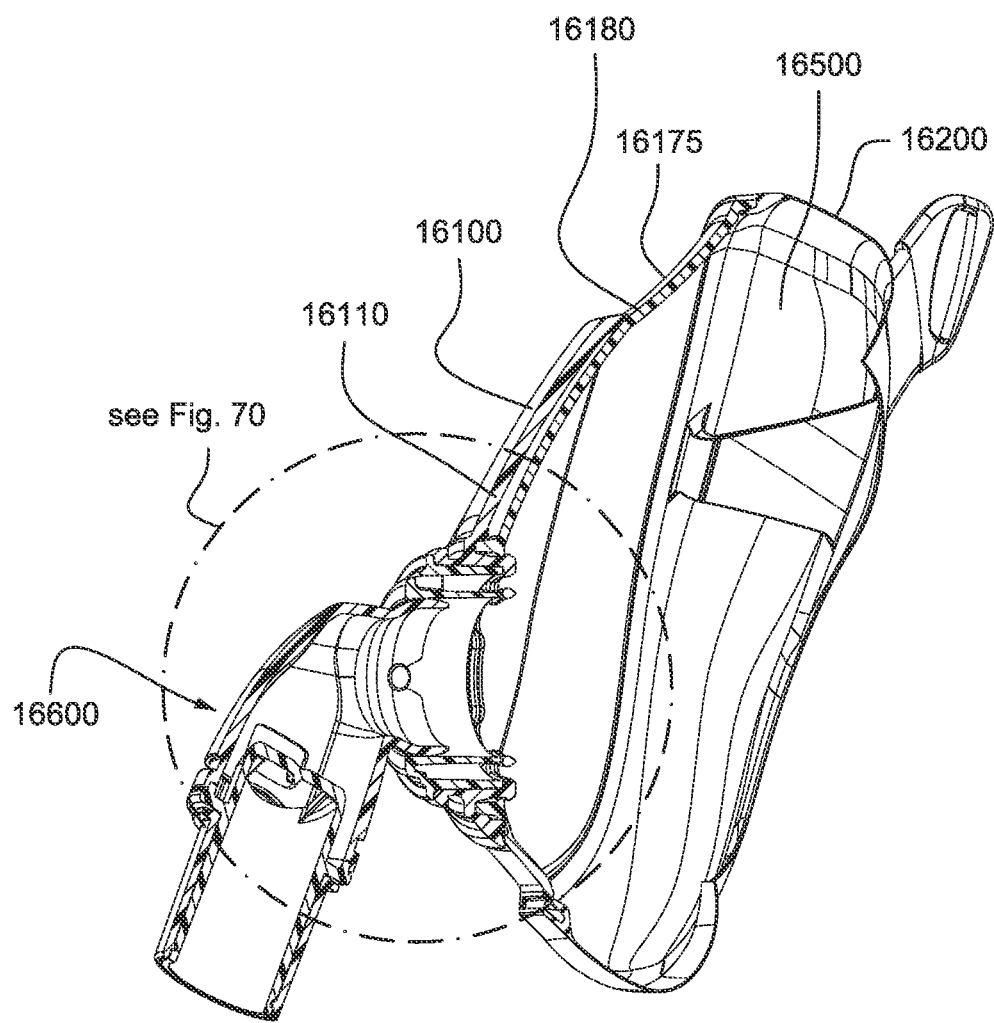

FIG. 69 is a cross-sectional view of the patient interface shown in FIG. 63.

Figure 70:
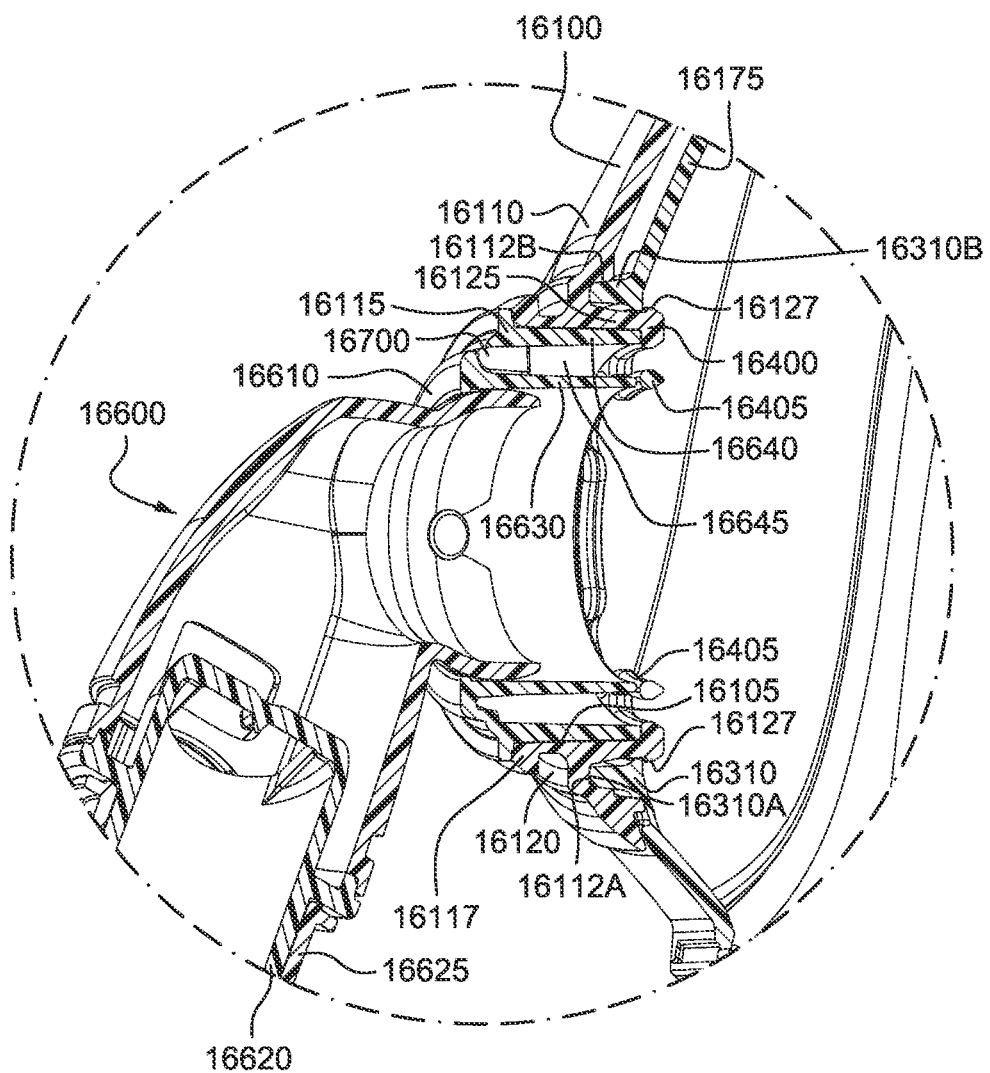

FIG. 70 is an enlarged view of the patient interface shown in FIG. 69.

Figure 71:
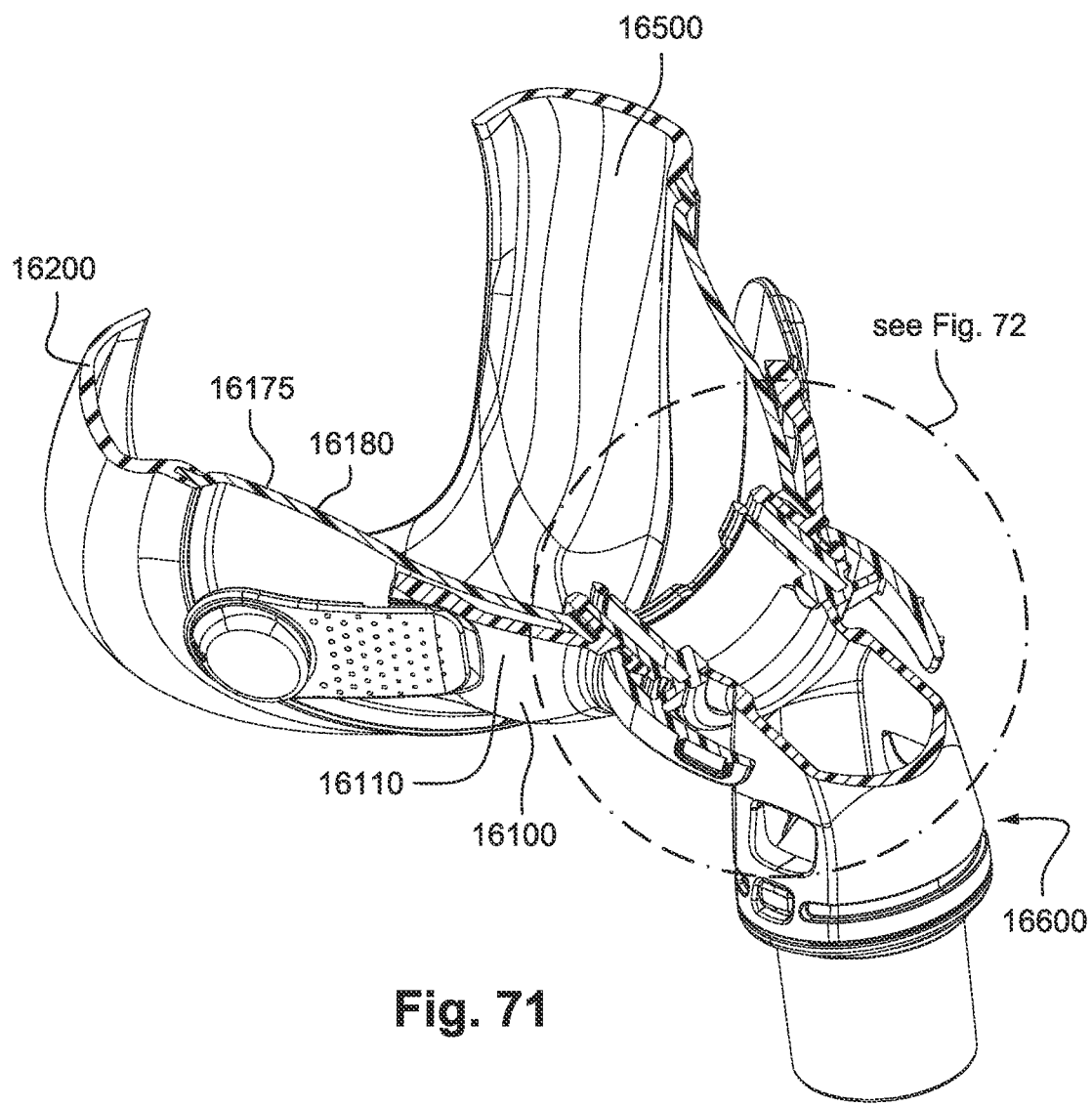

FIG. 71 is a cross-sectional view of the patient interface shown in FIG. 65.

Figure 72:
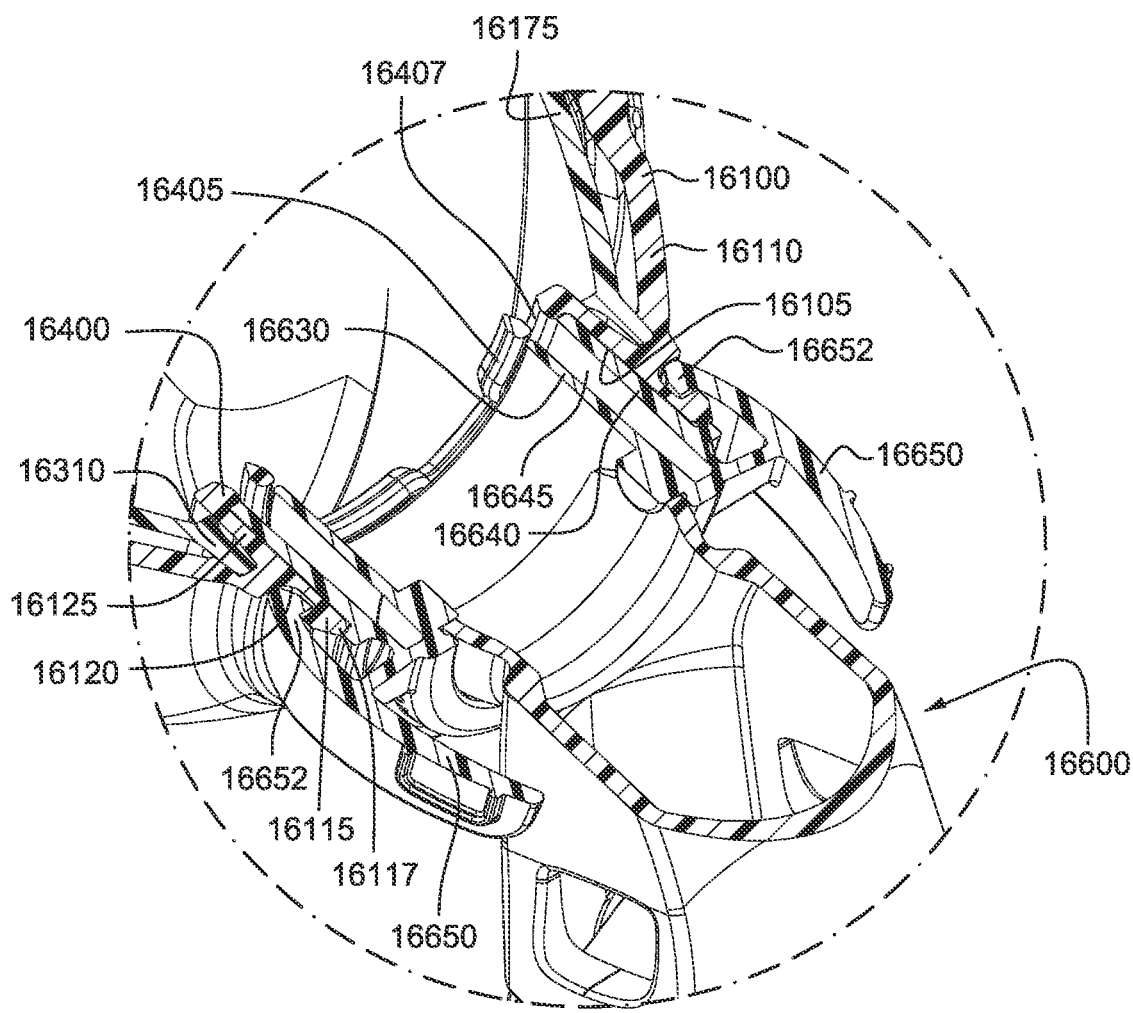

FIG. 72 is an enlarged view of the patient interface shown in FIG. 71.

Figure 73:
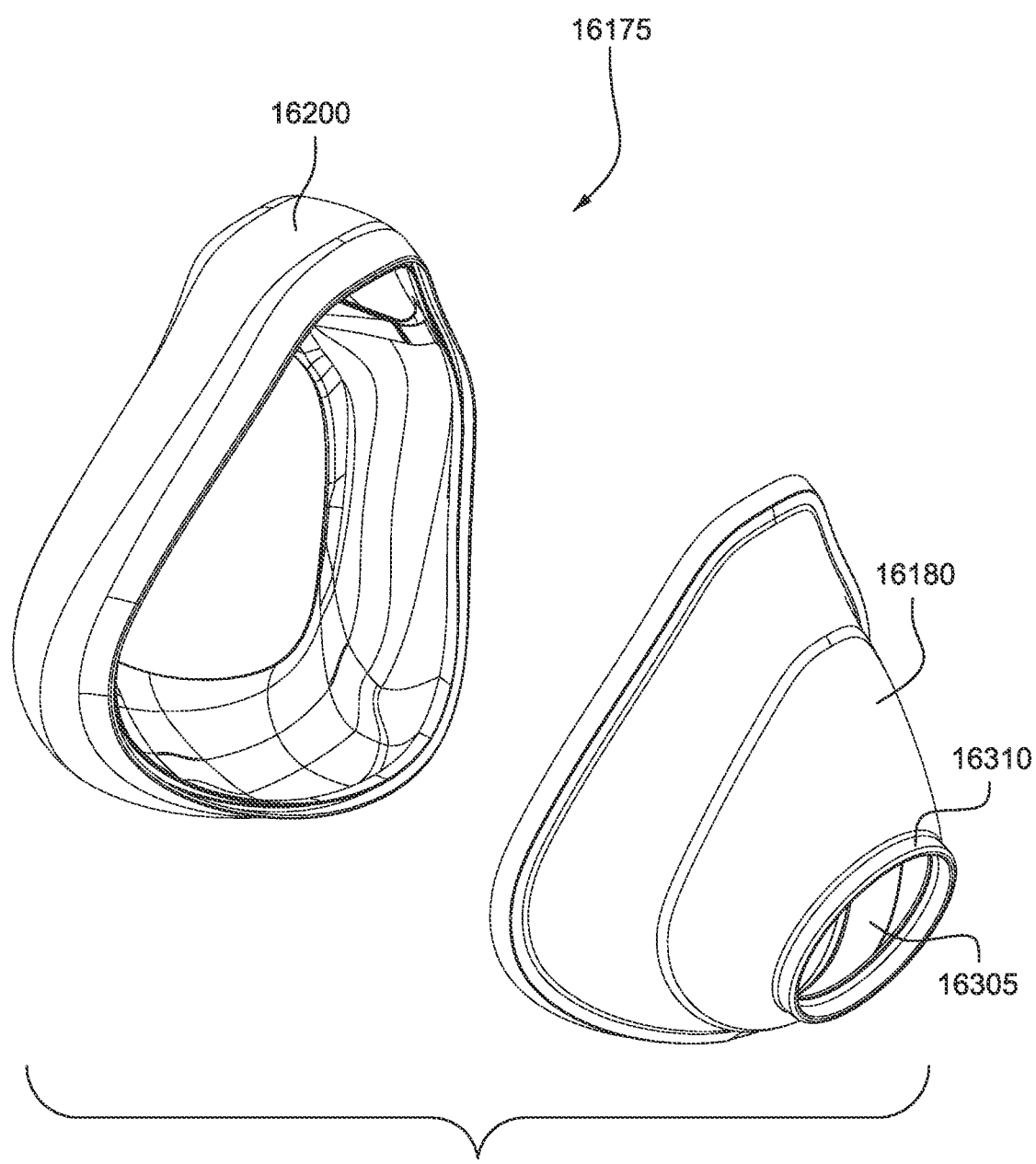

FIG. 73 is a front exploded view of a cushion assembly according to an example of the present technology.

Figure 74:
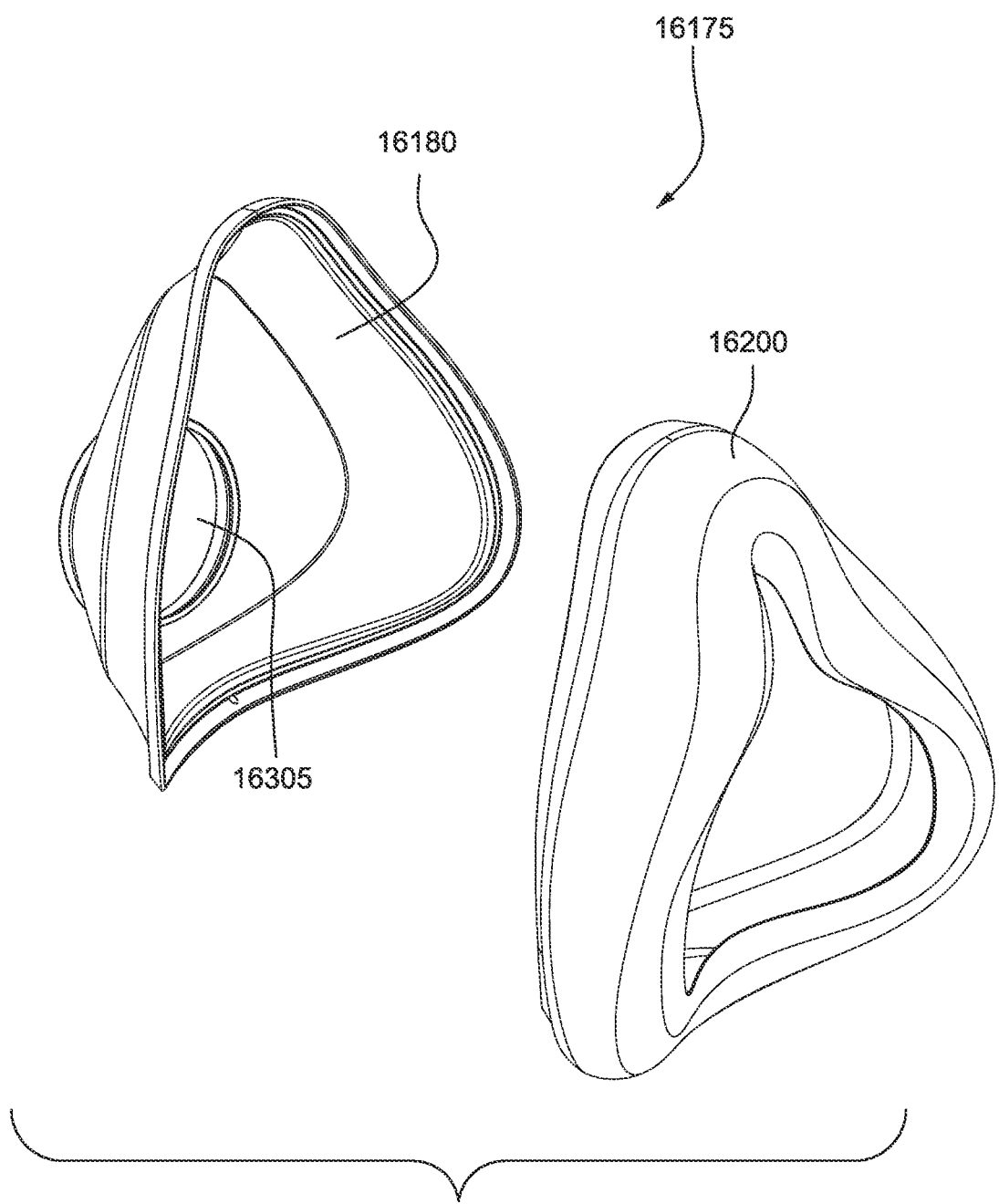

FIG. 74 is a rear exploded view of the cushion assembly shown in FIG. 73.

Figure 75:
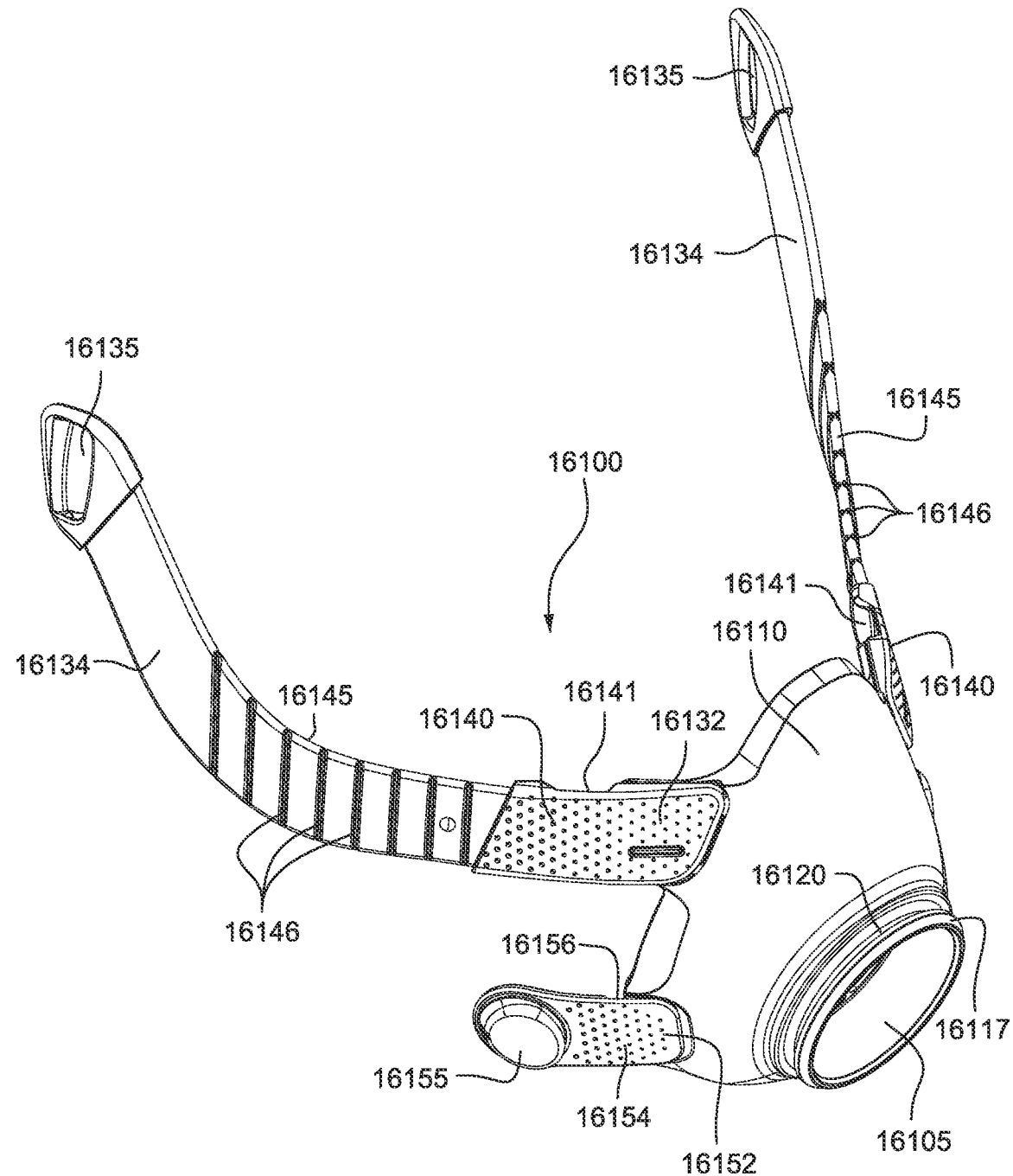

FIG. 75 is a front perspective view of a frame assembly according to an example of the present technology.

Figure 76:
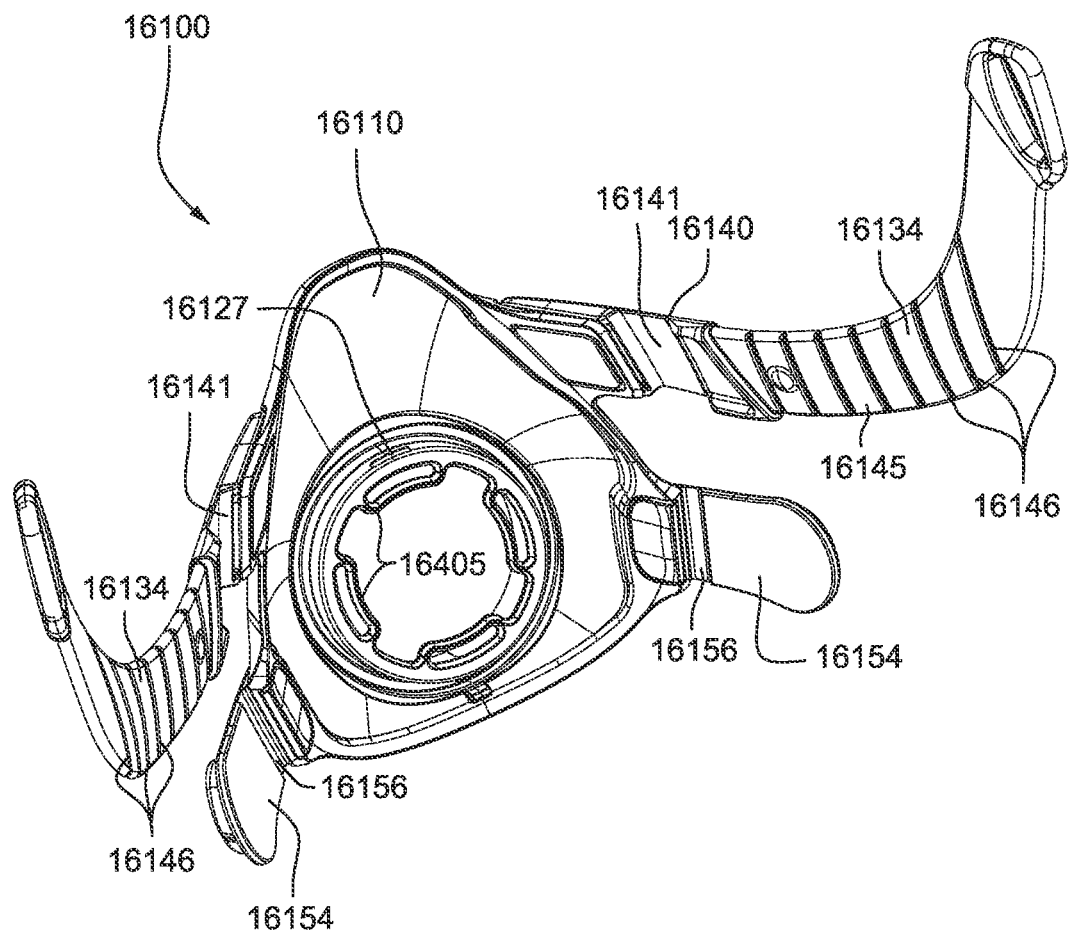

FIG. 76 is a rear perspective view of the frame assembly shown in FIG. 75.

Figure 77:
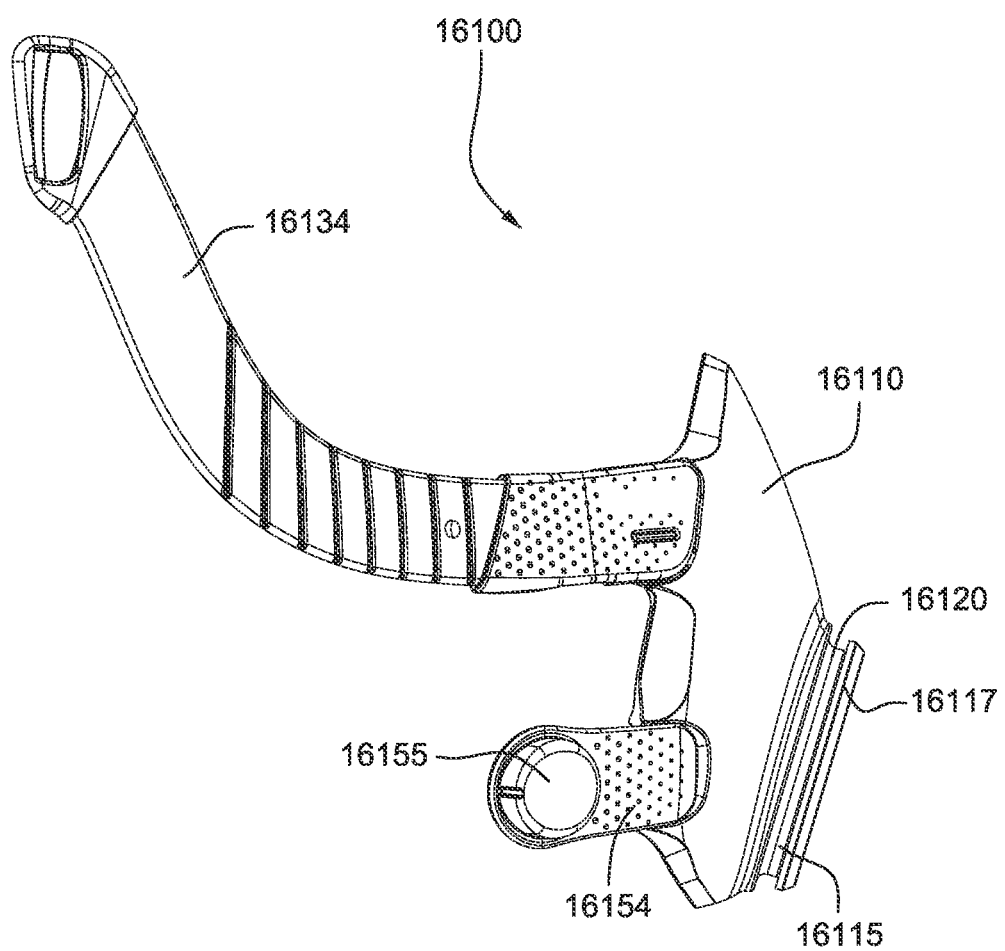

FIG. 77 is a side view of the frame assembly shown in FIG. 75.

Figure 78:
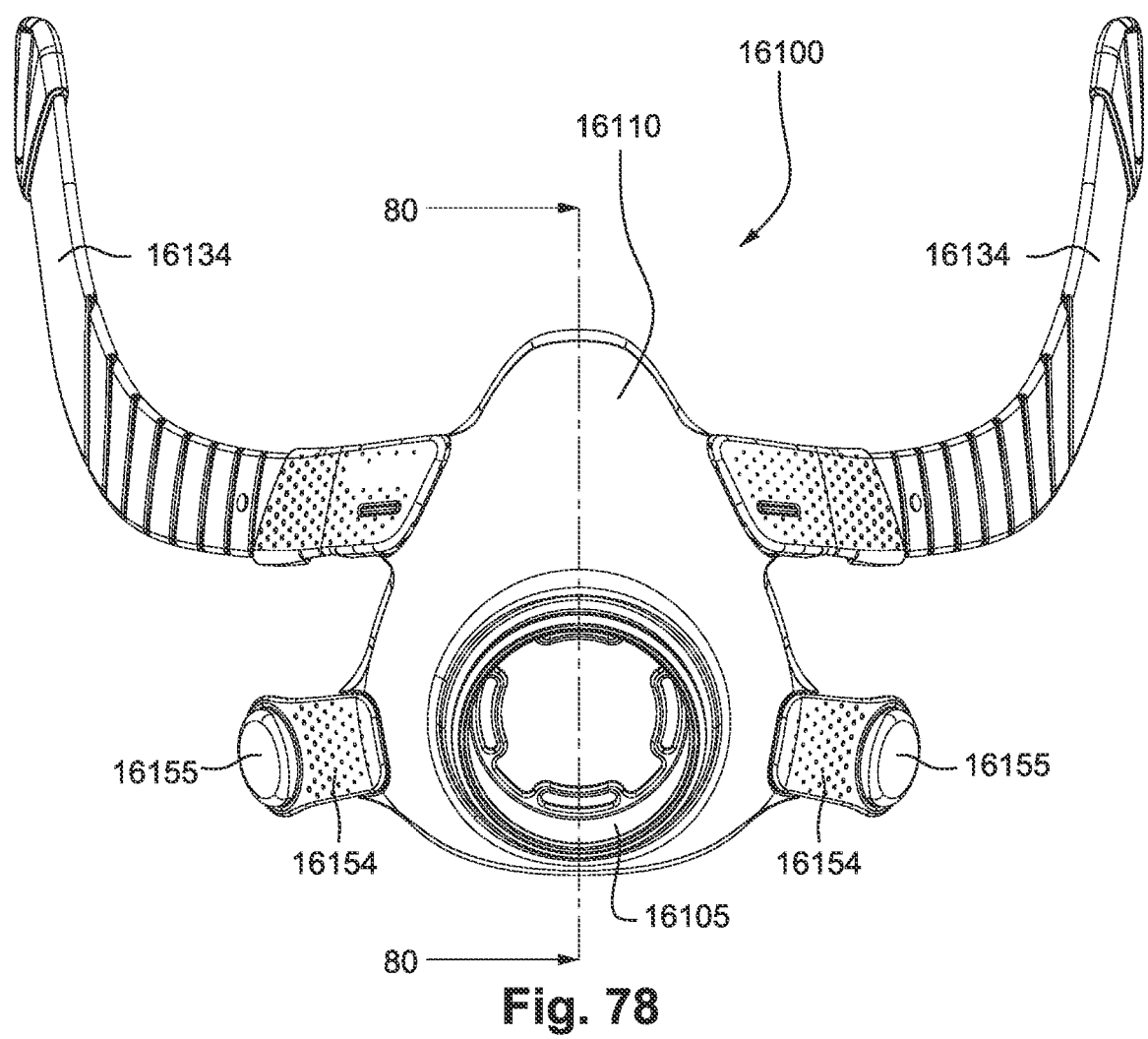

FIG. 78 is a front view of the frame assembly shown in FIG. 75.

Figure 79:
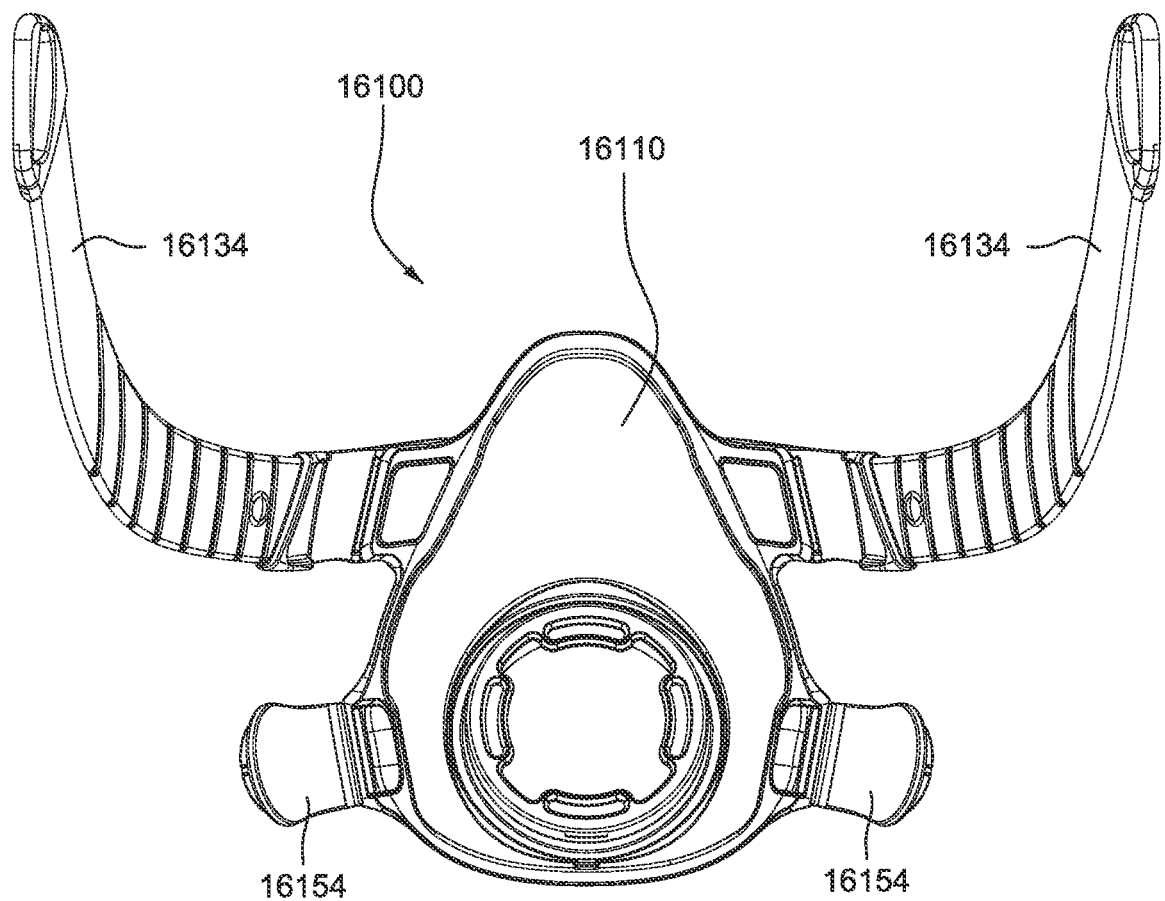

FIG. 79 is a rear view of the frame assembly shown in FIG. 75.

Figure 80:
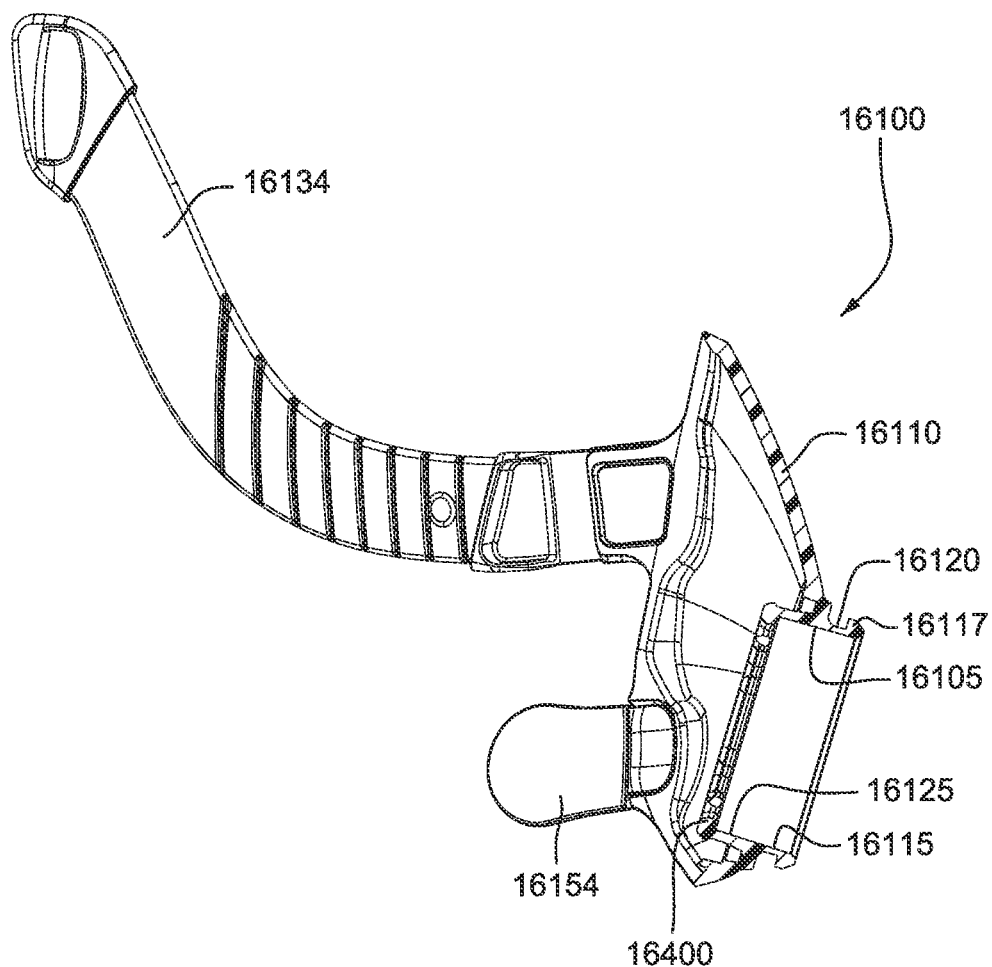

FIG. 80 is a cross-sectional view of the frame assembly shown in FIG. 78.

Figure 81:
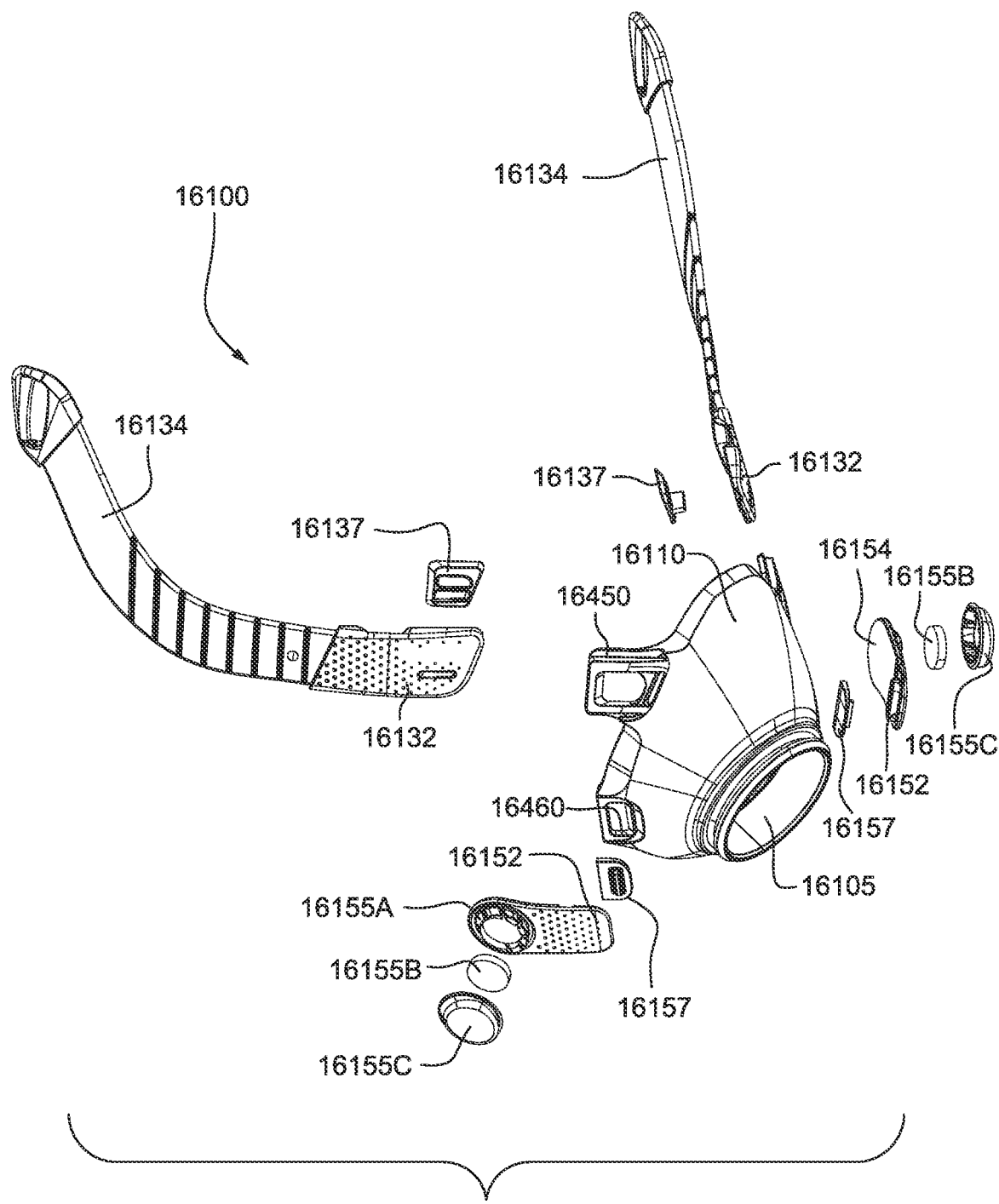

FIG. 81 is a front exploded view of the frame assembly shown in FIG. 75.

Figure 82:
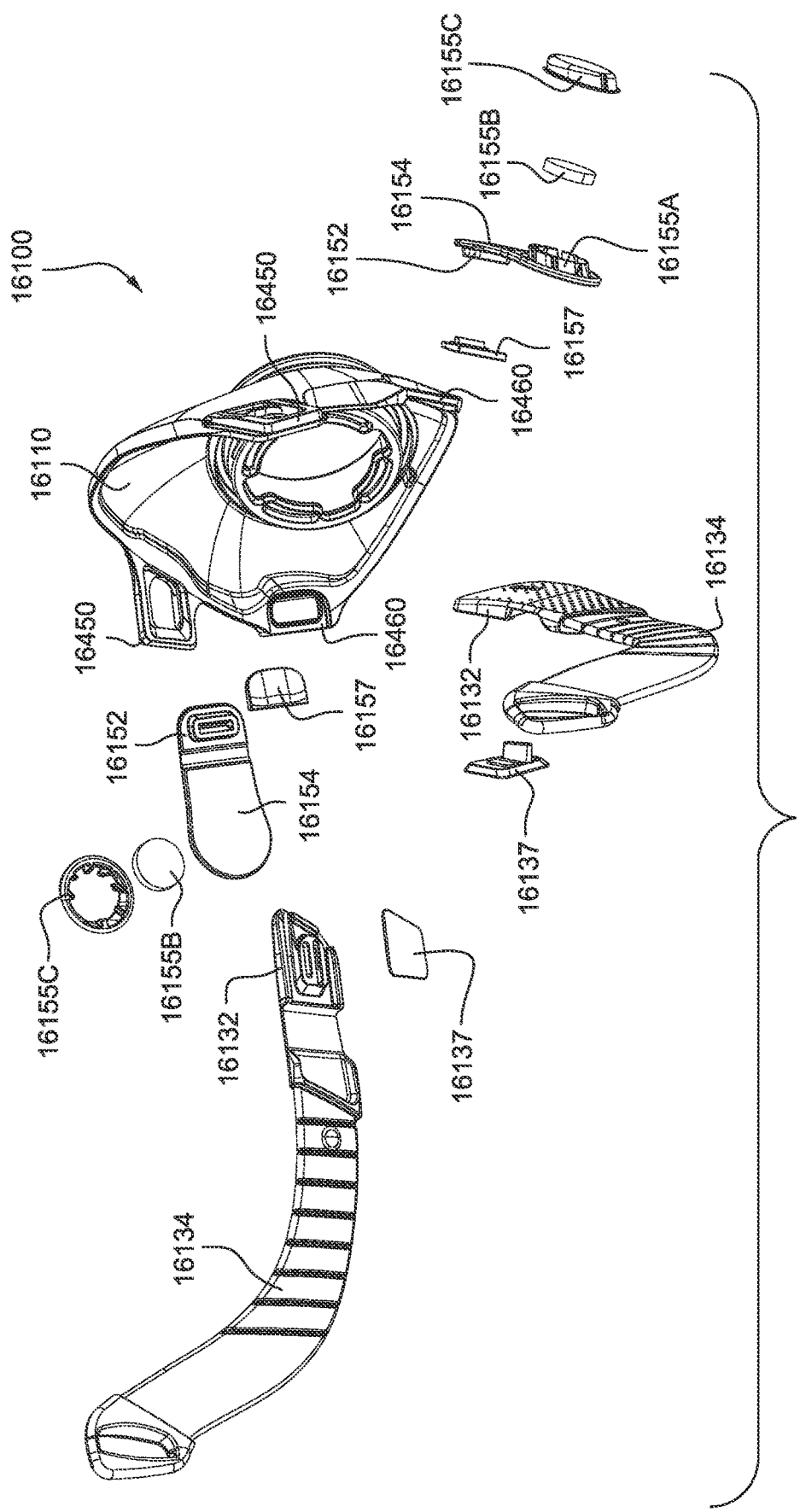

FIG. 82 is a rear exploded view of the frame assembly shown in FIG. 75.

Figure 83:
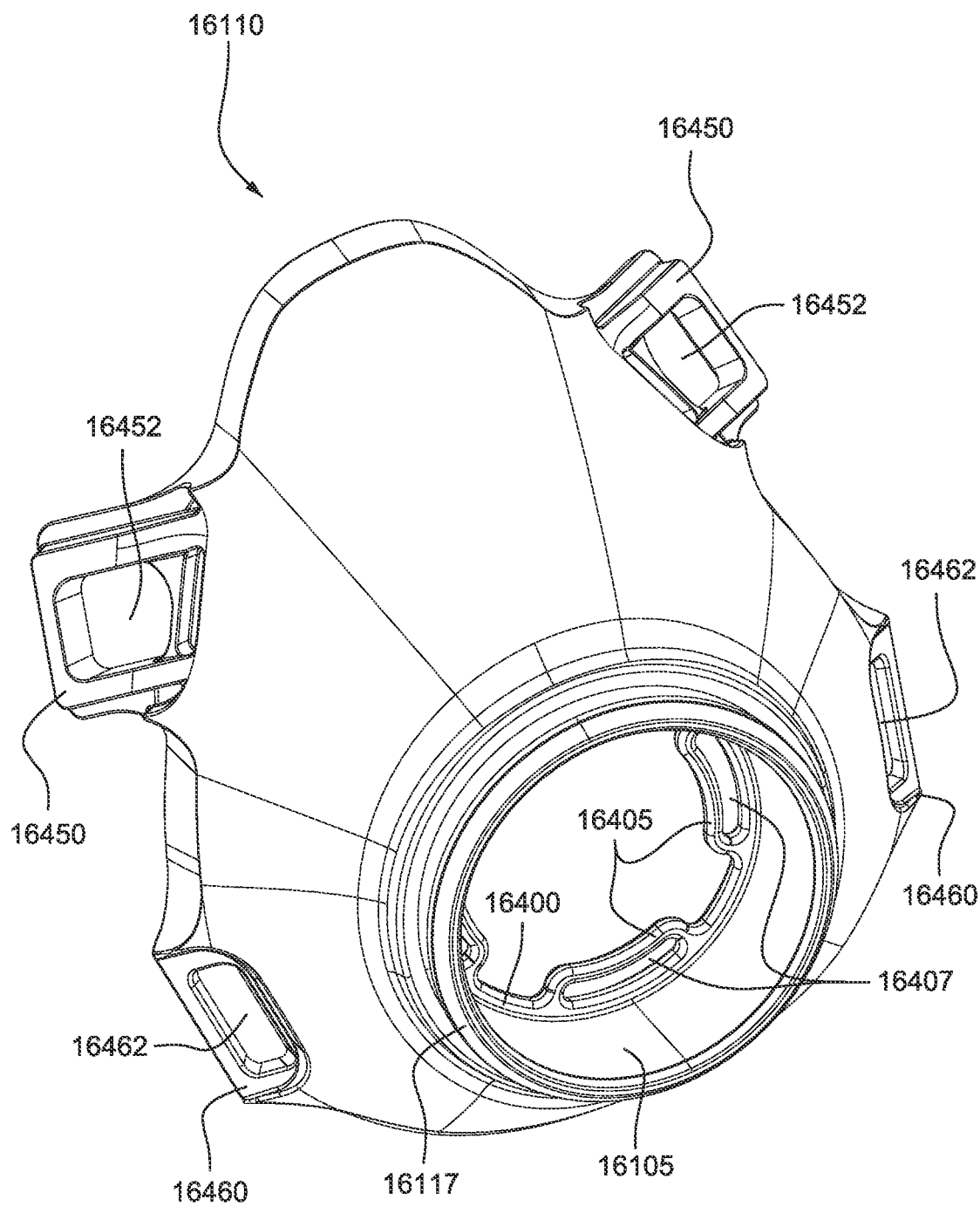

FIG. 83 a front perspective view of a shroud for a frame assembly according to an example of the present technology.

Figure 84:
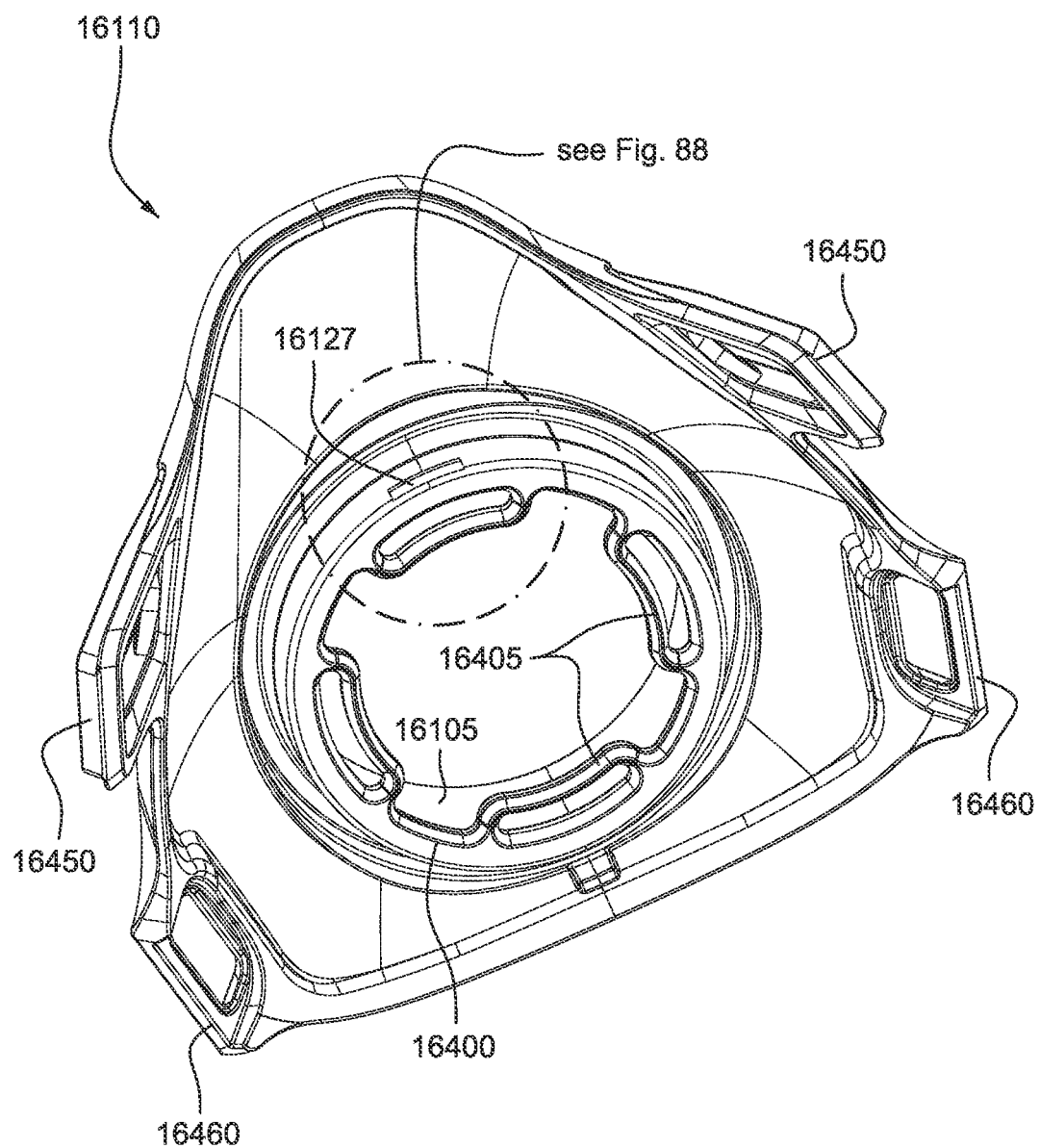

FIG. 84 is a rear perspective view of the shroud shown in FIG. 83.

Figure 85:
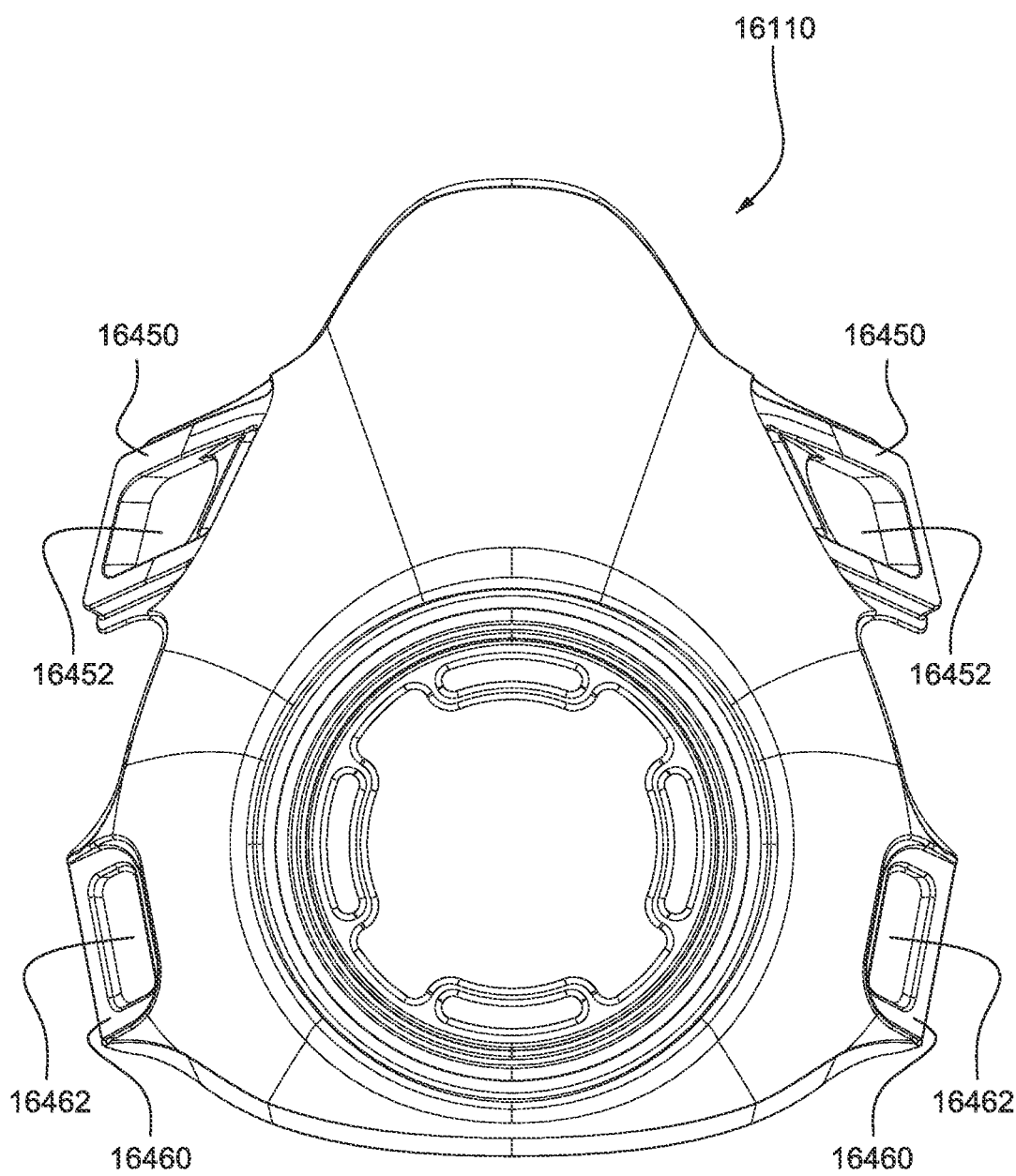

FIG. 85 is a front view of the shroud shown in FIG. 83.

Figure 86:
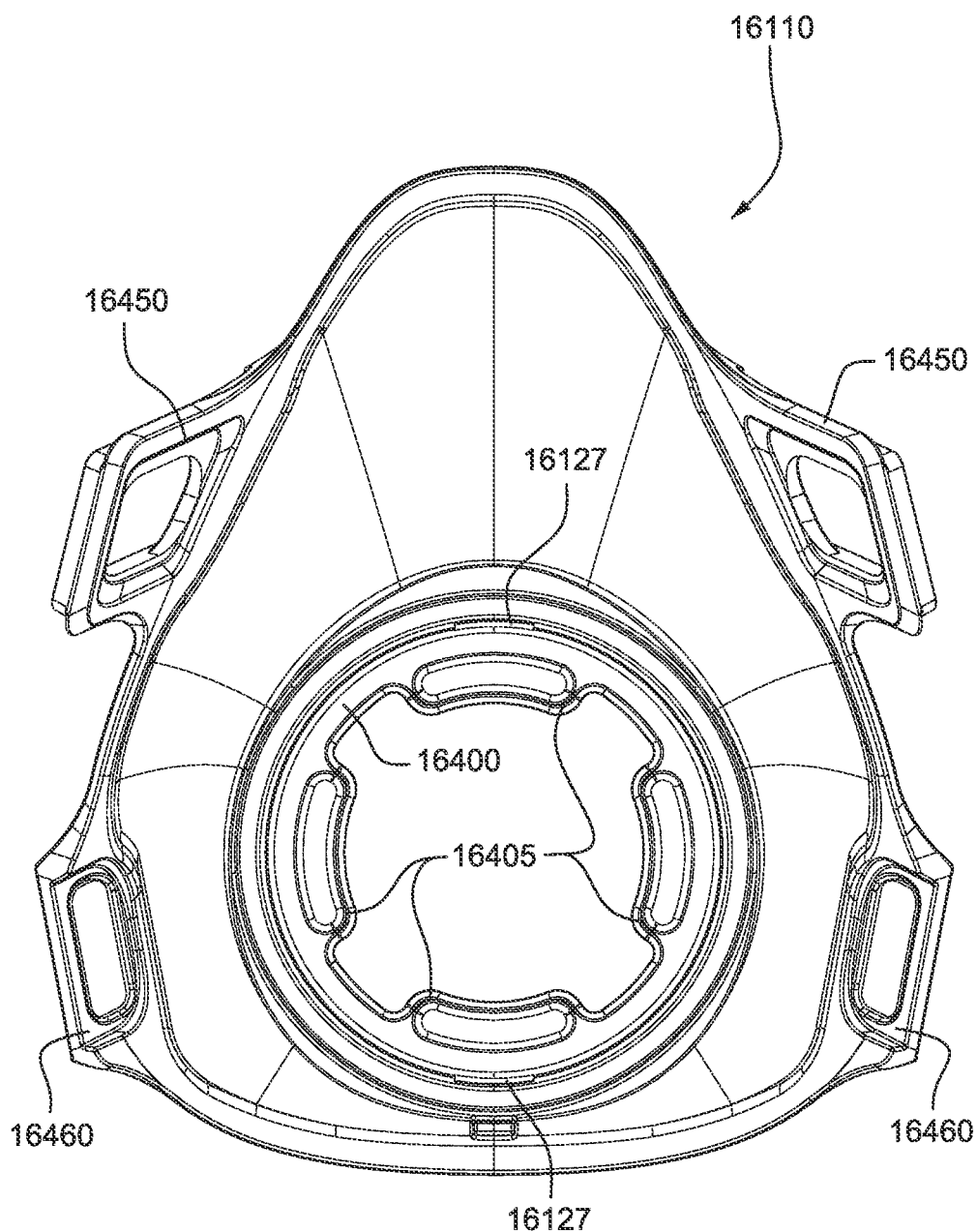

FIG. 86 is a rear view of the shroud shown in FIG. 83.

Figure 87:
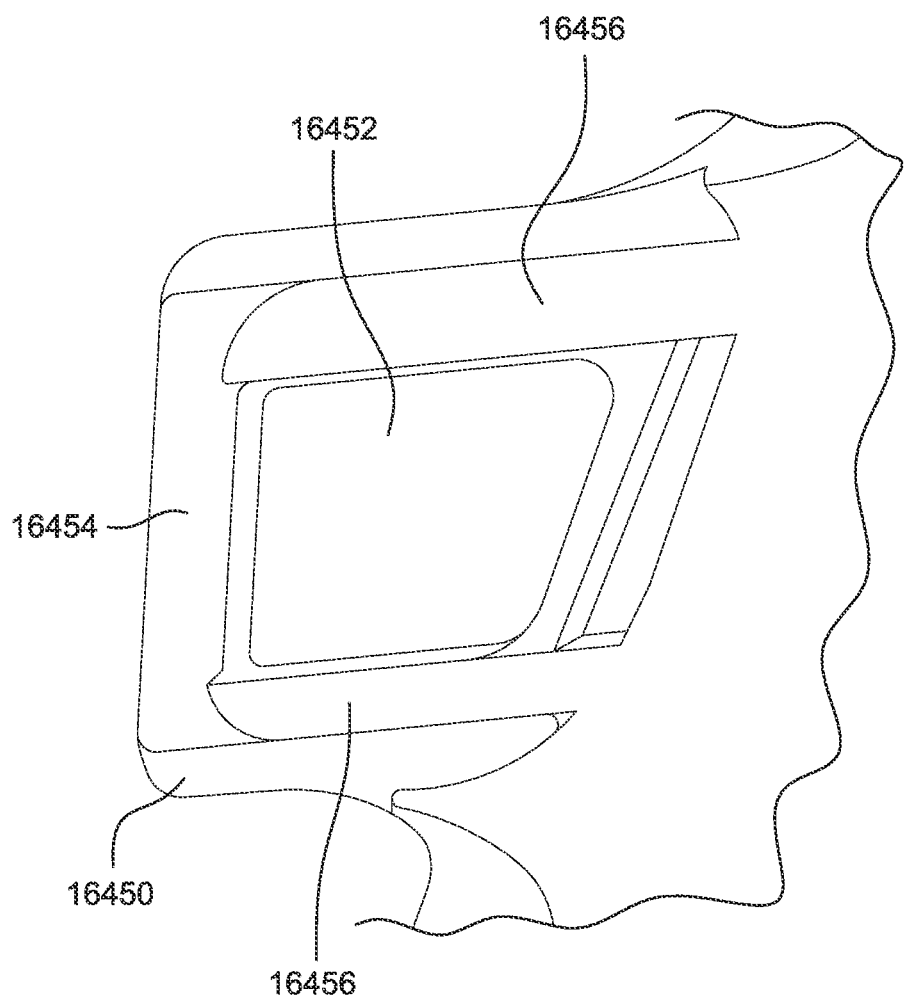

FIG. 87 is front view of an upper anchor or upper arm connector for a shroud according to an example of the present technology.

Figure 88:
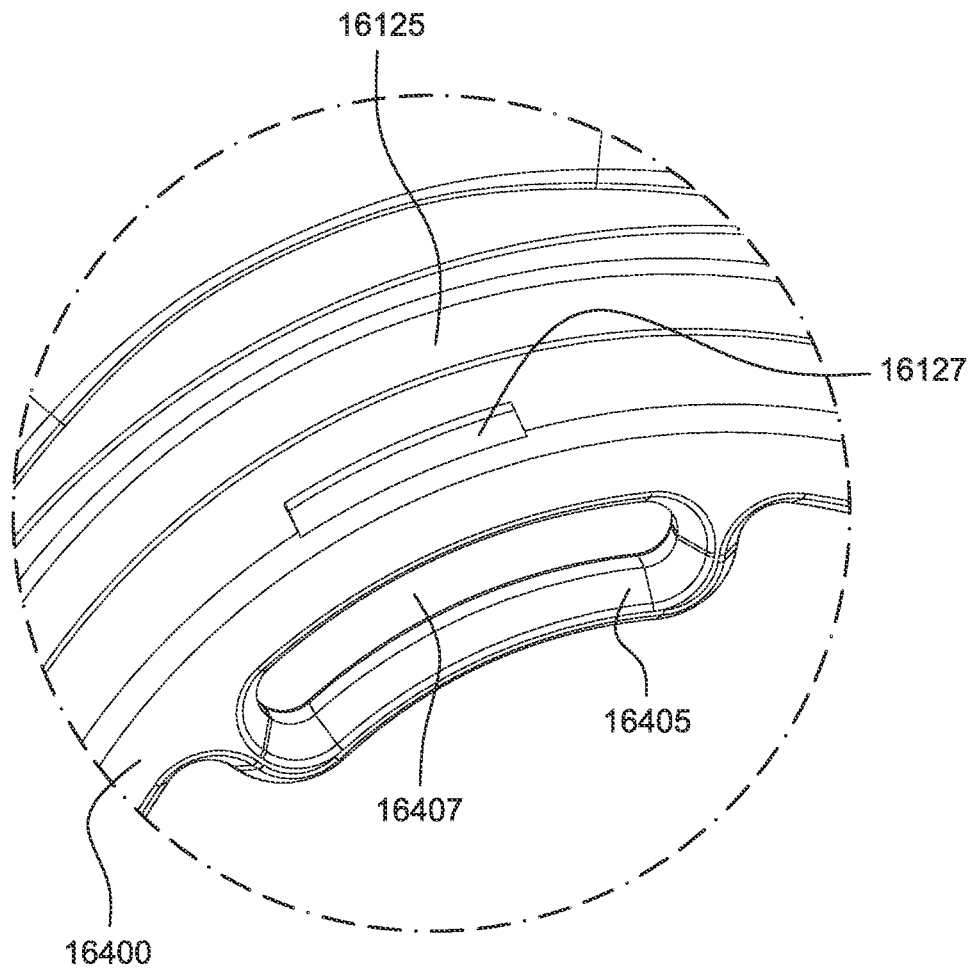

FIG. 88 is an enlarged view of the shroud shown in FIG. 84.

Figure 89A:
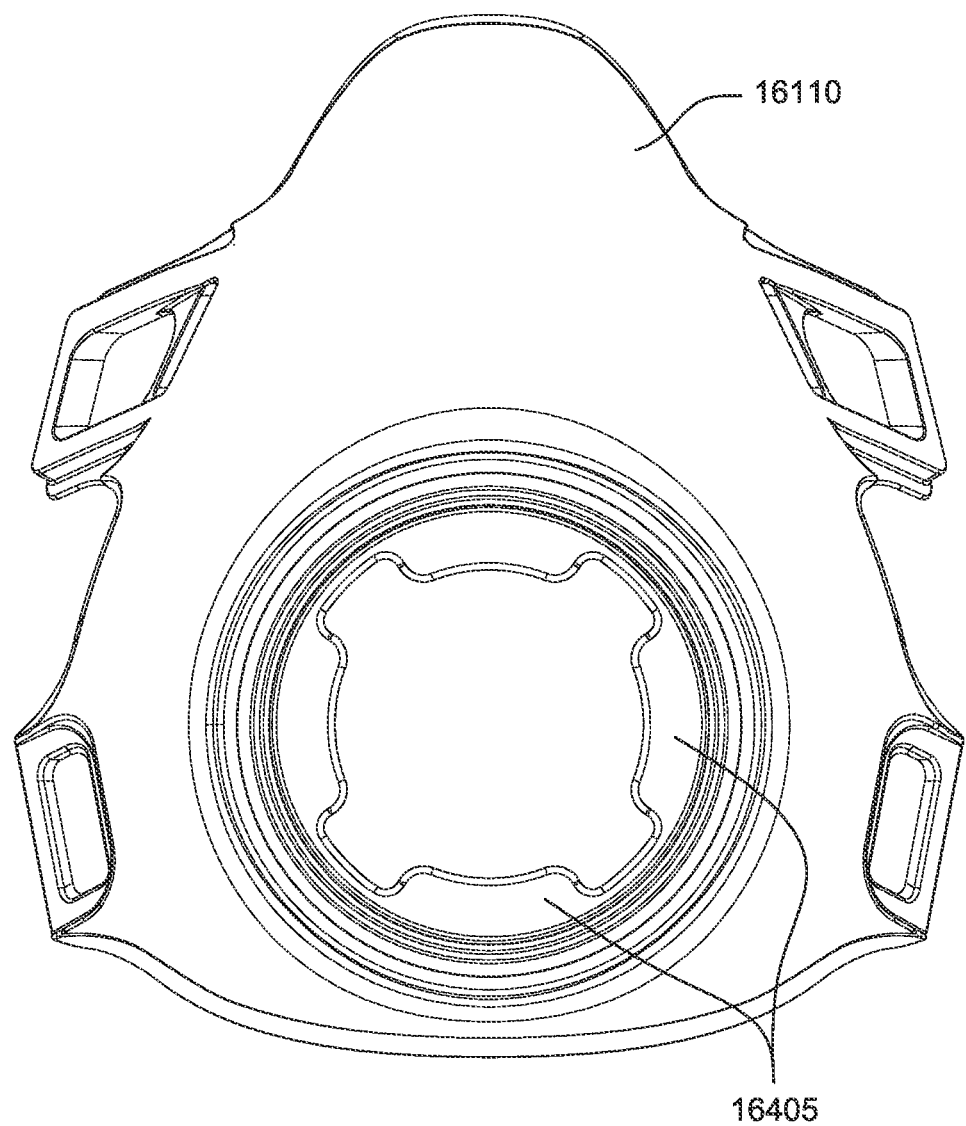

FIG. 89A is a front view of a shroud for a frame assembly according to another example of the present technology.

Figure 89B:
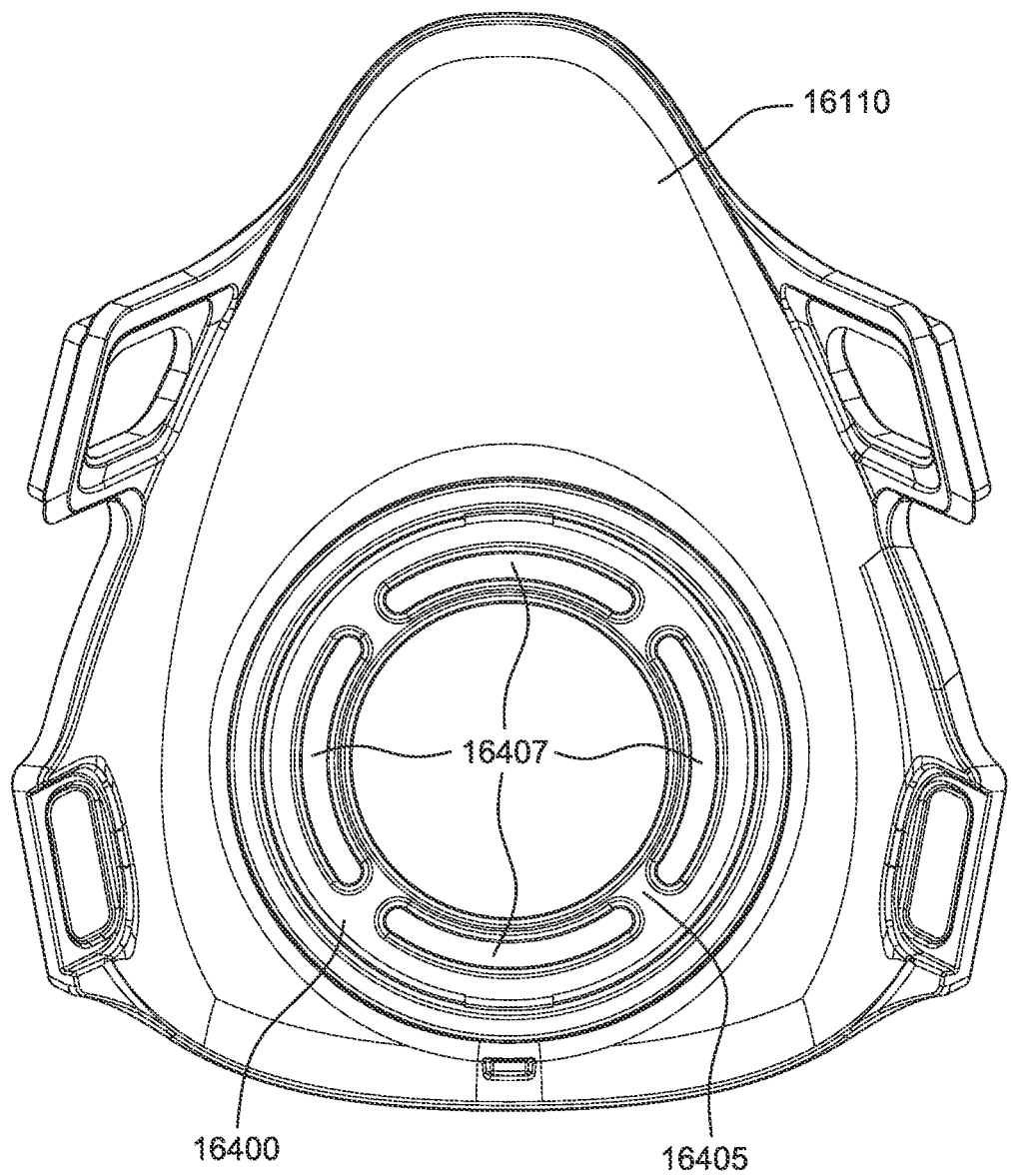

FIG. 89B is a rear view of a shroud for a frame assembly according to another example of the present technology.

Figure 90:
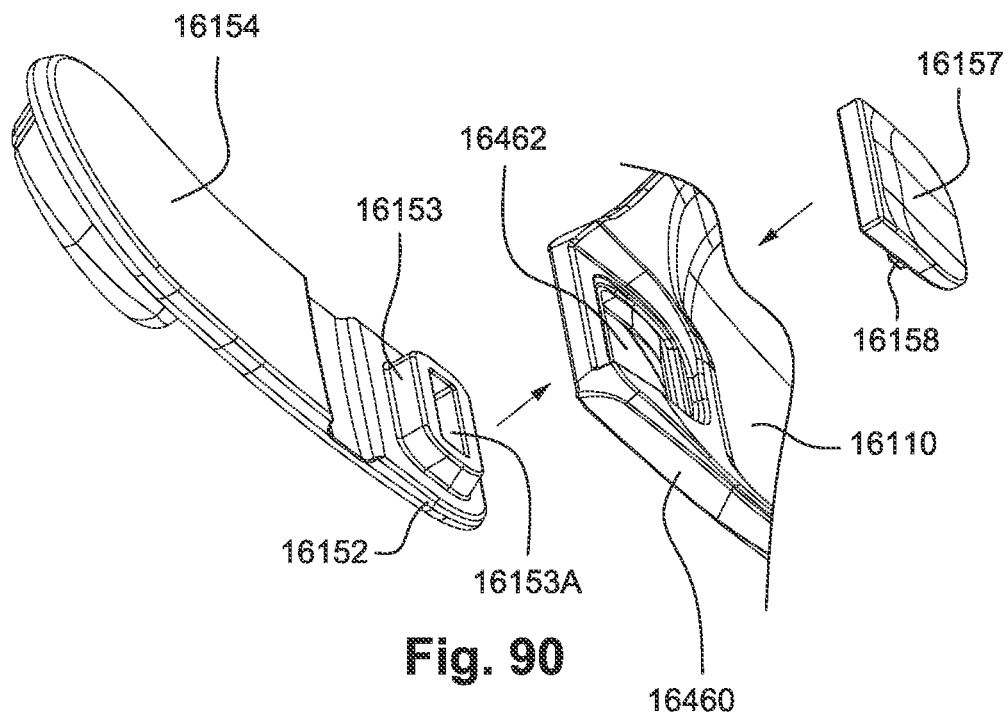

FIG. 90 is an exploded view showing connection of a lower headgear connector arm to the shroud of a frame assembly according to an example of the present technology.

Figure 91:
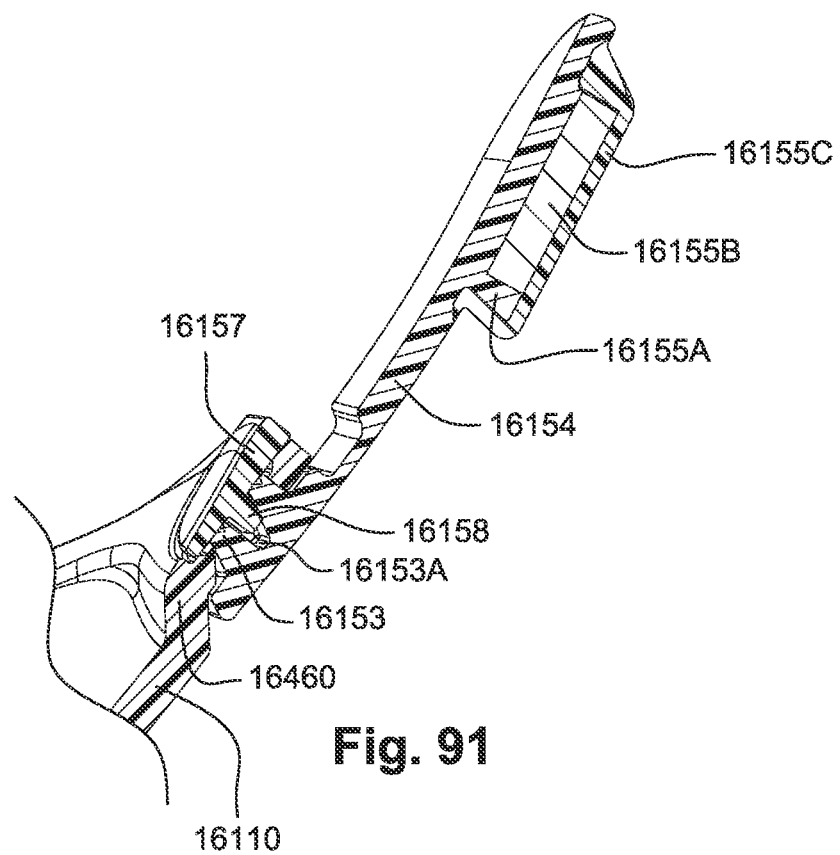

FIG. 91 is a cross-sectional view showing connection of a lower headgear connector arm to the shroud of a frame assembly according to an example of the present technology.

Figure 92:
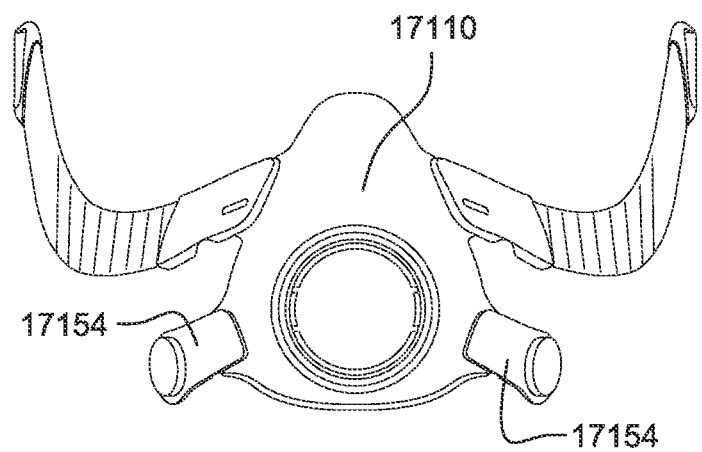

FIG. 92 is a front view of a frame assembly according to another example of the present technology.

Figure 93:
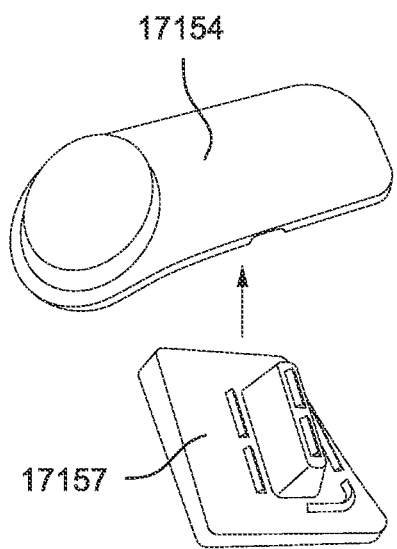
Figure 94:
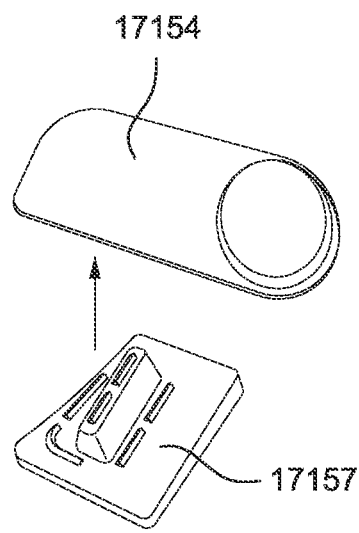

FIGS. 93 and 94 are exploded views of lower headgear connector arms for the frame assembly of FIG. 92.

Figure 95:
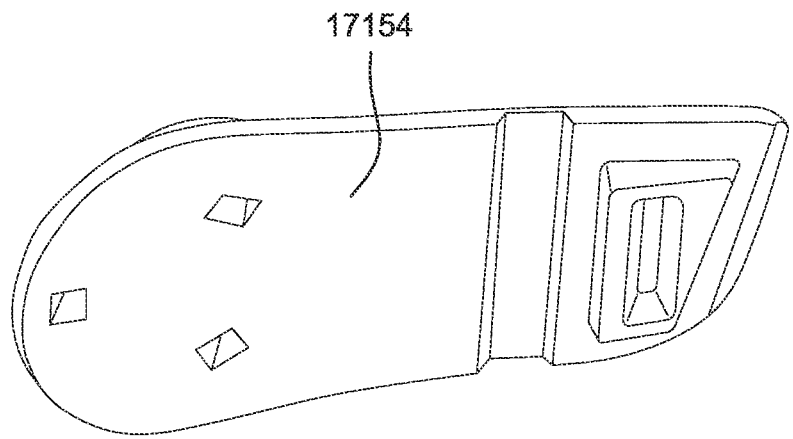

FIG. 95 is a rear perspective view of a lower headgear connector arm for the frame assembly of FIG. 92.

Figure 96:
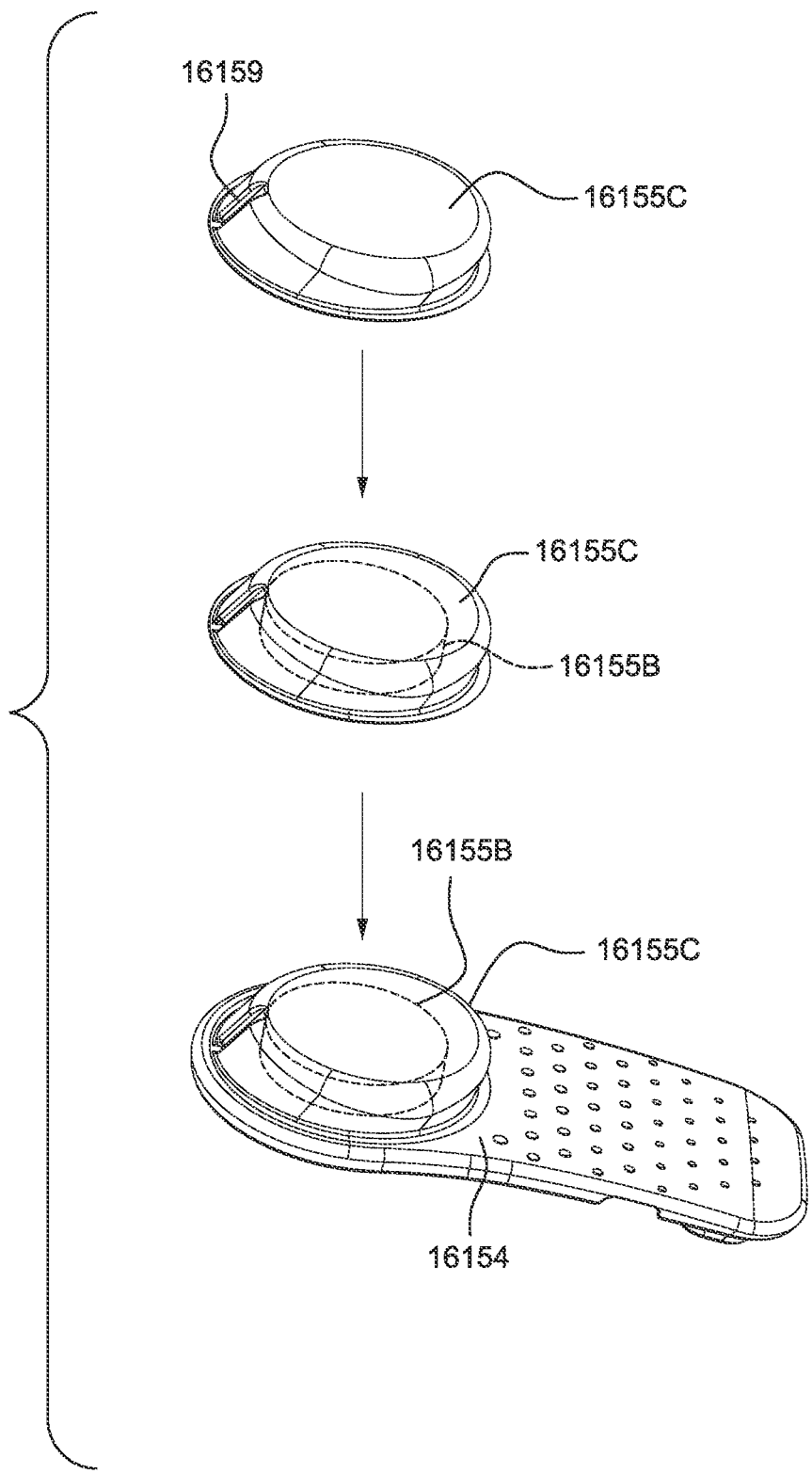

FIG. 96 shows a manufacturing process for a lower headgear connector arm according to an example of the present technology.

Figure 97:
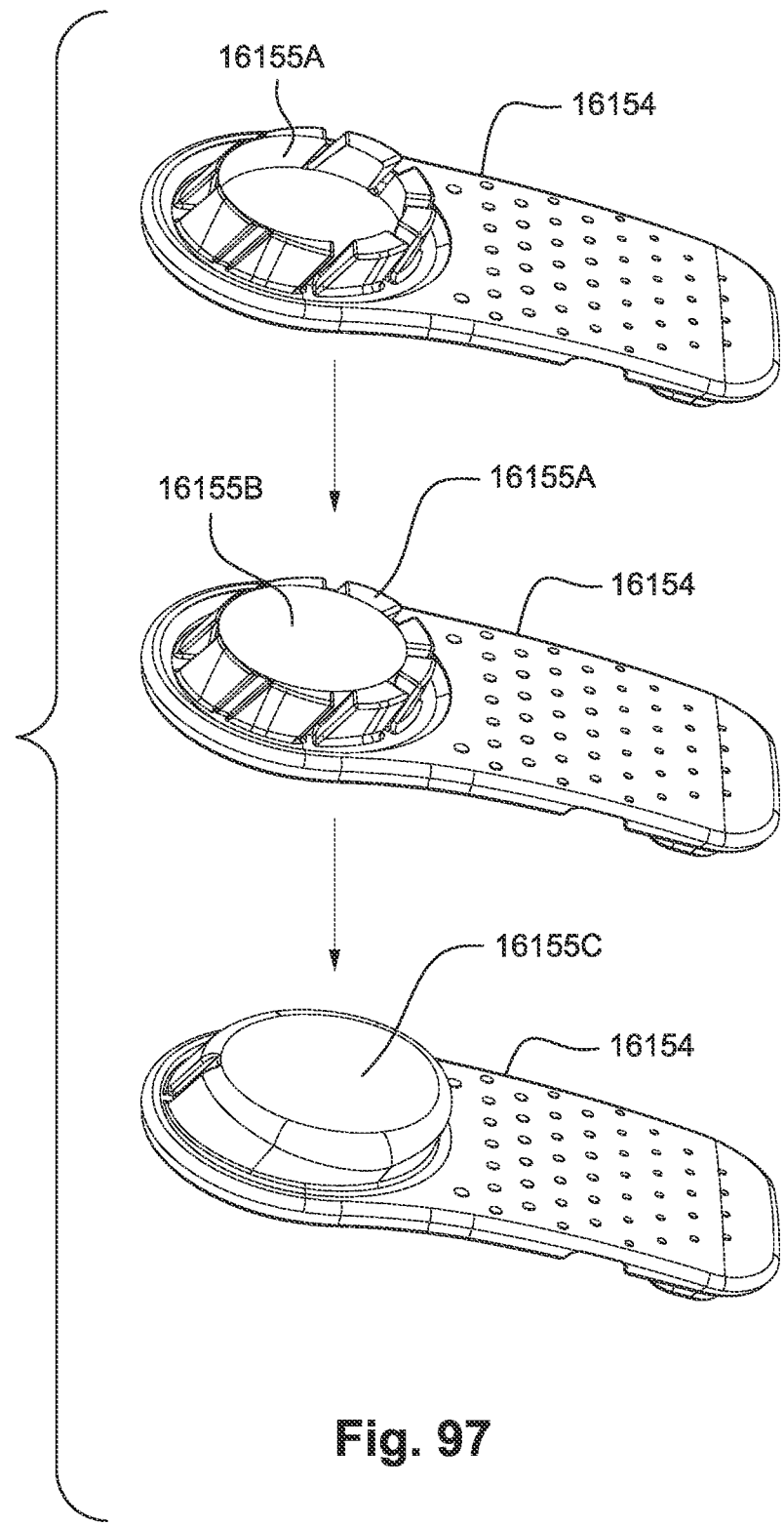

FIG. 97 shows a manufacturing process for a lower headgear connector arm according to another example of the present technology.

Figure 98:
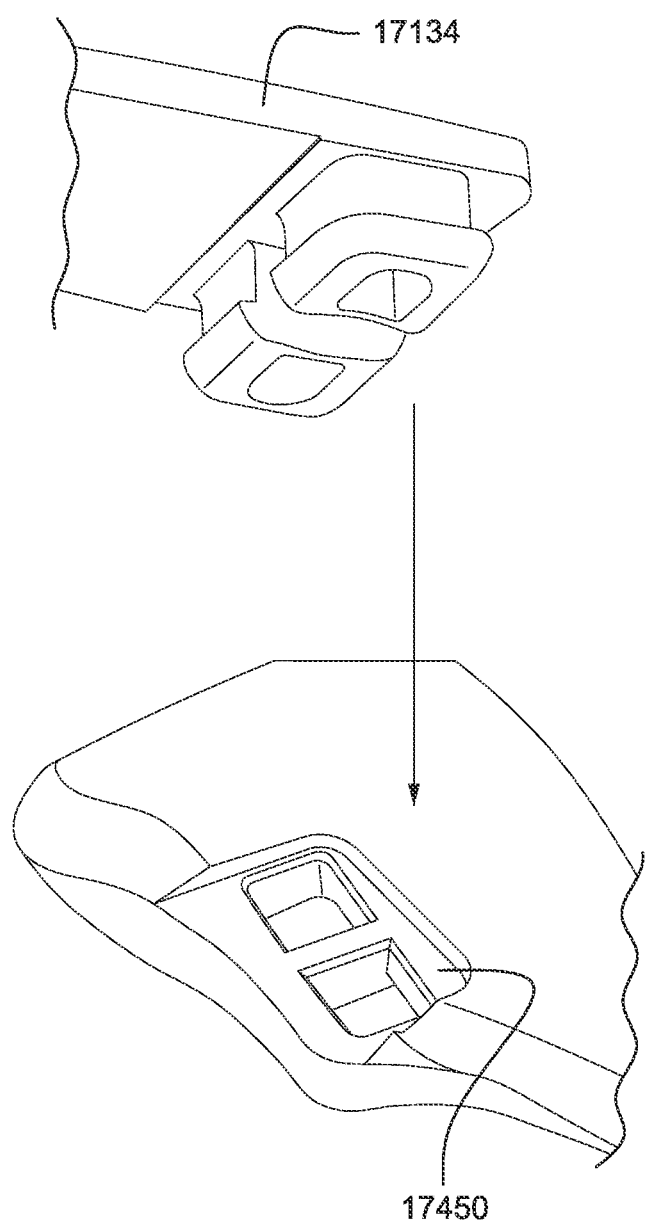

FIG. 98 is an exploded view showing connection of a lower headgear connector arm to the shroud of a frame assembly according to another example of the present technology.

Figure 99:
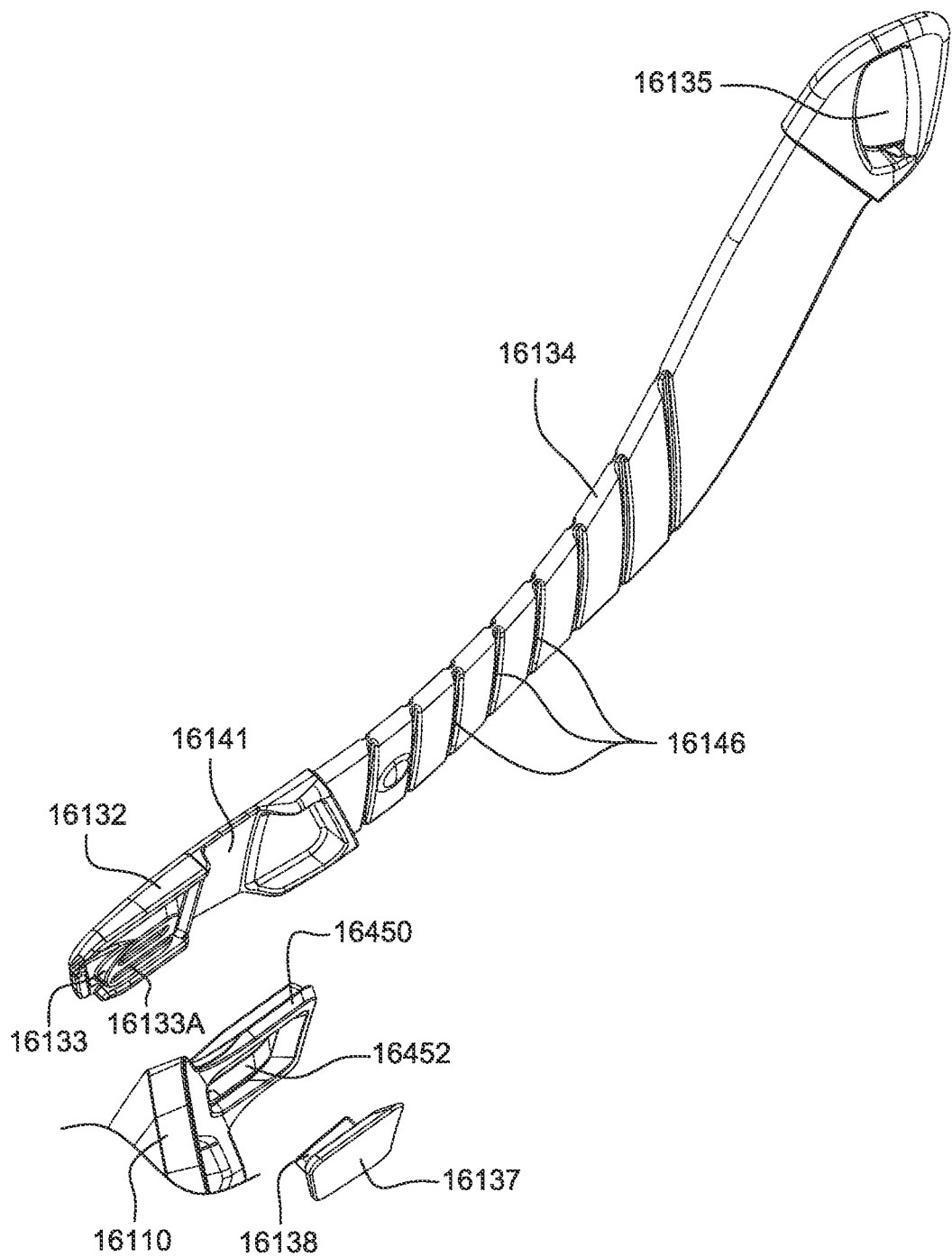

FIG. 99 is an exploded view showing connection of an upper headgear connector arm to the shroud of a frame assembly according to an example of the present technology.

Figure 100:
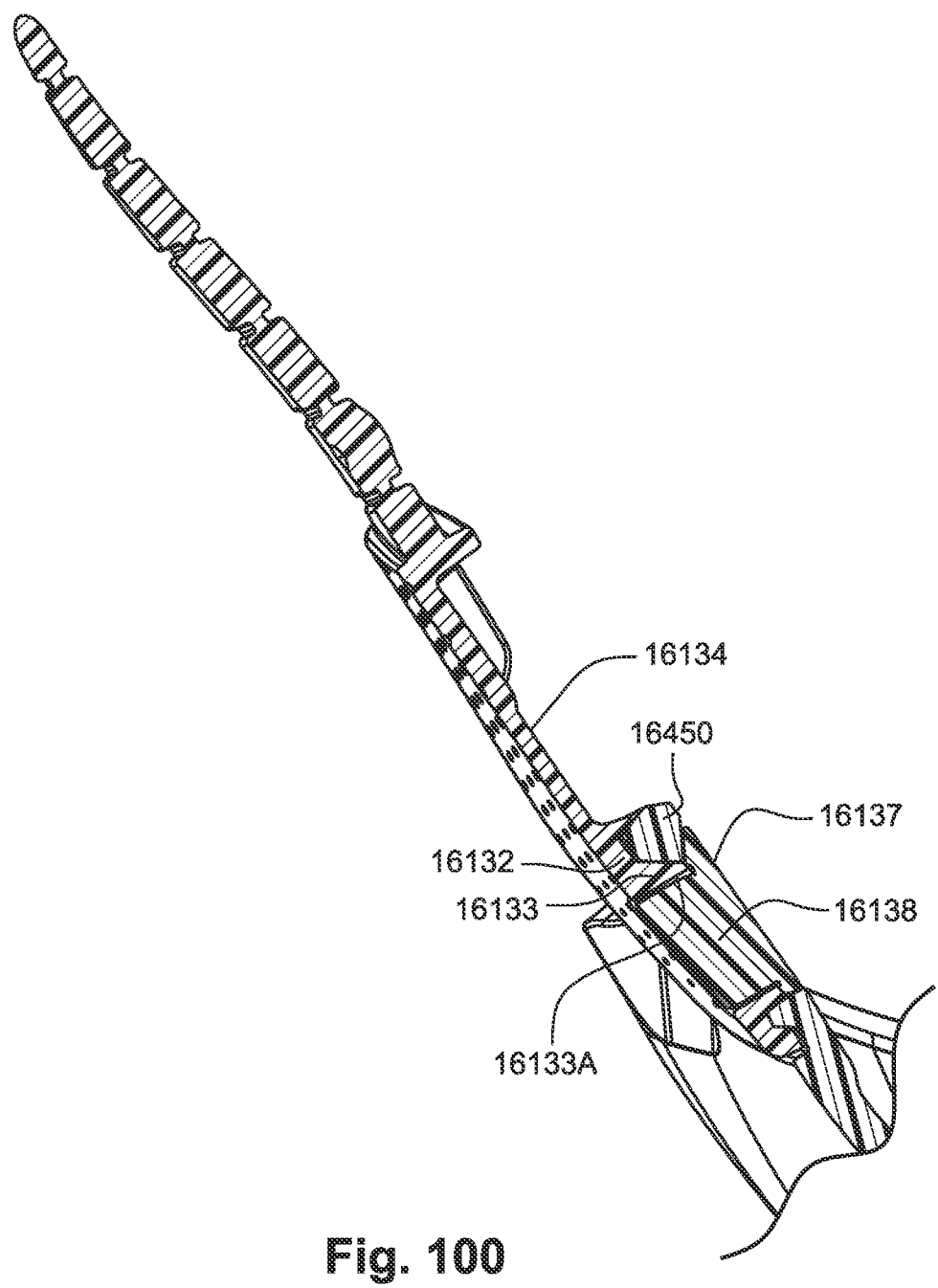

FIG. 100 is a cross-sectional view showing connection of an upper headgear connector arm to the shroud of a frame assembly according to an example of the present technology.

Figure 101:
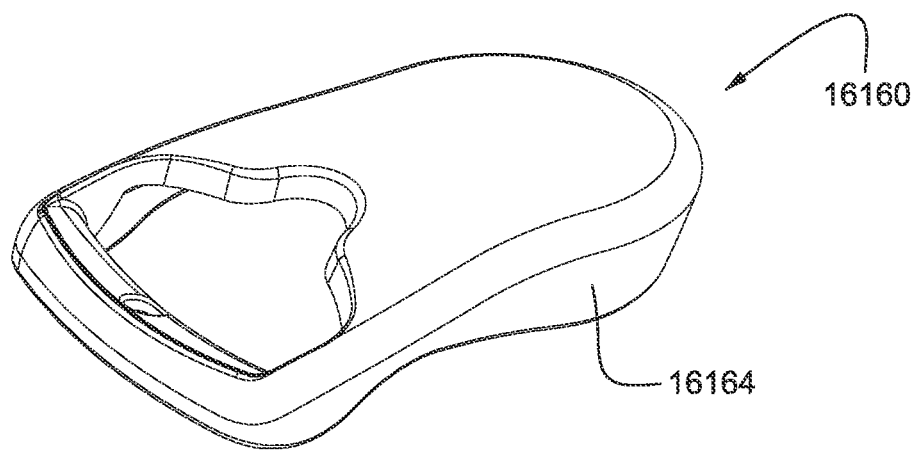

FIG. 101 is a front perspective view of a headgear clip according to an example of the present technology.

Figure 102:
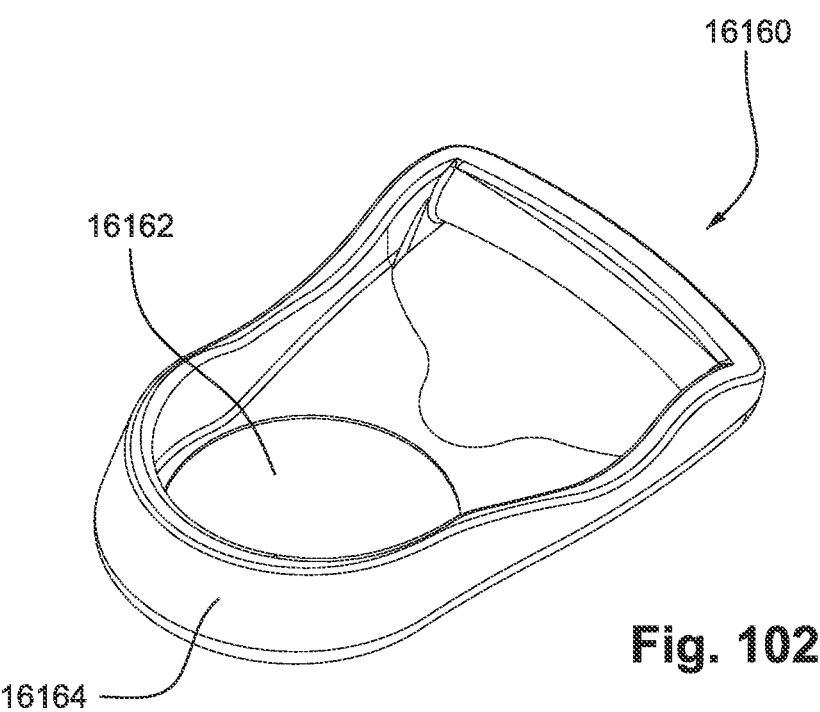

FIG. 102 is a rear perspective view of the headgear clip shown in FIG. 101.

Figure 103:
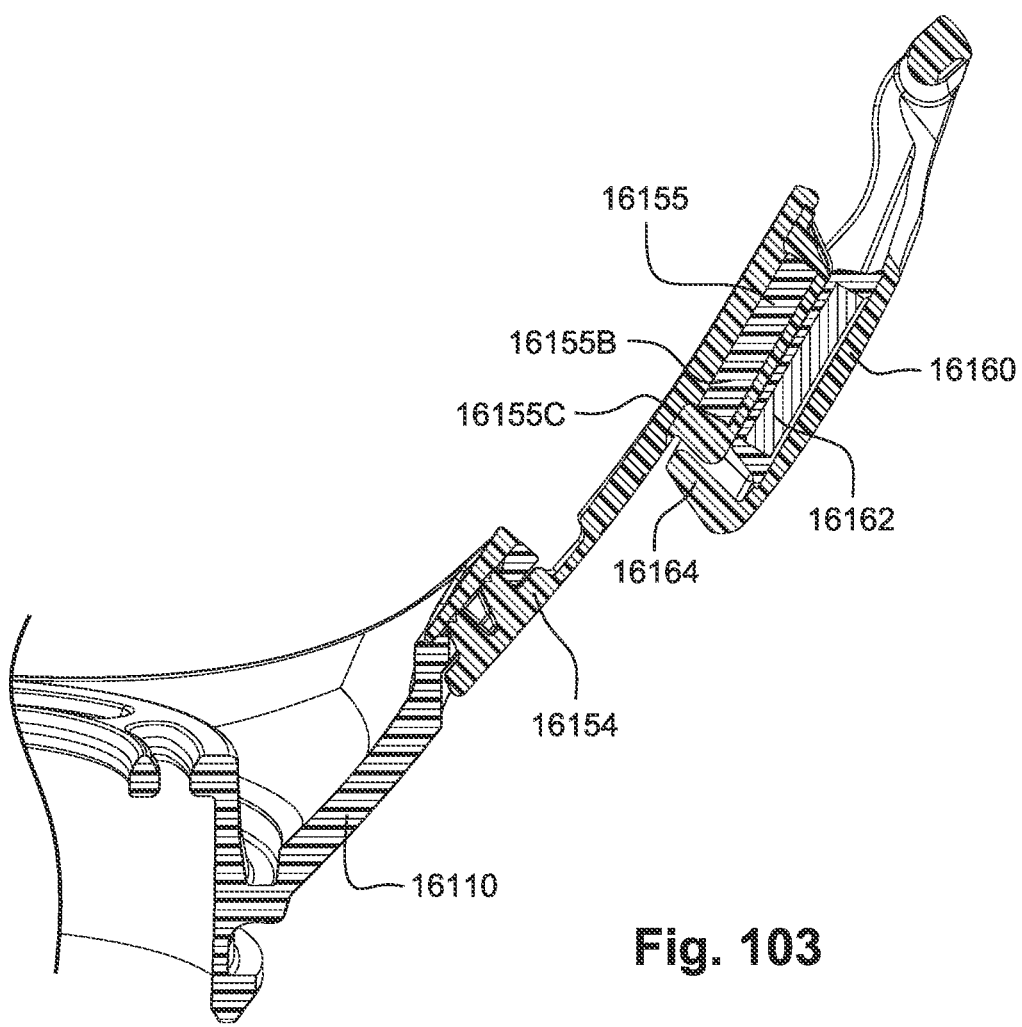

FIG. 103 is a cross-sectional view showing connection of the headgear clip of FIG. 101 to the lower headgear connector arm of a frame assembly according to an example of the present technology.

Figure 104:
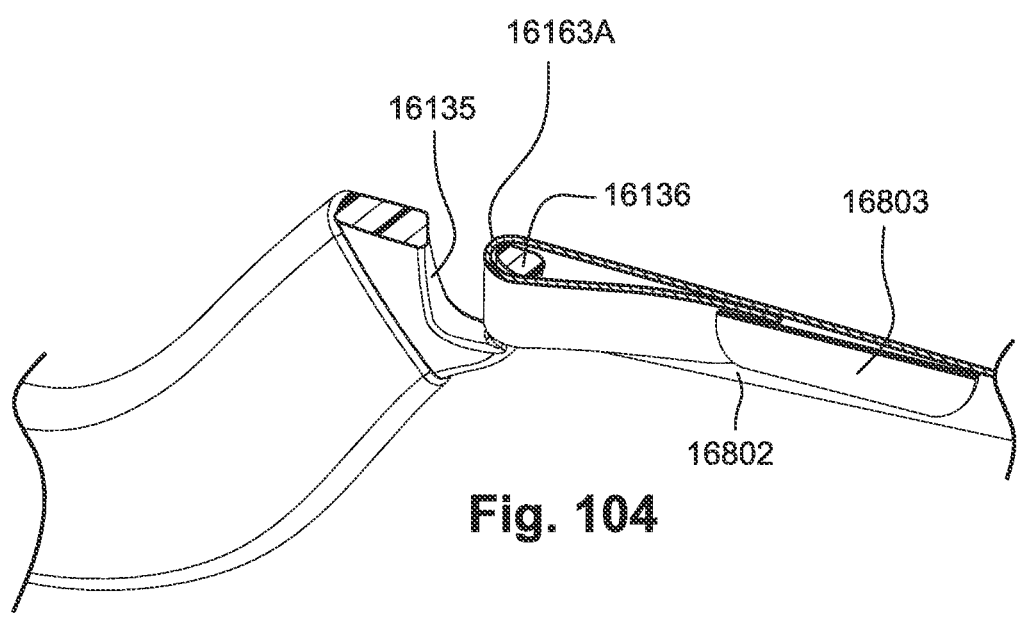

FIG. 104 is a cross-sectional view showing connection of an upper side strap of headgear to the upper headgear connection point of a frame assembly according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
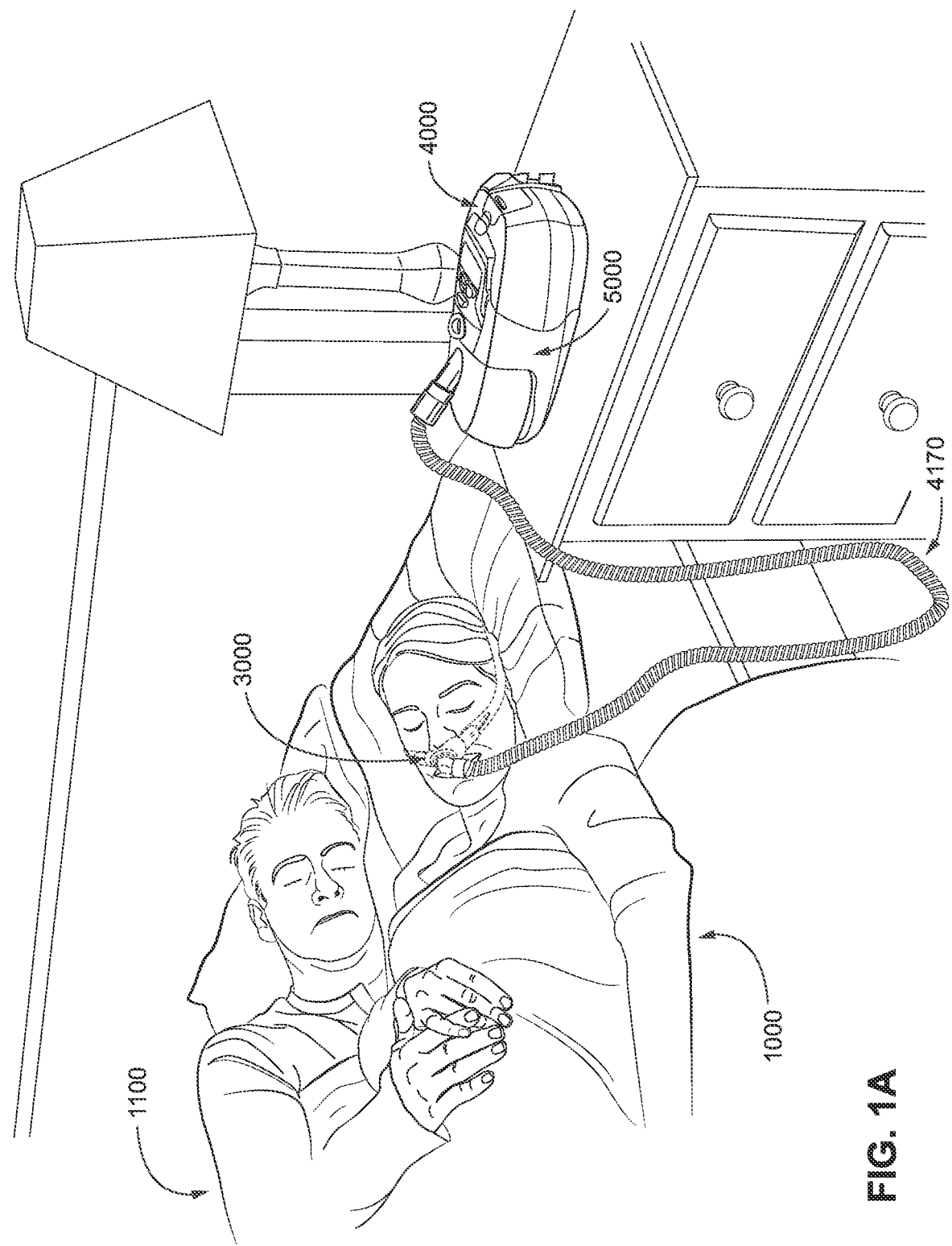
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
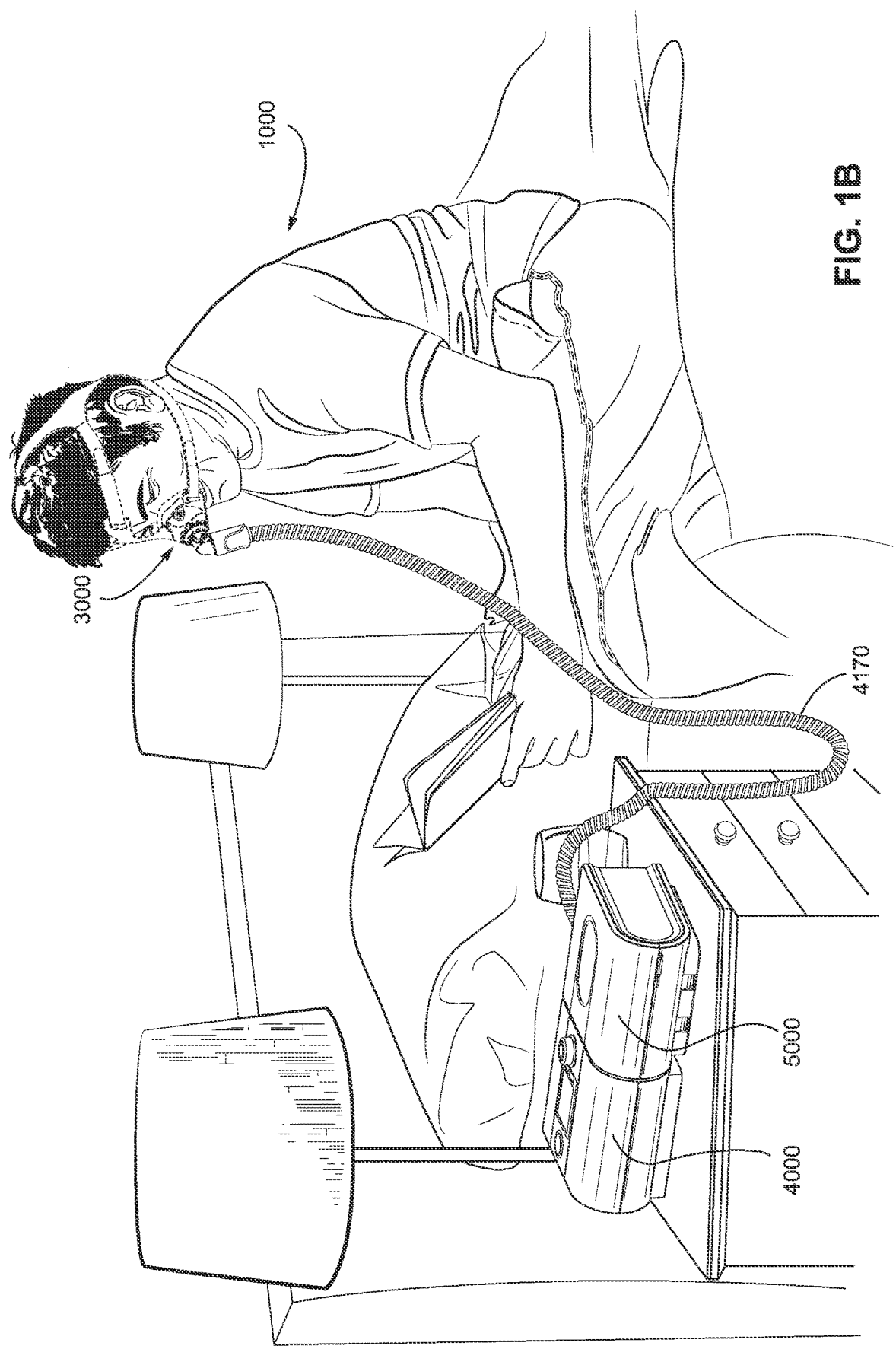
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

FIGS. 4 to 28 show a non-invasive patient interface 6000 in accordance with one aspect of the present technology comprising a frame assembly 6100, a cushion assembly 6175 including a seal-forming structure 6200, an air delivery connector (e.g., elbow assembly 6600), and a positioning and stabilising structure (e.g., headgear 6800). FIGS. 4 and 5 are exemplary views of the patient interface 6000 on a patient's head (with arm covers 6750 for upper arms 6134 of the frame assembly 6100 attached), and FIGS. 6 to 10 are exemplary views of the patient interface 6000 with the headgear 6800 and the arm covers 6750 removed. In use, one form of the seal-forming structure 6200 is arranged to surround an entrance to the airways of the patient 1000 so as to facilitate the supply of air at positive pressure to the airways. The seal-forming structure 6200 (e.g., constructed of silicone) may also be commonly referred to as a cushion. In some forms, a functional aspect may be provided by one or more physical components. In some forms, one physical component may provide one or more functional aspects.

In one form of the present technology, the frame assembly 6100 connects as an intermediate component to the cushion assembly 6175 and the elbow assembly 6600. That is, the cushion assembly 6175 connects to the frame assembly 6100 (via a first retention feature on the frame assembly) independently of the elbow assembly 6600 (see FIG. 11), and the elbow assembly 6600 connects to the frame assembly 6100 (via a second retention feature on the frame assembly) independently of the cushion assembly 6175 (see FIG. 12). However, the seal for the air flow path is formed between the elbow assembly 6600 and the cushion assembly 6175, i.e., the frame assembly 6100 is not in the air flow path (e.g., see FIGS. 13 and 14). Alternatively, a first seal for the air flow path may be formed between the elbow assembly 6600 and the frame assembly 6100, while a separate second seal may be formed between the frame assembly 6100 and the cushion assembly 6175. In this instance, the frame assembly 6100 may remain in the air flow path. The retention connections of the cushion assembly 6175 and the elbow assembly 6600 to the frame assembly 6100 are separate and distinct from one another and allow independent engagement/disengagement, e.g., such that the frame assembly 6100 may remain connected to either of the cushion assembly 6175 or elbow assembly 6600 when disconnecting either of these components. For example, this arrangement allows the cushion assembly 6175 to be disconnected from the frame assembly 6100 (e.g., to change cushion sizes) while maintaining connection between the frame assembly 6100 and the elbow assembly 6600, yet maintaining the ability to disconnect the elbow assembly 6600 from the frame assembly 6100.

In the illustrated example, the seal-forming structure 6200 of the patient interface 6000 of the present technology may be held in sealing position in use by the headgear 6800. As illustrated in FIGS. 4 and 5, the headgear 6800 includes a pair of upper side straps 6802 and a pair of lower side straps 6804 connected to a circular crown strap 6806 that encapsulates the crown of the patient's head. The upper side straps 6802 connect to the upper headgear connector 6130 of the frame assembly 6100 and the lower side straps 6804 connect to the lower headgear connector 6150 of the frame assembly 6100, e.g., via headgear clips 6160. The side straps 6802, 6804 may include an adjustable hook and loop (Velcro™) connection mechanism, e.g., Velcro™-like hook tabs, to facilitate connection and/or adjustment.

FIGS. 59 to 100 show a patient interface 16000 according to another example of the present technology. The patient interface includes a frame assembly 16100, a cushion assembly 16175 including a seal-forming structure 16200, an air delivery connector (e.g., elbow assembly 16600), and a positioning and stabilising structure (e.g., headgear 16800 including upper side straps 16802, lower side straps 16804, and crown strap 16806). FIGS. 59 to 61 are exemplary views of the patient interface 16000 with arm covers 16750 for upper arms 16134 of the frame assembly 16100 attached, and FIGS. 62 to 68 are exemplary views of the patient interface 16000 with the headgear 16800 and the arm covers 16750 removed.

Similar to the example described above, the cushion assembly 16175 connects to the frame assembly 16100 (via a first retention feature on the frame assembly) independently of the elbow assembly 16600 (see FIG. 67), and the elbow assembly 16600 connects to the frame assembly 16100 (via a second retention feature on the frame assembly) independently of the cushion assembly 16175 (see FIG. 68). That is, the retention connections of the cushion assembly 16175 and the elbow assembly 16600 to the frame assembly 16100 are separate and distinct from one another and allow independent engagement/disengagement.

In the example of patient interface 16000, a first seal for the air flow path is formed between the elbow assembly 16600 and the frame assembly 16100, and a separate second seal is formed between the frame assembly 16100 and the cushion assembly 16175. In this example, the frame assembly 16100 is provided in the air flow path. That is, the elbow assembly 16600 is structured to establish a hard-to-hard connection and dynamic seal with the frame assembly 16100, and the cushion assembly 16175 is structured to establish a separate hard-to-hard connection and static seal with the frame assembly 16100.

Also, in the example of patient interface 16000, the frame assembly 16100 includes a lockout feature along the opening 16105 that is structured and arranged to prevent direct connection or insertion of the air circuit 4170, e.g., air delivery tube. This arrangement requires use of the elbow assembly 16600 to interconnect the frame assembly 16100 and the air circuit 4170, thereby ensuring that the elbow assembly 16600 (and its vent and anti-asphyxia valve (AAV)) are present in the system.

In the example shown in FIGS. 4 to 28 and 59-100, the patient interface is a full-face/oro-nasal interface type including a seal-forming structure 6200 structured to form a seal around the patient's nose and mouth. However, aspects of the present technology may be adapted for use with other suitable interface types, e.g., nasal interface, nasal prongs.

For example, FIGS. 29 to 54C show a non-invasive patient interface 7000 in accordance with another aspect of the present technology. In this example, the patient interface is a nasal interface type including a seal-forming structure 7200 structured to form a seal around the patient's nose. The patient interface 7000 comprises a frame assembly 7100, a cushion assembly 7175 including the seal-forming structure 7200, an elbow assembly 7600, and a positioning and stabilising structure (e.g., headgear 7800). Similar to the above, the cushion assembly 7175 connects to the frame assembly 7100 independently of the elbow assembly 7600 (e.g., see FIG. 35), and the elbow assembly 7600 connects to the frame assembly 7100 independently of the cushion assembly 7175 (e.g., see FIG. 36). In this example, the seal for the air flow path is formed between the elbow assembly 7600 and the cushion assembly 7175 (e.g., see FIGS. 37 and 38).

Frame Assembly

As best shown in FIGS. 18 to 26, the frame assembly 6100 includes a shroud or wall member 6110, an upper headgear connector 6130 provided to an upper portion of the shroud 6110, and a lower headgear connector 6150 provided to a lower portion of the shroud 6110. The frame assembly 6100 provides a connection between the cushion assembly 6175 and the elbow assembly 6600, and also provides a connection between the cushion assembly 6175 and the headgear 6800, e.g., either in a removable fashion or a more permanent fashion, to allow sealing forces to be transferred to the cushion assembly 6175 from the headgear 6800. In the illustrated example, upper and lower headgear connectors 6130, 6150 provide a 4-point connection to the headgear 6800.

The shroud 6110 (e.g., constructed of a relatively hard plastic material such as polycarbonate) includes an opening 6105 through which the elbow assembly 6600 sealingly engages with the cushion assembly 6175 (e.g., see FIGS. 13 and 14).

In the illustrated example, the opening 6105 is bounded by an annular flange 6115 that protrudes forwardly from an anterior or front side of the shroud 6110. The flange 6115 includes a rim 6117 along its free end which defines a circular channel 6120 structured to interface with the elbow assembly 6600.

The posterior or rear side of the shroud 6110 includes a plurality of spring arms 6125 (e.g., 3, 4, 5, or more spring arms) spaced around the opening 6105. Each of the spring arms 6125 includes a barbed end structured to provide a mechanical interlock, e.g., snap-fit connection, with the cushion assembly 6175.

In an alternative example, as best shown in FIGS. 75 to 100, the frame assembly 16100 includes a shroud or wall member 16110, a pair (i.e., right and left) of upper headgear connector arms 16134 (each comprising two flexible portions 16140, 16145) extending from respective sides of an upper portion of the shroud 16110, and a pair (i.e., right and left) of lower headgear connector arms 16154 extending from respective sides of a lower portion of the shroud 16110.

In the illustrated example, the opening 16105 of the shroud 16110 (e.g., constructed of a relatively hard plastic material such as polycarbonate) is bounded by an outer annular flange 16115 and an inner annular flange 16125.

The outer annular flange 16115 protrudes forwardly from an anterior or front side of the shroud 16110. The flange 16115 includes a rim 16117 along its free end which defines a circular channel 16120 structured to interface with the elbow assembly 16600.

The inner annular flange 16125 protrudes rearwardly from a posterior or rear side of the shroud 16110. The flange 16125 includes a plurality of tabs or catches 16127 along its perimeter (e.g., see FIGS. 70, 76, 84, 86, and 88), e.g., 2, 3, 4 or more tabs, which are structured to provide a mechanical interlock, e.g., snap-fit connection, with the cushion assembly 16175 so as to releasably connect the frame assembly 16100 to the cushion assembly 16175. In the illustrated example, the tabs 16127 are provided on superior and inferior sides of the flange (i.e., north and south sides), however alternative arrangements are possible, e.g., tabs provided on anterior and posterior sides of the flange (i.e., east and west sides).

In addition, a radially inwardly extending ridge 16400 protrudes from the flange 16125 into the opening 16105. As described in more detail below, the ridge 16400 acts as a stop to prevent over-insertion of the elbow assembly 16600 into the frame assembly 16100. Also, the ridge 16400 provides a dynamic face seal with the elbow assembly 16600.

Also, the ridge 16400 includes a plurality of projections 16405 along its perimeter (e.g., 2, 3, 4, or more projections), which are structured to provide a lockout feature along the opening 16105 to prevent direct connection or insertion of the air circuit 4170, e.g., air delivery tube, to the frame assembly 16100. This arrangement ensures that the elbow assembly 16600 (and its vent and anti-asphyxia valve (AAV)) is used to interconnect the frame assembly 16100 and the air circuit 4170.

In the illustrated example, the plurality of projections 16405 are structured and arranged to have minimal or no impact on noise (from flow through the opening 16105), impedance to air delivery (inlet flow to the patient), and $CO_2$ washout (outlet flow to the vent of the elbow assembly 16100).

In the nasal interface example, e.g., see FIGS. 42 to 49, the frame assembly 7100 includes a shroud 7110 and a headgear connector 7130 provided to the shroud 7110 to provide a 4-point connection to the headgear 7800. The shroud 7110 (e.g., constructed of a relatively hard plastic material such as polycarbonate) includes an opening 7105 providing an annular edge structured to engage with the elbow assembly 7600. The posterior or rear side of the shroud 7110 includes a plurality of locking tabs or spring arms 7125 (e.g., 2, 3, 4, 5, or more tabs or spring arms) spaced around the opening 7105 and structured to provide a mechanical interlock, e.g., snap-fit connection, with the cushion assembly 7175.

Upper and Lower Headgear Connectors

The upper headgear connector 6130 includes a shroud connection portion 6132 provided to an upper portion of the shroud 6110 and a pair (i.e., right and left) of rigidised upper headgear connector arms 6134 (each comprising two flexible portions 6140, 6145) extending from respective sides of the shroud connection portion 6132 and structured to connect to respective upper headgear straps of the headgear. The lower headgear connector 6150 includes a shroud connection portion 6152 provided to a lower portion of the shroud 6110 and a pair (i.e., right and left) of lower headgear connector arms 6154 extending from respective sides of the shroud connection portion 6152 and structured to connect to respective lower headgear straps of the headgear.

In the illustrated example, each upper headgear connector arm 6134 includes an upper headgear connection point in the form of a slot 6135 structured to receive a respective upper headgear strap 6802 of the headgear. In the illustrated example, each lower headgear connector arm 6154 includes a lower headgear connection point in the form of a magnetic connector 6155 structured to locate and connect to a magnet 6162 associated with a headgear clip 6160 provided to a respective lower headgear strap 6804 of the headgear. However, it should be appreciated that the upper and lower headgear connector arms 6134, 6154 may be connected with headgear straps of the headgear in other suitable manners.

Each of the upper headgear connector arms 6134 is structurally rigid to resist torsion (twisting) and each includes central and peripheral flexible portions 6140, 6145 to conform to varying facial profiles. The central flexible portion 6140 of each arm 6134 is positioned proximal to the shroud 6110 and the shroud connection portion 6132. The peripheral flexible portion 6145 of each arm 6134 is positioned between the upper headgear connection point 6135 and the central flexible portion 6140. The central flexible portion 6140 is separated from the peripheral flexible portion 6145 by a first rigid portion 6143. The peripheral flexible portion 6145 is separated from the upper headgear connection point 6135 by a second rigid portion 6147.

Each upper arm 6134 extends and curves in an upwards direction between the eyes and ears to avoid obstructing patient's vision, position the headgear attachment point (e.g., slot 6135) so that the upper headgear straps extend above and avoid the patient's ears, and provide a force vector that extends generally parallel to the Frankfort horizontal line (e.g., see FIGS. 4 and 5).

The upper arms 6134 are also curved (orthogonal to the plane of the face) to conform to the facial profile e.g., the arms curve to generally match the curvature of the cheek bones and avoid load on the temple.

The upper arms 6134 are rigidised to resist deformation in order to maintain its predetermined shape to ensure the frame assembly 6100 positions the headgear attachment points in the same position and avoid translating headgear tension forces to compressive forces resulting in uncomfortable facial contact by the upper arms.

The upper arms 6134 are also rigidised to resist tension forces that may be provided by the headgear straps to prevent twisting of the arms.

In an example, the upper arms are rigidised or stiffened such that that they maintain a preformed 3D shape (not floppy) structured to conform to the facial profile and positions the headgear attachment points in the appropriate locations. Each upper arm maintains its preformed shape due to its rigidity or stiffness in particular orientations. The upper arms are structured to be less resistant (less stiff or rigid) to bending into and away from the face to adapt varying facial widths. The upper arms are rigidised such that they do not substantially deform under tension forces applied by the headgear straps, thereby acting as an intermediary between the headgear straps and the cushion assembly to convert the tension forces from the headgear straps to a compressive force applied on the seal-forming structure to provide seal and stability on the face. The upper arms are also shaped to apply the appropriate force vectors on the seal-forming structure via the shell to effect a stable and comfortable seal. In an example, the seal-forming structure is pulled into the face under the appropriate compressive force that is also in line with the Frankfort horizontal plane (that is pulled directly back into the face).

In an example, the upper arms are rigidised to provide torsional rigidity to be resistant to deformation under twisting. The upper arms are also resistant to bending deformation vertically up and down alongside the face (i.e., remain at the correct height above the ears. However, the upper arms are also structured to provide a predetermined level of deformation to allow bending (allows bending towards/away from the face) to adjust for varying facial width. In addition, the upper arms are resilient/elastic in this orientation to allow the upper arms to return to their original positions. This feature may also prevent discomfort by minimising the load/force exerted by the frame assembly on the face when the headgear straps are tightened by absorbing some of these tension forces due to its flexibility. In some locations, the upper arms may also provide substantially rigidity/stiffness to avoid contact of the face, wherein the arms may act as a strut to resist bending deformation or compression into the face from headgear tension. Conversely, in other locations, the flexibility of the arms may allow the arms to collapse under tension or compression from side load (e.g., when a patient sleeps on their side, thereby exerting a side load on the patient interface. The arms absorb the compressive force applied by the side load and prevent it from dislodging the seal-forming structure. This flexibility also allows for better conformation to the face, which increases comfort and also prevents seal instability from side load.

The central flexible portion 6140 is configured to allow the respective arm 6134 to flex to adapt to varying facial width (between patients). For example, for wide faces, the central flexible portion 6140 allows the arms 6134 to flex outwardly away from one another and away from the face, and for narrow faces, the central flexible portion 6140 allows the arms 6134 to flex towards one another and towards the face. In the illustrated example, the central flexible portion 6140 of each arm comprises a single slot 6141 (on an anterior side) forming a hinge.

It should be appreciated that the slot 6141 may include other suitable arrangements and configurations to modify the location and flexibility characteristics of the arm, e.g., more than one slot, slots on one or both sides of the arm (anterior and/or posterior sides), spacing between slots, width, depth, orientation or angle of slot on the arm. In an example, the slot 6141 may be filled with a flexible material. In alternative examples, the hinge may be provided by a number of different methods, e.g., such as a thinner cross section or the use of a flexible material joint.

The first and second rigid portions 6143, 6147 provide structural rigidity to the arms 6134 to support its predetermined shape.

The peripheral flexible portion 6145 is configured to allow the respective arm 6134 to conform to the varying curvature or profile of the user's face, e.g., conform to cheek variation between patients. For example, the peripheral flexible portion 6145 articulates to conform to the width and profile of the cheeks above the cheek bones of the user. In the illustrated example, the peripheral flexible portion 6145 of each arm 6134 comprises a plurality of slots 6146 (on each side of the arm, i.e., slots on anterior and posterior sides of the arm) forming a plurality of hinges over the cheek region. The hinges allow the arms 6134 to articulate and conform to micro variations of the cheek region and distribute load on the face more evenly upon headgear tension, e.g., when compared to a rigidiser arm without any flex.

In the illustrated example, the slots 6146 are generally parallel to one another, generally evenly spaced apart from one another, and include similar widths and depths into the thickness of the arm. However, it should be appreciated that the slots 6146 may include other suitable arrangements and configurations to modify the location and flexibility characteristics of the arm 6134, e.g., number of slots, slots on one or both sides of the arm (anterior and/or posterior sides), spacing between slots, width, depth, orientation or angle of slot on the arm (e.g., slots angled relative to one another to provide bending in different orientations). In an example, one or more of the slots 6146 may be filled with a flexible material. In an alternative example, the hinge may be provided by a plurality of flexible sections (by material) spaced apart by rigid segments.

In alternative examples, it should be appreciated that the upper headgear connector arms 6134 may include any suitable number of flexible portions along its length to modify its flexibility characteristics, e.g., one, two, three or more flexible portions.

In the illustrated example, to minimise discomfort, the upper arms 6134 may have a smooth and curved surface profile to distribute load and allow the arms rock over the face without a concentrated load or stabbing into the face. For example, as shown in FIG. 26, each upper arm 6134 may include a generally lozenge-shaped cross-section, e.g., generally flat but slightly dome shape on either side to increase contact comfort.

In an example, the lower headgear connector arms 6154 are relatively more flexible than the upper headgear connector arms 6134, e.g., the lower headgear connector arms 6154 have less resistance against torsion such that they may twist with the lower headgear straps of the headgear. This flexibility allows the lower arms 6154 to twist and turn with the lower headgear straps to prevent forced disconnection of the retention features under these forces, i.e., maintain connection of the lower arms with the lower headgear straps.

Each lower arm 6154 comprises the magnetic connector 6155 (e.g., encased magnet) structured to locate and connect to the headgear clip 6160 provided to the respective lower headgear strap of the headgear. The magnetic connector 6155 also provides a receptacle 6156, which allows insertion and retention of a corresponding protrusion (e.g., provided by the magnet 6162 of the headgear clip 6160) to resist disconnection from tension of the headgear straps. The retention allows connection to be maintained while allowing the headgear clip 6160 to rotate relative to respective lower arm 6154. That is, the protrusion/magnet 6162 of the headgear clip 6160 and the receptacle 6156 of the magnetic connector 6155 include corresponding cylindrical shapes to allow relative rotation. The magnets are used for locating the headgear clip in correct position for retaining engagement via engagement of the protrusion/magnet 6162 member into the receptacle 6156.

The upper and lower arms 6134, 6154 are connected to the shroud 6110 via the respective shroud connection portion 6132, 6152. In the illustrated example, the upper and lower arms 6134, 6154 are permanently (e.g., co-molded, overmolded) connected to the shroud 6110. As illustrated, each shroud connection portion 6134, 6154 includes a plurality of pins 6133, 6153 that are received in respective openings 6113, 6114 provided to the shroud 6110 which form rivets to mechanically secure the upper and lower arms 6134, 6154 to the shroud 6110 after the molding process (e.g., see FIGS. 21, 24, and 25). In the illustrated example, the shroud 6110 includes upper and lower grooves 6111, 6112 structured to receive respective shroud connection portions 6132, 6152 of the upper and lower headgear connectors, and the openings 6113, 6114 for securing the upper and lower headgear connectors are provided within the grooves 6111, 6112 (e.g., see FIGS. 24 and 25). However, it should be appreciated that the upper and lower headgear connector arms 6134, 6154 may be connected to the shroud 6110 in other suitable manners, e.g., removable connection.

In an example, the upper arms 6134 and/or the lower arms 6154 may be covered by a textile, e.g., for aesthetics, increase perception of softness/comfort. For example, FIGS. 4 and 5 show a textile arm cover or sock 6750 provided to the upper arms 6134, while FIGS. 6 to 10, for example, show the upper arms 6134 with the arm covers 6750 removed.

The upper and lower arms may provide targeted flexibility in alternative manners. For example, the arms may be formed by a single material with a varying cross sectional thickness for targeted flexibility, e.g., flexible areas may be thinner to provide a living hinge, while thickened areas will have a reduced flexibility. In another example, the arms may be formed by two or more materials, each material having different elastic properties/young's modulus, e.g., rigid sections may be formed in rigid materials such as polycarbonate, while each rigid section may be joined by an intermediary flexible/soft material such as liquid silicone rubber to provide targeted flex. In another example, the arms may be formed in layers of different materials, e.g., the arms may be formed by at least a bendable or flexible first layer. The flexible first layer may provide a substrate surface for multiple rigid portions that are spaced apart to form a second rigid layer. The rigid portions may flex relative to each other, while being supported by the first layer. In an example, the substrate layer in this example has the required stretch properties to provide the required tension forces to the patient interface. In the current example, the substrate layer has minimal to no stretch to prevent the tension forces from being absorbed by the substrate layer.

The arms provide the required stiffness (e.g. resist torsional forces, maintain a preformed shape, etc.) for maintaining the patient interface in the desired position. However, the arms may in some cases provide a reduction in comfort due to the hardness and rigidity of the component (i.e., resistance to conforming to the face). This discomfort is due to a combination of tactile feel and resistance in conforming to facial profile variations, which may provide an undesirable load on sensitive portions of the face. To overcome this aspect, the arms may be coated or covered with a softer and in some cases a less rigid material. The material may act to absorb some or all of the compressive forces applied by the arms on the user's face. Moreover, the soft and/or less rigid material may act to conform to facial profile variations, thereby acting as a conforming layer. In addition, the arm may be coated or covered with a tactile layer may have a desirable tactile feel for direct contact with the user's face. The tactile layer may comprise a desirable fabric with enhanced tactile feel and desirable predetermined stretch characteristics. The arm may further comprise a compliant layer comprising a less rigid and/or soft material such as foam for absorbing the compressive forces applied by the arm on the user's face and/or complying with facial variations by conforming the facial profile.

In an example, both the tactile layer and the compliant layer may be structured or comprise materials that substantially do not alter the function of the arms. That is, the layers should not alter the preformed shape of the arms. Moreover, the layers should allow for the arms to flex/bend in particular orientations as defined. Thus the layers should be structured or comprise selected materials to maintain the function of the arms. Furthermore, the layers may be permanently or semi-permanently fixed to the arms. Alternatively, the arms may comprise a removable layer to cover the arms. For example, the removable layer may be a textile cover or sock. The arm may comprise a superior surface for contact with the user's face. The superior surface may comprise a foam layer above the rigid material, which is subsequently covered by the tactile layer. The arm may also comprise an inferior surface covered by the tactile layer.

There are a number of ways to fix the layers to the arm. In one example, the compliant layer is a foam such as memory foam, which is glued, laminating, moulded, mechanically attached, etc. to the superior surface of the arm. The tactile layer is then attached to the foam compliant layer by laminating, stitching, gluing, etc. the tactile layer to the foam. In an example, in both cases the attachment means should not substantially alter the shape and rigidity of the arms. That is, the attachment means for the layers should not substantially change the flexing/bending of the arms nor change the ability of the arms to maintain its preformed shape.

In the alternative example shown in FIGS. 75 to 100, each upper headgear connector arm 16134 includes a shroud connection portion 16132 provided to a respective upper portion of the shroud 16110, and each lower headgear connector arm 16154 includes a shroud connection portion 16152 provided to a respective lower portion of the shroud 16110.

In the illustrated example, each upper headgear connector arm 16134 includes an upper headgear connection point in the form of a slot 16135 structured to receive a respective upper headgear strap 16802 of the headgear. As best shown in FIG. 104, the bridge or cross-bar 16136 defining the slot 16135 includes a leading edge 16136A that is tapered (e.g., like a knife edge) to facilitate assembly/disassembly to the upper headgear strap 16802 of the headgear. For example, the tapered leading edge 16136A may readily slide through and between the Velcro™-like hook tab 16803 and the remainder of the upper headgear strap 16802 to facilitate assembly/disassembly without fully releasing the Velcro™-like hook tab 16803 from the remainder of the upper headgear strap 16802. In the illustrated example, each lower headgear connector arm 16154 includes a lower headgear connection point in the form of a magnetic connector 16155 structured to locate and connect to a magnet associated with a headgear clip 16160 provided to a respective lower headgear strap 16804 of the headgear. However, it should be appreciated that the upper and lower headgear connector arms 16134, 16154 may be connected with headgear straps of the headgear in other suitable manners.

Similar to the upper headgear connector arms described above, each of the upper headgear connector arms 16134 is structurally rigid to resist torsion (twisting) and each includes central and peripheral flexible portions 16140, 16145 to conform to varying facial profiles. The central flexible portion 16140 (i.e., the first flexible portion) of each arm 16134 is positioned proximal to the shroud connection portion 16132. The peripheral flexible portion 16145 (i.e., the second flexible portion) of each arm 16134 is positioned between the upper headgear connection point 16135 and the central flexible portion 16140.

In the illustrated example, the central flexible portion 16140 of each arm 16134 comprises a single slot 16141 (on a posterior side) forming a hinge. In the illustrated example, the peripheral flexible portion 16145 of each arm 16134 comprises a plurality of slots 16146 (on each side of the arm, i.e., slots on anterior and/or posterior sides of the arm) forming a plurality of hinges over the cheek region.

In examples, the peripheral flexible portion 16145 of each arm need not include slots on the anterior or posterior sides. Instead, or in addition, the flexible portion may include one or more interconnecting elastomeric (e.g., silicone) sections that may form a flush or smooth transition between relatively harder plastic sections, but allow flexing, bending and/or pivoting. These can be made via insert or over molding, where the harder plastic sections are placed in the mold and the interconnecting sections are molded over the harder plastic sections.

Each lower headgear connector arm 16154 comprises the magnetic connector 16155 (including encased magnet 16155B) structured to locate and connect to the headgear clip 16160 (including encased magnet 16162) provided to the respective lower headgear strap of the headgear, e.g., see FIG. 103. In the illustrated example, the end of each lower arm 16154 includes a magnet receiving portion 16155A to receive and align a magnet 16155B and a cap 16155C to enclose and retain the magnet 16155B to the magnet receiving portion 16155A. As illustrated, the magnetic connector 16155 provides a protrusion which allows it to be inserted and retained within a corresponding receptacle provided by the headgear clip 16160, e.g., see FIG. 103. The headgear clip 16160 includes a catch or retaining wall 16164 that resists disconnection from tension of the headgear straps while allowing the headgear clip 16160 to rotate (e.g., allow for 360° rotation) relative to respective lower arm 16154. In the illustrated example, as shown in FIGS. 101, 102, and 103, the catch or retaining wall 16164 (e.g., semi-circular cross-section or U-shape) provides a mechanical retention member to mechanically engage with a semi-circular peripheral region of the connector 16155. In an example, the magnetic connector 16155 and/or the catch or retaining wall 16164 may be angled or sloped to provide an undercut to facilitate retention of the headgear clip 16160 on the magnetic connector 16155.

In an example, as shown in FIG. 96, each lower headgear connector arm 16154 and magnetic connector 16155 thereof may be manufactured by molding the cap 16155C, assembling the magnet 16155B in the cap 16155C, inserting the assembled cap/magnet in a lower arm molding tool, and then molding the lower arm 16154 to the cap/magnet. In an example, the cap 16155C may include an orientation feature, e.g., slot 16159, to facilitate correct orientation and alignment of the cap 16155C relative to the lower arm 16154.

In an alternative example, as shown in FIG. 97, each lower headgear connector arm 16154 and magnetic connector 16155 thereof may be manufactured by molding the lower arm 16154, assembling the magnet 16155B in the magnet receiving portion 16155A of the lower arm 16154, inserting the assembled lower arm/magnet in a cap molding tool, and then overmolding the cap 16155C to the lower arm/magnet.

In the illustrated example, each lower headgear connector arm 16154 comprises a single slot 16156 (on a posterior side) forming a hinge portion, e.g., see FIGS. 75 and 76. This hinging portion is structured and arranged to accommodate for facial width variation by allowing the lower arms 16154 to flex away from the patient's face in use, e.g., allows easy adjustment during initial fitting of the patient interface and allows adaption to various facial geometry without affecting seal of the patient interface. Also, the hinging portion allows the lower arms 16154 to move or flex with corresponding headgear clips 16160 in use, e.g., to prevent inadvertent detachment of the headgear clip 16160 from the respective magnetic connector 16155.

The upper and lower arms 16134, 16154 are connected to the shroud 16110 via the respective shroud connection portion 16132, 16152. In the illustrated example, the upper and lower arms 16134, 16154 are permanently connected (e.g., ultrasonically welded) to the shroud 16110.

As shown in FIGS. 83 to 86, the shroud 16110 includes a pair (i.e., right and left) of upper anchors or upper arm connectors 16450 on respective sides of an upper portion of the shroud 16110, and a pair (i.e., right and left) of lower anchors or lower arm connectors 16460 on respective sides of a lower portion of the shroud 16110. Each upper anchor 16450 provides an opening 16452 and each lower anchor 16460 provides an opening 16462.

As shown in FIGS. 90 and 91, the shroud connection portion 16152 of each lower arm 16154 includes a protrusion 16153 that is received in the opening 16462 of a respective lower anchor 16460. The protrusion 16153 includes an opening 16153A that receives a protrusion 16158 provided to a cap 16157 which engages and interlocks the shroud connection portion 16152 to the cap 16157. The shroud connection portion 16152 and the cap 16157 are ultrasonically welded to mechanically secure the shroud connection portion 16152 to the cap 16157, thereby securing the lower arm 16154 to the lower anchor 16460.

In the illustrated example, the caps 16157 are symmetrical to facilitate manufacturing and assembly. However, it should be appreciated that the caps for secruing the lower arms may be assymetrical. For example, FIGS. 92 to 95 show an alternative arrangement in which lower arms 17154 are secured to the shroud 17110 with respective asymmetrical caps 17157.

Similarly, as shown in FIGS. 99 and 100, the shroud connection portion 16132 of each upper arm 16134 includes a protrusion 16133 that is received in the opening 16452 of a respective upper anchor 16450. The protrusion 16133 includes an opening 16133A that receives a protrusion 16138 provided to a cap 16137 which engages and interlocks the shroud connection portion 16132 to the cap 16137. The shroud connection portion 16132 and the cap 16137 are ultrasonically welded to mechanically secure the shroud connection portion 16132 to the cap 16137, thereby securing the upper arm 16134 to the upper anchor 16450

However, it should be appreciated that the upper and lower headgear connector arms 16134, 16154 may be connected to the shroud 16110 in other suitable manners, e.g., removable connection. For example, FIG. 98 illustrates a connector arm 17134 connected to an anchor 17450 via a snap joint, e.g., push through snap joint arrangement including pegs structured to engage within respective openings with a snap fit.

In an example, the upper and/or lower anchors 16450, 16460 of the shroud 16110 may be structured to enhance robustness. For example, the sharp corners along the anchor may be eliminated to reduce stress concentration, e.g., edges along the opening of the anchor may be rounded (e.g., see FIG. 87). Also, the bridge member of the anchor may be provided with an increased thickness to increase section strength, e.g., see bridge member 16454 of upper anchor 16450 in FIG. 87. In addition, ribs may be provided to arms of the anchor to increase strength, e.g., see ribs 16456 provided to arms of upper anchor 16450 in FIG. 87.

In an example, the upper arms 16134 and/or the lower arms 16154 may be covered by a textile, e.g., for aesthetics, increase perception of softness/comfort, provide comfort on the face and minimise marking. For example, FIGS. 59 to 61 show a textile arm cover or sock 16750 provided to the upper arms 16134, while FIGS. 62 to 65, for example, show the upper arms 16134 with the arm covers 16750 removed. The cover 16750 conceals the upper arms 16134 making the outer surface smooth to increase comfort on the face, e.g., no marking and easier to slide over the facial surface. The cover 16750 may be optionally removable.

In an example, at least a portion of the upper arms 16134 and/or the lower arms 16154 may include dimples or a gold ball pattern, e.g., for aesthetics.

In the nasal interface example, e.g., see FIGS. 42 to 49, the headgear connector 7130 includes a shroud connection portion 7132 connected to the shroud 7110, a pair (i.e., right and left) of upper headgear connector arms 7134 structured to connect to respective upper headgear straps 7802 of the headgear 7800, a pair (i.e., right and left) of lower headgear connector arms 7154 structured to connect to respective lower headgear straps 7804 of the headgear 7800, and intermediate portions 7133 to interconnect the upper and lower arms 7134, 7154 with the shroud connection portion 7132.

In the illustrated example, each upper headgear connector arm 7134 includes an upper headgear connection point in the form of a slot 7135 structured to receive a respective upper headgear strap 7802 of the headgear 7800 (see FIG. 29). In the illustrated example, each lower headgear connector arm 7154 includes a lower headgear connection point in the form of a magnetic connector 7155 structured to locate and connect to a magnet associated with a headgear clip 7160 provided to a respective lower headgear strap 7804 of the headgear 7800 (see FIG. 29). However, it should be appreciated that the upper and lower headgear connector arms 7134, 7154 may be connected with headgear straps of the headgear in other suitable manners.

Similar to the above example, each intermediate portion 7133 of the headgear connector 7130 assembly includes a flexible portion 7140 to conform to varying facial profiles, e.g., accommodate facial width variations. In the illustrated example, the flexible portion 7140 comprises a single slot (on anterior and/or posterior sides) forming a hinging section adjacent the cushion assembly.

As shown in FIGS. 48 and 49, the headgear connector 7130 may include a multi-layered configuration, e.g., layers of different materials to provided desired flexibility.

Cushion Assembly

In one form of the present technology, the cushion assembly or cushion module 6175 includes a main body, chassis, or shell 6180 that is connected or otherwise provided to the seal-forming structure or cushion 6200 (see FIGS. 15 and 16). The shell 6180 may be permanently (e.g., co-molded, overmolded) or removably (e.g., mechanical interlock) connected to the cushion 6200. In an example, the cushion 6200 is constructed of a relatively flexible or pliable material (e.g., silicone) and the shell 6180 is constructed of a relatively rigid material (e.g., polycarbonate). The shell 6180 and the cushion 6200 cooperate to form the plenum chamber 6500.

The shell 6180 includes an opening 6305 by which breathable gas is delivered to the plenum chamber 6500. The opening 6305 is bounded by an annular flange 6310 which is adapted to be connected to the frame assembly 6100 and adapted to interface (e.g., seal) with the elbow assembly 6600 which is connected to the gas delivery tube 4180.

The shell 6180 has multiple functions. For example, it forms the plenum chamber for delivery of pressurised gases to the entrance of a patient's airways. The shell 6180 is a rigid structure that directs a force onto the seal-forming structure for sealing to a patients face. The force is provided by tension forces from tightening the headgear straps. These forces are translated from a pair of upper and lower headgear straps to the corresponding upper and lower arms. In an example, the upper and lower arms are provided the frame assembly, which provides the headgear tension forces to the shell 6180.

The shell 6180 also provides an outer (or anterior) surface for engaging the inner (or posterior) surface of the shroud of the frame assembly to effect a seal. The shell also comprises separate retention features or is otherwise structured to detachably engage to the inner surface of the frame assembly. The patient interface is modular in that a single frame assembly size is capable of connection to multiple cushion assembly sizes (e.g., small to large). Thus, the shell also detachably engages to the frame assembly such that the frame assembly is connected into a predetermined configuration that corresponds to its respective cushion assembly size. For example, smaller cushion assemblies have an overall reduced height relative to medium or large cushion assemblies. Thus the frame assembly connects in a position relative to the cushion assembly to position the upper headgear attachment point in their correct position (between the eyes and ears, while providing an attachment point where the upper headgear straps avoid the ears). This means that the frame assembly connects at a higher position on the shell when compared to medium or large cushion assembly sizes. In an example, medium and/or large sizes may not have this requirement and connect such that the frame assembly is positioned in substantially the same position.

In the alternative example shown in FIGS. 75 to 100, the cushion assembly 16175 includes shell 16180 that is connected or otherwise provided to the seal-forming structure or cushion 16200 (see FIGS. 73 and 74). The shell 16180 and the cushion 16200 cooperate to form the plenum chamber 16500 (e.g., see FIGS. 69 and 71). The shell 16180 includes an opening 16305 by which breathable gas is delivered to the plenum chamber 16500. The opening 16305 is bounded by an annular flange 16310 which is adapted to connect to the frame assembly 16100.

In the nasal interface example, e.g., see FIGS. 39 to 41, the cushion assembly 7175 includes a shell 7180 that is permanently (e.g., co-molded, overmolded) connected to the seal-forming structure or cushion 7200. In an example, the cushion 7200 is constructed of a relatively flexible or pliable material (e.g., silicone) and the shell 7180 is constructed of a relatively rigid material (e.g., polycarbonate). The shell 7180 and the cushion 7200 cooperate to form the plenum chamber 7500. In the illustrated example, the flexible flange or lip seal 7250 (i.e. seal 7250 provides a seal with the elbow assembly 7600) is provided in one-piece with the cushion 7200, e.g., connecting portion 7149 interconnects seal 7250 and cushion 7200 as shown in FIGS. 38 and 39.

Connection Between Cushion Assembly and Frame Assembly

In one form of the present technology, the shell 6180 of the cushion assembly 6175 is repeatedly engageable with and removably disengageable from the shroud 6110 of the frame assembly 6100 via a mechanical interlock, e.g., snap-fit connection.

The cushion assembly 6175 and the frame assembly 6100 include cooperating retaining structures to connect the cushion assembly 6175 to the frame assembly 6100. In an example, the frame assembly 6100 is releasably connectable to the cushion assembly 6175 to facilitate replacement and/or cleaning, and to allow alternative frame assemblies and cushion assemblies to be connected to one another. Such arrangement allows multiple seals (e.g., types and sizes) to be used with the patient interface and therefore provide a patient interface suitable for Multiple Patient Multiple Use (MPMU) usage situations. In an alternative example, the frame assembly 6100 may be permanently connected or integrally formed in one-piece with the cushion assembly 6175, e.g., co-molded In the illustrated example, the shell 6180 includes an opening 6305 bounded by an annular flange 6310 that protrudes forwardly from the shell 6180. The flange 6310 includes a plurality of tabs or catches 6315 along its perimeter (e.g., see FIGS. 15 and 17), e.g., 3, 4, 5 or more tabs, which are structured to engage or interlock with corresponding spring arms 6125 on the posterior side of the shroud 6110, e.g., with a snap-fit, to releasably connect the cushion assembly 6175 to the frame assembly 6100.

The cushion assembly 6175 also includes one or more recesses 6320 (e.g., see FIGS. 15 and 17) along the perimeter of the flange 6310 (e.g., upper and lower recesses) structured to engage or interlock with corresponding protrusions 6127 on the posterior side of the shroud 6110, e.g., to facilitate alignment, prevent relative rotation.

In the illustrated example, the shell 6180 of the cushion assembly 6175 and the shroud 6110 of the frame assembly 6100 are relatively rigid (e.g., both formed of a relatively hard material, e.g., such as polycarbonate) such that engagement between the shell 6180 and the shroud 6110 provides a hard-to-hard connection. Also, the perimeter, shape, and geometry of the mating surfaces provided by the shell 6180 and the shroud 6110 are predetermined to facilitate alignment and mechanical/structural engagement, e.g., clean, smooth, curved mating surfaces. That is, the relative rigidity or stiffness of the shroud and the shell are to maintain the preformed structure of the components. The stiffness allows for the components to maintain their shape so that they may be easily aligned for connection.

It should be appreciated that the cushion assembly may be connected or interlocked with the frame assembly in other suitable manners. For example, these components may be connected via a clip.

In the alternative example, as best shown in FIGS. 70 and 72, the inner annular flange 16125 of the shroud 16110 extends through the opening 16305 of the shell 16180, and the tabs or catches 16127 of the flange 16125 engage or interlock on a posterior side of the annular flange 16310 of the shell 16180 so as to releasably connect the frame assembly 16100 to the cushion assembly 16175. Such connection maintains ease of use, provides a sealed hard to hard connection, minimizes rattling and rocking movement between components, and reduces impact on stability. Also, such connection stably holds the cushion assembly 16175 in position, while allowing the appropriate force vectors to be imparted onto the cushion assembly 16175 for seal.

Also, the frame assembly 16100 is structured to form a static diametric seal and a static face seal with the cushion assembly 16175 to minimize and control leak. As illustrated in FIGS. 70 and 72, the shroud 16110 of the frame assembly 16100 includes a channel adapted to receive the flange 16310 of the cushion assembly 16175. The leading edge 16310A of the flange 16310 and the end wall 16112A of the channel are configured and arranged to provide a static face seal, and the outer side 16310B of the flange 16310 and the side wall 16112B of the channel are configured and arranged to provide a static diametric seal.

In the nasal interface example, e.g., see FIGS. 30 to 49, the shell 7180 includes a plurality of tabs or catches 7315 along the perimeter of flange 7310, which are structured to engage or interlock with corresponding tabs or arms 7125 on the posterior side of the shroud 7110, e.g., with a snap-fit, to releasably connect the cushion assembly 7175 to the frame assembly 7100.

The cushion assembly 7175 also includes one or more recesses 7320 (e.g., see FIG. 41) along the perimeter of the flange 7310 (e.g., lower recess) structured to engage or interlock with corresponding protrusions 7127 (e.g., see FIG. 43) on the posterior side of the shroud 7110, e.g., to facilitate alignment, prevent relative rotation.

In another example, as shown in FIGS. 55 to 58, the shell of the cushion assembly 8175 may include a central aperture with an internal surface structured to receive an annular central flange of the frame assembly 8100. The shell includes a retention feature that interlocks or connects to a retention feature on the frame assembly. In addition, a clearance is maintained within the aperture of the shell for a bellows structure 8250 of a vent adaptor 8900 (FIGS. 55 and 56) or elbow assembly 8600 (FIGS. 57 and 58) to engage with a surface 8275 of the shell to effect a face seal.

The cushion assembly 6175 and the frame assembly 6100 are structured to maintain engagement during use and prevent any unintentional or partial disassembly during use.

In one form of the present technology, the frame assembly 6100 is engageable with the cushion assembly 6175 by posteriorly moving the frame assembly 6100 towards the cushion assembly 6175 in a direction substantially parallel to the Frankfort horizontal, and the frame assembly 6100 is disengageable from the cushion assembly 6175 by anteriorly moving the frame assembly 6100 from the cushion assembly 6175 in a direction substantially parallel to the Frankfort horizontal.

Elbow Assembly

As shown in FIGS. 27 and 28, the elbow assembly 6600 includes a first end portion 6610 that is repeatedly engageable with and removably disengageable from the shroud 6110 of the frame assembly 6100 and a second end portion 6620 adapted to connect to the air circuit 4170, e.g., via a swivel connector 6625.

The first end portion 6610 includes a pair of resilient, quick release pinch arms 6650, i.e., cantilevered spring arm. Each of the spring or pinch arms 6650 includes a barbed end or tab 6652 structured to provide a mechanical interlock, e.g., snap-fit connection, with the flange 6115 of the shroud 6110.

The first end portion 6610 includes an annular side wall 6630 structured to extend through the frame assembly 6100 and form a seal with the cushion assembly 6175.

In the illustrated example, a vent 6700 is integrated into the first end portion 6610 to allow for the washout of exhaled air, e.g., vent exits of the vent provided along a perimeter of the first end portion 6610.

In the alternative example, as best shown in FIGS. 59, 65, 70, and 72, the elbow assembly 16600 includes a first end portion 16610 with pinch arms 16650 to releasably engage with the frame assembly 16100 and a second end portion 16620 adapted to connect to the air circuit 4170, e.g., via a swivel connector 16625.

In this example, the first end portion 16610 includes inner and outer radial walls 16630, 16640 defining a radial channel 16645 leading to a plurality of vent holes 16700 to permit the exit of exhausted gases from the patient interface.

In addition, the elbow assembly 16600 is structured to house an AAV assembly including AAVs structured to allow the patient to breathe through ports if pressurized gas is not of sufficient magnitude or not delivered.

FIGS. 50 and 51 show the elbow assembly 7600 structured for connection to the nasal type patient interface 7000. FIGS. 52 and 53 show an alternative elbow assembly 9600 structured for connection to the nasal type patient interface 7000.

In the illustrated examples, each side of the elbow assembly 7600, 9600 includes a cantilevered push button and grooves along sides of the push button that allow the push button to flex. Each push button includes a tab or catch that is adapted to engage the edge of the opening 7105 of the frame assembly 7100 with a snap fit to releasably secure the elbow assembly 7600, 9600 to the frame assembly 7100.

As best shown in FIGS. 51 and 53, a raised portion of the button and webbing within the grooves along sides of the button is constructed of a soft, tactile material, e.g., TPE. The raised portion provides a soft tactile feel for ease of use and grip, and the webbing provides seal, soft tactile feel, and spring (clip return) force. In an example, the raised portion and webbing are overmolded to the main elbow body including the push buttons.

As shown in FIGS. 50 and 51, the elbow assembly 7600 includes a vent assembly 7700 to allow for the washout of exhaled air.

Connection Between Elbow Assembly and Frame Assembly

The elbow assembly 6600 releasably connects and retains onto the frame assembly 6100 via the pinch arms 6650, e.g., quick release snap-fit. The flange 6115 of the shroud 6110 defines the circular channel 6120 which is structured to receive the barbed end 6652 of the pinch arms 6650 to releasably retain the elbow assembly 6600 to the frame assembly 6100 and form a swivel connection (e.g., see FIG. 6), e.g., allow 360° free rotation of the elbow assembly 6600 relative to the frame assembly 6100.

Because the elbow assembly 6600 connects to the frame assembly 6100 independently of the cushion assembly 6175, the patient is able to remove and swap different size cushion assemblies without the need for disconnecting the elbow assembly 6600, frame assembly 6100, and headgear.

Similarly, in the alternative example as best shown in FIG. 72, the circular channel 16120 of the frame assembly 16100 is structured to receive the barbed end 16652 of the pinch arms 16650 to releasably retain the elbow assembly 16600 to the frame assembly 16100.

Seal Between Elbow Assembly and Cushion Assembly

In an example, the cushion assembly 6175 comprises a flexible flange or lip seal 6250 to provide a seal with the elbow assembly 6600. The lip seal 6250 is provided to the flange 6310 of the shell 6180 and includes a free end that extends radially inwardly into the opening 6305. As shown in FIGS. 13 and 14, the elbow assembly 6600 is structured to mechanically interlock with the frame assembly 6100, but is structured and arranged to sealingly engage with sealing membrane 6250 of the cushion assembly 6175 to form a seal for the air flow path, i.e., sealing mechanism is separate from the retention features.

As illustrated, the leading edge of the side wall 6630 of the elbow assembly 6600 forms a face seal with the lip seal 6250. This form of engagement minimises surface area contact to reduce friction, thereby allowing a seal to form between the components while allowing the elbow assembly 6600 to swivel freely relative to the frame and cushion assemblies 6100, 6175.

In the nasal interface example, e.g., see FIGS. 37 and 38, the elbow assembly 7600 is structured to mechanically interlock with the frame assembly 7100, and the leading edge of the side wall 7630 of the elbow assembly 7600 is structured and arranged to sealingly engage with the lip seal 7250 of the cushion assembly 7175 to form a seal for the air flow path.

Seal Between Elbow Assembly and Frame Assembly

In an alternative example, the elbow assembly 16600 is structured to establish a hard-to-hard connection and seal with the frame assembly 16100. As best shown in FIG. 72, a dynamic diametric seal is formed between the cylindrical outer surface of the outer wall 16640 of the elbow assembly 16600 and the inner surface provided by the annular flanges 16115, 16125 of the frame assembly 16100. Also, the annular flange 16125 of the frame assembly 16100 comprises the radially inwardly extending ridge 16400 that acts as a stop to prevent over-insertion of the elbow assembly 16600 into the frame assembly 16100. The surface of the ridge 16400 also provides a dynamic face seal with the leading edge or surface of the outer wall 16640 of the elbow assembly 16600. The diametric seal and the face seal provided between surfaces of the outer wall 16640 and surfaces of the annular flanges 16115, 16125/ridge 16400 provide two mating surfaces of contact between the elbow assembly 16600 and the frame assembly 16100, which increases the surface area of contact between the elbow assembly 16600 and the frame assembly 16100. The two mating surfaces are configured and arranged to minimize and control leak by providing a tortuous leak path, i.e., leak path between the two mating surfaces extends radially to axially from interior the patient interface to atmosphere.

Lockout Feature

As noted above, the ridge 16400 of the frame assembly 16100 includes a plurality of projections 16405 structured to provide a lockout feature to prevent direct connection or insertion of the air circuit 4170 to the frame assembly 16100.

As best shown in FIG. 72, each projection 16405 extends to the inner wall 16630 of the elbow assembly so that the projections 16405 do not extend significantly into the inlet flow path to the patient. In addition, each projection 16405 includes an opening 16407 (e.g., see FIGS. 72, 83, and 88) so the projections 16405 do not significantly block outlet flow to the channel 16645 leading to the vent holes 16700 of the elbow assembly 16100. Thus, the plurality of projections 16405 are structured and arranged to have minimal or no impact on noise (from flow through the opening 16105), impedance to air delivery (inlet flow to the patient), and $CO_2$ washout (outlet flow to the vent of the elbow assembly 16100.

In an alternative example, as shown in FIG. 89A, each of the projections 16405 may be provided without an opening.

In another alternative, as shown in FIG. 89B, the lockout feature may be provided by a single annular projection 16405 that extends along the entire perimeter of the ridge 16400. As illustrated, openings 16407 are provided along the projection 16405, e.g., so the projection 16405 does not significantly block outlet flow to the channel 16645 leading to the vent holes 16700.

Vent Adaptor Connector

In an alternative example, a vent adaptor connector may be provided to the patient interface, e.g., as an alternative to the elbow assembly 6600. Similar to the arrangement described above, the vent adaptor connector may be releasably connected to the frame assembly 6100 independent of the cushion assembly 6175, and may sealingly engage with the sealing membrane 6250 of the cushion assembly 6175 to form a seal for the air flow path.

Alternative Connection/Seal of Elbow Assembly/Vent Adaptor Connector

As aforementioned, the patient interface is connectable to both an elbow assembly and a vent adaptor connector, e.g., elbow assembly/vent adaptor connector releasably connected to the frame assembly and sealingly engaged with the cushion assembly.

In an alternative example, as shown in FIGS. 55 to 58, the elbow assembly 8600/vent adaptor connector 8900 includes a seal or bellows structure 8250 (e.g., formed of silicone) structured to engage an inner surface 8275 provided to the shell of the cushion assembly 8175. The bellows structure is structured to move towards the inner surface of the shell when pressure is increased within the components, i.e., pressure supported seal. The bellows structure engages with the inner surface on the shell along the inlet opening to provide a bellows face seal.

The seal forming structures of the vent adaptor connector/elbow assembly and the shell are separate to the retention forming features. In an example, the frame comprises a retention feature including a resilient pair of arms adapted for insertion into corresponding grooves in the vent adaptor connector/elbow assembly. The connection is also a swivel connection allowing the vent adaptor connector/elbow assembly to swivel relative to the cushion assembly and frame assembly. Hence, the bellows face seal has another advantage in that it effects a seal between the components with minimal friction to allow substantial relative movement without breaking seal. In an example, the frame assembly is structured such that it does not form part of the air delivery path to the patient but is structured to removably retain both the cushion assembly and vent adaptor connector/elbow assembly in position. The vent adaptor connector/elbow assembly forms a seal directly with the shell of the cushion assembly through an aperture provided in the frame assembly.

This configuration allows a user to remove the vent adaptor connector/elbow assembly from the patient interface, without the need for disconnecting the frame assembly from the cushion assembly, i.e., the patient can stop therapy but leave the patient interface on the face. This configuration also allows a user to remove the cushion assembly from the frame assembly and vent adaptor connector/elbow assembly without the need for disconnecting the frame assembly from the vent adaptor connector/elbow assembly. In an example, the frame assembly is connected to the headgear, thus the headgear can remain connected to the frame assembly and vent adaptor connector/elbow assembly while the user tries various cushion assembly sizes (e.g., small, medium, large) without the need to reassemble multiple components.

Modularity

In the illustrated example, the frame assembly 6100 may be provided in one size (i.e., common frame assembly), which may be selectively engageable with multiple sizes of cushion assemblies 6175, e.g., small, medium, and large size cushion assemblies distinguished by volume/footprint on the patient's face. Thus, the patient has the freedom to change cushion sizes freely without the need to replace the frame assembly 6100. In an example, regardless of size, the patient interface provides similar locations for the headgear connectors (e.g., based on headgear vectors and clearance with the patient's eyes) and the connection for the elbow assembly (e.g., to optimize gas washout).

In such example, the shell of each of the different size cushion assemblies includes a connector (annular flange-type connector) that is common or similar for all sizes (e.g., common retention feature), which allows the one size or common frame assembly to be connected to each of the different size cushion assemblies, i.e., each cushion assembly includes a common frame retention feature on the shell for all cushion sizes.

Similar to the above, the frame assembly 7100 of the nasal interface type may be provided in one size (i.e., common frame assembly), which may be selectively engageable with multiple sizes of cushion assemblies 7175, e.g., small, medium, and large size cushion. For example, FIGS. 54A, 54B, and 54C are rear views of small, medium, and large cushion assemblies 7175 according to an example of the present technology. As illustrated, each size provides a different volume or footprint on the patient's face.

5.3.1 Seal-Forming Structure

In one form of the present technology, a seal-forming structure provides a seal-forming surface, and may additionally provide a cushioning function.

A seal-forming structure in accordance with the present technology may be constructed from a soft, flexible, resilient material such as silicone. In an alternative example, the seal-forming structure may include a foam cushion including a foam seal forming portion. In such example, such foam cushion may be provided to a shell to allow connection to the frame assembly 6100.

In one form, the seal-forming structure comprises a sealing flange and a support flange. The sealing flange comprises a relatively thin member with a thickness of less than about 1 mm, for example about 0.25 mm to about 0.45 mm, that extends around the perimeter of the plenum chamber. Support flange may be relatively thicker than the sealing flange. The support flange is disposed between the sealing flange and the marginal edge of the plenum chamber, and extends at least part of the way around the perimeter. The support flange is or includes a spring-like element and functions to support the sealing flange from buckling in use. In use the sealing flange can readily respond to system pressure in the plenum chamber acting on its underside to urge it into tight sealing engagement with the face.

In one form the seal-forming portion of the non-invasive patient interface comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface comprises a seal-forming portion that forms a seal in use on an upper lip region (that is, the lip superior) of the patient's face.

In one form the non-invasive patient interface comprises a seal-forming portion that forms a seal in use on a chin-region of the patient's face.

In certain forms of the present technology, a seal-forming structure is configured to correspond to a particular size of head and/or shape of face. For example one form of a seal-forming structure is suitable for a large sized head, but not a small sized head. In another example, a form of seal-forming structure is suitable for a small sized head, but not a large sized head.

5.3.2 Plenum Chamber

The plenum chamber has a perimeter that is shaped to be complementary to the surface contour of the face of an average person in the region where a seal will form in use. In use, a marginal edge of the plenum chamber is positioned in close proximity to an adjacent surface of the face. Actual contact with the face is provided by the seal-forming structure. The seal-forming structure may extend in use about the entire perimeter of the plenum chamber.

5.3.3 Positioning and Stabilising Structure

The seal-forming structure of the patient interface of the present technology may be held in sealing position in use by the positioning and stabilising structure.

In one form of the present technology, a positioning and stabilising structure is provided that is configured in a manner consistent with being worn by a patient while sleeping. In one example the positioning and stabilising structure has a low profile, or cross-sectional thickness, to reduce the perceived or actual bulk of the apparatus. In one example, the positioning and stabilising structure comprises at least one strap having a rectangular cross-section. In one example the positioning and stabilising structure comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure comprises a strap that is bendable and e.g. non-rigid. An advantage of this aspect is that the strap is more comfortable for a patient to lie upon while the patient is sleeping.

In certain forms of the present technology, a positioning and stabilizing structure provides a retaining force configured to correspond to a particular size of head and/or shape of face. For example one form of positioning and stabilizing structure provides a retaining force suitable for a large sized head, but not a small sized head. In another example, a form of positioning and stabilizing structure provides a retaining force suitable for a small sized head, but not a large sized head.

5.3.4 Vent

In one form, the patient interface includes a vent constructed and arranged to allow for the washout of exhaled gases, e.g. carbon dioxide.

One form of vent in accordance with the present technology comprises a plurality of holes, for example, about 20 to about 80 holes, or about 40 to about 60 holes, or about 45 to about 55 holes.

The vent may be located in the plenum chamber. Alternatively, the vent is located in a decoupling structure, e.g., a swivel.

5.3.5 Decoupling Structure(s)

In one form the patient interface includes at least one decoupling structure, for example, a swivel or a ball and socket.

5.3.6 Connection Port

Connection port allows for connection to the air circuit.

5.3.7 Forehead Support

In the illustrated example, the frame assembly 6100 is provided without a forehead support.

In another form, the patient interface may include a forehead support, e.g., the frame assembly may include a forehead support.

5.3.8 Anti-Asphyxia Valve

In one form, the patient interface includes an anti-asphyxia valve.

5.3.9 Ports

In one form of the present technology, a patient interface includes one or more ports that allow access to the volume within the plenum chamber. In one form this allows a clinician to supply supplemental oxygen. In one form, this allows for the direct measurement of a property of gases within the plenum chamber, such as the pressure.

5.4 Glossary

For the purposes of the present technology disclosure, in certain forms of the present technology, one or more of the following definitions may apply. In other forms of the present technology, alternative definitions may apply.

5.4.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory disease.

Pressure: Force per unit area. Pressure may be expressed in a range of units, including cmH$_2$O, g-f/cm$^2$ and hectopascal. 1 cmH$_2$O is equal to 1 g-f/cm$^2$ and is approximately 0.98 hectopascal. In this specification, unless otherwise stated, pressure is given in units of cmH$_2$O.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.4.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.4.1.2 Mechanical Properties

Resilience: Ability of a material to absorb energy when deformed elastically and to release the energy upon unloading.

'Resilient': Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

'Floppy' structure or component: A structure or component that will change shape, e.g. bend, when caused to support its own weight, within a relatively short period of time such as 1 second.

'Rigid' structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.4.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.4.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.4.4 Anatomy 5.4.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.4.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.4.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.4.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional Dead Space:

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.4.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.4.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill) See FIG. 3E (relatively small negative curvature compared to FIG. 3F) and FIG. 3F (relatively large negative curvature compared to FIG. 3E). Such curves are often referred to as convex.

5.4.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill)

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.4.6.3 Space Curves

Space curves: Unlike a plane curve, a space curve does not necessarily lie in any particular plane. A space curve may be considered to be a one-dimensional piece of three-dimensional space. An imaginary person walking on a strand of the DNA helix walks along a space curve. A typical human left ear comprises a left-hand helix, see FIG. 3P. A typical human right ear comprises a right-hand helix, see FIG. 3Q. FIG. 3R shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3O), or alternatively by a left-hand rule (FIG. 3N).

Osculating plane: The plane containing the unit tangent vector and the unit principal normal vector. See FIGS. 3N and 3O.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3R, since T2>T1, the magnitude of the torsion near the top coils of the helix of FIG. 3R is greater than the magnitude of the torsion of the bottom coils of the helix of FIG. 3R With reference to the right-hand rule of FIG. 3O, a space curve turning towards the direction of the right-hand binormal may be considered as having a right-hand positive torsion (e.g. a right-hand helix as shown in FIG. 3R). A space curve turning away from the direction of the right-hand binormal may be considered as having a right-hand negative torsion (e.g. a left-hand helix).

Equivalently, and with reference to a left-hand rule (see FIG. 3N), a space curve turning towards the direction of the left-hand binormal may be considered as having a left-hand positive torsion (e.g. a left-hand helix). Hence left-hand positive is equivalent to right-hand negative. See FIG. 3S.

5.4.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by the plane curve 301D.

A structure may have a two-dimensional hole, e.g. a hole bounded by a surface. For example, an inflatable tyre has a two dimensional hole bounded by the inside surface of the tyre. In another example, a bladder with a cavity for air or gel could have a two-dimensional hole. See for example the cushion of FIG. 3L and the example cross-section there through in FIG. 3M. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by surface 302D.

5.5 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

For example, it should be appreciated that one or more features of any one patient interface example (e.g., patient interfaces 6000, 7000, 16000) may be combinable with one or more features of another patient interface example (e.g., patient interfaces 6000, 7000, 16000) or other examples related thereto. For example, one or more aspects of the frame assembly 16100 (e.g., lockout feature, headgear connector arms, connection and sealing arrangement between components) may be incorporated into the patient interfaces 6000, 7000.

Also, it should be appreciated that one or more aspects of the present technology may be combinable with one or more aspects of: PCT Application No. PCT/AU2016/050892, filed Sep. 23, 2016 and entitled "Elbow Assembly", which claims the benefit of U.S. Provisional Application No. 62/222,435, filed Sep. 23, 2015 and U.S. Provisional Application No. 62/376,718, filed Aug. 18, 2016; U.S. Provisional Application No. 62/377,217, filed Aug. 19, 2016 and entitled "Patient Interface with a Seal-Forming Structure having Varying Thickness"; U.S. Provisional Application No. 62/377,158, filed Aug. 19, 2016 and entitled "Patient Interface with a Seal-Forming Structure having Varying Thickness"; PCT Application No. PCT/AU2016/050893, filed Sep. 23, 2016 and entitled "Vent Adaptor for a Respiratory Therapy System", which claims the benefit of U.S. Provisional Application No. 62/222,604, filed Sep. 23, 2015; and/or PCT Application No. PCT/AU2016/050228 filed Mar. 24, 2016 and entitled "Patient Interface with Blowout Prevention for Seal-Forming Portion", which claims the benefit of U.S. Provisional Application No. 62/138,009, filed Mar. 25, 2015 and U.S. Provisional Application No. 62/222,503, filed Sep. 23, 2015; each of the above-noted applications of which is incorporated herein by reference in its entirety.

5.6 Reference Signs List

| Number | Feature Item |
|---|---|
| 1000 | patient |
| 1100 | bed partner |
| 3000 | patient interface |
| 3100 | seal—forming structure |
| 3200 | plenum chamber |
| 3300 | positioning and stabilising structure |
| 3400 | vent |
| 3600 | connection port |
| 3700 | forehead support |
| 4000 | RPT device |
| 4170 | air circuit |
| 5000 | humidifier |
| 6000 | patient interface |
| 6100 | frame assembly |
| 6105 | opening |
| 6110 | shroud |
| 6111 | groove |
| 6112 | groove |
| 6113 | openings |
| 6114 | openings |
| 6115 | flange |
| 6117 | rim |
| 6120 | channel |
| 6125 | spring arm |
| 6127 | protrusion |
| 6130 | upper headgear connector |
| 6132 | shroud connection portion |
| 6133 | pins |
| 6134 | upper headgear connector arm |
| 6135 | upper headgear connection point |
| 6140 | central flexible portion |
| 6141 | slot |
| 6143 | first rigid portion |
| 6145 | peripheral flexible portion |
| 6146 | slot |
| 6147 | second rigid portion |
| 6150 | lower headgear connector |
| 6152 | shroud connection portion |
| 6153 | pins |
| 6154 | lower headgear connector arm |
| 6155 | magnetic connector |
| 6156 | receptacle |
| 6160 | headgear clip |
| 6162 | magnet |
| 6175 | cushion assembly |
| 6180 | shell |
| 6200 | seal—forming structure |
| 6250 | lip seal |
| 6305 | opening |
| 6310 | flange |
| 6315 | catch |
| 6320 | recess |
| 6500 | plenum chamber |
| 6600 | elbow assembly |
| 6610 | first end portion |
| 6620 | second end portion |
| 6625 | swivel connector |
| 6630 | side wall |
| 6650 | pinch arm |
| 6652 | tab |
| 6700 | vent |
| 6750 | arm cover |
| 6800 | headgear |
| 6802 | upper side strap |
| 6804 | lower side strap |
| 6806 | crown strap |
| 7000 | patient interface |
| 7100 | frame assembly |
| 7105 | opening |
| 7110 | shroud |
| 7125 | spring arm |
| 7127 | protrusion |
| 7130 | headgear connector |
| 7132 | shroud connection portion |
| 7133 | intermediate portion |
| 7134 | upper headgear connector arm |
| 7135 | slot |
| 7140 | flexible portion |
| 7149 | connecting portion |
| 7154 | lower headgear connector arm |
| 7155 | magnetic connector |
| 7160 | headgear clip |
| 7175 | cushion assembly |
| 7180 | shell |
| 7200 | seal—forming structure |
| 7250 | seal |
| 7310 | flange |
| 7315 | catch |
| 7320 | recess |
| 7500 | plenum chamber |
| 7600 | elbow assembly |
| 7630 | side wall |
| 7700 | vent assembly |
| 7800 | headgear |
| 7802 | upper headgear strap |
| 7804 | lower headgear strap |
| 8100 | frame assembly |
| 8175 | cushion assembly |
| 8250 | bellows structure |
| 8275 | surface |
| 8600 | elbow assembly |
| 8900 | vent adaptor connector |
| 9600 | elbow assembly |
| 16000 | patient interface |
| 16100 | frame assembly |
| 16105 | opening |
| 16110 | shroud |
| 16112A | end wall |
| 16112B | side wall |
| 16115 | outer annular flange |
| 16117 | rim |
| 16120 | channel |
| 16125 | inner annular flange |
| 16127 | tab or catch |
| 16132 | shroud connection portion |
| 16133 | protrusion |
| 16133A | opening |
| 16134 | upper headgear connector arm |
| 16135 | upper headgear connection point |
| 16136 | bridge |
| 16136A | leading edge |
| 16137 | cap |
| 16138 | protrusion |
| 16140 | central flexible portion |
| 16141 | slot |
| 16145 | peripheral flexible portion |
| 16146 | slot |
| 16152 | shroud connection portion |
| 16153 | protrusion |
| 16153A | opening |
| 16154 | lower headgear connector arm |
| 16155 | magnetic connector |
| 16155A | magnet receiving portion |
| 16155B | magnet |
| 16155C | cover |
| 16156 | slot |
| 16157 | cap |
| 16158 | protrusion |
| 16159 | slot |
| 16160 | headgear clip |
| 16162 | magnet |
| 16164 | catch |

-continued

| Number | Feature Item |
|---|---|
| 16175 | cushion assembly |
| 16180 | shell |
| 16200 | seal—forming structure |
| 16305 | opening |
| 16310 | flange |
| 16310A | leading edge |
| 16310B | outer side |
| 16400 | ridge |
| 16405 | projections |
| 16407 | opening |
| 16450 | upper anchor |
| 16452 | opening |
| 16454 | bridge member |
| 16456 | ribs |
| 16460 | lower anchor |
| 16462 | opening |
| 16500 | plenum chamber |
| 16600 | elbow assembly |
| 16610 | first end portion |
| 16620 | second end portion |
| 16625 | swivel connector |
| 16630 | inner wall |
| 16640 | outer wall |
| 16645 | channel |
| 16650 | pinch arm |
| 16652 | barbed end |
| 16700 | vent holes |
| 16750 | arm cover |
| 16800 | headgear |
| 16802 | upper side strap |
| 16803 | tab |
| 16804 | lower side strap |
| 16806 | crown strap |
| 17110 | shroud |
| 17134 | connector arm |
| 17154 | lower arm |
| 17157 | cap |
| 17450 | anchor |

The invention claimed is:

1. A frame assembly for a patient interface for treatment of sleep disordered breathing, the frame assembly configured to connect headgear of the patient interface to a cushion assembly of the patient interface, the frame assembly comprising:
a shroud constructed of a rigid plastic material and including an opening formed therein to receive a flow of air from an air delivery tube, the shroud being structured to, in use, facilitate support of a cushion assembly on a patient's face; and
a pair of upper headgear connector arms extending from respective sides of an upper portion of the shroud and, in use, configured to extend along respective sides of the patient's face, each upper headgear connector arm having a shape that, in use, curves in an upwards direction such that the upper headgear connector arm extends between the patient's eye and ear;
each upper headgear connector arm including:
an upper headgear connection point adapted to receive a respective upper headgear strap;
a shroud connection portion that is connected to the respective side of the upper portion of the shroud; and
a first flexible portion positioned proximal the shroud connection portion and between the shroud connection portion and the upper headgear connection point, the first flexible portion being configured to, in use, allow the upper headgear connector arm to flex outwardly away from the patient's face and inwardly towards the patient's face to adapt to varying facial widths,
wherein the first flexible portion is a living hinge formed by a relatively thinner portion of the upper headgear connector arm disposed immediately between relatively thicker portions of the upper headgear connector arm to form a flexible area,
wherein each upper headgear connector arm further comprises a second flexible portion provided between the first flexible portion and the upper headgear connection point,
wherein the second flexible portion allows the upper headgear connector arm to, in use, flex along its length to conform to the width and profile of patient cheek regions,
wherein a textile material covers a portion of each upper headgear connector arm to provide a patient-contacting surface,
wherein each upper headgear connector arm includes a textile receiving area extending from a first shoulder of the upper headgear connection point to a second shoulder of the first flexible portion to receive the textile material,
wherein the textile receiving area has a reduced thickness as compared to the first shoulder, an upper end of the textile material being adjacent the first shoulder when the textile material is positioned in the textile receiving area, and
wherein the textile receiving area has a reduced thickness as compared to the second shoulder, a lower end of the textile material being adjacent the second shoulder when the textile material is positioned in the textile receiving area.

2. The frame assembly of claim 1, wherein the shroud is constructed of polycarbonate.

3. The frame assembly of claim 2, wherein the pair of upper headgear connector arms are made of a different material than the polycarbonate of the shroud.

4. The frame assembly of claim 3, wherein the pair of upper headgear connector arms comprise a plastic material.

5. The frame assembly of claim 1, wherein each upper headgear connection point includes a slot adapted to receive the respective upper headgear strap.

6. The frame assembly of claim 1, wherein the textile material is less rigid as compared to a material of the upper headgear connector arm.

7. The frame assembly of claim 1, wherein the reduced thickness of the textile receiving area forms the second flexible portion, the reduced thickness permitting the upper headgear connector arm to flex along its length.

8. The frame assembly of claim 1, wherein the second shoulder extends diagonally across a width of the upper headgear connector arm from an upper longitudinal edge to a lower longitudinal edge of the upper headgear connector arm.

9. The frame assembly of claim 1, wherein the shroud includes a pair of upper arm connectors at respective sides of the upper portion of the shroud, and
wherein the shroud connection portion of each upper headgear connector arm is directly connected to a respective one of the upper arm connectors of the shroud.

10. The frame assembly of claim 1, wherein each upper headgear connector arm is structurally rigid to resist torsion.

11. The frame assembly of claim 1, wherein the second flexible portion allows the upper headgear connector arm to, in use, articulate to conform to the width and profile of the patient cheek regions.

12. The frame assembly of claim 11, wherein the second flexible portion includes a plurality of slots formed in the upper headgear connector arm to create a plurality of hinges to allow the upper headgear connector arm to, in use, articulate and conform to variations in patient cheek regions.

13. The frame assembly of claim 12, wherein the textile material covers the plurality of slots but does not cover the living hinge.

14. The frame assembly of claim 12, wherein the plurality of slots of the second flexible portion are substantially parallel to one another, and wherein the plurality of slots of the second flexible portion are substantially evenly spaced apart from one another.

15. The frame assembly of claim 11, wherein the second flexible portion and the flexible area of the first flexible portion are separated by a first rigid portion.

16. The frame assembly of claim 15, wherein the first rigid portion includes an upper wall along an upper edge of the upper headgear connector arm and a lower wall along a lower edge of the upper headgear connector arm.

17. The frame assembly of claim 1, wherein each shroud connection portion is removably attached to the upper portion of the shroud.

18. The frame assembly of claim 1, wherein each shroud connection portion is permanently attached to the upper portion of the shroud.

19. The frame assembly of claim 1, further comprising a pair of lower headgear connector arms extending from respective sides of a lower portion of the shroud, each lower headgear connector arm including a lower headgear connection point adapted to connect with a lower headgear strap.

20. The frame assembly of claim 1, further comprising a pair of lower headgear connector arms extending from respective sides of a lower portion of the shroud, each lower headgear connector arm including a lower headgear connection point adapted to connect with a lower headgear strap,
wherein the shroud is constructed of polycarbonate,
wherein the pair of upper headgear connector arms comprise a plastic material, the polycarbonate of the shroud being more rigid than the plastic of the upper headgear connectors,
wherein each upper headgear connection point includes a slot adapted to receive the respective upper headgear strap,
wherein the textile material is less rigid as compared to a material of the upper headgear connector arm,
wherein the shroud includes a pair of upper arm connectors at respective sides of the upper portion of the shroud,
wherein the shroud connection portion of each upper headgear connector arm is directly connected to a respective one of the upper arm connectors of the shroud,
wherein each upper headgear connector arm further comprises a second flexible portion provided between the first flexible portion and the upper headgear connection point,
wherein the second flexible portion includes a plurality of slots formed in the upper headgear connector arm to create a plurality of hinges to allow the upper headgear connector arm to, in use, articulate and conform to variations in patient cheek regions,
wherein the plurality of slots of the second flexible portion are substantially parallel to one another,
wherein the plurality of slots of the second flexible portion are substantially evenly spaced apart from one another,
wherein the second flexible portion and the flexible area of the first flexible portion are separated by a first rigid portion, and
wherein the first rigid portion includes an upper wall along an upper edge of the upper headgear connector arm and a lower wall along a lower edge of the upper headgear connector arm.

21. The frame assembly of claim 20, wherein each shroud connection portion is permanently attached to the upper portion of the shroud.

22. The frame assembly of claim 1, further comprising a pair of lower headgear connector arms extending from respective sides of a lower portion of the shroud, each lower headgear connector arm including a lower headgear connection point adapted to connect with a lower headgear strap,
wherein the shroud is constructed of polycarbonate,
wherein the pair of upper headgear connector arms comprise a plastic material, the polycarbonate of the shroud being more rigid than the plastic of the upper headgear connectors,
wherein each upper headgear connection point includes a slot adapted to receive the respective upper headgear strap,
wherein the textile material is less rigid as compared to a material of the upper headgear connector arm,
wherein the shroud includes a pair of upper arm connectors at respective sides of the upper portion of the shroud,
wherein the shroud connection portion of each upper headgear connector arm is directly connected to a respective one of the upper arm connectors of the shroud,
wherein the relatively thicker portions of the first flexible portion of the upper headgear connector arm include a first rigid portion positioned proximal the flexible area of the first flexible portion and between the flexible area and the upper headgear connection point, and
wherein the first rigid portion includes an upper wall along an upper edge of the upper headgear connector arm and a lower wall along a lower edge of the upper headgear connector arm.

23. A patient interface to deliver a supply of air to a patient for treatment of sleep disordered breathing, comprising:
a frame assembly according to claim 1; and
a cushion assembly, the cushion assembly including a shell and a seal-forming structure, the seal-forming structure being configured to, in use, form a seal with the patient's face,
wherein the shell has greater rigidity as compared to the seal-forming structure, and
wherein an opening is formed in the shell to receive the flow of air from the air delivery tube.

24. The patient interface of claim 23, wherein the shell of the cushion assembly is constructed of polycarbonate, and the seal-forming structure comprises an elastomer material,
wherein the shell and the shroud have mating shapes, such that an inner surface of the shroud has a shape that corresponds to an exterior surface of the shell.

25. The patient interface of claim 24, wherein the shell includes a ridge formed therein that surrounds the opening in the shell, the shroud having a perimeter that corresponds to the ridge when the shroud facilitates support of the cushion assembly on the patient's face.

26. A treatment system used for treatment of sleep disordered breathing, comprising:
- a patient interface according to claim 23;
- a respiratory pressure therapy (RPT) device to supply breathable gas at positive pressure; and
- an air delivery tube to pass the breathable gas from the RPT device to the patient interface.

27. The frame assembly of claim 1, wherein the relatively thinner portion of the upper headgear connector arm is spaced from the shroud connection portion such that a first portion of the upper headgear connector arm is configured to pivot relative to a second portion of the upper headgear connector arm at the living hinge, and wherein the upper headgear connector arm is not configured to pivot about the upper portion of the shroud at an attachment point of the shroud connection portion with the upper portion of the shroud.

28. The frame assembly of claim 27, wherein the shroud is constructed of polycarbonate, and wherein the pair of upper headgear connector arms are made of a different material than the polycarbonate of the shroud.

29. The frame assembly of claim 27, wherein the shroud connection portion includes a protruding connector fastened to the shroud, and wherein the relatively thinner portion of the upper headgear connector arm and the relatively thicker portions of the headgear connector arm are spaced and separate from the protruding connector.

30. A frame assembly for a patient interface for treatment of sleep disordered breathing, the frame assembly configured to connect headgear of the patient interface to a cushion assembly of the patient interface, the frame assembly comprising:
- a shroud constructed of a rigid plastic material and including an opening formed therein to receive a flow of air from an air delivery tube, the shroud being structured to, in use, facilitate support of a cushion assembly on a patient's face; and
- a pair of upper headgear connector arms extending from respective sides of an upper portion of the shroud and, in use, configured to extend along respective sides of the patient's face, each upper headgear connector arm having a shape that, in use, curves in an upwards direction such that the upper headgear connector arm extends between the patient's eye and ear;
- each upper headgear connector arm including:
  - a first side configured to face towards the patient's face in use, and a second side opposite the first side and configured to face away from the patient's face in use;
  - an upper headgear connection point adapted to receive a respective upper headgear strap;
  - a shroud connection portion that is connected to the respective side of the upper portion of the shroud;
  - a first flexible portion positioned proximal the shroud connection portion and between the shroud connection portion and the upper headgear connection point, the first flexible portion being configured to, in use, allow the upper headgear connector arm to flex outwardly away from the patient's face and inwardly towards the patient's face to adapt to varying facial widths; and
  - a second flexible portion provided between the first flexible portion and the upper headgear connection point, the second flexible portion allowing the upper headgear connector arm to, in use, articulate to conform to the width and profile of patient cheek regions,
- wherein the second flexible portion includes a first plurality of slots formed in the first side of the upper headgear connector arm and a second plurality of slots formed in the second side of the upper headgear connector arm, the first plurality of slots and the second plurality of slots forming a plurality of hinges,
- wherein the first flexible portion is structurally different than the second flexible portion, and
- wherein each upper headgear connector arm has sufficient rigidity such that, in use, when tension forces are applied to the upper headgear connector arm by the respective upper headgear strap the upper headgear connector arm resists extension and maintains a preformed three-dimensional shape to convert the tension forces into a compressive force adapted to be applied by the cushion assembly on the patient's face.

31. The frame assembly of claim 30, wherein the first flexible portion is a living hinge formed by a relatively thinner portion of the upper headgear connector arm adjacent relatively thicker portions of the upper headgear connector arm to form a flexible area.

32. The frame assembly of claim 31, wherein the second flexible portion and the flexible area of the first flexible portion are separated by a first rigid portion, and
- wherein the first rigid portion includes an upper wall along an upper edge of the upper headgear connector arm and a lower wall along a lower edge of the upper headgear connector arm.

33. A frame assembly for a patient interface for treatment of sleep disordered breathing, the frame assembly configured to connect headgear of the patient interface to a cushion assembly of the patient interface, the frame assembly comprising:
- a shroud constructed of a rigid plastic material and including an opening formed therein to receive a flow of air from an air delivery tube, the shroud being structured to, in use, facilitate support of a cushion assembly on a patient's face; and
- a pair of upper headgear connector arms extending from respective sides of an upper portion of the shroud and, in use, configured to extend along respective sides of the patient's face, each upper headgear connector arm having a shape that, in use, curves in an upwards direction such that the upper headgear connector arm extends between the patient's eye and ear;
- each upper headgear connector arm including:
  - a first side configured to face towards the patient's face in use, and a second side opposite the first side and configured to face away from the patient's face in use;
  - an upper headgear connection point adapted to receive a respective upper headgear strap;
  - a shroud connection portion that is connected to the respective side of the upper portion of the shroud;
  - a first flexible portion positioned proximal the shroud connection portion and between the shroud connection portion and the upper headgear connection point, the first flexible portion being configured to, in use, allow the upper headgear connector arm to flex outwardly away from the patient's face and inwardly towards the patient's face to adapt to varying facial widths; and a second flexible portion provided between the first flexible portion and the upper headgear connection point, the second flexible portion allowing the upper headgear connector arm to, in use, articulate to conform to the width and profile of patient cheek regions, wherein the second flexible portion includes a first plurality of slots formed in the first side of the upper headgear connector arm and a second plurality of slots formed in the second side of the upper headgear connector arm, the first plurality of slots and the second plurality of slots forming a plurality of hinges, wherein the first flexible portion is structurally different than the second flexible portion, and wherein a portion of each upper headgear connector arm spanning from the upper headgear connection point to the first flexible portion comprises entirely a same material.

\* \* \* \* \*